United States Patent
Goldfless et al.

(10) Patent No.: US 12,049,667 B2
(45) Date of Patent: Jul. 30, 2024

(54) HIGH-THROUGHPUT POLYNUCLEOTIDE LIBRARY SEQUENCING AND TRANSCRIPTOME ANALYSIS

(71) Applicant: AbVitro LLC, Wilmington, DE (US)

(72) Inventors: Stephen Jacob Goldfless, Seattle, WA (US); Adrian Wrangham Briggs, Seattle, WA (US); Rajagopal Chari, Seattle, WA (US); Yue Jiang, Seattle, WA (US); Ronald Hause, Seattle, WA (US); Francois Vigneault, Seattle, WA (US)

(73) Assignee: ABvitro LLC, Wilmington, DE (US)

( * ) Notice: Subject to any disclaimer, the term of this patent is extended or adjusted under 35 U.S.C. 154(b) by 32 days.

(21) Appl. No.: 16/616,424

(22) PCT Filed: May 25, 2018

(86) PCT No.: PCT/US2018/034768
§ 371 (c)(1),
(2) Date: Nov. 22, 2019

(87) PCT Pub. No.: WO2018/218222
PCT Pub. Date: Nov. 29, 2018

(65) Prior Publication Data
US 2020/0354784 A1    Nov. 12, 2020

Related U.S. Application Data

(60) Provisional application No. 62/511,949, filed on May 26, 2017.

(51) Int. Cl.
*C12Q 1/6855* (2018.01)

(52) U.S. Cl.
CPC ..... *C12Q 1/6855* (2013.01); *C12Q 2525/155* (2013.01); *C12Q 2525/179* (2013.01); *C12Q 2525/191* (2013.01); *C12Q 2563/159* (2013.01); *C12Q 2563/179* (2013.01)

(58) Field of Classification Search
CPC ............ C12Q 1/6855; C12Q 2525/155; C12Q 2525/179; C12Q 2525/191; C12Q 2563/159; C12Q 2563/179
See application file for complete search history.

(56) References Cited

U.S. PATENT DOCUMENTS

| | | |
|---|---|---|
| 4,656,134 A | 4/1987 | Ringold |
| 4,683,195 A | 7/1987 | Mullis et al. |
| 4,683,202 A | 7/1987 | Mullis |
| 4,766,067 A | 8/1988 | Biswas |
| 4,795,699 A | 1/1989 | Tabor |
| 4,800,159 A | 1/1989 | Mullis |
| 4,889,818 A | 12/1989 | Gelfand |
| 4,921,794 A | 5/1990 | Tabor |
| 4,965,188 A | 10/1990 | Mullis |
| 4,988,617 A | 1/1991 | Landegren |
| 4,994,370 A | 2/1991 | Silver |
| 5,066,584 A | 11/1991 | Gyllensten |
| 5,091,310 A | 2/1992 | Innis |
| 5,122,464 A | 6/1992 | Wilson |
| 5,130,238 A | 7/1992 | Malek |
| 5,142,033 A | 8/1992 | Innis |
| 5,168,038 A | 12/1992 | Tecott |
| 5,210,015 A | 5/1993 | Gelfand |
| 5,242,794 A | 9/1993 | Whiteley |
| 5,494,810 A | 2/1996 | Barany |
| 5,925,517 A | 7/1999 | Tyagi |
| 6,174,670 B1 | 1/2001 | Wittwer |
| 6,306,597 B1 | 10/2001 | Macevicz |
| 6,569,627 B2 | 5/2003 | Wittwer |
| 6,582,938 B1 | 6/2003 | Su |
| 6,797,470 B2 | 9/2004 | Barany |
| 7,037,687 B2 | 5/2006 | Ashton, II |
| 7,083,917 B2 | 8/2006 | Barany |
| 7,166,434 B2 | 1/2007 | Barany |
| 7,169,560 B2 | 1/2007 | Lapidus |
| 7,232,656 B2 | 6/2007 | Balasubramanian |

(Continued)

FOREIGN PATENT DOCUMENTS

| | | |
|---|---|---|
| WO | WO9312227 A1 | 6/1993 |
| WO | WO9951773 A1 | 10/1999 |

(Continued)

OTHER PUBLICATIONS

Al-Lazikani, B. et al. (1997). "Standard Conformations for the Canonical Structures of Immunoglobulins," J. Mol. Biol. 273:927-948.

Aljanabi et al., "Universal and Rapid Salt-Extraction of High Quality Genomic DNA for PCR-based Techniques," Nucleic Acids Res (1997) 25(22): 4692-4693.

Altschul, S.F. et al. (1997). "Gapped BLAST and PSI-BLAST: A New Generation of Protein Database Search Programs," Nucleic Acids Res. 25(17):3389-3402.

Arguel et al., "A cost effective 5' selective single cell transcriptome profiling approach with improved UMI design." Nucleic Acids Res. (2017) 45(7): e48.

Becker-Andre et al., "Absolute mRNA Quantification Using the Polymerase Chain Reaction (PCR). A Novel Approach by a PCR Aided Transcript Titration Assay (PATTY)," Nucleic Acids Res (1989) 17(22): 9437-9444.

(Continued)

*Primary Examiner* — Sahana S Kaup
(74) *Attorney, Agent, or Firm* — Morrison & Foerster LLP

(57) ABSTRACT

Provided herein are methods for target gene sequencing and single cell barcoding in conjunction with analysis of gene expression in single cells. In some embodiments, the target gene is an immune molecule, such as an antibody or TCR. In some embodiments, the methods can be used to carry out transcriptome sequencing, e.g., RNA sequencing, to capture transcriptome of single cells paired with full receptor immune receptor sequences such that information about the immune repertoire and transcriptome of a cell can be determined. Also provided are polynucleotide libraries for use in carrying out transcriptome analysis and immune molecule, e.g., antibody or TCR, sequencing.

33 Claims, 5 Drawing Sheets

Specification includes a Sequence Listing.

(56) References Cited

U.S. PATENT DOCUMENTS

| | | | |
|---|---|---|---|
| 7,320,865 B2 | 1/2008 | Barany | |
| 7,332,285 B2 | 2/2008 | Barany | |
| 7,364,858 B2 | 4/2008 | Barany | |
| 7,429,453 B2 | 9/2008 | Barany | |
| 7,598,035 B2 | 10/2009 | Macevicz | |
| 7,622,280 B2 | 11/2009 | Holliger | |
| 7,645,596 B2 | 1/2010 | Williams | |
| 7,769,400 B2 | 8/2010 | Backholm | |
| 9,816,088 B2 | 11/2017 | Vigneault | |
| 9,902,950 B2 | 2/2018 | Church | |
| 10,119,134 B2 | 11/2018 | Vigneault | |
| 10,208,338 B2 * | 2/2019 | Makarov | C12N 9/1252 |
| 10,246,703 B2 | 4/2019 | Church | |
| 10,392,614 B2 | 8/2019 | Vigneault | |
| 10,392,726 B2 | 8/2019 | Church | |
| 10,393,743 B2 | 8/2019 | Vigneault | |
| 10,590,483 B2 | 3/2020 | Vigneault et al. | |
| 11,061,030 B2 | 7/2021 | Vigneault et al. | |
| 2012/0010091 A1 | 1/2012 | Linnarson | |
| 2013/0274117 A1 | 10/2013 | Church | |
| 2013/0296535 A1 | 11/2013 | Church | |
| 2014/0357500 A1 * | 12/2014 | Vigneault | C12Q 1/6809 506/4 |
| 2014/0378349 A1 * | 12/2014 | Hindson | C12N 15/1065 506/26 |
| 2015/0376609 A1 * | 12/2015 | Hindson | C40B 20/04 506/4 |
| 2016/0032282 A1 | 2/2016 | Vigneault | |
| 2016/0244742 A1 | 8/2016 | Linnarsson et al. | |
| 2016/0244825 A1 | 8/2016 | Vigneault | |
| 2017/0268056 A1 | 9/2017 | Vigneault | |
| 2018/0127743 A1 | 5/2018 | Vigneault | |
| 2018/0148715 A1 | 5/2018 | Church | |
| 2018/0274021 A1 | 9/2018 | Vigneault | |
| 2019/0024145 A1 | 1/2019 | Vigneault, V | |
| 2019/0025299 A1 | 1/2019 | Vigneault | |
| 2019/0025304 A1 | 1/2019 | Vigneault | |
| 2019/0048067 A1 | 2/2019 | Vigneault | |
| 2019/0064173 A1 | 2/2019 | Bharadwaj et al. | |
| 2019/0161750 A1 | 5/2019 | Church | |
| 2019/0264198 A1 | 8/2019 | Vigneault | |
| 2019/0352201 A1 | 11/2019 | Nakayama | |
| 2020/0048630 A1 | 2/2020 | Vigneault | |
| 2020/0078404 A1 | 3/2020 | Ports et al. | |
| 2020/0088725 A1 | 3/2020 | Vigneault et al. | |
| 2020/0239910 A1 | 7/2020 | Bonyhadi et al. | |
| 2020/0239955 A1 | 7/2020 | Vigneault et al. | |
| 2020/0292526 A1 | 9/2020 | Hause et al. | |
| 2021/0180014 A1 | 6/2021 | Amin et al. | |

FOREIGN PATENT DOCUMENTS

| | | | | |
|---|---|---|---|---|
| WO | WO0140803 A1 | 6/2001 | | |
| WO | WO0189788 A2 | 11/2001 | | |
| WO | WO03020763 A2 | 3/2003 | | |
| WO | WO2004002627 A2 | 1/2004 | | |
| WO | WO2004033685 A1 | 4/2004 | | |
| WO | WO2004091763 A2 | 10/2004 | | |
| WO | WO2005021151 A1 | 3/2005 | | |
| WO | WO2006040551 A2 | 4/2006 | | |
| WO | WO2006040554 A1 | 4/2006 | | |
| WO | WO2006096571 A2 | 9/2006 | | |
| WO | WO2007081385 A2 | 7/2007 | | |
| WO | WO2007089541 A2 | 8/2007 | | |
| WO | WO2008063227 A2 | 5/2008 | | |
| WO | WO2010036352 A1 | 4/2010 | | |
| WO | WO2011044186 A1 | 4/2011 | | |
| WO | WO2012048340 A2 | 4/2012 | | |
| WO | WO2012048341 A1 | 4/2012 | | |
| WO | WO2013033271 A2 | 3/2013 | | |
| WO | WO2014108850 A2 | 7/2014 | | |
| WO | WO-2014108850 A2 * | 7/2014 | | C12Q 1/6806 |
| WO | WO2014144495 A1 | 9/2014 | | |
| WO | WO2014182197 A1 | 11/2014 | | |
| WO | WO 2014/210353 | 12/2014 | | |
| WO | WO 2015/044428 | 4/2015 | | |
| WO | WO2015164212 A1 | 10/2015 | | |
| WO | WO2016040476 A1 | 3/2016 | | |
| WO | WO2016044227 A1 | 3/2016 | | |
| WO | WO-2016044227 A1 * | 3/2016 | | C12N 15/1093 |
| WO | WO 2016/100977 | 6/2016 | | |
| WO | WO-2016126871 A2 * | 8/2016 | | C12Q 1/6806 |
| WO | WO 2016/168584 | 10/2016 | | |
| WO | WO2016176322 A1 | 11/2016 | | |
| WO | WO2017053902 A1 | 3/2017 | | |
| WO | WO2017053903 A1 | 3/2017 | | |
| WO | WO2017053905 A1 | 3/2017 | | |
| WO | WO2017053906 A1 | 3/2017 | | |
| WO | WO2018057051 A1 | 3/2018 | | |
| WO | WO2018218222 A1 | 11/2018 | | |
| WO | WO 2019/051335 | 3/2019 | | |

OTHER PUBLICATIONS

Bibkova, M. et al. (2006). "High-Throughput DNA Methylation Profiling Using Universal Bead Arrays," Genome Res. 16:383-393.

Bird et al. "Single-Chain Antigen-Binding Proteins," Science (1988) 242: 423-426.

Brenner, C. "A Cultivated Taste for Yeast," Genome Biol (2000) 1:1.

Brenner, C. "Chemical Genomics in Yeast," Genome Biol (2004) 5(9): 240.

Brown et al., "Chemical Synthesis and Cloning of a Tyrosine tRNA Gene," Methods Enzymol (1979) 68: 109-151.

Clackson, T. et al. (Aug. 15, 1991). "Making Antibody Fragments Using Phage Display Libraries," Nature 352:624-628.

Cloonan et al., "Stem Cell Transcriptome Profiling via Massive-Scale mRNA Sequencing," Nat Methods (2008) 5(7): 613-619.

De Wildt et al., "Antibody Arrays for High-Throughput Screening of Antibody-Antigen Interactions," Nat Biotechnol (2000) 18(9): 989-94.

Dear, P. "One by One: Single Molecule Tools for Genomics," Brief Funct Genomic Proteomic (2003) 1(4): 397-416.

Diviacco et al., "A Novel Procedure for Quantitative Polymerase Chain Reaction by Coamplification of Competitive Templates," Gene (1992) 122(2): 313-20.

Duhaime et al., "Towards Quantitative Metagenomics of Wild Viruses and Other Ultra-Low Concentration DNA Samples: A Rigorous Assessment and Optimization of the Linker Amplification Method," Environ Microbiol (2012) 14(9): 2526-2537.

Eason et al., "Characterization of Synthetic DNA Bar Codes in *Saccharomyces* Cerevisiae Gene-Deletion Strains," Proc Natl Acad Sci U S A (2004) 101(30): 11046-11051.

Edd et al., "Controlled Encapsulation of Single-Cells Into Monodisperse Picoiitre Drops," Lab Chip (2008) 8(8): 1262-1264.

Freeman et al., "Quantitative RT-PCR: Pitfalls and Potential," Biotechniques (1999) 26(1): 112-225.

Gansauge et al., "Single-stranded DNA Library Preparation From Highly Degraded DNA Using T4 DNA Ligase," Nucleic Acids Res (2017) 45(10): e79.

Ge, H. "UPA, a Universal Protein Array System for Quantitative Detection of Protein-Protein, protein-DNA, protein-RNA and Protein-Ligand Interactions," Nucleic Acids Res (2000) 28(2): e3.

Giaever et al., "Chemogenomic Profiling: Identifying the Functional Interactions of Small Molecules in Yeast," Proc Natl Acad Sci U S A (2004) 101(3): 793-798.

Grabherr et al., "Full-length Transcriptome Assembly From RNA-Seq Data Without a Reference Genome," Nat Biotechnol (2011) 29(7): 644-652.

Gu et al., "Depletion of Abundant Sequences by Hybridization (DASH): Using Cas9 to Remove Unwanted High-Abundance Species in Sequencing Libraries and Molecular Counting Applications," Genome Biol (2016) 17: 41.

Gustincich et al., "A Fast Method for High-Quality Genomic DNA Extraction From Whole Human Blood," Biotechniques (1991) 11(3): 298-300, 302.

(56) References Cited

OTHER PUBLICATIONS

Hammond et al., "Extraction of DNA From Preserved Animal Specimens for Use in Randomly Amplified Polymorphic DNA Analysis," Anal Biochem (1996) 240(2): 298-300.
Harris, T.D. et al. (2008). "Singie-Molecule DNA Sequencing of a Viral Genome", Science 320:106-109.
Hashimshony et al., "CEL-Seq: single-cell RNA-Seq by multiplexed linear amplification." Cell Rep. (2012) 2(3):666-673.
Hollyman et al., "Manufacturing Validation of Biologically Functional T Cells Targeted to CD19 Antigen for Autologous Adoptive Cell Therapy." Journal of Immunotherapy. 2009. 32(2):169-180.
Honegger et al., "Yet another numbering scheme for immunoglobulin variable domains: an automatic modeling and analysis tool," J Mol Biol, (2001) 8:309(3):657-70.
Huston, J.R. et al. (Aug. 1988). "Protein engineering of antibody binding sites: recovery of specific activity in an anti-digoxin single-chain Fv analogue produced in *Escherichia coli*," Proc. Natl. Acad. Sci. U.S.A. 85(16)5879-5883.
Islam et al., Highly Multiplexed and Strand-Specific Single-Cell RNA 5' End Sequencing, Nat Protoc (2012) 7(5): 813-828.
Karlin et al., "Applications and statistics for multiple high-scoring segments in molecular sequences", Proc. Natl. Acad. Sci. USA (1993) 90:5873-5787.
Kindt et al., Kuby Immunology 6th ed., W.H. Freeman and Co. (2007) p. 91.
Klaver et al., "T Cell maturation Stage Prior to and During GMP Processing Informs on CAR T Cell Expansion in Patients." Frontiers in Immunology. (2016) 7:648 (7 pages.).
Klein et al., "Droplet Barcoding for Single-Cell Transcriptomics Applied to Embryonic Stem Cells," Cell (2015) 161(5): 1187-1201.
Kumar et al., "Emerging Technologies in Yeast Genomics," Nat Rev Genet (2001) 2(4): 302-312.
Larrick et al., "Polymerse Chain Reaction Using Mixed Primers: Cloning of Human Monoclonal Antibody Variable Region Genes from Single Hybridoma Cells," Nat Biotechnol (1989) 7: 934-938.
Lefranc et al., "IMGT unique numbering for immunoglobulin and T cell receptor variable domains and Ig superfamily V-like domains," Dev Comp Immunol (2003) 27(1):55-77.
Lueking et al., "Protein Microarrays for Gene Expression and Antibody Screening," Anal Biochem (1999) 270(1): 103-111.
MacAbeath et al., "Printing Proteins as Microarrays for High-Throughput Function Determination," Science (2000) 289(5485): 1760-1763.
MacCallum et al., "Antibody-antigen interactions: Contact analysis and binding site topography," J. Mol. Biol. (1996) 262, 732-745.
Mackay et al., "Real-time PCR in Virology," Nucleic Acids Res (2002) 30(6): 1292-1305.
Macosko et al., "Highly Parallel Genome-wide Expression Profiling of Individual Cells Using Nanoliter Droplets," Cell (2015) 161(5): 1202-1214.
Margulies, M. et al. (Sep. 15, 2005, e-pub. Jul. 31, 2005). "Genome Sequencing in Open Microfabricated High Density Picoliter Reactors," Nature 437(7057):376-380.
McCaughan et al., "Single-molecule Genomics," J Pathol (2010) 220(2): 297-306.
Muyldermans et al., "Sequence and Structure of VH Domain From Naturally Occurring Camel Heavy Chain Immunoglobulins Lacking Light Chains," Protein Eng (1994) 7(9): 1129-1135.
Narang et al., "Improved Phosphotriester Method for the Synthesis of Gene Fragments," Methods Enzymol (1979) 68: 90-98.
Nicholls et al., "An Improved Method for Generating Single-Chain Antibodies From Hybridomas," J Immunol Methods (1993) 165(1): 81-91.
Osbourn et al., "Directed Selection of MIP-1 Alpha Neutralizing CCR5 Antibodies From a Phage Display Human Antibody Library," Nat Biotechno! (1998) 16(8): 778-781.
Portolano et al., "Lack of promiscuity in autoantigen-specific H and L chain combinations as revealed by human H and L chain "roulette"," J. Immunol. (1993) 150:880-887.

Quail et al., "Evaluation and Optimisation of Preparative Semi-Automated Electrophoresis Systems for Illumina Library Preparation," Electrophoresis (2012) 33(23): 3521-3528.
Raine et al., "SPlinted Ligation Adapter Tagging (SPLAT), a Novel Library Preparation Method for Whole Genome Bisulphite Sequencing," Nucleic Acids Res (2017) 45(6): e36.
Reddy et al., "Clinical Potential of Neurosteroids for CNS Disorders." Trends in Pharmacological Sciences. (2016) 37(7): 543-561.
Robertson et al. "De Novo Assembly and Analysis of RNA-seq Data," Nat Methods (2010) 7(11): 909-912.
Schulz et al., "Oases: Robust De Novo RNA-seq Assembly Across the Dynamic Range of Expression Levels," Bioinformatics (2012) 28(8): 1086-1092.
Scmueck-Henneresse et al., "Comprehensive Approach for Identifying the T Cell Subset Origin of CD3 and CD28 Antibody Activated Chimeric Antigen Receptor Modified T Cells." The Journal of Immunology. 2017. 199(1): 348-362.
Shugay et al., "Towards Error-Free Profiling of Immune Repertoires," Nat Methods (2014) 11(6): 653-655.
Soni, G.V. et al. (2007). "Progress toward Ultrafast DNA Sequencing Using Solid-State Nanopores" Clin. Chem. 53(11):1996-2001.
Sunnucks et al., "Microsatellite and Chromosome Evolution of Parthenogenetic Sitobion Aphids in Australia," Genetics (1996) 144(2): 747-756.
Surget-Groba et al., "Optimization of De Novo Transcriptome Assembly From Next-Generation Sequencing Data," Genome Res (2010) 20(10): 1432-1440.
Unpublished U.S. Appl. No. 16/335,877, filed Mar. 22, 2019, titled "Affinity-Oligonucleotide Conjugates and Uses Thereof" (Copy not provided). (Copy not submitted herewith pursuant to the waiver of 37 C.F. R. § 1.98(a)(2)(iii) issued by the Office on Sep. 21, 2004).
Unpublished U.S. Appl. No. 16/531,038, filed Aug. 3, 2019, titled "Methods of Selecting T Cell Receptors Using Affinity Oligonucleotide Conjugates" (Copy not provided).(Copy not submitted herewith pursuant to the waiver of 37 C.F. R. § 1.98(a)(2)(iii) issued by the Office on Sep. 21, 2004).
Unpublished U.S. Appl. No. 16/780,234, filed Feb. 2, 2020, titled "High-Throughput Nucleotide Library Sequencing" (Copy not provided). (Copy not submitted herewith pursuant to the waiver of 37 C.F. R. § 1.98(a)(2)(iii) issued by the Office on Sep. 21, 2004).
Wang et al., "Clinical manufacturing of Car T cells: foundation of a promising therapy," Mol Ther Oncolytics (2016)3:16015.
Wang et al., "Manufacture of Tumor and Virus Specific T Lymphocytes for Adoptive Cell Therapies." Cancer Gene Therapy, 2015. 22(2): 85-94.
Ward, E.S. et al. (Oct. 12, 1989). "Binding activities of a repertoire of single immunoglobulin variable domains secreted from *Escherichia coli*," Nature 341(6242):544-546.
Winzeler et al., "Functional Characterization of the S. Cerevisiae Genome by Gene Deletion and Parallel Analysis," Science (1999) 285(5429): 901-906.
Xie et al., "SOAPdenovo-Trans: De Novo Transcriptome Assembly With Short RNA-Seq Reads," Bioinformatics (2014) 30(12): 1660-1666.
Zapata et al., "Engineering Linear F(ab')2 Fragments For Efficient Production in *Escherichia coli* and Enhanced Antiproliferative Activity," Protein Engineering (1995) 8(10): 1057-1062.
Zimmerman et al., "Technical Aspects of Quantitative Competitive PCR," Biotechniques (1996) 21(2): 268-72, 274-9.
Fox et al., "Applications of Ultra-high-Throughput Sequencing," Methods Mol Biol (2009) 553:79-108.
Morozova et al., "Applications of next-generation sequencing technologies in functional genomics," Genomics (2008) 92(5):255-264.
Shendure et al., "Accurate multiplex polony sequencing of an evolved bacterial genome,"Science (2005) 309:1728-1732.
Jiang et al., "Whole transcriptome analysis with sequencing: methods, challenges and potential solutions," Cellular and Molecular Life Sciences (2015) vol. 72(18), pp. 3425-3439.
Levsky et al., "Single-Cell Gene Expression Profiling," Science. (2002) 297; 836-840.

(56) References Cited

OTHER PUBLICATIONS

Gansauge et al., ""Single-stranded DNA library preparation for the sequencing of ancient or damaged DNA,"" Nature Protocols (2013) 8(4):737-748.

* cited by examiner

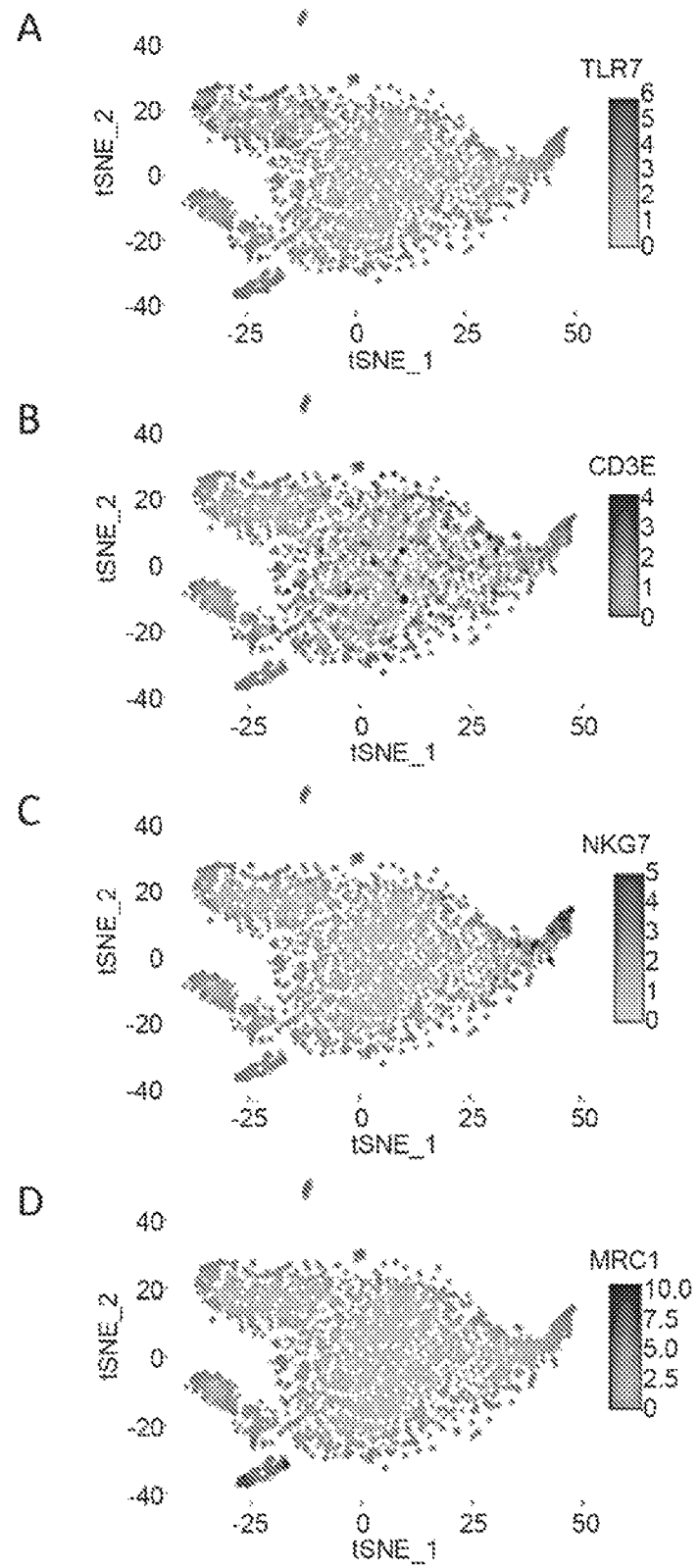

HIGH-THROUGHPUT POLYNUCLEOTIDE LIBRARY SEQUENCING AND TRANSCRIPTOME ANALYSIS

CROSS-REFERENCE TO RELATED APPLICATIONS

This application is a National Stage application under 35 U.S.C. § 371 of International Application No. PCT/US2018/034768, filed on May 25, 2018 which claims priority from U.S. provisional application No. 62/511,949, filed May 26, 2017, entitled "HIGH-THROUGHPUT POLYNUCLEOTIDE LIBRARY SEQUENCING AND TRANSCRIPTOME ANALYSIS," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042011700SeqList.txt, created Nov. 22, 2019, which is 28.1 KB in size. The information in the electronic format of the Sequence Listing is incorporated by reference in its entirety.

FIELD

The present disclosure relates to methods for target gene sequencing and single cell barcoding in conjunction with analysis of gene expression in single cells. In some embodiments, the target gene is an immune molecule, such as an antibody or TCR. In some embodiments, the methods can be used to carry out transcriptome sequencing, e.g., RNA sequencing, to capture a transcriptome of single cells paired with full receptor immune receptor sequences such that information about the immune repertoire and transcriptome of a cell can be determined. The present disclosure also relates to polynucleotide libraries for use in carrying out transcriptome analysis and immune molecule, e.g., antibody or TCR, sequencing.

BACKGROUND

The determination of the transcriptomic content of a cell or tissue (i.e., "gene expression profiling") provides a method for the functional analysis of normal and diseased cells or tissues, including providing characterization information about the "state" of the cell or tissue or identifying characteristics of subpopulations of cells. Existing tools for single-cell transcriptome sequencing are limited in their throughput and/or are not capable of capturing full length immune receptor sequences. Thus, improved methods are needed. Provided are methods and compositions that meet such needs.

SUMMARY

Provided are methods of producing a polynucleotide library from individual cells or a plurality of cells, wherein one or more full-length barcoded target polynucleotide sequences or selected fragments thereof are produced, while co-generating a multitude of barcoded polynucleotide sequences, the collection of which substantially represents the transcriptome or genome of a cell or plurality of cells. The barcoding permits analysis and quantification of expression or presence of polynucleotides from the same cell. Also provided are polynucleotide libraries produced by the methods herein. Also provided are methods of transcriptome analysis from a single cell or a multitude of cells and combining transcriptome analysis with analysis of target sequence(s).

In some embodiments, the methods include producing a polynucleotide library, which includes adding a second adaptor to each of a plurality of barcoded single-stranded polynucleotides at or near a terminal end that is opposite a first adaptor attached to each of the barcoded single-stranded polynucleotides, the plurality of barcoded single-stranded polynucleotides containing: (i) one or more target single-stranded polynucleotide(s), including an amplicon of one or more target polynucleotide(s), or a complement(s) thereof, present in a cell of a population of cells; and (ii) a collection of single-stranded polynucleotides that each contain an amplicon of a polynucleotide, or a complement thereof, in the cell; and wherein each of the plurality of barcoded single-stranded polynucleotides includes a vessel barcode that is the same for all polynucleotides from (i) and (ii) from the same cell of the population of cells.

In some embodiments, the plurality of barcoded single-stranded polynucleotides includes polynucleotides of (i) and (ii) of a plurality of cells in the population of cells. In some embodiments, the plurality of barcoded single-stranded polynucleotides further contains a molecular barcode that is unique to each single-stranded polynucleotide or an amplified product thereof.

In some embodiments, the collection of single-stranded polynucleotides from each cell of the population of cells, collectively, contain complementary DNA (cDNA) strands of a transcriptome or a partial transcriptome. In some embodiments, the transcriptome or partial transcriptome, collectively, contain at least 60%, 70%, 75%, 80%, 85% 90% 95%, 96%, 97%, 98%, 99% or 100% of the transcripts present in the genome of the cell.

In some embodiments of the method, each of the barcoded single-stranded polynucleotides has a size that is greater than or greater than about 50 base pairs, greater than 100 base pairs, or greater than 200 base pairs. In some embodiments, each of the barcoded single-stranded polynucleotides have a size from or from about 50 base pairs (bp) to 1500 bp, 50 bp to 1250 bp, 50 bp to 1000 bp, 50 bp to 750 bp, 50 bp to 500 bp, 100 bp to 1500 bp, 100 bp to 1250 bp, 100 bp to 1000 bp, 100 bp to 750 bp, 100 bp to 500 bp, 200 bp to 1500 bp, 200 bp to 1250 bp, 200 bp to 1000 bp, 200 bp to 750 bp or 250 bp to 500 bp.

In some embodiments of the method, the second adaptor is added in a homogenous mixture containing the plurality of barcoded-single stranded polynucleotides.

In some embodiments, the first adaptor contains the vessel barcode.

In some embodiments of the methods of producing a polynucleotide library, the method includes: (a) lysing cells within each of a plurality of vessels, wherein each of said vessels contains a cell from a sample containing a population of cells; (b) producing, in each vessel, a plurality of complementary polynucleotides, said producing of said plurality of complementary polynucleotides including (i) producing one or more target polynucleotide(s) that is complementary to one or more target polynucleotide(s) present in the cell using one or more target-specific primers; and (ii) producing a collection of polynucleotides, each of which is complementary to a polynucleotide in the cell. In some embodiments, the collection of polynucleotides in (ii) is produced using random and/or degenerate and/or non-specific oligo primers. In some embodiments, the collection of polynucleotides in (ii) is produced using oligo dT primers.

In some embodiments, each of said vessels further contains a plurality of molecular barcoded oligonucleotides, a pool of vessel barcoded oligonucleotides, and, optionally, a first adaptor, and the method further includes: (c) attaching to a plurality of, optionally each of the plurality of, complementary polynucleotides one of the plurality of molecular barcoded oligonucleotides, thereby generating a plurality of barcoded polynucleotides, such as molecular barcoded polynucleotides, each containing a molecular barcode, optionally wherein the molecular barcode is distinct from the molecular barcodes contained by other barcoded polynucleotides within the plurality and/or is a unique molecular barcode; (d) attaching one of the one or a pool of vessel barcoded oligonucleotides, or an amplified products thereof, to a plurality of, optionally each of, the barcoded polynucleotides, thereby generating a plurality of dual-barcoded polynucleotides, wherein each of the dual-barcoded polynucleotides in the same vessel contain the same vessel barcode. In some embodiments, step (d) comprises attaching one of the one or a pool of vessel barcoded oligonucleotides, or an amplified product thereof, and the first adaptor or one of the pool of first adaptors, or an amplified product thereof, to a plurality of, optionally each of, the molecular barcoded polynucleotides, thereby generating a plurality of dual-barcoded polynucleotides, optionally single-stranded dual-barcoded polynucleotides, each comprising a molecular barcode and a vessel barcode, wherein each of the dual-barcoded polynucleotides in the same vessel comprise the same vessel barcode In some embodiments, the methods further include (e) producing a single-stranded amplicon of a plurality of, optionally each of, the plurality of dual-barcoded polynucleotides and/or (f) adding a second adaptor to each of the single-stranded amplicons, thereby adding the adaptor to a dual-barcoded single-stranded polynucleotide, wherein the first adaptor and second adaptor are present at or near opposite ends of each of the dual-barcoded single-stranded polynucleotides.

In some embodiments, the methods of producing a polynucleotide library include the steps of: (a) lysing cells within each of a plurality of vessels, wherein each of said vessels contains a cell from a sample containing a population of cells, a plurality of molecular barcoded oligonucleotides, and one or a pool of vessel barcoded oligonucleotides, and, optionally, a first adaptor or pool of first adaptors; (b) producing, in each vessel, a plurality of complementary polynucleotides, said producing said plurality, including (i) producing one or more target polynucleotide(s) that is complementary to one or more target polynucleotide(s) present in the cell; and (ii) producing a collection of polynucleotides that each are individually complementary to a polynucleotide in the cell; (c) attaching to each complementary polynucleotide one of the plurality of molecular barcoded oligonucleotides, thereby generating a plurality of barcoded polynucleotides each containing a unique molecular barcode; (d) attaching one of the one or a pool of vessel barcoded oligonucleotides, or an amplified product thereof, and the first adaptor or one of the pool of first adaptors, or an amplified product thereof, to each of the barcoded polynucleotides, thereby generating a plurality of dual-barcoded polynucleotides, optionally single-stranded dual-barcoded polynucleotides, wherein each of the dual-barcoded polynucleotides comprises a molecular barcode and a vessel barcode, and each of the dual-barcoded polynucleotides in the same vessel comprises the same vessel barcode; (e) producing a single-stranded amplicon of each of the plurality of dual-barcoded polynucleotides; and (f) adding a second adaptor to each of the single-stranded amplicons, thereby adding the second adaptor to a dual-barcoded single-stranded polynucleotide, wherein the first adaptor and second adaptor are present at or near opposite ends of each of the dual-barcoded single-stranded polynucleotides.

In some embodiments, the adaptor, such as the first adaptor, contains the vessel barcoded oligonucleotide. In some embodiments, the vessel barcoded oligonucleotide contains the first adaptor. In some embodiments, the collection of polynucleotides from each cell of the population of cells, collectively, contain sequences complementary to transcripts of a transcriptome or a partial transcriptome of a cell. In some embodiments, the transcriptome or partial transcriptome contains at least 60%, 70%, 75%, 80%, 85% 90% 95%, 96%, 97%, 98%, 99% or 100% of the transcripts present in the genome of the cell.

In some embodiments, the one or more target polynucleotide(s) and/or the polynucleotide in the cell is a DNA. In some embodiments, the one or more target polynucleotide(s) from (i) and/or the polynucleotide from (ii), from which the amplicon in (i) and/or the amplicon in (ii) is/are derived, is/are a DNA. In some embodiments, the one or more target polynucleotide(s) and/or the polynucleotide in the cell is an RNA, such as an mRNA. In some embodiments, the one or more target polynucleotide(s) from (i) and/or the polynucleotide from (ii), from which the amplicon in (i) and/or the amplicon in (ii) is/are derived, is an RNA, such as an mRNA.

In some embodiments, each of or one or more of the complementary polynucleotide of (b) is a cDNA. In some embodiments, each of or one or more of the barcoded single-stranded polynucleotide(s) is a strand of a cDNA.

In some embodiments of the methods, the first adaptor and/or second adaptor contain at least one universal priming site. In some embodiments, the first adaptor and second adaptor are different; and/or the first adaptor contains a first universal priming site and the second adaptor contains a second universal priming site, optionally wherein the first universal priming site and second universal priming site are different. In some embodiments, the first universal priming site and/or second universal priming site is or contains a P7 priming site (C7) or a contiguous portion thereof or a P5 priming site or a contiguous portion thereof, optionally wherein the contiguous portion thereof is sufficient to anneal to a complementary sequence. In some embodiments, the first universal priming site is or contains the P7 priming site (C7) or a contiguous portion thereof and the second universal priming site is or contains the P5 priming site (C5) or a contiguous portion thereof. In some embodiments, the P7 priming site (C7) contains the sequence AGATCGGAAGAGCACACGTCTGAACTCCA (SEQ ID NO:77), or is a contiguous portion thereof. In some embodiments, the P5 priming site contains the sequence AGATCGGAAGAGCGTCGTGTAGGGAAAGAGTGTA-GATCTCGGTGGTCGCC GTATCATT (SEQ ID NO:78), or is a contiguous portion thereof. In some embodiments, the contiguous portion contains at least or at least about 15, 20, 25 or 30 nucleotides in length. In some embodiments, the P5 priming site is a contiguous portion set forth in SEQ ID NO:25 (AGATCGGAAGAGCGTCGTGT).

In some embodiments, adding the second adaptor includes hybridizing a splint oligonucleotide to each of the barcoded single-stranded polynucleotides in the presence of an oligonucleotide including a second universal priming site, wherein the splint oligonucleotide contains (i) a sequence complementary to the second universal priming site and (ii) a degenerate overhang sequence capable of randomly annealing to the 3' end of the barcoded single-stranded polynucleotide. In some cases, prior to the hybridizing, the splint oligonucleotide and the oligonucleotide containing the second universal priming site are annealed to form a splint-adaptor duplex. In some aspects, the degenerate overhang sequence contains the sequence $(N)_{3-12}$, wherein N is any nucleotide.

In some of any such embodiments, the degenerate overhang sequence contains the sequence NNNNNN, wherein N is any nucleotide (SEQ ID NO:24). In some embodiments, the splint oligonucleotide contains the sequence ACACGACGCTCTTCCGATC wherein N is any amino acid (SEQ ID NO:26). In some of any such embodiments, the oligonucleotide containing the second universal priming site contains the sequence AGATCGGAAGAGCGTCGTGT (SEQ ID NO:25).

In some of any such embodiments, the vessel barcoded oligonucleotide contains at least or about at least 3, 4, 5, 6, 7, 8, 9, 10, 15, 20, 30, 40 or 50 nucleotides. In some of any such embodiments, the vessel barcoded oligonucleotide contains from or from about 10 to 30 nucleotides. In some of any such embodiments, the vessel barcoded oligonucleotide contains a degenerate sequence. In some of any such embodiments, the vessel barcoded oligonucleotide contains the sequence $(N)_{14-17}$, wherein N is any nucleotide, optionally wherein at least one or two N in the sequence is W, wherein W is adenine or thymine. In some of any such embodiments, the vessel barcoded oligonucleotide contains the sequence NNNNWNNNNWNNNN (SEQ ID NO:80), WNNNNWNNNNWNNNN (SEQ ID NO:81), NWNNNWNNNNWNNNN (SEQ ID NO:82) or NNWNNNNWNNNNWNNNN (SEQ ID NO:83), wherein N is any nucleotide and W is adenine or thymine.

In some of any such embodiments, each vessel contains a pool of first adaptors, wherein each vessel barcoded oligonucleotide of the pool of first adaptors contain at least one base-shift or base addition compared to at least one of the other vessel barcoded oligonucleotides in the pool. In some of any such embodiments, the vessel barcoded oligonucleotides of the pool of first adaptors contains the sequences NNNNWNNNNWNNNN (SEQ ID NO:80), WNNNNWNNNNWNNNN (SEQ ID NO:81), NWNNNWNNNNWNNNN (SEQ ID NO:82) and NNWNNNNWNNNNWNNNN (SEQ ID NO:83), wherein N is any nucleotide and W is adenine or thymine.

In some of any such embodiments, in step (d) the method further includes amplifying the one or pool of vessel barcoded oligonucleotides or one or pool of the first adaptors, wherein the first adaptors comprise the one or pool of vessel barcoded oligonucleotides, wherein the amplifying is performed prior to or simultaneously with attaching the vessel barcoded oligonucleotide to the molecular barcoded polynucleotide. In some embodiments, attaching the vessel barcoded oligonucleotide includes hybridizing a region of the vessel barcoded oligonucleotide to a region of each of the complementary polynucleotides or to a region of each of the molecular barcoded polynucleotides containing a molecular barcode. In some cases, the region contains a 3' tagging polynucleotide that is complementary to a 3' terminal region of the molecular barcode of the barcoded polynucleotides. In some embodiments, the region contains a 3' tagging polynucleotide that is complementary to a 5' terminal region of the molecular barcoded oligonucleotide.

In some of any such embodiments, in step (b), the one or more target polynucleotide(s) are produced by reverse transcription of the target polynucleotide(s) in the presence of a reverse transcriptase and one or more target-specific primer(s) complementary to a target sequence of the target polynucleotide(s); and/or the collection of polynucleotides are produced by reverse transcription of polynucleotides, such as polynucleotide transcripts, in the cell in the presence of a reverse transcriptase and a one or more transcriptome primers complementary to a polynucleotide, such as a polynucleotide transcript, in the cell.

In some of any such embodiments, the one or more target polynucleotide(s) contains a polynucleotide of an immune molecule or chain thereof. In some of any such embodiments, the one or more target polynucleotide(s) contains at least two target polynucleotides, each containing a polynucleotide of an immune molecule chain.

In some of any such embodiments, the one or more target polynucleotide(s) contains a polynucleotide of a TCR or a chain thereof. In some of any such embodiments, the one or more target polynucleotides contain a first polynucleotide of a T-cell receptor alpha (TCRα) and a second polynucleotide of a T-cell receptor (TCRβ). In some embodiments, the one or more target polynucleotide(s) contains a first polynucleotide of a T-cell receptor gamma (TCRγ) and a second polynucleotide of a T-cell receptor delta (TCRdelta).

In some of any such embodiments, the one or more target polynucleotide(s) contains a polynucleotide of an antibody or a chain thereof. In some embodiments, the one or more target polynucleotide(s) contains a first polynucleotide of a heavy chain immunoglobulin (IgH) polynucleotide and a second polynucleotide of a light chain immunoglobulin (IgL) polynucleotide. In some embodiments, the one or more target-specific primers and/or the one or more transcriptome primers include a poly (T) sequence.

In some of any such embodiments, the one or more transcriptome primers contain a mixture of random hexamer oligonucleotide primers. In some embodiments, the one or more target-specific primers contain one or more primers complementary to a sequence(s) of the target sequence(s) of the target polynucleotide. In some cases, the one or more target-specific primers contain at least two primers, e.g., a first primer and a second primer. In some embodiments, the one or more target-specific primers contain primers to a target sequence of a plurality of target polynucleotides each encoding an immune molecule or a chain thereof. In some aspects, the immune molecule is a T cell receptor or an antibody.

In some of any such embodiments, at least the first primer is complementary to a target sequence of a polynucleotide of a first chain of an immune molecule and a second primer is complementary to a target sequence of a polynucleotide of a second chain of the immune molecule. In some embodiments, the first and second primers are complementary to a target sequence of different TCR chain polynucleotides of a TCR.

In some of any such embodiments, the first primer is complementary to a target sequence of a TCRalpha polynucleotide sequence and the second primer is complementary to a target sequence of a TCRbeta polynucleotide sequence; or the first primer is complementary to a target sequence of a TCRgamma polynucleotide sequence and the second primer is complementary to a target sequence of a TCRdelta polynucleotide sequence. In some aspects, the target sequence of the TCR chain polynucleotides is a constant region sequence.

In some of any such embodiments, the first primer is complementary to a target sequence of a TCRalpha constant region polynucleotide sequence and the second primer is complementary to a target sequence of a TCRbeta constant region polynucleotide sequence; or the first primer is complementary to a target sequence of a TCRgamma constant region polynucleotide sequence and the second primer is complementary to a target sequence of a TCRdelta constant region polynucleotide sequence. In some embodiments, at least the first and second primer are complementary to a target sequence of different antibody chain polynucleotides of an antibody. In some embodiments, the first primer is complementary to a target sequence of a heavy chain immunoglobulin (IgH) polynucleotide sequence and the second primer is complementary to a target sequence of a light chain immunoglobulin (IgL) polynucleotide sequence. In some embodiments, the target sequence of the antibody chain polynucleotides is a constant region sequence.

In some of any such embodiments, the first primer is complementary to a target sequence of a heavy chain constant region (CH) polynucleotide sequence and the second primer is complementary to a target sequence of a light chain constant region (CL) polynucleotide sequence. In some cases, the target sequence of the CH polynucleotide is from IgM, IgD, IgA, IgE or IgG, or combinations thereof; and/or the target sequence of the CL polynucleotide sequence is from Igkappa, Iglambda or combinations thereof.

In some of any such embodiments, the one or more target polynucleotide(s) contains a full-length coding sequence. In some of any such embodiments, the one or more target polynucleotide(s) and the collection of polynucleotides are produced in the vessel in the same reaction volume.

In some of any such embodiments of the method, in step (b), producing the plurality of complementary polynucleotides contains use of a non-template terminal transferase, wherein three or more non-template nucleotides, ribonucleotides or analogs thereof are added to the 3' end of each produced complementary polynucleotide. In some cases, the non-template terminal transferase is a reverse transcriptase or a polymerase. In some aspects, the non-template terminal transferase is a reverse transcriptase, and wherein the reverse transcriptase is selected from Superscript II reverse transcriptase, Maxima reverse transcriptase, Protoscript II reverse transcriptase, Maloney murine leukemia virus reverse transcriptase (MMLV-RT), HighScriber reverse transcriptase, avian myeloblastosis virus (AMV) reverse transcriptase, any reverse transcriptase including terminal deoxynucleotidyl transferase activity, and combinations thereof.

In some of any such embodiments of the method, in step (c), the attaching includes hybridizing a region of one of the plurality of molecular barcoded oligonucleotides to the three or more non-template nucleotides of each of the complementary polynucleotides. In some embodiments, the plurality of molecular barcoded oligonucleotides are provided as a plurality of template switch oligonucleotides each including a 3' portion complementary to the three or more non-template nucleotides. In some cases, the template switch oligonucleotide further includes a 5' terminal region that is complementary to a 3' tagging polynucleotide of the first adaptor including the vessel barcode. In some cases, the template switch oligonucleotide further comprises a 5' terminal region that is complementary to a portion of the first adaptor, wherein the first adaptor comprises the vessel barcoded oligonucleotide.

In some of any such embodiments, the reverse transcriptase has template switching activity; at least some strands of the plurality of produced complementary polynucleotides contains a 3' overhang containing three or more non-template nucleotides; the plurality of molecular barcoded oligonucleotides are provided as a plurality of template switch oligonucleotides each containing (1) a 5' terminal region that is complementary to a 3' tagging oligonucleotide comprising the first adaptor and the vessel barcoded oligonucleotide, (2) the molecular barcode and (3) a 3' portion complementary to the three of more non-template nucleotides of the 3' overhang; and the template switch oligonucleotide serves as a template for the reverse transcriptase, such that the molecular barcode is incorporated into each complementary polynucleotide to produce the molecular barcoded polynucleotides.

In some of any such embodiments, the 3' portion complementary to the three or more non-template nucleotides includes a nucleotide, ribonucleotide or analog thereof. In some of any such embodiments, the three or more non-template nucleotides includes three or more C nucleotides and the 3' portion complementary to three of more non-template nucleotides contain one or more G nucleotides or a ribonucleotide or analog thereof.

In some of any such embodiments, the template switch oligonucleotide further contains a 3' modified nucleotide that blocks extension of the template switch oligonucleotide by a reverse transcriptase or a DNA polymerase. In some cases, the modification is a deoxy, phosphate, amino, or alkyl modification of the 3' terminal nucleotide.

In some of any such embodiments of the method, step (d) further includes extending each of the plurality of complementary polynucleotides after the attaching. In some embodiments, step (d) further comprises extending each of the plurality of the molecular barcoded polynucleotides after the attaching to generate the plurality of dual-barcoded polynucleotides.

In some of any such embodiments, the vessel is a well, an emulsion, a droplet, or a microcapsule.

In some of any such embodiments, the method includes, prior to step (e), combining the contents of two or more of the plurality of vessels, thereby generating a homogenous mixture including the two or more of the plurality of dual-barcoded single-stranded polynucleotides. In some aspects, combining the contents of the plurality of vessels includes breaking two or more of the plurality of vessels and pooling the dual-barcoded single-stranded polynucleotides from the two or more broken vessels.

In some embodiments, the method includes, prior to step (e), selecting or purifying dual-barcoded single-stranded polynucleotides having a size that is greater than or greater than about 50 base pairs, greater than 100 base pairs, or greater than 200 base pairs. In some embodiments, the method includes, prior to step (e), selecting or purifying dual-barcoded single-stranded polynucleotides having a size from or from about 50 base pairs (bp) to 1500 bp, 50 bp to 1250 bp, 50 bp to 1000 bp, 50 bp to 750 bp, 50 bp to 500 bp, 100 bp to 1500 bp, 100 bp to 1250 bp, 100 bp to 1000 bp, 100 bp to 750 bp, 100 bp to 500 bp, 200 bp to 1500 bp, 200 bp to 1250 bp, 200 bp to 1000 bp, 200 bp to 750 bp or 250 bp to 500 bp.

In some of any such embodiments, the dual-barcoded single-stranded polynucleotides contain in order (5' to 3'): the first adaptor, the vessel barcode, the molecular barcode and the second adaptor. In some of any such embodiments, the first adaptor is positioned at or near the 5' region of the single-stranded barcoded polynucleotide, optionally the dual-barcoded single-stranded polynucleotide. In some of any such embodiments, the second adaptor is positioned at or near the 3' region of the single-stranded barcoded polynucleotide, optionally the dual-barcoded single-stranded polynucleotide.

In some of any such embodiments of the method, one or more of steps (a)-(f) is carried out in solution and/or is not carried out in the presence of a solid support, optionally wherein the support is a bead. In some of any such embodiments, at least steps (c) and (d) are carried out in solution and/or are not carried out in the presence of a solid support, optionally wherein the support is a bead. In some embodiments, each of steps (a)-(e) is carried out in solution and/or is not carried out in the presence of a solid support, optionally wherein the support is a bead.

In some of any such embodiments, the population of cells contains at least or about at least $1\times10^3$, $5\times10^3$, $1\times10^4$, $5\times10^4$, $1\times10^5$, $5\times10^5$, $1\times10^6$, or $5\times10^6$ cells. In some embodiments, the population of cells is from a biological sample from a subject. In some examples, the biological sample is or contains a whole blood sample, a buffy coat sample, a peripheral blood mononuclear cells (PBMC) sample, an unfractionated T cell sample, a lymphocyte sample, a white blood cell sample, an apheresis product, or a leukapheresis product.

In some of any such embodiments, the population of cells contains immune cells. In some embodiments, the immune cells contain lymphocytes or antigen presenting cells. In some of any such embodiments, the immune cell is a lymphocyte or a subtype thereof, a B cell or a subtype thereof, a T cell or a subtype thereof, or a combination thereof. In some examples, the immune cell is a T cell that is a CD4+ and/or CD8+ T cell.

In some of any such embodiments, the population of cells is enriched for or contains central memory T cells, effector memory T cells, naïve T cells, stem central memory T cells, effector T cells and regulatory T cells. In some of any such embodiments, the population of cells is enriched for memory B-cells, naïve B-cells or plasmablast B-cells.

In some of any such embodiments, the subject is a human subject. In some embodiments, the subject has a cancer, an infection or an autoimmune condition. In some cases, the infection is a viral, bacterial or fungal infection.

In some of any such embodiments, the method further includes amplifying the plurality of barcoded single-stranded polynucleotides, thereby generating a plurality of polynucleotide templates. In some of any such embodiments, the amplification of the plurality of barcoded single-stranded polynucleotides is carried out in the presence of a first primer set including a first primer complementary to the first adaptor sequence and a second primer complementary to the second adaptor sequence. In some aspects, the first and/or second primer is a universal primer. In some cases, the first and/or second primer is complementary to the P7 priming site (C7) or a contiguous portion thereof or the P5 priming site (C5) or a contiguous portion thereof. In some cases, the first primer is complementary to the P7 priming site (C7) or a contiguous portion thereof and the second primer is complementary to the P5 priming site (C5) or a contiguous portion thereof. In some embodiments, the primer that is complementary to the P7 priming site (C7) or a contiguous portion thereof has or contains the sequence CAAGCAGAAGACGGCATACGAGAT (SEQ ID NO:39); and/or the primer that is complementary to the P5 priming site (C5) or a contiguous portion thereof contains the sequence ACACGACGCTCTTCCGATCT (SEQ ID NO:27). In some of any such embodiments, the first and/or second primer further contains a sequencing adaptor. In some embodiments, the primer that is complementary to the P7 priming site (C7) or a contiguous portion thereof further contains the sequence CAAGCAGAAGACGGCATACGAGAT[NNNNNN]GTGACTGGAGTTCAGACGTGTGCT CTTCCGATCT (SEQ ID NO:28); and/or the primer that is complementary to the P5 priming site (C5) or a contiguous portion thereof contains the sequence AATGATACGGCGACCACCGAGATCTACACTCTTTCCCTACACGACGCTCTTCC (SEQ ID NO:76).

In some embodiments, the method further includes purifying each of the plurality of single-stranded barcoded polynucleotides, optionally single-stranded dual barcoded polynucleotides.

Provided is a polynucleotide library containing a plurality of barcoded polynucleotides produced by the method of any of the embodiments described. Also provided is a polynucleotide library, containing a plurality of barcoded polynucleotides, wherein the plurality of barcoded polynucleotides contain (i) one or more target polynucleotide(s) containing an amplicon of one or more target polynucleotide(s) present in a cell of a population of cells; and (ii) a collection of polynucleotides that each contain amplicon of a polynucleotide in the cell, wherein each barcoded polynucleotide contains a first adaptor including a first universal priming site that is complementary to a first universal primer; a vessel barcoded oligonucleotide, comprising a vessel barcode, wherein the vessel barcode is the same for all barcoded polynucleotides from (i) and (ii) from the same cell of the population of cells; and a second adaptor sequence containing a second universal priming site that is complementary to a second universal primer.

In some embodiments, each of the plurality of barcoded polynucleotides contains a molecular barcode that is unique to each polynucleotide or polynucleotide template. In some aspects, the collection of barcoded polynucleotide templates from each cell of the population of cells, collectively, contain complementary DNA (cDNA) strands of a transcriptome or a partial transcriptome or a complement thereof. In some embodiments, the transcriptome or partial transcriptome, collectively, contains at least 60%, 70%, 75%, 80%, 85% 90% 95%, 96%, 97%, 98%, 99% or 100% of the transcripts present in the genome of the cell.

In some of any such embodiments, each of the barcoded polynucleotides has a size that is greater than or greater than about 50 base pairs, greater than 100 base pairs, or greater than 200 base pairs. In some embodiments, each of the barcoded single-stranded polynucleotides have a size from or from about 50 base pairs (bp) to 1500 bp, 50 bp to 1250 bp, 50 bp to 1000 bp, 50 bp to 750 bp, 50 bp to 500 bp, 100 bp to 1500 bp, 100 bp to 1250 bp, 100 bp to 1000 bp, 100 bp to 750 bp, 100 bp to 500 bp, 200 bp to 1500 bp, 200 bp to 1250 bp, 200 bp to 1000 bp, 200 bp to 750 bp or 250 bp to 500 bp.

In some of any such embodiments, the first adaptor contains the vessel barcode. In some embodiments the barcoded polynucleotides are single-stranded. In some embodiments the barcoded polynucleotides are double-stranded. In some embodiments, the first adaptor and second adaptor are different.

In some of any such embodiments, the first universal priming site and/or second universal priming site is or contains a P7 priming site (C7) or a contiguous portion thereof or a P5 priming site (C5) or a contiguous portion thereof, optionally wherein the contiguous portion thereof is sufficient to anneal to a complementary sequence. In some embodiments, the first universal priming site is or contains the P7 priming site (C7) or a contiguous portion thereof and the second universal priming site is or contains the P5 priming site (C5) or a contiguous portion thereof. In some aspects, the P7 priming site (C7) contains the sequence AGATCGGAAGAGCACACGTCTGAACTCCA (SEQ ID NO:77), or is a contiguous portion thereof. In some examples, the P5 priming site contains the sequence AGATCGGAAGAGCGTCGTGTAGGGAAAGAGTGTA-GATCTCGGTGGTCGCCGTATCA TT (SEQ ID NO:78), or is a contiguous portion thereof.

In some of any such embodiments, the contiguous portion contains at least or at least about 15, 20, 25 or 30 nucleotides in length. In some embodiments, the P5 priming site is a contiguous portion set forth in SEQ ID NO:25 (AGATCG-GAAGAGCGTCGTGT).

In some of any such embodiments, the vessel barcoded oligonucleotide contains at least or about at least 3, 4, 5, 6, 7, 8, 9, 10, 15, 20, 30, 40 or 50 nucleotides. In some embodiments, the vessel barcoded oligonucleotide contains from or from about 10 to 30 nucleotides.

In some of any such embodiments, the one or more target polynucleotide(s) contains a polynucleotide of an immune molecule or chain thereof. In some embodiments, the one or more target polynucleotide(s) contains at least two target polynucleotides, each containing a polynucleotide of an immune molecule chain.

In some of any such embodiments, the one or more target polynucleotide(s) contains one or more polynucleotide(s) of a TCR or a chain thereof. In some embodiments, the one or more target polynucleotide(s) contains a first polynucleotide of a T-cell receptor alpha (TCRα) and a second polynucleotide of a T-cell receptor (TCRβ). In some embodiments, the one or more target polynucleotide(s) contains a first polynucleotide of a T-cell receptor gamma (TCRγ) and a second polynucleotide of a T-cell receptor delta (TCRdelta).

In some of any such embodiments, the one or more target polynucleotide(s) contains one or more polynucleotide(s) of an antibody or a chain thereof. In some embodiments, the one or more target polynucleotide(s) contains a first polynucleotide of a heavy chain immunoglobulin (IgH) polynucleotide and a second polynucleotide of a light chain immunoglobulin (IgL) polynucleotide.

In some of any such embodiments, the barcoded polynucleotides contain in order (5' to 3'): the first adaptor, the vessel barcode, the molecular barcode and the second adaptor. In some embodiments, the first adaptor is positioned at or near the 5' region of the dual-barcoded single-stranded polynucleotide. In some embodiments, the second adaptor is positioned at or near the 3' region of the dual-barcoded single-stranded polynucleotide.

Provided are methods for sequencing including sequencing one or more the plurality of polynucleotides, such as barcoded polynucleotides (e.g., dual-barcoded polynucleotides), produced by any of the embodiments described or from the any of the embodiments of the polynucleotide libraries described. In some examples, the transcriptome from the plurality of polynucleotides, such as polynucleotide templates, is sequenced. In some cases, the method further includes amplifying the whole transcriptome or a portion thereof prior to the sequencing. In some aspects, amplification is carried out using a first primer set containing a first primer and second primer specific for the first and second adaptor sequences, respectively.

In some embodiments, the one or more target polynucleotide(s) from the plurality of polynucleotide templates is sequenced. In some cases, the method further includes amplifying the one or more target polynucleotide(s) from the plurality of polynucleotide templates prior to the sequencing. In some examples, the full-length sequence(s) of the one or more target polynucleotide(s) is amplified.

In some embodiments, amplification is carried out in the presence of a second primer set containing one or more first primer complementary to one or more target polynucleotide and a second primer complementary to the first adaptor sequence. In some cases, the second primer of the second primer set is complementary to the P7 priming site (C7) or a contiguous portion thereof or the P5 priming site (C5) or a contiguous portion thereof. In some aspects, the second primer of the second primer set is complementary to the P7 priming site (C7) or a contiguous portion thereof. In some embodiments, the second primer of the second primer set has or contains the sequence CAAGCAGAAGACGGCAT-ACGAGAT (SEQ ID NO:39) or CAAGCAGAAGACGG-CATACGAGAT[NNNNNN]GTGACTGGAGTTCA-GACGTGTGCT CTTCCGATCT (SEQ ID NO:28).

In some embodiments, the one or more first primer complementary to the one or more target polynucleotide is specific to a target sequence of an immune molecule or a chain thereof. In some cases, the immune molecule is a T cell receptor or an antibody. In some aspects, the one or more first primer(s) is specific to a target sequence of a constant region of the immune molecule.

In some embodiments, the immune molecule is a TCR and the one or more first primers include AGTCTCTCAGCTGGTACACGG (SEQ ID NO:37), ATGGCTCAAACACAGCGACCTC (SEQ ID NO:38) or a combination thereof. In some embodiments, the immune molecule is an antibody and the one or more first primers includes any of SEQ ID NOS: 29-36 or a combination thereof.

In some of any such embodiments, the method includes determining the cell origin of the one or more barcoded polynucleotides(s), optionally dual barcoded polynucleotides. In some cases, determining the cell origin includes identifying sequence information, or sequences of dual barcoded polynucleotides, that have the same vessel barcode as being from the same cell.

In some of any such embodiments, the target polynucleotide is an immune molecule containing a first polynucleotide chain and a second polynucleotide chain and the method includes matching the first polynucleotide chain and the second polynucleotide chain to the same cell by the presence of the same vessel barcode in the sequenced dual barcoded polynucleotides. In some embodiments, the method further includes quantitating or determining the number of polynucleotides with the same barcode, optionally the same molecular barcode and/or vessel barcode.

In some of any such embodiments, the plurality of barcoded polynucleotides are dual barcoded polynucleotides comprising a molecular barcode and a vessel barcode, and the method further includes identifying transcriptome sequences and target polynucleotide sequences that have the same vessel barcode, thereby identifying transcriptome information of the cell bearing the target polynucleotide(s).

Provided are methods for transcriptome analysis including (a) sequencing one or more target polynucleotide(s) from the plurality of barcoded polynucleotides produced by any of the methods described or from the plurality of barcoded polynucleotides of any of the polynucleotide libraries described, wherein the barcoded polynucleotides are dual-barcoded polynucleotides comprising a molecular barcode and a vessel barcode, thereby generating sequence information for the target polynucleotide from the plurality of cells; (b) sequencing the whole transcriptome or a portion thereof from the from the plurality of barcoded polynucleotides produced by any of the methods described or from the plurality of barcoded polynucleotides of any of the polynucleotide libraries described, wherein the barcoded polynucleotides are dual-barcoded polynucleotides comprising a molecular barcode and a vessel barcode, thereby generating transcriptome data from the plurality of cells; and (c) identifying sequence information from (a) and from (b) that have the same vessel barcode as being from the same cell.

Provided are methods for analyzing a transcriptome of a selected single cell, including (a) amplifying and sequencing one or more target polynucleotide(s) from a plurality of the plurality of barcoded polynucleotides produced by any of the methods described or from the plurality of barcoded polynucleotides of any of the polynucleotide libraries described, wherein the barcoded polynucleotides are dual-barcoded polynucleotides comprising a molecular barcode and a vessel barcode, thereby generating sequence information for each of the target polynucleotides in at least one of the plurality of cells; (b) identifying the vessel barcode(s) associated with one of the target polynucleotide sequenced in (a), thereby identifying a selected single cell bearing the target polynucleotide; (c) amplifying and sequencing the transcriptome or a portion thereof from the plurality of barcoded polynucleotides of the cell bearing the vessel barcode identified in (b), thereby generating transcriptome data from the selected target polypeptide-expressing cell. In some embodiments, the transcriptome or portion thereof is amplified or sequenced from the selected cell using a primer specific to the vessel barcode identified in (b) and a primer specific to the second adaptor sequence of the barcoded polynucleotides.

In some embodiments, the method includes matching sequence information of the transcriptome or a portion thereof and at least one of the target polynucleotide(s) that are from the same cell, wherein the sequence information is determined from the plurality of barcoded polynucleotides produced by any of the methods described or from the plurality of barcoded polynucleotides of any of the polynucleotide libraries described or is determined from the any of the methods described, wherein the barcoded polynucleotides are dual-barcoded polynucleotides comprising a molecular barcode and a vessel barcode. In some cases, sequences that have the same vessel barcode are matched as being from the same cell. In some embodiments, the transcriptome data includes a parameter, characteristic, feature or phenotype associated with the function or activity of the cell. In some cases, the transcriptome data is associated with the activation, exhaustion or proliferation activity of the cell.

BRIEF DESCRIPTION OF THE DRAWINGS

FIG. 4 depicts the t-SNE plots of single-cell transcriptome data of FIG. 3, colored to identify cells expressing identified sequences: Toll-like receptor 7 (TLR7; A), T-cell surface glycoprotein CD3 epsilon chain (CD3E; B), natural killer cell granule protein 7 (NKG7; C), mannose receptor C-type 1 (MRC1; D)

DETAILED DESCRIPTION

Figure 1A:
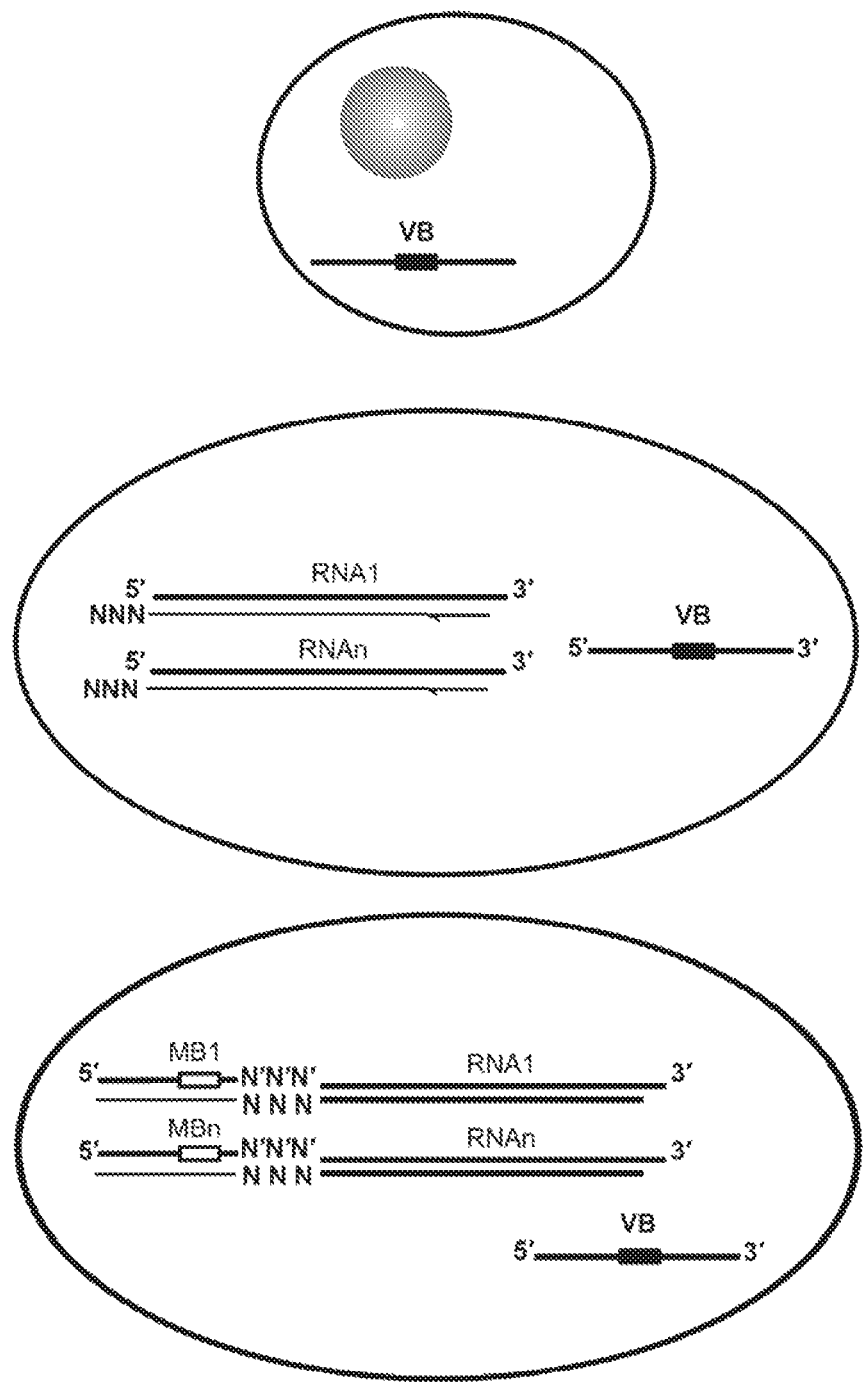
FIG. 1A depicts a schematic of a barcoding phase: an exemplary method described herein. The sketch represents a method of amplifying and barcoding two or more polynucleotides, such as a target polynucleotide and one or more genomic or transcriptomic polynucleotides, or paired sequences, such as paired variable Ig (e.g., $V_H$ and $V_L$ mRNAs) or TCR sequences (e.g., $V\alpha/V\beta$ and $V\gamma/V\delta$ mRNAs), for library preparation and immune sequencing. Vessel Barcode (VB); Molecular Barcode (MB). (Top) A single droplet (of a plurality of droplets) of an emulsion, as an exemplary vessel, containing a single cell and other reaction components (e.g., enzymes, buffers, oligonucleotides). (Middle) Exemplary methods of cell lysis and reverse transcription of lysed cell RNAs utilizing target-specific, random, and/or oligo-dT reverse transcription primers. (Bottom) Template switch phase and Molecular Barcode (MB) tagging of single molecules during reverse transcription phase.

Provided herein are methods and compositions for the analysis of gene expression in single cells or in a plurality of single cells. The provided methods permit the efficient generation of a plurality of single cell high quality polynucleotide (e.g., DNA) sequencing libraries containing polynucleotides from the full transcriptome, or a portion thereof, and one or more full-length polynucleotide sequences of a target gene of interest, such as a full-length paired immune receptor product, e.g., a TCR or an antibody, whereby target polynucleotide(s) and the polynucleotides from the full or partial transcriptome, originating from the same cell, can be identified. In some embodiments, each of the plurality of polynucleotides in the library contains adaptor sequences (e.g., a first adaptor and a second adaptor) that allow for next-generation sequencing of the total recovered products, as opposed to specific genes that must be decided upon performing the experiment. Thus, in some aspects of the provided method, subsequent PCR amplification can be carried out using primers specific for these adaptor sequences and/or primers specific to the target polynucleotides of interest and/or cell-specific primers. In some embodiments, the provided methods permit processing of tens or hundreds of thousands of cells in a single experiment, thereby yielding single-cell sequencing data, e.g., RNA-seq data, such as mRNA counts, combined with full-length immune molecule sequences, e.g., antibody or TCR in an efficient and high-throughput manner.

In some cases, direct sequencing of the all, or parts, of the genomic and mRNA content of a tissue is being increasingly used to enable analysis of alternative splicing, regulatory/promoter regions, and polyadenylation signals without having to preselect previously known genes (Cloonan et al., Nat Methods 5(7):613-9 (2008)). However, current methods of analyzing the mRNA content of cells by direct sequencing rely on analyzing bulk mRNA obtained from tissue samples typically containing millions of cells. This means that much of the functional information present in single cells is lost or blurred when gene expression is analyzed in bulk mRNA. In addition, gene expression during dynamic processes, such as the cell cycle, is difficult to observe in population averages. Therefore, in some applications, single-cell based approaches of direct sequencing are preferable to bulk samples.

In some instances, it is desirable to analyze the genomic or mRNA content of a selected cell, such as a cell that expresses a particular gene or genes of interest, such as a target gene. In some instances, it is desirable to obtain the genomic or transcriptomic content of a selected cell while also obtaining the full-length sequence of a target gene, such as an immune receptor. Existing tools for single-cell transcriptome sequencing include microarrays, 96-well based methods, such as traditional FACS sorting into wells, and microfluidic instruments, such as the Fluidigm C1. These tools can be used to prepare whole transcriptome and target libraries, but their throughput is limited, because they are limited in the number of cells that can be analyzed (e.g., hundreds to thousands of cells).

In some instances, it is desirable to analyze the genomic or mRNA content of a selected cell, such as a cell that expresses a particular gene or genes of interest, such as a target gene (e.g., an immune receptor). Ultra high throughput methods using microwell arrays or emulsions have been described to allow whole single-cell transcriptome sequencing (see e.g., Klein et al., Cell (2015) 161(5):1187-1201; Macosko et al., Cell (2015) 161(5): 1202-1214; WO/2015/164212; WO/2016/040476), but efficient capture of full-length target sequences, such as full-length immune receptor sequences, is not possible with the existing technology. These methods are also limited to smaller numbers of cells, typically in the low thousands, due to limitations imposed by the bead-based approach, which requires larger droplets and larger reaction volumes per cell.

In embodiments of the provided methods, target sequences, such as target immune molecules (e.g., antibody or TCR), and the genome or transcriptome sequences of a plurality of cells are produced in one simultaneous reaction, and provide a mechanism for linking sequence information of sequences derived from the same cell. In some aspects, the presently disclosed methods, when coupled with high-throughput sequencing technology allows analyzing a large number of single cells and achieving the analysis in one single reaction assay. In principle, one can sequence any number of cells and any number of targeted regions per cell. In some aspects, the number of single cells that can be processed is limited only by practical constraints, such as the speed of high throughput sequencing. In some embodiments, the methods disclosed herein are adaptable for use with beads. In other embodiments, the methods disclosed herein do not include a bead-based sequencing or amplification step.

In some aspects, the provided methods overcome, or reduce, the problems of existing methods by providing a method of preparing cDNA libraries which can be used to analyze gene expression in a plurality of single cells. In some embodiments, the provided methods result in the production of a polynucleotide library, for ultra-high throughput sequencing, that allows the recovery of synthesis-ready, full-length target sequences, including sequences of paired heterodimeric or multimeric targets, while simultaneously capturing complementary quantitative genomic or transcriptomic information of the cells identified as expressing the target sequence(s).

In particular, the provided methods are for preparing a polynucleotide library, e.g., cDNA library, from a plurality of single cells. The methods are based on determining gene expression levels from a population of individual cells, which can be used to identity natural variations in gene expression on a cell by cell level. The methods can also be used to identify and characterize the cellular composition of a population of cells, including in the absence of suitable cell-surface marker. The methods described herein also provide the advantage of generating a cDNA library representative of RNA content in a cell population using single cells, whereas cDNA libraries prepared by classical methods typically require total RNA isolated from a large population. Thus, in some aspects, a cDNA library produced using the provided methods permit at least equivalent representation of RNA content in a population of cells by utilizing a smaller subpopulation of individual cells along with additional advantages as described herein.

The provided embodiments are based on emulsion-based methods for single-cell target sequencing, such as immune target sequencing, and transcriptome analysis. In some aspect, cells from a sample containing a population of cells are encapsulated in single cell vessels (e.g. droplets), such as using microfluidic emulsion-based methods. Methods are then carried out to attach vessel (e.g. droplet)-specific barcodes to target polynucleotides (e.g., amplicons of target mRNA transcripts) and/or a plurality of polynucleotides (e.g., amplicons of mRNA transcripts of the full or partial transcriptome) within emulsion droplets, thereby allowing high-throughput genetic and/or expression analysis of single cells contained within the droplets. In some aspects, the vessel barcodes are present initially as single molecule DNA templates with a randomized central sequence portion flanked by known primer sites. The templates can be reverse transcribed to generate an amplicon and/or PCR amplified to yield one or more amplicons within the vessels, such as droplets, and can become attached to cell-derived nucleic acids by sequence overlap. In some aspects of the method, a cell-derived nucleic acid is amplified using a gene-specific PCR primer to amplify a target gene or target genes of interest, e.g., an immune molecule, such as an antibody or a T cell receptor (TCR). In some cases, the ability to amplify several target genes can provide information about various features of the cells, such as the phenotype, activity or other feature of the cell.

In some cases, adding additional target genes can link information about a particular immune molecule, e.g. TCR, to cell phenotype information of the cell. In further aspects of the method, barcoded whole transcriptomic cell-derived nucleic acids can be amplified using primers that permit the full transcriptome or a portion thereof of the cells to be sequenced, and transcripts originating from the same cell matched. In some aspects, random reverse transcription primers are used to generate amplicons corresponding to transcripts of the transcriptome. In certain embodiments, a universal priming site can be added to the ends of the barcoded polynucleotides, such as by added first and second adaptors, such that the entire library can be amplified in bulk and sequenced in a high throughput shotgun manner.

In some embodiments, the reaction to amplify a cell-derived nucleic acid can be carried out in a one-pot reaction that can perform a) cell lysis; b) target mRNA reverse transcription; c) molecular barcoding of each cDNA; d) PCR amplification of a vessel-specific DNA barcode; and e) attachment of a copy of the vessel barcode to each cDNA. In some embodiments, the products can be recovered and sequenced, such as using any of a variety of sequencing platforms. For example, an Illumina MiSeq platform can be used using 325×300 bp to sequence the entire length of each product. In some aspects, the droplet barcodes allow identification of all products from each single cell. In certain aspects, the molecular barcodes allow expression quantitation for each cell and, in some cases, elimination of sequencing and RT-PCR errors.

In the provided embodiments, the process of transcriptome sequencing can be performed separately from targeted sequencing of a few chosen transcripts, such as a TCR, since the amplified library can be processed separately. This permits the method to be performed a number of times on separate aliquots on the same amplified barcoded library. A variety of useful approaches can be realized by the provided methods due to the ability to perform different experiments at different times on the same amplified barcoded library. In one example, the methods can be used to first carry out targeted sequencing of a target molecule of interest, e.g. TCR, in a sample, which may lead to identification of a few particular cells of interest. In some aspects, PCR or capture oligonucleotides can then be designed to target the vessel barcodes that represent those cells of interest, allowing capture and sequencing of all barcoded transcripts of those cells only. In some aspects, this greatly reduces sequencing costs of sequencing the whole library.

In certain aspects, the methods and compositions described herein are useful for single cells analysis, such as, e.g., for the study of genomes, transcriptomes, proteomes, metabolic pathways and the like of complex cell samples. Analyses of multiple cells in heterogeneous cell populations are particularly useful when studying complex samples or mixtures. Complex samples or cell mixtures include, for example, peripheral blood mononuclear cell (PBMCs) samples, metagenomic samples, normal and cancerous tissue sections, embryonic and stem cell colonies. Genome and transcriptome sequencing is desirable to identify divergent cell types or in cells at certain stages, such as different stages of activation, exhaustion or proliferation. Particular applications include molecular T- and B-cell receptor profiling, haplotyping, and HLA typing.

"Metagenomic samples" refers to samples containing genomes from multiple origins, such as species. For example, the present approach may be applied to mixtures of bacterial species to allow sequencing of nucleic acids from multiple bacteria in one assay followed by correlating the sequences to the same bacterial cell. Similarly, nucleic acid sequences of one cell type among cells of another cell type, such as immune cells infiltrating a tumor. In such instances, the nucleic acids of an immune cell infiltrating a tumor can be correlated with the full-length sequence(s) of the immune receptor or binding fragment thereof using the methods provided herein.

Embodiments of the provided methods also permit sampling of a large number of single cells. Using similarity of expression patterns, a map of cells can be built showing how the cells relate. This map can be used to distinguish cell types in silico, by detecting clusters of closely related cells. By sampling not just a few, but large numbers of single cells, similarity of expression patterns can be used to build a map of cells and how they are related. This method permits access to undiluted expression data from every distinct type of cell present in a population, without the need for prior purification of those cell types, In addition, where known markers are available, these can be used in silico to delineate cells of interest.

Among the provided embodiments is a method of preparing a polynucleotide library, e.g., a cDNA library, from a plurality of single cells by releasing mRNA from each single cell to provide a plurality of individual samples, wherein the mRNA in each individual mRNA sample is from a single cell, synthesizing a first strand of cDNA (i.e., amplicon) from the mRNA in each individual mRNA sample and incorporating a nucleotide barcode (e.g., molecular barcode and/or vessel barcode) into the cDNA amplicon to provide a plurality of barcoded (e.g., dual barcoded) cDNA samples (i.e., wherein the cDNA in each barcoded cDNA sample is complementary to an mRNA from a single cell pooling the barcoded cDNA samples, and amplifying the pooled cDNA samples to generate a cDNA library comprising barcoded double-stranded cDNA). In some embodiments, the resulting amplicon is dual barcoded single-stranded cDNA, such as dual barcoded single-stranded cDNA that corresponds to one or more mRNA template(s). In some embodiments, the barcoded double-stranded cDNA is denatured to generate barcoded single-stranded cDNA to facilitate addition of an adaptor, such as an adaptor to facilitate sequencing. By utilizing the above method, it is feasible to prepare samples for sequencing from several hundred single cells in a short time. Traditional methods for preparing a fragment library from RNA for sequencing include gel excision steps that are laborious. In some aspects of the methods described herein, a plurality of cells is prepared as a single sample (after cDNA synthesis), which makes it feasible to prepare a plurality, such as several hundred, cells for sequencing. Additionally, technical variation can be minimized because each set of the plurality of cells is prepared together (in a single tube).

In some aspects of the invention, each cDNA sample obtained from a single cell is tagged with a barcode, which allows gene expression to be analyzed at the level of a single cell. This allows expression during dynamic processes, such as the cell cycle, to be studied and distinct cell types in a complex tissue (e.g., the brain) to be analyzed. In some aspects, the cDNA samples can be pooled prior to analysis. Pooling the samples simplifies handling of the samples from each single cell and reduces the time required to analyze gene expression in the single cells, which allows for high throughput analysis of gene expression. Pooling of the cDNA samples prior to amplification also provides the advantage that technical variation between samples is virtually eliminated. In addition, because the cDNA samples are pooled before amplification, less amplification is required to generate sufficient amounts of cDNA for subsequent analysis compared to amplifying and treating cDNA samples from each single cell separately. This reduces amplification bias, and also means that any bias will be similar across all the cells used to provide pooled cDNA samples. RNA purification, storage and handling are also not required, which helps eliminate problems caused by the unstable nature of RNA.

T cell receptor chain pairs and antibody immunoglobulin chain pairs are both types of immune receptors contemplated to be sequenced using the presently disclosed methods. In some embodiments, the provided methods allow the generation of polynucleotide libraries for high-throughput sequencing and gene expression analysis that include sequences of one or more target sequences, such as one or more sequences of an immune receptor, and sequences that can be combined to provide genomic and/or transcriptomic sequencing information. In some embodiments, a polynucleotide library can be developed that is a human derived library panel for antibody and/or TCR discovery from patient or cohorts with specific common attributes. In some embodiments of the provided method, the starting material can be any source that contains a population of cells of interest that does or is likely to contain the target polynucleotide of interest, such as the immune molecule or receptor, e.g., antibody or TCR. In some embodiments, starting material can be peripheral blood or from a tissue biopsy, from which immune cells are globally isolated or sub-sorted for naïve, memory and/or antibody secreting cells (ASC) if desired. In some embodiments, the provided method can be applied to multiple different types of singular or paired variable sequences, e.g., T-cell receptor chain pairs and antibody immunoglobulin chain pairs.

In some aspects, the cDNA libraries produced by the provided methods are suitable for the analysis of gene expression profiles of single cells by direct sequencing, and it is possible to use these libraries to study the expression of genes, including expression of genes associated with, or cells bearing, a particular target polynucleotide of interest, such as an immune molecule or receptor, e.g., antigen, antibody or TCR. In some embodiments, gene expression profiles which were not previously known can be analyzed. In some embodiments, the provided methods can be used to characterize or compare each of a plurality of cells from a sample for their transcriptional cell state, e.g., activated, exhausted, proliferating or other desired parameter or attribute of cells. In some embodiments, the provided methods can be used to facilitate the discovery of therapeutic candidates, such as TCRs, by looking at the response of particular cells bearing a particular TCR specific to an antigen of interest. In some embodiments of the provided methods, it is possible to identify cells expressing a TCR that is associated with a desired response, e.g., nature or degree of T cell activation. In some embodiments, the provided methods make it possible to capture a richer data set by analysis of the whole transcriptome as opposed to existing methods which require prior knowledge and/or selection of a smaller panel of candidate genes.

I. Polynucleotide Library for Target and Transcriptome Analysis

In some embodiments, methods provided herein are directed to amplification and sequencing of one or more target polynucleotide molecules and amplification and sequencing a collection of polynucleotides, such as one or more target molecules and a collection of polynucleotides from a single cell or a population of cells. In some embodiments, the methods and compositions described herein are useful for single cells analysis, such as, e.g., for the study of genomes, transcriptomes, proteomes, metabolic pathways and the like of complex cell samples. In other aspects, the methods and compositions described herein can be used for immunoreceptor discovery, e.g., by pairing heavy and light immunoglobulin or T-cell receptor chains in single B and T cells, as well as for HLA typing. In other embodiments, antibody pairing information and single-cell analysis can be combined to associate cell function or cell status information with expression of the identified immune receptor sequence. In still other aspects, the methods and compositions described herein can be used to monitor the impact of small molecule and drugs or immunotherapies and their effect(s) in complex normal or cancerous samples for diagnostics or the discovery of new drugs or treatment regimens. In yet other embodiment, the methods and composition can be used to detect and analyze target pathogens such as bacteria or viruses in biological samples.

In some embodiments, the provided methods can include various features of the methods as described in International Publication Nos. WO2012/048341, WO2014/144495, WO2016/044227, WO2016/176322, or WO2017/053902, each incorporated by reference in their entirety.

The present invention utilizes steps in which nucleic acids are manipulated in order to generate libraries of polynucleotides for sequencing. In some embodiments, the present invention utilizes steps in which nucleic acids are manipulated in order to produce target polynucleotide molecules, include sequences comprising variable regions of an immune receptor, such as an antibody or TCR produced by an immune cell. In some cases that target polynucleotide molecule includes recombinant monoclonal antibodies. In some embodiments, the present invention utilizes steps in which nucleic acids are manipulated in order to produce polynucleotides that represent the transcriptome or genome of one or more cells. In a general sense, in some embodiments of the invention, amplification of a cell's, such as an immune cell's and/or T cell's, genetic material, e.g., reverse transcription polymerase chain reaction (reverse transcription-PCR), is employed to generate cDNA amplification of immune cell genetic material.

In some embodiments, the methods can be used to obtain sequence information about a target polynucleotide of interest within a cell, such as a TCR or an antibody. The target genes can be obtained from genomic DNA or mRNA of a cell from a sample or population of cells. The sample or population of cells can include immune cells. For example, for target antibody molecules, the immunoglobulin genes can be obtained from genomic DNA or mRNA of immune cells or T cells. RNA can be heavy chain (V, D, J segments), or light chain (V, J segments). In some embodiments, the starting material is RNA from immune cells composed of V, D, J gene segments that encodes for an antibody, and contains a constant region.

In some embodiments, in addition to obtaining full-length sequence data of a target polynucleotide of interest, e.g., immune molecule, such as antibody or TCR, the provided methods also permit efficient generation of high quality DNA sequencing libraries from both the whole transcriptome product and the full-length target, including multisubunit target, polynucleotide(s), e.g., antibody or TCR, including full-length paired immune receptor product.

In some embodiments, such methods include the addition (e.g., ligation) of adaptor DNA sequence to the single-stranded polynucleotide products, which can permit amplification and next-generation sequencing of the transcriptome of a single cell or a plurality of single cells.

A. Polynucleotide Libraries

A library produced according to the methods described herein can be a library comprising a large or full-length target sequence, such as an antibody or TCR sequence, with appropriate barcodes, such as vessel barcodes and molecular barcodes. In some embodiments, the library contains a large or full-length target sequence, e.g., antibody or TCR sequence, including both chains of the antibody or TCR, and sequences corresponding to one or more transcripts of a partial or complete transcriptome of the cell from which the target sequence, e.g., antibody or TCR, originated, each with a vessel barcode and a molecular barcode. In such embodiments, the large or full-length target sequence, e.g., antibody or TCR sequence, and the sequence(s) corresponding to one or more transcripts of a partial or complete transcriptome of the cell from which the target sequence, e.g., antibody or TCR, originated contain the same vessel barcode and contain a molecular barcode that is unique to each original transcript of the transcriptome. In some aspects, the vessel barcode is included in a first adaptor that is attached to each target polynucleotide and each polynucleotide of the collection of polynucleotides representing transcripts of the transcriptome.

In some embodiments, methods are provided for producing a polynucleotide library, whereby an adaptor (hereinafter also called a second adaptor) is added to each of a plurality of previously or first adaptor-tagged, barcoded single-stranded polynucleotides, such that the adaptors are at opposite ends of the polynucleotides, wherein the plurality of barcoded single-stranded polynucleotides include (i) one or more target single-stranded polynucleotide(s) that is complementary to one or more target polynucleotide(s) present in a cell of a population of cells; and (ii) a collection of single-stranded polynucleotides that each are complementary to a polynucleotide in the cell, wherein each of the plurality of barcoded single-stranded polynucleotides, contains a vessel barcode that is the same for all complementary polynucleotides from the same cell of the population of cells. The adaptor, such as each of the first and second adaptor, contains a universal priming sequence, which can be used for amplification or sequencing of the adaptor-tagged dual barcoded polynucleotides.

In some embodiments, the library of polynucleotides can be sequenced. In some embodiments, a library produced according to the methods described herein can contain appropriate clustering segments for sequencing. In some embodiments, many copies of identical molecular barcodes can be generated. In some embodiments, many copies of polynucleotides containing identical molecular barcodes can be generated for each starting unique target polynucleotide molecule. In some embodiments, many copies of polynucleotides containing identical molecular barcodes can be generated for each starting unique target polynucleotide molecule tagged with a vessel barcode. Any or all of the sequences can be sequenced and paired, for example, to determine the full or partial transcriptome of a cell expressing the target sequence(s).

Starting material can be RNA or DNA from a cell, such as from immune cells or T-cells. In some cases, the cell can be one that is known to or suspected of containing a desired target polynucleotide, such as an immune receptor, for example a TCR or an antibody. For example in the case of an antibody, a target cell is one that comprises the V, D, J gene segments that encode for an antibody, and contains the constant region. In some embodiments, the target polynucleotide comprises heavy chain segments (V, D, J segments), or light chain segments (V, J segments).

The polynucleotide starting material, such as RNA, can be reverse transcribed into cDNA using one or a pool of polynucleotides. Examples of primers in a pool of polynucleotides for reverse transcribing a target polynucleotide can comprise a portion complementary to a region of the target polynucleotide and/or can comprise sequences for reverse transcription of the whole transcriptome or a portion thereof. In some cases, the polynucleotides can comprise a portion complementary to a region of the target RNA, such as in a constant region of the target or to a poly-A tail of the mRNA. In some cases, multiple oligonucleotides, such as primers, can be used to anneal one or more target sequences, such as constant regions. In some aspects, the one or more polynucleotides include sequence specific, polydT, and/or random hexamer primers.

A reverse transcriptase can be employed to carry out the reverse transcription reaction. In particular embodiments, a reverse transcriptase can comprise a non-template terminal transferase activity. When a reverse transcriptase comprising non-template terminal transferase activity reaches the end of a template, it can add three or more non-template residues, such as three or more non-template cytosine residues. In some embodiments, Superscript II™ reverse transcriptase is used for this purpose. In some embodiments, Maxima™ reverse transcriptase is used for this purpose. In some embodiments, Protoscript II™ reverse transcriptase is used for this purpose. In some embodiments, Maloney murine leukemia virus reverse transcriptase (MMLV-RT) is used for this purpose. In some embodiments, HighScriber™ Reverse Transcriptase is used for this purpose. In some embodiments a terminal deoxynucleotidyl transferase is used for this purpose. In some embodiments avian myeloblastosis virus (AMV) reverse transcriptase is used for this purpose. Any reverse transcriptase capable of transcribing RNA that has non-template terminal transferase activity can be used. Any reverse polymerase capable of transcribing RNA that has non-template terminal transferase activity can be used. Any reverse polymerase capable of transcribing DNA that has non-template terminal transferase activity can be used. cDNA resulting from reverse transcription can be tagged with one or more barcodes. In some examples, the cDNA resulting from reverse transcription can be tagged with a vessel barcode and a molecular barcode. Various oligonucleotides of particular design can be used for barcode tagging.

In some embodiments, template switching can be used to generate libraries, such as for immune repertoire sequencing and/or transcriptome analysis. For example, template switching can be employed during reverse transcription to generate a region on the product of the reverse transcription that is complementary to a polynucleotide harboring a barcode, such as a vessel barcoded polynucleotide or a molecular barcoded polynucleotide. Template switching can be employed during reverse transcription to remove issues of PCR bias. These methods can be used for antibody sequencing, such as through the use of a high-throughput sequencing platform.

In some embodiments, a vessel barcode includes a randomized sequence portion flanked by known primer sites. For example the cDNA can be tagged with a vessel barcode, which can include a stretch of ~20 degenerate nucleotides with or without one or more known intercalating base position(s), such as NNNNWNNNNWNNNNWNNNNW (SEQ ID NO: 99; where N is any nucleotide and W is a known intercalating base that is A or T) or NNNNWISCNNNWISCNNN (SEQ ID NO: 100; where N is any nucleotide; W is a known intercalating base that is A or T; I is a known intercalating base that is A, T, G or C (i.e., N); S is an intercalating base that is G or C; and C is a known intercalating cytosine). Other exemplary sequences included in vessel barcoded oligonucleotides include NNNNWNNNNWNNNN (SEQ ID NO:80), WNNNNWNNNNWNNNN (SEQ ID NO:81), NWNNNWNNNNWNNNN (SEQ ID NO:82) or NNWNNNNWNNNNWNNNN (SEQ ID NO:83), wherein N is any nucleotide and W is adenine or thymine. The vessel barcode also can include known primer sites that are able to be recognized by a forward and reverse primer for amplification of vessel barcodes in a reaction mixture prior to their attachment or tagging, such as by annealing, to transcripts. Exemplary vessel barcode primers are set forth in SEQ ID NO: 4 and SEQ ID NO:5 or SEQ ID NO:10 and SEQ ID NO:11. In some cases, a pool of vessel barcodes containing the same primer sites but base-shifted in the degenerate portion, such as two or more vessel barcodes set forth in any of SEQ ID NOS: 80, 81, 83, 99 or 100, is provided to a vessel to result in tagged polynucleotide products that are base-shifted to increase diversity during sequencing. In some embodiments, an oligonucleotide containing a vessel barcode is part of an adaptor, such as a first adaptor, containing a universal primer site (e.g. P7). A first adaptor as described herein can include a universal priming site and a vessel barcode. Exemplary of such oligonucleotides containing vessel barcodes, including a universal primer site, degenerate portion and primers, are set forth in SEQ ID NOS: 2, 6, 7, 8 or 9, or are a pool of any two or more of SEQ ID NOS: 6, 7, 8 or 9. In some cases, the vessel barcode, or a pool of vessel barcodes, can be used to tag the cDNA molecules processed in the same vessel. In particular examples, the cDNA molecules processed in the same vessel are complementary to RNA molecules from the same cell.

In some embodiments, a molecular barcode includes a degenerate sequence to uniquely tag polynucleotide transcripts from the reverse transcription reaction. In some aspects, the molecular barcode is part of a template switch oligonucleotide, whereby the template switch oligonucleotide includes template sequences for the reverse transcriptase such that the molecular barcode is incorporated into each complementary polynucleotide. In some embodiments, a template switch oligonucleotide can contain (1) a 5' terminal region that is complementary to a 3' tagging polynucleotide of the first adaptor containing the vessel barcode, (2) the molecular barcode and (3) a 3' portion complementary to a 3' overhang. In some embodiments, a template switching molecule, such as a template switch oligonucleotide containing a barcode (e.g., a molecular barcode) can incorporate modified bases to minimize artifact formation. An exemplary template switch oligonucleotide, containing an exemplary molecular barcode is set forth in SEQ ID NO: 3.

Reverse transcription reactions, such as those described above, can be conducted in the presence of a 3' tagging polynucleotide. A 3' tagging polynucleotide can be a polynucleotide used to add nucleic acids to a 3' end of a selected polynucleotide, such as a target cDNA, or to a polynucleotide (e.g., cDNA) that is complementary to a transcript of the transcriptome in a cell. A 3' tagging polynucleotide can be a polynucleotide used as a template to add nucleic acids to a 3' end of a target polynucleotide, such as a cDNA. A 3' tagging polynucleotide can be a polynucleotide that hybridizes to a 3' end of a target polynucleotide, such as a cDNA. A 3' tagging polynucleotide can be a polynucleotide that contains a 3' region, such as a 3' terminal region, that hybridizes to a 3' end of a target polynucleotide, such as a cDNA. For example, a 3' tagging polynucleotide can comprise a segment, such as a segment that anneals to three or more non-template residues. In some embodiments, a 3' tagging polynucleotide is a molecular barcode polynucleotide. In some embodiments, a 3' tagging polynucleotide can comprise a molecular barcode. In some embodiments, a 3' tagging polynucleotide can comprise 3' riboguanosine residues or analogues thereof on the 3' end (rGrGrG) (RNA bases) that are complementary to and annealed to the strand produced by the reverse transcription enzyme (e.g., the sequence CCC). In some embodiments, three or more guanine residues can be used instead of riboguanosine residues (DNA nucleotides instead of RNA nucleotides). In some embodiments, a 3' tagging polynucleotide can comprise 1 or 2 riboguanosine residues on the 3' end and a riboguanosine residue or analogue thereof on the 3' end (rGrGG) that are complementary to and annealed to the strand produced by the reverse transcription enzyme (e.g., CCC).

Upon annealing of a 3' tagging polynucleotide to a CCC of the cDNA strand, a reverse transcriptase can continue extending the cDNA into the tagging polynucleotide, thereby attaching a molecular barcode or complement thereof, to a target population of polynucleotides, such as cDNAs, in the reaction. For example, 3' tagging polynucleotide can be a polynucleotide that contains a region 5' to the 3' region that hybridizes to a 3' end of a target polynucleotide. The region 5' to the 3' region that hybridizes to a 3' end of a target polynucleotide can comprise a region that is not complementary to the target polynucleotide, such as a cDNA. The region 5' to the 3' region that hybridizes to a 3' end of a target polynucleotide can comprise a molecular barcode. The region 5' to the 3' region that hybridizes to a 3' end of a target polynucleotide can comprise a region complementary to a vessel barcoded polynucleotide or complement thereof. In other experiments, template switching can be performed in separate reactions. For example, a 3' tagging polynucleotide can be added after the reverse transcription reaction, and enzymes such as a reverse transcriptase or polymerase can be used to extend into the tagging polynucleotide. Because a tagging polynucleotide can harbor a unique degenerate molecular barcode on each molecule in a vessel, each cDNA in a vessel can be uniquely tagged with a molecular barcode. In some embodiments, template switching can be performed at the same time as a reverse transcription reaction is conducted.

In some embodiments, a 3' tagging polynucleotide, such as a molecular barcoded polynucleotide, can further comprise a 5' region, such as a 5' terminal region that is complementary to a 3' tagging polynucleotide or complement thereof containing another barcode, such as a vessel barcode. In some embodiments, a target polynucleotide that contains a molecular barcode or complement thereof, such as a tagged cDNA molecule, can comprise a 3' region, such as a 3' terminal region that is complementary to a 3' tagging polynucleotide or complement thereof containing another barcode, such as a vessel barcode.

In some embodiments, a 3' tagging polynucleotide is a vessel barcoded polynucleotide. Upon generation of a polynucleotide containing a molecular barcode or complement thereof from a target polynucleotide, a vessel barcode can be added to the molecular barcoded target polynucleotide. A 3' tagging polynucleotide can be a polynucleotide used to add nucleic acids to a 3' end of a target polynucleotide, such as a molecular barcoded target polynucleotide. A 3' tagging polynucleotide can be a polynucleotide used as a template to add nucleic acids to a 3' end of a target polynucleotide, such as a molecular barcoded target polynucleotide. A 3' tagging polynucleotide can be a polynucleotide that hybridizes to a 3' end of a target polynucleotide, such as a molecular barcoded target polynucleotide. A 3' tagging polynucleotide can be a polynucleotide that contains a 3' region, such as a 3' terminal region, that hybridizes to a 3' end of a target polynucleotide, such as a molecular barcoded target polynucleotide. A vessel barcoded polynucleotide can comprise a 3' region, such as a 3' terminal region, that hybridizes to a 3' end of a molecular barcoded target polynucleotide.

Upon annealing of a 3' tagging polynucleotide to a molecular barcoded target polynucleotide, a reverse transcriptase can continue extending the cDNA into the 3' tagging polynucleotide, such as a vessel barcoded polynucleotide, thereby attaching a vessel barcode or complement thereof, to a target population of polynucleotides, such as molecular barcoded target polynucleotides, in the reaction. For example, 3' tagging polynucleotide can be a polynucleotide that contains a region 5' to the 3' region that hybridizes to a 3' end of a molecular barcoded target polynucleotide. The region 5' to the 3' region that hybridizes to a 3' end of a molecular barcoded target polynucleotide can comprise a region that is not complementary to the target polynucleotide or the molecular barcoded target polynucleotide. The region 5' to the 3' region that hybridizes to a 3' end of a molecular barcoded target polynucleotide can comprise a vessel barcode.

In some embodiments, a 3' tagging polynucleotide is an amplified product. In some embodiments, a 3' tagging polynucleotide is an amplified product originating from a single molecule. In some embodiments, a 3' tagging polynucleotide is an amplified product of a vessel barcoded polynucleotide. In some embodiments, a 3' tagging polynucleotide is an amplified product originating from a single vessel barcoded polynucleotide. The region 5' to the 3' region that hybridizes to a 3' end of a molecular barcoded target polynucleotide can comprise a region complementary to a primer or complement thereof. The region 5' to the 3' region that hybridizes to a 3' end of a molecular barcoded target polynucleotide can comprise a region complementary to a primer or complement thereof that was used to amplify the vessel barcoded polynucleotide.

In some embodiments, the 3' tagging polynucleotide can act as a primer, such as a forward primer, for amplification of the molecular barcoded cDNA, and DNA polymerase can extend the sequence to generate a dual barcoded single stranded polynucleotide molecule that is complementary to the cDNA and contains the vessel barcode, molecular barcode, and coding sequence for the target gene or transcript. In some embodiments, the dual barcoded single stranded polynucleotide molecule contains 5' to 3': a vessel barcode, a molecular barcode, a coding sequence for the target gene or transcript, and a first adapter. In some embodiments the oligonucleotide containing the vessel barcode contains a second adaptor, and the dual barcoded single stranded polynucleotide molecule contains 5' to 3': a second adaptor, a vessel barcode, a molecular barcode, a coding sequence for the target gene or transcript, and the first adaptor.

Tagged cDNA resulting from reverse transcription can be amplified one or more times, such as by PCR amplification. Various primers of particular design can be used for the amplification. A product of a first amplification reaction, such as PCR, can be amplified using a second amplification reaction, such as a first or second PCR phase. Various primers can be used for the amplification step. A library of amplified polynucleotides can be generated using the methods described herein. In some examples, a resulting library can comprise a full or partial antibody or TCR sequence with appropriate molecular and vessel barcodes. The library also can contain sequences corresponding to one or more transcripts of a partial or complete transcriptome with appropriate molecular and vessel barcodes.

A dual barcoded target polynucleotide, such as a cDNA containing a molecular barcode and a vessel barcode can then be amplified, such as by PCR. The PCR can then be conducted, for example, by using a primer set. A product of the aforementioned PCR reaction can then be amplified one or more times, such as by one or more rounds of PCR, or directly sequenced. In some embodiments, the primer set can involve forward and/or reverse primer(s) that is/are specific for the first and/or second adaptor(s). In some embodiments, the primer set can include the vessel barcode-containing oligonucleotide as a forward primer and a reverse primer that is specific for the first adaptor. In some embodiments, the primer set can include primer sets that include forward and reverse primers that bind the second and first adaptors and the vessel barcode-containing oligonucleotide as an additional primer, such as an additional forward primer. Exemplary primers are described in Examples herein.

Upon sequencing, sequences with identical molecular barcodes can be matched or paired. Upon sequencing, sequences with identical vessel barcodes can be matched or paired. Upon sequencing, sequences with identical target sequences can be matched or paired. In some embodiments, sequencing reads can be collapsed into consensus sequences. Collapsing matched or paired sequencing reads into a consensus sequence can thereby reduce or eliminate sequencing and PCR errors. Sequencing can be performed using a first primer site for a first read. Sequencing can be performed using the first primer site for a second read. Sequencing can be performed using a second primer site for a second read.

In some embodiments, chains of an immune receptor, such as chains of a TCR or an antibody, containing the same vessel barcodes can be paired. In some cases, antibody heavy and light chains containing the same vessel barcodes, can be paired. In some embodiments, paired chains can be cloned in a mammalian vector system. The immune receptor, such as antibody, construct can be expressed in other human or mammalian host cell lines. The construct can then be validated by transient transfection assays and Western blot analysis of the expressed antibody or TCR of interest.

In certain aspects, the invention provides a method of making a library of uniquely barcoded heavy and light chain antibody sequences and/or alpha and beta chain TCR sequences and/or gamma and delta chain TCR sequences including obtaining a plurality of nucleic acid constructs in which each construct includes a unique N-mer and a functional N-mer. The functional N-mer can be a random N-mer, a PCR primer, a universal primer, an antibody, a sticky end, or any other sequence. The method can include making M sets of a number N of fluid compartments each containing one or more copies of a unique construct. The method can create barcode libraries of higher complexity by adding an additional construct to each compartment in a set, and repeating that for each set to produce M compartments each containing a unique pair of constructs. The pairs can be hybridized or ligated to produce new constructs. In each construct in a barcode library, each unique N-mer can be adapted for identification by sequencing, probe hybridization, other methods, or a combination of methods.

Methods of amplification of RNA or DNA are well known, and can be used according to the present invention without undue experimentation based on the teaching and guidance presented herein. Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al.; U.S. Pat. No. 4,994,370 to Silver, et al.; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference (see, e.g., Current Protocols in Molecular Biology (CPMB) (Fred M. Ausubel, et al. ed., John Wiley and Sons, Inc.); or J. Sambrook et al., "Molecular Cloning: A Laboratory Manual," 1989, 2nd Ed., Cold Spring Harbour Laboratory Press: New York, N.Y.).

Conveniently, the method steps described herein, such as amplification, sequencing, and the like, may or may not be carried out in a multiplex assay format employing a solid phase on which a plurality of substrates, e.g., antigens, and the like, are immobilized, such as an array. In some embodiments, the array is a protein biochip. Using protein biochips, hundreds and even thousands of antigens can be screened. As used herein, "array," "microarray," or "biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes. A "protein biochip" refers to a biochip adapted for the capture of polypeptides. Many protein biochips are described in the art. Methods of producing polypeptide arrays are described, e.g., in De Wildt et al, 2000, Nat. Biotechnol. 18:989-994; Lueking et al., 1999, Anal. Biochem. 270: 103-1 11; Ge, 2000, Nucleic Acids Res. 28, e3, 1-VH; MacBeath and Schreiber, 2000, Science 289: 1760-1763; WO 01/40803 and WO 99/51773A1. Use of arrays allows a number of the steps, such as screening, to be performed robotically and/or in a high-throughput manner. Polypeptides for the array can be spotted at high speed, e.g., using a commercially available robotic apparatus, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

Upon capture on a biochip, analytes can be detected by a variety of detection methods selected from, for example, a gas phase ion spectrometry method, an optical method, an electrochemical method, atomic force microscopy and a radio frequency method. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods Immunoassays in various formats (e.g., ELISA) are popular methods for detection of analytes captured on a solid phase. Electrochemical methods include voltammetry and amperometry methods. Radio frequency methods include multipolar resonance spectroscopy.

In some embodiments of the invention, techniques which have been established for working with single cells or selecting particular populations of cells are employed. One exemplary technique incorporates a special accessory which can be used in FACS to deflect single cells into separate containers. Such accessories are commercially available and well-known in the art. Such accessories are useful for dispensing single cells into selected compartments of, for example, standard 96 well microtiter culture plates. Alternatively, cells may be deposited into a microtiter plate at a limiting dilution to ensure single cell deposition.

A second technique is PCR performed on single immune cells to amplify the $V_H$ and $V_L$ or $V\alpha$ and $V\beta$ or $V\gamma$ and $V\delta$ segments in addition optional amplification of the transcriptome of the single immune cells. In some embodiments, single cell PCR is used to retain the native pairing of $V_L$ and $V_H$ or $V\alpha$ and $V\beta$ or $V\gamma$ and $V\delta$ in the single cell. The specificity of an antibody, or a TCR, is determined by the complementarity determining regions (CDRs) within the $V_L$ region and $V_H$ region, or the $V\alpha$ and $V\beta$ or $V\gamma$ and $V\delta$ regions, respectively.

Methods for performing single-cell PCR are well known (e.g., Larrick, J. W. et al., Bio/Technology 7:934 (1989)). For example, antibody-producing B-cells from the B cell library or TCR-producing T-cells from the T-cell library may be fixed with a fixative solution or a solution containing a chemical such as formaldehyde, glutaraldehyde or the like. The cells are then permeabilized with a permeabilization solution comprising for example a detergent. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular mRNA, including $V_H$ and $V_L$ or $V\alpha$ and $V\beta$ or $V\gamma$ and $V\delta$ mRNA, for example, into the corresponding cDNA sequences. In other examples, single cell PCR can be performed in solution from lysed, non-fixed cells as described herein.

Reverse transcription may be performed in a single step or optionally together with a PCR procedure, using a reverse transcriptase, sufficient quantities of the four dNTPs, and primers that bind to the mRNA providing a 3' hydroxyl group for reverse transcriptase to initiate polymerization. Target-specific primers and/or random hexamer oligonucleotide primers can be used to initiate the reverse transcription reaction and generate high quality sequencing libraries.

For target sequences, any primer complementary to the target mRNA may be used, but it is preferred to use primers complementary to a 3'-terminal end of the $V_H$ and $V_L$ or $V\alpha$ and $V\beta$ or $V\gamma$ and $V\delta$ molecules so as to facilitate selection of variable region mRNA. Numerous studies have indicated that degenerate polynucleotides can be prepared to serve as the 5'-end primers for $V_H$ and $V_L$ or $V\alpha$ and $V\beta$ or $V\gamma$ and $V\delta$. The combinatorial library method of making targeting molecules relies on such primers. Furthermore, numerous experiments have shown that PCR can amplify the gene segments of interest, such as $V_H$ and $V_L$ or $V\alpha$ and $V\beta$ or $V\gamma$ and $V\delta$, from a single cell. Because of the ability to work with even a single cell, this PCR approach can generate antibodies even where the immune cells of interest occur at low frequency.

In some embodiments, after FACS sorting, the cells of immune cell library are pooled and the reverse transcription-PCR is performed on the entire pool of cells. Generation of mRNA for cloning antibody or TCR purposes is readily accomplished by well-known procedures for preparation and characterization of antibodies or TCRs (see, e.g., Antibodies: A Laboratory Manual, 1988; incorporated herein by reference). For example, total RNA from the B-cell library is extracted by appropriate methods which are standard and conventional in the art. cDNA is then synthesized from the RNA by appropriate methods, e.g., using random hexamer polynucleotides, or C-gene or C-gene family-specific primers, or V-gene or V-gene family-specific primers. Again these are processes known to persons skilled in the art as explained above. Libraries of nucleic acid molecules derived from B-cell or T-cell libraries, e.g., a library of RNA or cDNA molecules derived from such B or T lymphocytes, may be cloned into expression vectors to form expression libraries. In some embodiments, only the $V_H$ or Vα or Vγ domain, derived from the immune cell library, is amplified to generate a library of $V_H$ or Vα or Vγ domains. A $V_L$ or Vβ or Vδ library from another source is used in combination with the $V_H$ or Vα or Vγ library to generate antibodies or TCRs using methods described herein. Libraries of antibody or TCR fragments can be constructed by combining $V_H$ and $V_L$ or Vα and Vβ or Vγ and Vδ libraries together in any number of ways as known to the skilled artisan. For example, each library can be created in different vectors, and the vectors recombined in vitro, or in vivo. Alternatively, the libraries may be cloned sequentially into the same vector, or assembled together by PCR and then cloned. PCR assembly can also be used to join $V_H$ and $V_L$ or Vα and Vβ or Vγ and Vδ DNAs with DNA encoding a flexible peptide spacer to form single chain Fv (scFv) libraries as described elsewhere herein. In yet another technique, in-cell PCR assembly is used to combine $V_H$ and $V_L$ or Vα and Vβ or Vγ and Vδ genes within lymphocytes by PCR and then clone repertoires of linked genes.

1. Target Polynucleotides

In embodiments, methods provided herein are directed to amplification and sequencing of a target polynucleotide molecule, such as a polynucleotide molecule from a cell. In some cases, methods provided herein are directed to amplification and sequencing of two or more regions of a target polynucleotide molecule. In some cases, methods provided herein are directed to amplification and sequencing of two or more target polynucleotide molecules, such as two or more naturally paired molecules. In one aspect, target polynucleotides are RNA. In one aspect, target polynucleotides are genomic nucleic acids. DNA derived from the genetic material in the chromosomes of a particular organism can be genomic DNA.

In some embodiments, reference to a "target nucleic acid molecule," "target polynucleotide," "target polynucleotide molecule," refers to any nucleic acid of interest.

In some embodiments, target polynucleotides include sequences comprising variable regions of an immune receptor, such as an antibody or TCR produced by an immune cell.

In some embodiments, target polynucleotides include two or more chains of an immune receptor that are naturally paired to generate an immune receptor or binding fragment thereof. In some embodiments, target polynucleotides include sequences comprising a variable region of a heavy chain of an antibody produced by an immune cell. In some embodiments, target polynucleotides include sequences comprising a variable region of a light chain of an antibody produced by an immune cell. In some embodiments, target polynucleotides include sequences comprising a variable region of a heavy chain and sequences comprising a variable light chain of an antibody produced by the same immune cell.

The term "antibody" herein thus is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, and CDR-H3) and three CDRs in each light chain variable region (CDR-L1, CDR-L2, and CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme).

Thus, unless otherwise specified, a "CDR" or "complementary determining region," or individual specified CDRs (e.g., "CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given $V_H$ or $V_L$ amino acid sequence, it is understood that such a CDR has a sequence of the corresponding CDR (e.g., CDR-H3) within the variable region, as defined by any of the aforementioned schemes. In some embodiments, specified CDR sequences are specified.

Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments. In particular embodiments, the antibodies are single-chain antibody fragments comprising a variable heavy chain region and/or a variable light chain region, such as scFvs.

Immunoglobulins (Igs) expressed by B-cells are in some aspects proteins consisting of four polypeptide chains, two heavy chains (IgHs) and two light chains (IgLs), forming an H2L2structure. Each pair of IgH and IgL chains contains a hypervariable domain, consisting of a VL and a VH region, and a constant domain. The IgH chains of Igs are of several types, $\delta$, $\gamma$, $\alpha$, and $\beta$. The diversity of Igs within an individual is mainly determined by the hypervariable domain. Similar to the TCR, the V domain of IgH chains is created by the combinatorial joining of the VH, DH, and JH gene segments. Independent addition and deletion of nucleotides at the VH-DH, DH-JH, and VH-JH junctions during the process of Ig gene rearrangement further increases hypervariable domain sequence diversity. Here, immunocompetence is reflected in the diversity of Igs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

A "hypervariable region" refers to the amino acid residues of an antibody or TCR which are responsible for antigen-binding. The hypervariable region comprises amino acid residues from a complementarity determining region or CDR. Framework or FR residues are those variable domain residues other than the hypervariable region residues as herein defined.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the VH region of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called VHH domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the VH or VHH regions. The CDR3 in the camel VHH region is characterized by its relatively long length, averaging 16 amino acids (Muyldermans et al., 1994, Protein Engineering 7(9): 1129).

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

In some embodiments, target polynucleotides include sequences comprising a variable region of an alpha chain of a TCR produced by an immune cell. In some embodiments, target polynucleotides include sequences comprising a variable region of a beta chain of a TCR produced by an immune cell. In some embodiments, target polynucleotides include sequences comprising a variable region of an alpha chain of a TCR and sequences comprising a variable region of a beta chain of a TCR produced by the same immune cell. In some embodiments, target polynucleotides include sequences comprising a variable region of a gamma chain of a TCR produced by an immune cell. In some embodiments, target polynucleotides include sequences comprising a variable region of a delta chain of a TCR produced by an immune cell. In some embodiments, target polynucleotides include sequences comprising a variable region of a gamma chain of a TCR and sequences comprising a variable region of a delta chain of a TCR produced by the same immune cell.

In some embodiments, a TCR encompasses full TCRs as well as antigen-binding portions or antigen-binding fragments (also called MHC-peptide binding fragments) thereof. In some embodiments, the TCR is an intact or full-length TCR. In some embodiments, the TCR is an antigen-binding portion that is less than a full-length TCR but that binds to a specific antigenic peptide bound to (i.e., in the context of) an MHC molecule, i.e., an MHC-peptide complex. In some cases, an antigen-binding portion or fragment of a TCR can contain only a portion of the structural domains of a full-length or intact TCR, but yet is able to bind the epitope (e.g., MHC-peptide complex) to which the full TCR binds. In some cases, an antigen-binding portion or fragment of a TCR contains the variable domains of a TCR, such as variable α chain and variable β chain of a TCR, sufficient to form a binding site for binding to a specific MHC-peptide complex, such as generally where each chain contains three complementarity determining regions. Polypeptides or proteins having a binding domain which is an antigen-binding domain or is homologous to an antigen-binding domain are included. Complementarity determining region (CDR) grafted antibodies and TCRs and other humanized antibodies and TCRs (including CDR modifications and framework region modifications) are also contemplated by these terms. It should be noted that while reference may be made only to immunoglobulin chains (e.g., heavy chains and lights chains), the disclosed invention can be applied to multiple other different types of paired sequences, e.g., T-cell receptor chain pairs (TCRα and TCRβ chains and TCRγ and TCRδ chains), and is not limited to immunoglobulins.

The ability of T-cells to recognize antigens associated with various cancers or infectious organisms is conferred by its TCR, which is made up of both an alpha (α) chain and a beta (β) chain or a gamma (γ) and a delta (δ) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to the antigenic peptide on the APC is a central event in T-cell activation, which occurs at an immunological synapse at the point of contact between the T-cell and the APC.

Each TCR comprises variable complementarity determining regions (CDRs), as well as framework regions (FRs). The amino acid sequence of the third complementarity-determining region (CDR3) loops of the α and β chain variable domains largely determines the sequence diversity of αβ T-cells arising from recombination between variable (Vβ), diversity (Dβ), and joining (Jβ) gene segments in the β chain locus, and between analogous Vα and Jα gene segments in the α chain locus, respectively. The existence of multiple such gene segments in the TCR α and β chain loci allows for a large number of distinct CDR3 sequences to be encoded. Independent addition and deletion of nucleotides at the Vβ-Dβ, Dβ-Jβ, and Vα-Jα junctions during the process of TCR gene rearrangement further increases CDR3 sequence diversity. In this respect, immunocompetence is reflected in the diversity of TCRs.

Also provided are TCR fragments, including antigen-binding fragments. In some embodiments, the TCR is an antigen-binding portion thereof, such as a variant of a full-length TCR not containing the transmembrane and/or cytoplasmic region(s) thereof, which may be referred to as a full soluble TCR. In some embodiments, the TCR is a dimeric TCR (dTCR). In some embodiments, the TCR is a single-chain TCR (scTCR), such as a scTCR having a structure as described in PCT patent publication numbers WO 03/020763, WO 04/033685, or WO 2011/044186. In certain embodiments, the TCR is a single-chain TCR fragment comprising an alpha chain variable region linked to a beta chain variable region, such as a scTv. In some embodiments, an scTv is also referred to as an scFv A single-chain Fv or scFv refers in some aspects to antibody or TCR fragments that comprise the variable heavy chain (VH) and variable light chain (VL) domains of an antibody or the variable alpha or gamma chain (Vα or Vγ) and variable beta or delta chain (Vβ or Vδ) domains of a TCR, wherein these domains are present in a single polypeptide chain. Generally, the Fv polypeptide further comprises a polypeptide linker between the VH and VL domains or Vα and Vβ domains or Vγ and Vδ domains which enables the scFv to form the desired structure for antigen binding.

A diabody refers in some aspects to small antibody and/or TCR fragments with two antigen-binding sites, which fragments comprise a VH connected to a VL in the same polypeptide chain (VH-VL) or a Vα connected to a Vβ in the same polypeptide chain (Vα-Vβ) or a Vγ connected to a Vδ in the same polypeptide chain (Vγ-Vδ). By using a linker that is too short to allow pairing between the two domains on the same chain, the domains are forced to pair with the complementary domains of another chain and create two antigen-binding sites. Exemplary diabodies are described more fully in, for example, EP404097 and WO93111161.

A bispecific antibody or bispecific TCR refers in some aspects to an antibody or TCR that shows specificities to two different types of antigens. The terms as used herein specifically include, without limitation, antibodies and TCRs which show binding specificity for a target antigen and to another target that facilitates delivery to a particular tissue. Similarly, multi-specific antibodies and TCRs have two or more binding specificities.

A linear antibody or "linear TC refers in some aspects to a pair of tandem Fd segments (e.g., VH-CH1-VH-CH1 or Vα-Cal-Vα-Cal) which form a pair of antigen binding regions. Linear antibodies and TCRs can be bispecific or monospecific, for example, as described by Zapata et al., Protein Eng. 8(10):1057-1062 (1995).

An antigen-binding domain refers in some aspects to one or more fragments of an antibody or TCR that retain the ability to specifically bind to an antigen. Non-limiting examples of antibody fragments included within such terms include, but are not limited to, (i) a Fab fragment, a monovalent fragment consisting of the VL, VH, CL and CH1 domains; (ii) a F(ab')2 fragment, a bivalent fragment containing two Fab fragments linked by a disulfide bridge at the hinge region; (iii) a Fd fragment consisting of the VH and CH1 domains; (iv) a Fv fragment containing the VL and VH domains of a single arm of an antibody, including scFvs, (v) a dAb fragment (Ward et al., (1989) Nature 341:544 546), which containing a VH domain; and (vi) an isolated CDR. Additionally included in this definition are antibodies comprising a single heavy chain and a single light chain or TCRs with a single alpha chain or a single beta chain.

"F(ab')2" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which a light chain composed of VL and CL, and a heavy chain fragment composed of VH and CHγ1 (γ1 region in the constant region of the heavy chain) are connected at their C terminal regions through a disulfide bond. Each of these two homologous antibody fragments is called 'Fab'. Pepsin also cleaves IgG downstream of the disulfide bonds existing between the hinge regions in each of the two heavy chains to generate an antibody fragment slightly larger than the fragment in which the two above-mentioned 'Fab' are connected at the hinge region. This antibody fragment is called F('ab')2. The Fab fragment also contains the constant domain of the light chain and the first constant domain (CH1) of the heavy chain. 'Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally are produced as pairs of Fab' fragments which have hinge cysteines between them.

Fv refers in some aspects to an antibody or TCR fragment which contains a complete antigen-recognition and antigen-binding site. This region consists of a dimer of one heavy chain and one light chain variable domain or one TCRα chain and one TCRβ chain or one TCRγ chain and one TCR chain in tight, non-covalent association. It is in this configuration that the three CDRs of each variable domain interact to define an antigen-binding site on the surface of the VH-VL dimer or Vα-Vβ dimer or Vγ-Vδ dimer. Collectively, a combination of one or more of the CDRs from each of the VH and VL chains or Vα and Vβ chains or Vγ and Vδ chains confers antigen-binding specificity to the antibody or TCR. For example, it would be understood that, for example, the CDRH3 and CDRL3 could be sufficient to confer antigen-binding specificity to an antibody or TCR when transferred to $V_H$ and $V_L$ chains or Vα and Vβ chains or Vγ and Vδ chains of a recipient selected antibody, TCR, or antigen-binding fragment thereof and this combination of CDRs can be tested for binding, affinity, etc. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment (VL and VH or Vα and Vβ or Vγ and Vδ), are coded for by separate genes, they can be joined using recombinant methods by a synthetic linker that enables them to be made as a single protein chain in which the VL and VH or Vα and Vβ or Vγ and Vδ chain regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any VH and VL sequences of specific scFv can be linked to an Fc region cDNA or genomic sequences, in order to generate expression vectors encoding complete Ig (e.g., IgG) molecules or other isotypes. VH and VL can also be used in the generation of Fab, Fv or other fragments of Igs using either protein chemistry or recombinant DNA technology.

A "germline sequence" refers to a genetic sequence from the germline (the haploid gametes and those diploid cells from which they are formed). Germline DNA contains multiple gene segments that encode a single Ig heavy or light chain, or a single TCRα or TCRβ chain, or a single TCRγ or TCRδ chain. These gene segments are carried in the germ cells but cannot be transcribed and translated until they are arranged into functional genes. During B-cell and T-cell differentiation in the bone marrow, these gene segments are randomly shuffled by a dynamic genetic system capable of generating more than 108 specificities. Most of these gene segments are published and collected by the germline database.

In some embodiments, the immune molecule may be or may likely be a neutralizing antibody or neutralizing TCR. In some aspects, a neutralizing antibody or TCR is an antibody or TCR that inhibits replication of a pathogen, such as a virus or bacteria, regardless of the mechanism by which neutralization is achieved.

In some embodiments, the sample, such as a population of cells or a single cell can contain an immune repertoire, e.g., antibody repertoire or TCR repertoire, and such can be elucidated by the provided methods. In some embodiments, an antibody repertoire or TCR repertoire refers to a collection of antibodies, TCRs, or fragments thereof. In some embodiments, an antibody repertoire can, for example, be used to select a particular antibody or screen for a particular property, such as binding ability, binding specificity, ability of gastrointestinal transport, stability, affinity, and the like. The term specifically includes antibody and TCR libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

Target polynucleotides can be obtained from virtually any source and can be prepared using methods known in the art. For example, target polynucleotides can be directly isolated without amplification using methods known in the art, including without limitation extracting a fragment of genomic DNA or mRNA from an organism or a cell (e.g., an immune cell) to obtain target polynucleotides. A target polynucleotide can also encompass cDNA generated from RNA (such as mRNA) through reverse transcription-PCR. In some cases, a target polynucleotide is an RNA molecule. In some cases, a target polynucleotide is an mRNA molecule, or a cDNA produced from the mRNA molecule. In some cases, a target polynucleotide is an mRNA molecule, or cDNA molecule produced from the mRNA molecule, from a single immune cell. In some cases, target polynucleotides are mRNA molecules, or cDNA molecules produced from the mRNA molecules, from individual immune cells. In some cases, target polynucleotides are mRNA molecules encoding an antibody sequence from a single immune cell. In some cases, target polynucleotides are mRNA molecules encoding heavy chain antibody sequences from individual immune cells. In some cases, target polynucleotides are mRNA molecules encoding a heavy chain antibody sequence from a single immune cell. In some cases, target polynucleotides are mRNA molecules encoding light chain antibody sequences from individual immune cells. In some cases, target polynucleotides are mRNA molecules encoding a light chain antibody sequence from a single immune cell. In some cases, target polynucleotides are mRNA molecules encoding antibody variable sequences from individual immune cells. In some cases, target polynucleotides are mRNA molecules encoding a variable antibody sequence from a single immune cell. In some cases, target polynucleotides are mRNA molecules encoding variable light chain antibody sequences from individual immune cells. In some cases, target polynucleotides are mRNA molecules encoding a variable light chain antibody sequence from a single immune cell. In some cases, target polynucleotides are mRNA molecules encoding variable heavy chain antibody sequences from individual immune cells. In some cases, target polynucleotides are mRNA molecules encoding a variable heavy chain antibody sequence from a single immune cell. In some cases, a target polynucleotide can be a cell-free nucleic acid, e.g., DNA or RNA. In some cases, target polynucleotides are mRNA molecules encoding variable alpha, beta, gamma, and/or delta chain TCR sequences from individual immune cells.

The methods described herein can be used to generate a library of polynucleotides from one or more target polynucleotides for sequencing. Target polynucleotides include any polynucleotides of interest that are not products of an amplification reaction. For example, a target polynucleotide can include a polynucleotide in a biological sample. For example, target polynucleotides do not include products of a PCR reaction. For example, target polynucleotides may include a polynucleotide template used to generate products of an amplification reaction, but do not include the amplification products themselves. For example, target polynucleotides may include a polynucleotide template used to generate products of a reverse transcription reaction or primer extension reaction, and also include the reverse transcription reaction or primer extension reaction products themselves. For example, target polynucleotides include polynucleotides of interest that can be subjected to a reverse transcription reaction or a primer extension reaction. For example, target polynucleotides include RNA or DNA. For example, target polynucleotides include cDNA. In some embodiments, target RNA polynucleotides are mRNA. In some embodiments, target RNA polynucleotides are polyadenylated. In some embodiments, the RNA polynucleotides are not polyadenylated. In some embodiments, the target polynucleotides are DNA polynucleotides. The DNA polynucleotides may be genomic DNA. The DNA polynucleotides may comprise exons, introns, untranslated regions, or any combination thereof.

In some embodiments, libraries can be generated from two or more regions of a target polynucleotide. In some embodiments, methods libraries can be generated from two or more target polynucleotides. In some embodiments, target polynucleotides are genomic nucleic acids or DNA derived from chromosomes. In some embodiments, target polynucleotides include sequences comprising a variant, such as a polymorphism or mutation. In some embodiments, target polynucleotides include DNA and not RNA. In some embodiments, target polynucleotides include RNA and not DNA. In some embodiments, target polynucleotides include DNA and RNA. In some embodiments, a target polynucleotide is an mRNA molecule. In some embodiments, a target polynucleotide is a DNA molecule. In some embodiments, a target polynucleotide is a single stranded polynucleotide. In some embodiments, a target polynucleotide is a double stranded polynucleotide. In some embodiments, a target polynucleotide is a single strand of a double stranded polynucleotide.

Target polynucleotides can be obtained from any biological sample and prepared using methods known in the art. In some embodiments, target polynucleotides are directly isolated without amplification. Methods for direct isolation are known in the art. Non-limiting examples include extracting genomic DNA or mRNA from a biological sample, organism or, cell.

In some embodiments, one or more target polynucleotides are purified from a biological sample. In some embodiments, a target polynucleotide is not purified from the biological sample in which it is contained. In some embodiments, a target polynucleotide is isolated from a biological sample. In some embodiments, a target polynucleotide is not isolated from the biological sample in which it is contained. In some embodiments, a target polynucleotide can be a cell-free nucleic acid. In some embodiments, a target polynucleotide can be a fragmented nucleic acid. In some embodiments, a target polynucleotide can be a transcribed nucleic acid. In some embodiments, a target polynucleotide is a modified polynucleotide. In some embodiments, a target polynucleotide is a non-modified polynucleotide.

In some embodiments, a target polynucleotide is polynucleotide from a single cell. In some embodiments, target polynucleotides are from individual cells. In some embodiments, a target polynucleotide is polynucleotide from a sample containing a plurality of cells.

In some embodiments, a target polynucleotide encodes a biomarker sequence. In some embodiments, a target polynucleotide encodes two or more biomarker sequences. In some embodiments, a plurality of target polynucleotides encodes a biomarker sequence. In some embodiments, a plurality of target polynucleotides encodes two or more biomarker sequences. In some embodiments, a plurality of target polynucleotides encodes 3, 4, 5, 6, 7, 8, 9, 10, 20, 30, 40, 50, 60, 70, 80, 90, or 100 or more biomarker sequences.

In some embodiments, a plurality of target polynucleotides comprises a panel of immunoglobulin sequences. In some embodiments, a plurality of target polynucleotides comprises a panel of TCR sequences. For example, a panel of immunoglobulin sequences can be $V_H$ and/or $V_L$ sequences. In some embodiments, a panel of immunoglobulin or TCR sequences contains 1, 2, 3, 4, 5, 6, 7, 8, 9, or 10 immunoglobulin or TCR sequences. In some embodiments, a panel of immunoglobulin or TCR sequences contains at least about 10, 20, 30, 40, 50, 60, 70, 80, 90, 100, 150, 200, 250, 300, 350, 400, 3000, 4000, 5000, 6000, 7000, 450, 500, 550, 600, 650, 700, 750, 800, 850, 900, 1000, 1500, 2000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $510^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin or TCR sequences. In some embodiments, a panel of immunoglobulin or TCR sequences contains at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600, 000, 700,000, 800,000, 900,000, $1\times10^6$, $2\times10^6$, $3\times10^6$, $4\times10^6$, $510^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin or TCR sequences. In some embodiments, a panel of immunoglobulin or TCR sequences contains from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, 5000-10000, $1-1\times10^5$, $1-2\times10^5$, $1-3\times10^5$, $1-4\times10^5$, $1-5\times10^5$, $1-6\times10^5$, $1-7\times10^5$, $1-8\times10^5$, $9\times10^5$, $1-1\times10^6$, $1-2\times10^6$, $1-3\times10^6$, $1-4\times10^6$, $1-5\times10^6$, $1-6\times10^6$, $1-7\times10^6$, $1-8\times10^6$, $9\times10^6$, $1-1\times10^7$, $1-2\times10^7$, $1-3\times10^7$, $1-4\times10^7$, $1-5\times10^7$, $1-6\times10^7$, $1-7\times10^7$, $1-8\times10^7$, $1-9\times10^7$, $1-1\times10^8$, $1-2\times10^8$, $1-3\times10^8$, $1-4\times10^8$, $1-5\times10^8$, $1-6\times10^8$, $1-7\times10^8$, $1-8\times10^8$, $1-9\times10^8$, $1-1\times10^9$, $1-2\times10^9$, $1-3\times10^9$, $1-4\times10^9$, $1-5\times10^9$, $1-6\times10^9$, $1-7\times10^9$, $1-8\times10^9$, $1-9\times10^9$, $1-1\times10^{10}$, $1-2\times10^{10}$, $1-3\times10^{10}$, $1-4\times10^{10}$, $1-5\times10^{10}$, $1-6\times10^{10}$, $1-7\times10^{10}$, $1-810^{10}$, $1-9\times10^{10}$, $1-1\times10^{11}$, $1-2\times10^{11}$, $1-3\times10^{11}$, $1-4\times10^{11}$, $1-5\times10^{11}$, $1-6\times10^{11}$, $1-7\times10^{11}$, $1-8\times10^{11}$, $1-9\times10^{11}$, $1-1\times10^{12}$, $1-2\times10^{12}$, $1-3\times10^{12}$, $1-4\times10^{12}$, $1-5\times10^{12}$, $1-6\times10^{12}$, $1-7\times10^{12}$, $1-8\times10^{12}$, or $1-9\times10^{12}$ immunoglobulin or TCR sequences.

In some embodiments, a target polynucleotide is about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, or 5000-10000 bases or base-pairs in length. In some embodiments, the average length of the target polynucleotides, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some embodiments, a target sequence from a relative short template, such as a sample containing a target polynucleotide, is about 40, 45, 50, 55, 60, 65, 70, 75, 80, 85, 90, 95, or 100 bases. In certain embodiments, sequencing data are aligned against known or expected sequences using a database containing sequences or immunoglobulin or TCR sequences associated with a disease or condition.

2. Collections of Polynucleotides, e.g., Transcriptome

A collection of polynucleotides corresponding to genomic or transcriptomic polynucleotides can be obtained from virtually any source, such as one cell or a plurality of cells, and can be prepared using methods known in the art. For example, the collection of polynucleotides can be directly isolated from a single cell or a plurality of cells without amplification using methods known in the art, including without limitation extracting a fragment of genomic DNA or mRNA from an organism or a cell (e.g., an immune cell) to obtain the collection of polynucleotides. The collection of genomic or transcriptomic polynucleotides can also encompass cDNA generated from RNA (such as mRNA) through reverse transcription-PCR. In some cases, the collection of polynucleotides is a collection of RNA molecules. In some cases, the collection of polynucleotides is a collection of mRNA molecules, or a collection of cDNA molecules produced from the mRNA molecules. In some cases, the collection of polynucleotide is a collection of mRNA molecules, or cDNA molecules produced from the mRNA molecules, from a single immune cell. In some cases, the collection of polynucleotides is collection of mRNA molecules, or cDNA molecules produced from the mRNA molecules, from individual immune cells.

The methods described herein can be used to generate a library containing a collection of polynucleotides from one or more cells for sequencing. The collection of polynucleotides can be derived from genomic DNA or RNA, such as mRNA transcripts of one or a plurality of cells from a biological sample. For example, genomic DNA or cellular RNA, such as mRNA can be used as a template to generate products of an amplification reaction, such as a reverse transcription reaction or primer extension reaction. In some examples, the collection of polypeptides can be generated from cDNA. In some embodiments, the collection of polynucleotides is generated from RNA polynucleotides are mRNA, and the collection substantially represents the transcriptome of one or more cells from a biological sample. In some embodiments, the collection of polynucleotides is generated from RNA polynucleotides that are polyadenylated. In some embodiments, the RNA polynucleotides are not polyadenylated. In some embodiments, the collection of polynucleotides is generated from DNA polynucleotides. The DNA polynucleotides may be genomic DNA. The DNA polynucleotides may comprise exons, introns, untranslated regions, or any combination thereof. For example, the collection of polynucleotides of the present invention can contain the genomic or transcriptomic information of at least 5, 10, 100, 250, 500, 750, 1,000, 2,500, 5,000, 10,000, 25,000, 50,000, 75,000, 10,000, 250,000, 500,000, 750,000, 1,000,000, 2,500,000, 5,000,000, 7,500,000, or 10,000,000 subsets or individual cells, such as subsets of or individual immune cells expressing different antibodies or TCRs.

In some embodiments, the collection of polynucleotides can be generated by reverse transcriptase or primer extension reaction using random hexamer primers. In some embodiments, the collection of polynucleotides can be generated by reverse transcriptase or primer extension reaction using a primer directed against a polyA nucleotide sequence. In some examples, the collection the collection of polynucleotides can be generated by reverse transcriptase or primer extension reaction using an oligo-dT. In some examples, the primers can be biotinylated. Collections of polynucleotides, optionally, can be purified following reverse transcription or primer extension reactions. For example, collections of polynucleotides generated using biotinylated primers can optionally be purified using streptavidin purification techniques. In other embodiments, polynucleotides can be purified by one or more of affinity purification, agarose gel electrophoresis.

3. Droplet Libraries

In general, a droplet library is made up of a number of library elements that are pooled together in a single collection. Libraries may vary in complexity from a single library element to $1 \times 10^{15}$ library elements or more. Each library element is one or more given components at a fixed concentration. The element may be, but is not limited to, cells, beads, amino acids, proteins, polypeptides, nucleic acids, polynucleotides or small molecule chemical compounds. The element may contain an identifier such as a molecular barcode, a vessel barcode, or both.

A cell library element can include, but is not limited to, hybridomas, B-cells, T-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picoliter drops." Lab Chip, 8(8): 1262-1264, 2008. The discreet nature of cells allows for libraries to be prepared in mass with a plurality of cell variants, such as immune cells producing one antibody or TCR each, all present in a single starting media and then that media is broken up into individual vessels, such as droplets or capsules, that contain at most one cell. The cells within the individual vessels, e.g., droplets or capsules, are then lysed, and the polynucleotides released within the vessel, such as cellular mRNA and genomic DNA including target mRNA or DNA (e.g., heavy chain and light chain polynucleotides and/or alpha and beta chain polynucleotides and/or gamma and delta chain polynucleotides), from the lysed cells are barcoded with molecular barcodes and vessel barcodes and amplified. The dual barcoded polynucleotide products are then combined or pooled to form a library consisting of the transcriptome or genome and target (e.g., heavy and light chain and/or alpha and beta chain and/or gamma and delta chain) library elements. In particular, the transcriptome and target libraries are pooled.

A bead based library element contains one or more beads, and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, the library elements will be prepared from a variety of starting fluids. It is desirable to have exactly one cell per droplet with only a few droplets containing more than one cell when starting with a plurality of cells. In some cases, variations from Poisson statistics can be achieved to provide an enhanced loading of droplets such that there are more droplets with exactly one cell per droplet and few exceptions of empty droplets or droplets containing more than one cell.

In some embodiments, it is desirable to have exactly one vessel barcoded polynucleotide per droplet with only a few droplets containing more than one vessel barcoded polynucleotide when starting with a plurality of vessel barcoded polynucleotide. In some cases, variations from Poisson statistics can be achieved to provide an enhanced loading of droplets such that there are more droplets with exactly one vessel barcoded polynucleotide per droplet and few exceptions of empty droplets or droplets containing more than one vessel barcoded polynucleotide.

Examples of droplet libraries are collections of droplets that have different contents, ranging from beads, cells, small molecules, DNA, primers, antibodies, and barcoded polynucleotides. The droplets range in size from roughly 0.5 micron to 500 microns in diameter, which corresponds to about 1 picoliter to 1 nanoliter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are preferably uniform in size. That is, the diameter of any droplet within the library will vary less than 5%, 4%, 3%, 2%, 1% or 0.5% when compared to the diameter of other droplets within the same library. The uniform size of the droplets in the library may be critical to maintain the stability and integrity of the droplets and also may be essential for the subsequent use of the droplets within the library for the various biological and chemical assays described herein.

The invention provides a droplet library comprising a plurality of aqueous droplets within an immiscible fluid, wherein each droplet is preferably substantially uniform in size and comprises a different library element. The invention provides a method for forming the droplet library comprising providing a single aqueous fluid comprising different library elements, encapsulating each library element into an aqueous droplet within an immiscible fluid.

In certain embodiments, different types of elements (e.g., cells or beads), are pooled in a single source contained in the same medium. After the initial pooling, the elements are then encapsulated in droplets to generate a library of droplets wherein each droplet with a different type of bead or cell is a different library element. The dilution of the initial solution enables the encapsulation process. In some embodiments, the droplets formed will either contain a single element or will not contain anything, i.e., be empty. In other embodiments, the droplets formed will contain multiple copies of a library element. The elements being encapsulated are generally variants of a type. In one example, elements are immune cells of a blood sample, and each immune cell is encapsulated to amplify and barcode the antibody sequences of the nucleotides in the immune cells.

For example, in one type of emulsion library, there are library elements that have different particles, i.e., cells or barcoded polynucleotides in a different medium and are encapsulated prior to pooling. In one example, a specified number of library elements, i.e., n number of different cells, or barcoded polynucleotides, is contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevent the exchange of the contents of the library between droplets.

B. Methods of Producing Single-Cell Dual Barcoded Polynucleotide Library

In some embodiments, methods are provided for producing a polynucleotide library, that include the steps of (a) lysing cells within each of a plurality of vessels, wherein each of said vessels comprises a cell from a sample comprising a population of cells, a plurality of molecular barcoded oligonucleotides, and a first adaptor comprising a vessel barcoded oligonucleotide; (b) producing, in each vessel, a plurality of single-stranded polynucleotides comprising (i) one or more target single-stranded polynucleotide(s) that is complementary to one or more target polynucleotide(s) present in the cell; and (ii) a collection of single-stranded polynucleotides that each are complementary to a polynucleotide in the cell; (c) attaching to each single-stranded polynucleotide one of the plurality of molecular barcoded oligonucleotides, thereby generating a plurality of barcoded single-stranded polynucleotides each comprising a unique molecular barcode; (d) attaching the first adaptor comprising the vessel barcoded oligonucleotide, or an amplified product thereof, to each of the barcoded single-stranded polynucleotides, thereby generating a plurality of dual-barcoded single-stranded polynucleotides, wherein each of the dual-barcoded single-stranded polynucleotides in the same vessel comprise the same vessel barcode; and (e) adding a second adaptor to each of the dual-barcoded single-stranded polynucleotides, wherein the first adaptor and second adaptor are present at or near opposite ends of each of the dual-barcoded single-stranded polynucleotides. Exemplary vessels in which the polynucleotide library is produced include a well, emulsion, droplet or a microcapsule.

1. Sample Preparation

Any biological sample, including a sample containing a population of cells, containing polynucleotides can be used in the methods described herein. Any sample containing a cell generally can be used in the methods described herein. For example, a sample can be a biological sample from a subject or from a sample derived therefrom containing RNA or DNA. The polynucleotides can be extracted from the biological sample, or the sample can be directly subjected to the methods without extraction or purification of the polynucleotides. The sample can be extracted or isolated DNA or RNA. A sample can also be total RNA or DNA extracted from a biological specimen, a cDNA library, viral, or genomic DNA. In one embodiment, polynucleotides are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism.

In certain embodiments, the polynucleotides are obtained from a single cell, such as a cell present in a population of cells. Polynucleotides can be obtained directly from an organism or from a biological sample obtained from an organism. Any tissue or body fluid specimen may be used as a source for nucleic acid for use in the invention. Polynucleotides can also be isolated from cultured cells, such as a primary cell culture or a cell line. In some embodiments the cell can be a blood cell, an immune cell, a tissue cell, or a tumor cell. In some embodiments, the cell is an immune cell, such as a B cell or T cell. The B cell can be a plasmablast, a memory B cell, or a plasma cell. The cells or tissues from which template nucleic acids are obtained can be infected with a virus or other intracellular pathogen.

In some embodiments, the population of cells, such as a population containing immune cells, can be isolated from the blood or other biological samples of a subject or host, such as a human or other animal, such as a human or other animal that has been immunized or that is suffering from an infection, cancer, an autoimmune condition, or any other disease. In some embodiments, the human may be diagnosed with a disease, be exhibiting symptoms of a disease, not be diagnosed with a disease, or not be exhibiting symptoms of a disease. In some embodiments, the subject or host, e.g., a human subject, may be one that was exposed to and/or who can produce TCRs against an infectious agent (e.g., viruses, bacteria, parasites, prions, etc.), antigen, disease or an antigen associated with a disease or condition, e.g., a tumor-associated antigen. In some embodiments, the immune cells can be from any biological sample containing T cells, such as cells present in PBMCs, spleen or other lymphoid organ. In some embodiments, the immune cells are from a T cell source of a normal of healthy subject. In some embodiments, the immune cells are from a T cell source of a diseased subject. In some embodiments, $CD4^+$ or $CD8^+$ cells can be isolated or obtained. In some cases, peripheral blood mononuclear cells (PBMCs) can be isolated or obtained. In some cases, tumor-infiltrating lymphocytes (TILs) can be isolated or obtained.

In certain embodiments, antibody or TCR-producing immune cells can be isolated from the blood or other biological samples of a subject or host, such as a human or other animal, such as a human or other animal that has been immunized or that is suffering from an infection, cancer, autoimmune condition, or any other diseases to identify a pathogen-, tumor-, and/or disease-specific antibody or TCR of potential clinical significance. For example, the human may be diagnosed with a disease, be exhibiting symptoms of a disease, not be diagnosed with a disease, or not be exhibiting symptoms of a disease. For example, the human may be one that was exposed to and/or who can make useful antibodies or TCRs against an infectious agent (e.g., viruses, bacteria, parasites, prions, etc.), antigen, or disease. For example, the animal may be one that was exposed to and/or who can make useful antibodies or TCRs against an infectious agent (e.g., viruses, bacteria, parasites, prions, etc.), antigen, or disease. In some examples, the animal, such as a human, no longer exhibits symptoms of a disease or condition. Certain immune cells from immunized hosts make antibodies or TCRs to one or more target antigens and/or one or more unknown antigens. In the present invention the lymphocyte pool can be enriched for the desired immune cells by any suitable method, such as screening and sorting the cells using fluorescence-activated cell sorting (FACS), magnetic activated cell sorting (MACS), panning or other screening method to generate a plurality of immune cells from a sample, such as an immune cell library, before antibody chains are sequenced, antibodies are made, or an expression library or libraries is/are made. In contrast to prior art enrichment methods, which provide only a few subsets of immune cells expressing different antibodies, and therefore only a few naturally occurring combinations of variable domains, the immune cell library of the present invention contains at least 2 subsets of, or individual, immune cells expressing different antibodies or TCRs. For example, the immune cell library of the present invention can contain at least 5, 10, 100, 250, 500, 750, 1,000, 2,500, 5,000, 10,000, 25,000, 50,000, 75,000, 10,000, 250,000, 500,000, 750,000, 1,000,000, 2,500,000, 5,000,000, 7,500,000, or 10,000,000 subsets of, or individual, immune cells expressing different antibodies or TCRs. The methods of the present invention maximize immune cell recovery, and afford very high diversity.

T cells can be obtained from a number of sources, including peripheral blood mononuclear cells, bone marrow, thymus, tissue biopsy, tumor, lymph node tissue, gut associated lymphoid tissue, mucosa associated lymphoid tissue, spleen tissue, or any other lymphoid tissue, and tumors. T cells can be obtained from T cell lines and from autologous or allogeneic sources. T cells may be obtained from a single individual or a population of individuals, for example, a population of individuals who all suffer from the same disease, such as a cancer or an infectious disease. In some embodiments, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis or leukapheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate, a washing step may be accomplished by methods known to those in the art, such as by using a semi-automated "flow-through" centrifuge.

After washing, the cells may be resuspended in a variety of biocompatible buffers, such as, for example. Ca++/Mg++ free PBS. Alternatively, the undesirable components of the apheresis sample may be removed and the cells directly resuspended in culture media. In other embodiments, T cells are isolated from peripheral blood lymphocytes by lysing the red blood cells and by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, CD3+, CD28+ T cells can be positively selected using CD3/CD28 conjugated magnetic beads (e.g., DYNABEADS® M-450 CD3/CD28 T Cell Expander).

In some embodiments, enrichment of a T cell population by negative selection can be accomplished with a combination of antibodies directed to surface markers unique to the negatively selected cells. One such method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Another method for preparing T cells for stimulation is to freeze the cells after the washing step, which does not require the monocyte-removal step. The freeze and subsequent thaw step can provide a more uniform product by removing granulocytes and, to some extent, monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80°

C. at a rate of 1° C. per minute and stored in the vapor phase of a liquid nitrogen storage tank.

In some embodiments, the population of cells is enriched from a sample. In some embodiments, cells are enriched for a particular subset or subtype of cell. In some embodiments, the population of cells is enriched for or contains T cells or B cells. In some embodiments, the population of cells is enriched for or contains CD4+ or CD8+ cells. In some embodiments, the population of cells is enriched for or contains central memory T cells, effector memory T cells, naïve T cells, stem central memory T cells, effector T cells and regulatory T cells. In some embodiments, the population of cells is enriched for or contains memory B-cells, naïve B-cells or plasmablast B-cells.

In some embodiments, immune cells can be selected based on the affinity of the immune receptors from the cell for a selected target antigen or complex. In some aspects, affinity refers to the equilibrium constant for the reversible binding of two agents and is expressed as $K_D$. Affinity of a binding protein to a ligand such as affinity of an antibody for an epitope or such as affinity for a TCR for a MHC-peptide complex can be, for example, from about 100 nanomolar (nM) to about 0.1 nM, from about 100 nM to about 1 picomolar (pM), or from about 100 nM to about 1 femtomolar (fM). The term "avidity" refers to the resistance of a complex of two or more agents to dissociation after dilution.

In some embodiments, an epitope refers in some aspects to a portion of an antigen or other macromolecule capable of forming a binding interaction with the variable region binding pocket of an antibody or TCR. Such binding interactions can be manifested as an intermolecular contact with one or more amino acid residues of one or more CDRs. Antigen binding can involve, for example, a CDR3, a CDR3 pair, or in some instances, interactions of up to all six CDRs of the $V_H$ and $V_L$ chains. An epitope can be a linear peptide sequence (i.e., "continuous") or can be composed of non-contiguous amino acid sequences (i.e., "conformational" or "discontinuous"). An antibody or TCR can recognize one or more amino acid sequences; therefore an epitope can define more than one distinct amino acid sequence. In some aspects, a TCR can recognize one or more amino acid sequences or epitopes in the context of an MHC. Epitopes recognized by antibodies and TCRs can be determined by peptide mapping and sequence analysis techniques well known to one of skill in the art. Binding interactions are manifested as intermolecular contacts with one or more amino acid residues of a CDR.

In some embodiments, reference to an immune receptor, such as expressed on an immune cells, e.g., an antibody or TCR, with specific binding refers to a situation in which an antibody or TCR will not show any significant binding to molecules other than the antigen containing the epitope recognized by the antibody or TCR. The term is also applicable where for example, an antigen binding domain is specific for a particular epitope which is carried by a number of antigens, in which case the selected antibody, TCR, or antigen-binding fragment thereof carrying the antigen binding domain will be able to bind to the various antigens carrying the epitope.

The terms "preferentially binds" or "specifically binds" mean that the antibodies, TCRs, or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody, TCR, or fragment thereof for unrelated amino acid sequences. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

In some embodiments, the term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

In some embodiments, immune cells can be selected based on the affinity of the immune receptor, e.g., TCR, from the cell for a tetramer or other MHC-peptide multimer. In some embodiments, the term "tetramer" may refer to a complex comprising four subunits bound to a single molecule of streptavidin, which can bind to and thus identify a population of cells. A subunit can be a MHC-peptide complex. A subunit may be a MHC without an associated peptide. A subunit can be a B-cell receptor antigen. A population of cells identified by a tetramer can be a population that expresses a receptor, such as a TCR or BCR, that binds to a subunit of the tetramer. The population of cells can be antigen specific T cells. The population of cells can be antigen specific B cells. A tetramer can be fluorescently labeled. As used herein MHC-peptide tetramer can be used interchangeably with pMHC.

In some examples, immune cells can be selected based on affinity for an affinity oligonucleotide conjugate (see, e.g., WO 2017/053905). Cells selected based on binding to or recognition of selected target antigen or complex, such as an affinity oligonucleotide conjugate can be further isolated by positive or negative selection techniques described herein.

In some embodiments, immune cells from non-immunized human or non-human donors are utilized. The naïve repertoire of an animal (the repertoire before antigen challenge) provides the animal with antibodies or TCRs that can bind with moderate affinity (KA of about $1 \times 10^{-6}$ to $1 \times 10^{-7}$ M) to essentially any non-self-molecule. The sequence diversity of antibody or TCR binding sites is not encoded directly in the germline but is assembled in a combinatorial manner from V gene segments. Immunizations trigger any immune cell making a $V_H$-$V_L$ or $V_\alpha$-$V_\beta$ or $V_\gamma$-$V_\delta$ combination that binds the immunogen to proliferate (clonal expansion) and to secrete the corresponding antibody as noted above. However, the use of spleen cells and/or immune cells or other peripheral blood lymphocytes (PBLs) from an unimmunized subject can provide a better representation of the possible antibody or TCR repertoire, and also permits the construction of a subsequent B-cell or T-cell antibody or TCR library using any animal species.

In some embodiments, the sample is saliva. In some embodiments, the sample is whole blood. In some embodiments, in order to obtain sufficient amount of polynucleotides for testing, a blood volume of at least about 0.001, 0.005, 0.01, 0.05, 0.1, 0.5, 1, 2, 3, 4, 5, 10, 20, 25, 30, 35, 40, 45, or 50 mL is drawn. In some cases, in order to obtain sufficient nucleic acid for testing, a blood volume of at least 0.001, 0.005, 0.01, 0.05, 0.1, 0.5, 1, 2, 3, 4, 5, 10, 20, 25, 30, 35, 40, 45, or 50 mL is drawn.

In some cases, the starting material is peripheral blood. The peripheral blood cells can be enriched for a particular cell type (e.g., mononuclear cells; red blood cells; CD4+ cells; CD8+ cells; immune cells; T cells, NK cells, or the like). The peripheral blood cells can also be selectively depleted of a particular cell type (e.g., mononuclear cells; red blood cells; CD4+ cells; CD8+ cells; immune cells; T cells, NK cells, or the like).

In some cases, the starting material can be a tissue sample comprising a solid tissue, with non-limiting examples including skin, brain, liver, lung, kidney, prostate, ovary, spleen, lymph node (including tonsil), thyroid, pancreas, heart, skeletal muscle, intestine, larynx, esophagus, and stomach. In other cases, the starting material can be cells containing nucleic acids, immune cells, and in particular B-cells or T-cells. In some cases, the starting material can be a sample containing nucleic acids, from any organism, from which genetic material can be obtained. In some cases, a sample is a fluid, e.g., blood, saliva, lymph, or urine.

A sample can be taken from a subject with a condition. In some cases, the subject from whom a sample is taken can be a patient, for example, a cancer patient or a patient suspected of having cancer. The subject can be a mammal, e.g., a human, and can be male or female. In some cases, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some cases, non-nucleic acid materials can be removed from the starting material using enzymatic treatments (such as protease digestion).

In some cases, blood can be collected into an apparatus containing a magnesium chelator including but not limited to EDTA, and is stored at 4° C. Optionally, a calcium chelator, including but not limited to EGTA, can be added. In another case, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers.

In some cases when the extracted material comprises single-stranded RNA, double-stranded RNA, or DNA-RNA hybrid, these molecules can be converted to double-stranded DNA using techniques known in the field. For example, reverse transcriptase can be employed to synthesize DNA from RNA molecules. In some cases, conversion of RNA to DNA can require a prior ligation step, to ligate a linker fragment to the RNA, thereby permitting use of universal primers to initiate reverse transcription. In other cases, the poly-A tail of an mRNA molecule, for example, can be used to initiate reverse transcription. Following conversion to DNA, the methods detailed herein can be used, in some cases, to further capture, select, tag, or isolate a desired sequence.

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures).

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, 2nd Ed., Cold Spring Harbour Laboratory Press: New York, N.Y.). Other methods include: salting out DNA extraction (P. Sunnucks et al., Genetics, 1996, 144: 747-756; S. M. Aljanabi et al., Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, CA): Epicentre Technologies (Madison, WI); Gentra Systems, Inc. (Minneapolis, MN); MicroProbe Corp. (Bothell, WA); Organon Teknika (Durham, NC); and Qiagen Inc. (Valencia, CA)).

Methods of RNA extraction are also well known in the art (e.g., J. Sambrook et al., "Molecular Cloning: A Laboratory Manual" 1989, 211d Ed., Cold Spring Harbour Laboratory Press: New York) and kits for RNA extraction from bodily fluids are commercially available (e.g., Ambion, Inc. (Austin, TX); Amersham Biosciences (Piscataway, NJ); BD Biosciences Clontech (Palo Alto, CA); BioRad Laboratories (Hercules, CA); Dynal Biotech Inc. (Lake Success, NY); Epicentre Technologies (Madison, WI); Gentra Systems, Inc. (Minneapolis, MN); GIBCO BRL (Gaithersburg, MD); Invitrogen Life Technologies (Carlsbad, CA); MicroProbe Corp. (Bothell, WA); Organon Teknika (Durham, NC); Promega, Inc. (Madison, WI); and Qiagen Inc. (Valencia, CA)).

One or more samples can be from one or more sources. One or more of samples may be from two or more sources. One or more of samples may be from one or more subjects. One or more of samples may be from two or more subjects.

One or more of samples may be from the same subject. One or more subjects may be from the same species. One or more subjects may be from different species. The one or more subjects may be healthy. The one or more subjects may be affected by a disease, disorder or condition.

In some embodiments, a sample is a fluid, such as blood, saliva, lymph, urine, cerebrospinal fluid, seminal fluid, sputum, stool, or tissue homogenates.

A sample can be taken from a subject with a condition. In some embodiments, the subject from whom a sample is taken can be a patient, for example, a cancer patient or a patient suspected of having cancer. The subject can be a mammal, e.g., a human, and can be male or female. In some embodiments, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some embodiments, the polynucleotides are bound to other target molecules such as proteins, enzymes, substrates, antibodies, binding agents, beads, small molecules, peptides, or any other molecule. In some embodiments, the polynucleotides are not bound to a solid support. Nucleic acids can be extracted from a biological sample by a variety of techniques (Sambrook et al., Molecular Cloning: A Laboratory Manual, Third Edition, Cold Spring Harbor, N.Y. (2001)).

In some embodiments, cell suspensions can be preheated before analysis. In some embodiments, cell suspensions are heated immediately before emulsion generation (described in Section B.2 below) to a temperature and for a sufficient duration to enhance the activity of the DNA polymerase inside the cell, but minimize undesired effects, such as RNA degradation. Thus, the cells are heated to optimize the yield of the methods provided herein. In some examples, the cells are heated to approximately 30° C. to 70° C., such as 30 to 60° C., 25 to 60° C., 30 to 60° C., 40 to 60° C., 45 to 55° C., for a duration of 1, 2 3, 4, 5, 6, 7, 8, 9, 10, 11, 12, 13, 14, 15, 16, 17, 18, 19, or 20 minutes. After heating the cells, the cell suspension can be held at room temperature or placed on ice for 30 seconds to up to 4 hours, such as 30 seconds, 45 seconds, 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 1 hour, 1.5 hours, 2 hours, 2.5 hours, 3 hours, 3.5 hours or 4 hours prior to forming the emulsion.

A plurality of samples may comprise at least 2, 3, 4, 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples.

The one or more polynucleotides in a first sample may be different from one or more polynucleotides in a second sample. The one or more polynucleotides in a first sample may be different from one or more polynucleotides in a plurality of samples. One or more polynucleotides in a sample can comprise at least about 80%, 85%, 90%, 95%, 96%, 97%, 98%, 99%, or 100% sequence identity. In some embodiments, one or more polynucleotides in a sample can differ by less than about 100, 90, 80, 70, 60, 50, 40, 30, 25, 20, 25, 10, 9, 8, 7, 6, 5, 4, 3, 2, or 1 nucleotide or base pair. A plurality of polynucleotides in one or more samples of the plurality of samples can comprise two or more identical sequences. At least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99% or 100% of the total polynucleotides in one or more of the plurality of samples can comprise the same sequence. A plurality of polynucleotides in one or more samples of the plurality of samples may comprise at least two different sequences. At least about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the total polynucleotides in one or more of the plurality of samples may comprise at least two different sequences. In some embodiments, one or more polynucleotides are variants of each other. For example, one or more polynucleotides may contain single nucleotide polymorphisms or other types of mutations. In another example, one or more polynucleotides are splice variants.

A first sample may comprise one or more cells and the second sample may comprise one or more cells. The one or more cells of the first sample may be of the same cell type as the one or more cells of the second sample. The one or more cells of the first sample may be of a different cell type as one or more different cells of the plurality of samples.

The plurality of samples may be obtained concurrently. A plurality of samples can be obtained at the same time. The plurality of samples can be obtained sequentially. A plurality of samples can be obtained over a course of years, e.g., 100 years, 10 years, 5 years, 4 years, 3 years, 2 years or 1 year of obtaining one or more different samples. One or more samples can be obtained within about one year of obtaining one or more different samples. One or more samples can be obtained within 12 months, 11 months, 10 months, 9 months, 8 months, 7 months, 6 months, 5 months, 4 months, 3 months, 2 months or 1 month of obtaining one or more different samples. One or more samples can be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or 1 day of obtaining one or more different samples. One or more samples can be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples can be obtained within about 60 seconds, 45 seconds, 30 seconds, 20 seconds, 10 seconds, 5 seconds, 2 seconds or 1 second of obtaining one or more different samples. One or more samples can be obtained within less than one second of obtaining one or more different samples.

The different polynucleotides of a sample can be present in the sample at different concentrations or amounts (e.g., different number of molecules). For example, the concentration or amount of one polynucleotide can be greater than the concentration or amount of another polynucleotide in the sample. In some embodiments, the concentration or amount of at least one polynucleotide in the sample is at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of at least one other polynucleotide in the sample. In another example, the concentration or amount of one polynucleotide is less than the concentration or amount of another polynucleotide in the sample. The concentration or amount of at least one polynucleotide in the sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of at least one other polynucleotide in the sample.

In some embodiments, two or more samples may contain different amounts or concentrations of the polynucleotides. In some embodiments, the concentration or amount of one polynucleotide in one sample may be greater than the concentration or amount of the same polynucleotide in a different sample. For example, a blood sample might contain a higher amount of a particular polynucleotide than a urine sample. Alternatively, a single sample can divided into two or more subsamples. The subsamples may contain different amounts or concentrations of the same polynucleotide. The concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of the same polynucleotide in another sample. Alternatively, the concentration or amount of one polynucleotide in one sample may be less than the concentration or amount of the same polynucleotide in a different sample. For example, the concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of the same polynucleotide in another sample.

2. Droplet Generation and Single Cell Barcoding

For single cell barcoding with a vessel barcode and molecular barcode, vessels, such as water in oil emulsions, can be created in such way that resulting vessels contain 1 cell or less per vessel. The vessels can be created in such way that resulting vessels also contain 1 vessel barcode per vessel. The vessels can be created in such way that resulting vessels also contain 1 molecular barcoded polynucleotide per vessel. The vessels can be created in such way that resulting vessels also contain two or more, or a plurality of, molecular barcoded polynucleotides per vessel. The cells/vessels can be subject to an RNA or DNA single barcoding protocol as described herein, and the vessel barcode and one or more molecular barcode of each vessel can be fused with a target of interest, such as a cell polynucleotide. In some embodiments, matching vessel barcoded polynucleotides can be fused to cell components present in the same vessel as the one or more molecular barcoded polynucleotides. Following sequencing, vessel barcode and molecular barcode deconvolution can be used to identify which RNA (or DNA) originated from which cell. In some embodiments, vessels, such as water in oil emulsions, can be created in such way that resulting emulsions contained 1 cell or more per emulsion. In some embodiments, water in oil emulsions can be created in such way that resulting emulsions contain 1 vessel barcoded polynucleotide and two or more molecular barcoded polynucleotides per vessel. In some embodiments, vessels can be created in such way that resulting vessels contain more than 1 vessel barcoded polynucleotide and two or more molecular barcoded polynucleotides per vessel. In some embodiments, a vessel barcode and molecular barcode can be introduced into vessels when in solution. In some embodiments, a vessel barcode and molecular barcode can be introduced into vessels when not attached to a solid support, such as a bead. Exemplary vessels include a well, an emulsion, a droplet and a microcapsule.

In some aspects, single cells can be isolated inside an emulsion, which can act as a compartment (e.g., a vessel). The cells can be lysed and transcripts from the cell can be barcoded. Each of the transcripts can be fused with a molecular barcode or vessel barcode, in such way that when two or more RNA transcripts are detected with the same vessel barcode, they can be determined to have originated from the same starting cell. This can be applied to many different types of sequences. One particular application can be linking VH and VL or Vα and Vβ or Vγ and Vδ chains of antibody and TCR sequences.

One or more single cells can be isolated in one or more emulsions, in the presence of a vessel barcode and molecular barcodes, so that one vessel, such as a droplet, of the one or more emulsions can contain a maximum of 1 cell or less. Cells can be lysed chemically by a buffer contained in an emulsion or by freeze thaw, thereby releasing the contents of a cell in an emulsion.

RNAs of a single cell can be reverse transcribed into cDNA. A reverse transcription reaction can be done with a reverse transcriptase that possesses non-template terminal transferase activity which adds about 3 cytosine residues as described above. All reverse transcription buffers, enzymes, and nucleotides can be present when forming an emulsion. In some embodiments, a primer can be generalized (such as polynucleotide comprising a poly dT sequence) to target all mRNA. In some embodiments, DNA can be used. In some embodiments, more than 2 RNAs can be targeted.

In some embodiments, a vessel barcode can be linked to an RNA during reverse transcription. In some embodiments, a molecular barcode can be linked to an RNA during reverse transcription. In some embodiments, a vessel barcode and molecular barcode can be linked to a RNA during reverse transcription. Splitting a sample of a plurality of cells into small reaction volumes coupled with molecular and vessel barcoding of polynucleotides from, or derived from, an individual cell from the plurality of cells can enable high throughput sequencing of a repertoire of sequences, such as biomarker sequences.

Splitting a sample of a plurality of cells into small reaction volumes, or vessels containing one or more cells, coupled with molecular and vessel barcoding of polynucleotides from, or derived from, an individual cell from the plurality of cells can enable high throughput sequencing of a repertoire of sequences, such as sequences representing a percentage of the transcriptome of an organism. For example, a repertoire of sequences can comprise a plurality of sequences representing at least about 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, 10%, 15%, 20%, 30%, 35%, 40%, 45, 50%, 55%, 60%, 65%, 70%, 75%, 80%, 85%, 90%, 95%, 98%, 99%, or 100% of the transcriptome of an organism.

Splitting a sample of immune cells into small reaction volumes, or vessels containing one or more immune cells, coupled with molecular and vessel barcoding of polynucleotides from, or derived from, an individual immune cell from the plurality of immune cells can enable high throughput sequencing of a repertoire of heavy and light chain sequences. These methods can also allow for pairing of the heavy and light chains after sequencing based on the barcoded sequences. Splitting a sample into small reaction volumes as described herein can also enable the use of reduced amounts of reagents, thereby lowering the material cost of the analysis.

In some cases, the reverse transcription reaction and/or the amplification reaction (e.g., PCR) are carried out in droplets, such as in droplet digital PCR. In certain aspects, the invention provides fluidic compartments, or vessels, to contain all or a portion of a target material. In some embodiments, a compartment or vessel is droplet. While reference is made to "droplets" throughout the specification, that terms are used interchangeably with fluid compartment and fluid partition unless otherwise indicated. A vessel can comprise or consist of such a fluid compartment or fluid partition. Except where indicated otherwise, "droplet" is used for convenience and any fluid partition or compartment may be used. The droplets, used herein can include emulsion compositions (or mixtures of two or more immiscible fluids), such as described in U.S. Pat. No. 7,622,280. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets described herein are designed to prevent mixing between compartments, with each compartment protecting its contents from evaporation and/or coalescing with the contents of other compartments.

The mixtures or emulsions described herein can be stable or unstable. The emulsions can be relatively stable and have minimal coalescence. Coalescence occurs when small droplets combine to form progressively larger droplets. In some cases, less than 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets or vessels. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

A droplet or vessel can be formed by flowing an oil phase through an aqueous sample. The aqueous phase can comprise a buffered solution and reagents for performing an amplification reaction, including cells, nucleotides, nucleotide analogues, molecular barcoded polynucleotides, vessel barcoded polynucleotides primers, template nucleic acids, and enzymes, such as a DNA polymerase, RNA polymerase, and/or reverse transcriptase. In some embodiments, the aqueous phase can contain a cell lysing reagent, such as a chemical cell lysing reagent.

The aqueous phase can comprise a buffered solution and reagents for performing an amplification reaction with or without a solid surface, such as a bead. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, and dTTP, in concentrations of about, more than about, or less than about 50, 100, 200, 300, 400, 500, 600, or 700 µM each. In some cases dUTP is added within the aqueous phase to a concentration of about, more than about, or less than about 50, 100, 200, 300, 400, 500, 600, or 700, 800, 900, or 1000 µM. In some cases, magnesium chloride or magnesium acetate (MgCl is added to the aqueous phase at a concentration of about, more than about, or less than about 1.0, 2.0, 3.0, 4.0, or 5.0 mM). The concentration of MgCl can be about 3.2 mM. In some cases, magnesium acetate or magnesium is used. In some cases, magnesium sulfate is used.

A non-specific blocking agent such as BSA or gelatin from bovine skin can be used, wherein the gelatin or BSA is present in a concentration range of approximately 0.1-0.9% w/v. Other possible blocking agents can include beta-lactoglobulin, casein, dry milk, or other common blocking agents. In some cases, preferred concentrations of BSA and gelatin are about 0.1% w/v.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µM. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µM. The concentration of primers can be about 0.5 µM. Amenable ranges for target nucleic acid concentrations in PCR include, but are not limited to between about 1 pg and about 500 ng.

In some cases, the aqueous phase can also comprise additives including, but not limited to, non-specific background/blocking nucleic acids (e.g., salmon sperm DNA), biopreservatives (e.g., sodium azide), PCR enhancers (e.g., Betaine, Trehalose, etc.), and inhibitors (e.g., RNAse inhibitors). Other additives can include, e.g., dimethyl sulfoxide (DMSO), glycerol, betaine (mono)hydrate (N,N,N-trimethylglycine=[carboxymethyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-C1) and tetrapropylammonium chloride (TPrACl), non-ionic detergent (e.g., Triton X-100, TWEEN® 20, Nonidet P-40 (NP-40)), or PREXCEL-Q. In some cases, the aqueous phase can comprise 0, 1, 2, 3, 4, 5, 6, 7, 8, 9, or 10 different additives. In other cases, the aqueous phase can comprise at least 0, 1, 2, 3, 4, 5, 6, 7, 8, 9, or 10 different additives.

In some cases, a non-ionic Ethylene Oxide/Propylene Oxide block copolymer can be added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, and Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

Vessels that exhibit a liquid-like or solid-like interface with a surrounding phase are contemplated. For example, in some embodiments, the emulsion can be formulated to produce highly monodisperse droplets, serving as vessels, having a liquid like interfacial film that can be converted by heating into microcapsules having a solid-like interfacial film; such microcapsules can behave as bioreactors able to retain their contents through a reaction process such as PCR amplification. The conversion of the vessel to microcapsule form can occur upon heating. For example, such conversion can occur at a temperature of greater than about 50° C., 60° C., 70° C., 80° C., 90° C., or 95° C. In some cases this heating occurs using a thermocycler. During the heating process, a fluid or mineral oil overlay can be used to prevent evaporation. Excess continuous phase oil can or cannot be removed prior to heating. The biocompatible capsules can be resistant to coalescence and/or flocculation across a wide range of thermal and mechanical processing. Following conversion, the capsules can be stored at about, more than about, or less than about 3° C., 4° C., 5° C., 6° C., 7° C., 8° C., 9° C. 10° C., 15° C., 20° C., 25° C., 30° C., 35° C., or 40° C. These vessels in capsule form can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more polynucleotides and can resist coalescence, particularly at high temperatures. Accordingly, PCR amplification reactions can occur at a very high density (e.g., number of reactions per unit volume). In some cases, greater than 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a reverse transcription, primer extension, and/or PCR reaction to occur, e.g., primers, probes, dNTPs, DNA or RNA polymerases, etc. These vessels in capsule form exhibit resistance to coalescence and flocculation across a wide range of thermal and mechanical processing.

In some cases, the amplifying step is carried out by performing digital PCR, such as microfluidic-based digital PCR or droplet digital PCR.

In some embodiments, the vessels can be droplets. Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some cases. In some cases, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021 151; WO 2006/096571; WO 2007/089541; WO 2007/081385 and WO 2008/063227.

A droplet generally includes an amount of a first sample fluid in a second carrier fluid. Any technique known in the art for forming droplets may be used with methods of the invention. An exemplary method involves flowing a stream of the sample fluid containing the target material (e.g., immune cell) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets, which can serve as vessels, containing the target material.

The carrier fluid may be any fluid that is immiscible with the sample fluid. An exemplary carrier fluid is oil. In certain embodiments, the carrier fluid includes a surfactant.

The same method may be applied to create individual droplets or vessels that contain other reagents such as reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases, forward and reverse primers, deoxynucleotide triphosphates (dNTPs), and one or more buffers.

In certain embodiments, fluidic compartments are formed by providing a first fluid partition (e.g., a droplet) comprising a target material (e.g., an immune cell and/or a solid support such as a bead) and a second fluid (e.g., as a fluid stream or within droplets). The first and second fluids are merged to form a droplet, which can serve as a vessel for the provided methods. Merging can be accomplished by application of an electric field to the two fluids. In certain embodiments, the second fluid contains reagents for conducting an amplification reaction, such as a polymerase chain reaction or an amplification reaction.

Higher mechanical stability can be useful for microfluidic manipulations and higher-shear fluidic processing (e.g., in microfluidic capillaries or through 90 degree turns, such as valves, in fluidic path). Pre- and post-thermally treated droplet vessels or capsule vessels can be mechanically stable to standard pipet manipulations and centrifugation.

3. Reverse Transcription

In some cases, the target polynucleotides are prepared from RNA, such as mRNA, by reverse transcription. In some cases, the target polynucleotides are prepared from a DNA by primer extension, such as using a polymerase. During the reverse transcription reaction, cellular RNA, such as mRNA is reverse transcribed to yield complementary DNA (cDNA) and a unique molecular barcode is added to each cDNA to generate a barcoded single-stranded polynucleotide complementary to the cellular transcript. Such barcoded single-stranded polynucleotides can be generated for each transcript in the transcriptome.

The methods described herein can be used in coupled reverse transcription-PCR (reverse transcription-PCR). For example, reverse transcription and PCR can be carried out in two distinct steps. First a cDNA copy of the sample mRNA can be synthesized using either a polynucleotide dT primer, a sequence specific primer, a universal primer, a mixture of random hexamer oligonucleotide primers, or any primer described herein. In some examples, a cDNA copy of the RNA can be generated using a mixture of primers, such as a sequence specific primer and a mixture of random hexamer oligonucleotide primers, for example, to capture specific target RNA molecules of a cell in addition to a collection of polynucleotides that are substantially corresponds to the transcriptome of the same cell.

Reverse transcription and PCR can be carried out in a single closed vessel reaction. For example, a multitude of primers can be employed, one or more primers for reverse transcription and two or more primers for PCR in the same closed vessel. The primer(s) for reverse transcription can bind to the mRNA 3' to the position of the first PCR amplicon. In some embodiments, the conditions of the PCR can be modified to substantially restrict amplification to the first adaptor, or pool of first adaptors, using primers specific thereto, and limit amplification of the larger molecular-barcoded cDNA. Although not essential, the reverse transcription primer(s) can include RNA residues or modified analogs such as 2'-O-methyl RNA bases, which will not form a substrate for RNase H when hybridized to the mRNA.

The temperature to carry out the reverse transcription reaction depends on the reverse transcriptase being used. In some cases, a thermostable reverse transcriptase is used and the reverse transcription reaction is carried out at about 37° C. to about 75° C., at about 37° C. to about 50° C., at about 37° C. to about 55° C., at about 37° C. to about 60° C., at about 55° C. to about 75° C., at about 55° C. to about 60° C., at about 37° C., or at about 60° C. In some cases, a reverse transcriptase that transfers 3 or more non-template terminal nucleotides to an end of the transcribed product is used.

A reverse transcription reaction and the PCR reaction described herein can be carried out in various formats known in the art, such as in tubes, microtiter plates, microfluidic devices, or, preferably, droplets.

A reverse transcription reaction can be carried out in volumes ranging from 5 µL to 100 µL, or in 10 µL to 20 µL reaction volumes. In droplets, reaction volumes can range from 1 pL to 100 nL, or 10 pL to 1 nL. In some cases, the reverse transcription reaction is carried out in a droplet having a volume that is about or less than 1 nL.

Target polynucleotides, such as RNA, can be reverse transcribed into cDNA using one or more reverse transcription primers. The one or more reverse transcription primers can comprise a region complementary to a region of the RNA, such as a constant region (e.g., a heavy or light chain constant region or a poly-A tail of mRNA). In some embodiments, the reverse transcription primers can comprise a first reverse transcription primer with a region complementary to a constant region of a first RNA, and a second reverse transcription primer with a region complementary to a constant region of a second RNA. In some embodiments, the reverse transcription primers can comprise a first reverse transcription primer with a region complementary to a constant region of a first RNA, and one or more reverse transcription primers with a region complementary to a constant region of one or more RNAs, respectively.

In some embodiments, the reverse transcription primers can be modified to minimize artifact formation by exponential amplification of primer-dimer or primer-template switch products in the reaction. In some embodiments, the reverse transcription primers are modified by the addition of a 2'-O-methylation of one or more bases of the primer. In some embodiments, the one or more 2'-O-methylated bases are located near the center of the primer sequence. Such modified primers are typically used in reactions containing a DNA polymerase that cannot incorporate a base opposite the 2'O-methyl-modified residue. Exemplary 2'O-methyl-modified primers are set forth in SEQ ID NOS: 12-22).

In some embodiments the reverse transcription primers are a mixture of random hexamer oligonucleotides. Such primers can bind RNA at random locations, thereby priming the reverse transcription reaction of unknown sequences. In such examples, sufficient supplies of random hexamer primers are used to effect reverse transcription of essentially the transcriptome of the cell. Thus, in such embodiments, a collection of polynucleotides is generated, such as a collection of cDNA polynucleotides that corresponds to the transcriptome of the cell.

In some embodiments, reverse transcription primers do not comprise a barcode.

Reverse transcription primers can further comprise a region that is not complementary to a region of the RNA. In some embodiments, the region that is not complementary to a region of the RNA is 5' to a region of the primers that is complementary to the RNA. In some embodiments, the region that is not complementary to a region of the RNA is 3' to a region of the primers that is complementary to the RNA. In some embodiments, the region that is not complementary to a region of the RNA is a 5' overhang region. In some embodiments, the region that is not complementary to a region of the RNA comprises a priming site for amplification and/or a sequencing reaction, such as an adaptor. Using the one or more primers described herein, the RNA molecules are reverse transcribed using suitable reagents known in the art.

In particular embodiments, a reverse transcriptase can comprise a non-template terminal transferase activity. When a reverse transcriptase comprising non-template terminal transferase activity reaches the end of a template, it can add three or more non-template residues, such as three or more non-template cytosine residues. In some embodiments, Superscript II™ reverse transcriptase is used for this purpose. In some embodiments, Maxima™ reverse transcriptase is used for this purpose. In some embodiments, Protoscript II™ reverse transcriptase is used for this purpose. In some embodiments, Maloney murine leukemia virus reverse transcriptase (MMLV-RT) is used for this purpose. In some embodiments, HighScriber™ Reverse Transcriptase is used for this purpose. In some embodiments a terminal deoxynucleotidyl transferase is used for this purpose. In some embodiments avian myeloblastosis virus (AMV) reverse transcriptase is used for this purpose. Any reverse transcriptase capable of transcribing RNA that has non-template terminal transferase activity can be used. Any reverse polymerase capable of transcribing RNA that has non-template terminal transferase activity can be used. Any reverse polymerase capable of transcribing DNA that has non-template terminal transferase activity can be used.

Reverse transcription reactions, such as those described above, can be conducted in the presence of a 3' tagging polynucleotide. A 3' tagging polynucleotide can be a polynucleotide used to add nucleic acids to a 3' end of a target polynucleotide, such as a cDNA. A 3' tagging polynucleotide can be a polynucleotide used as a template to add nucleic acids to a 3' end of a target polynucleotide, such as a cDNA. A 3' tagging polynucleotide can be a polynucleotide that hybridizes to a 3' end of a target polynucleotide, such as a cDNA. A 3' tagging polynucleotide can be a polynucleotide that contains a 3' region, such as a 3' terminal region, that hybridizes to a 3' end of a target polynucleotide, such as a cDNA. For example, a 3' tagging polynucleotide can comprise a segment, such as a segment that anneals to three or more non-template residues. In some embodiments, a 3' tagging polynucleotide is a molecular barcode polynucleotide. In some embodiments, a 3' tagging polynucleotide can comprise a molecular barcode. In some embodiments, a 3' tagging polynucleotide can comprise 3' riboguanosine residues or analogues thereof on the 3' end (rGrGrG) (RNA bases) that are complementary to and annealed to the strand produced by the reverse transcription enzyme. In some embodiments, three or more guanine residues can be used instead of riboguanosine (DNA nucleotide instead of RNA nucleotide). In some embodiments, a 3' tagging polynucleotide can comprise 1 or 2 riboguanosine residues on the 3' end and a riboguanosine residue or analogue thereof on the 3' end (rGrGG) that are complementary to and annealed to the strand produced by the reverse transcription enzyme.

Upon annealing of a 3' tagging polynucleotide to a CCC of the cDNA strand, a reverse transcriptase can continue extending the cDNA into the tagging polynucleotide, thereby attaching a molecular barcode or complement thereof, to a target population of polynucleotides, such as cDNAs, in the reaction. For example, 3' tagging polynucleotide can be a polynucleotide that contains a region 5' to the 3' region that hybridizes to a 3' end of a target polynucleotide. The region 5' to the 3' region that hybridizes to a 3' end of a target polynucleotide can comprise a region that is not complementary to the target polynucleotide, such as a cDNA. The region 5' to the 3' region that hybridizes to a 3' end of a target polynucleotide can comprise a molecular barcode. The region 5' to the 3' region that hybridizes to a 3' end of a target polynucleotide can comprise a region complementary to a vessel barcoded polynucleotide or complement thereof. In other experiments, template switching can be performed in separate reactions. For example, a 3' tagging polynucleotide can be added after the reverse transcription reaction, and enzymes such as a reverse transcriptase or polymerase can be used to extend into a tagging polynucleotide. Because a tagging polynucleotide can harbor a unique degenerate molecular barcode on each molecule in a vessel, each cDNA in a vessel can be uniquely tagged with a molecular barcode. In some embodiments, template switching can be performed at the same time as a reverse transcription reaction is conducted.

A reverse transcription reaction can be conducted in a presence of a 3' tagging polynucleotide. A 3' tagging polynucleotide can comprise a P7 segment which can be used for annealing a sequencing primer. A 3' tagging polynucleotide can comprise a vessel barcode or a molecular barcode. A 3' tagging polynucleotide can comprise 3' riboguanosine residues on a 3' end (rGrGrG) (RNA bases) that can be complementary to and annealed to a strand produced by a reverse transcription enzyme. Thus, a vessel barcode and molecular barcode can be added to a terminal end of a cDNA in this same emulsion by reverse transcription enzymes. In some embodiments, guanine residues can be used instead of riboguanosine (DNA nucleotide instead of RNA nucleotide). Upon annealing of a 3' tagging polynucleotide to a CCC of a cDNA strand, a reverse transcriptase continues extending a cDNA into a 3' tagging polynucleotide, thereby creating a molecular barcoded tag to all cDNAs in a reaction. Upon annealing of a 3' tagging polynucleotide to a region of a molecular barcoded cDNA, a reverse transcriptase or polymerase continues extending a molecular barcoded cDNA into another 3' tagging polynucleotide, thereby creating a vessel barcoded tag to all cDNAs in a reaction.

In some embodiments, template switching can be done in a separate reaction instead of being done at the same time a reverse transcription reaction can be conducted. In some embodiments, a 3' tagging polynucleotide can be added after a reverse transcription reaction, and enzymes such as a reverse transcriptase or polymerase can be used to extend into a tagging polynucleotide in a similar fashion. Because a 3' tagging polynucleotide can harbor a unique degenerate molecular barcode on each single molecule, each cDNA can be uniquely tagged with a molecular barcode. Because a 3' tagging polynucleotide can harbor a same degenerate vessel barcode on each single molecule from a single vessel, each cDNA can be tagged with a vessel barcode unique to the vessel.

In some embodiments, a template switching molecule, such as a template switch oligonucleotide containing a barcode (e.g., a molecular barcode) can incorporate modified bases to minimize artifact formation. In some examples, a template-switch oligonucleotide can contain 2'deoxy uridine, which can be reverse transcribed, but cannot be copied by DNA polymerase. In some embodiments, riboguanosine can be incorporated in the template-switch oligonucleotide. In some embodiments, the template-switch oligonucleotide can modified at the 3' end to prevent extension by reverse transcriptase or DNA polymerase. Such modifications include 3'deoxy, 3'phosphate, 3'amino, and 3'alkyl modification to effect blockage of primer extension.

4. Polymerase Chain Reaction (PCR)

After performing the reverse transcription reactions of the RNA molecules, the resulting single bar-coded cDNA molecules can be simultaneously barcoded with a vessel barcode and amplified by one or more PCR reaction(s) to yield one or more amplicons. In some examples, PCR is used to generate the dual barcoded cDNA strand that contains the coding sequence corresponding to the mRNA transcript sequence and is complementary to the cDNA strand generated during the reverse transcriptase reaction. Enzymes and primer design for PCR are known and non-limiting examples of such reagents are described herein. Any of such reagents can be selected and used for the PCR in the provided methods.

In some cases, a PCR reaction is in a droplet having a reaction volume ranges from 1 pL to 100 nL preferably 10 pL to 1 nL. In some cases, the PCR reaction is carried out in a droplet having a volume that is about or less than 1 nL. In some cases, a reverse transcription reaction and a PCR reaction are carried out in the same droplet having a reaction volume ranges from 1 pL to 100 nL or 10 pL to 1 nL. In some cases, the reverse transcription reaction and the PCR reaction are carried out in a droplet having a volume that is about or less than 1 nL or a volume that is about or less than 1 pL. In some cases, a reverse transcription reaction and a PCR reaction are carried out in a different droplet. In some cases, a reverse transcription reaction and a PCR reaction are carried out in a plurality of droplets each having a reaction volume ranges from 1 pL to 100 nL or 10 pL to 1 nL. In some cases, the reverse transcription reaction and the PCR reaction are carried out in a plurality of droplets each having a volume that is about or less than 1 nL.

In some cases, a first PCR reaction is in a first droplet having a reaction volume ranges from 1 pL to 100 nL preferably 10 pL to 1 nL and a second PCR reaction is in a second droplet having a reaction volume ranges from 1 pL to 100 nL preferably 10 pL to 1 nL. In some cases, a first PCR reaction is in a first droplet having a volume that is about or less than 1 nL, and a second PCR reaction is in a second droplet having a volume that is about or less than 1 nL.

In some cases, a first PCR reaction and a second PCR reaction are carried out in a plurality of droplets each having a reaction volume ranges from 1 pL to 100 nL or 10 pL to 1 nL. In some cases, a first PCR reaction and a second PCR reaction are carried out in a plurality of droplets each having a volume that is about or less than 1 nL.

In some embodiments of the methods provided herein, the conditions of the reactions can be modified to effect amplification of selected sequences and minimize the amplification of other sequences. Such modifications can include altering the temperature, such as the melting temperature during PCR thermocycling. For example, "cold" cycles of PCR can be used to selectively amplify shorter oligonucleotides. "Cold" PCR cycles, differ from "hot" PCR cycles in their denaturation temperature. "Cold" cycles of PCR effect denaturation at a lower temperature to preferably amplify shorter sequences which are more readily denatured than longer, double-stranded sequences. Thus "cold" cycles of PCR are used to amplify shorter sequences, while limiting amplification of longer sequences. In some examples, a combination of "cold" cycles and "hot cycles" are used to generate desired amplicons.

In some embodiments, the duration of the denaturing, priming and/or elongation steps of the PCR can be modified to selectively or preferably amplify particular sequences in the reaction volume. In some examples, the primers used for the PCR amplification can be selected or modified to reduce or enhance PCR amplification under particular conditions. In some examples, heat labile accessory groups can be added to the 3' end of most bases via phophotriester linkages to render the oligonucleotide primers inactive a lower temperatures, but active once exposed to warmer temperatures. In some examples, oligonucleotides, linked to a heat-labile accessory group at the 3' end are used in the provided methods, such that the oligonucleotides are incapable of primer extension at lower temperatures, such as temperatures at which reverse transcriptase reactions occur, but are rendered active upon exposure to a higher temperature, such as prior to or during PCR.

After performing the reverse transcription reactions of the RNA molecules or primer extension of genomic molecules, the oligonucleotide containing the vessel barcode is amplified by polymerase chain reaction to generate multiple copies to be appended to molecular barcoded polynucleotides. In some examples, the oligonucleotides containing the vessel barcode are amplified using primers that have been modified by the addition of a heat-labile accessory group at the 3' end to prevent primer extension during the reverse transcriptase reaction, but enable primer extension and subsequent amplification during PCR. In some embodiments, amplification of the oligonucleotide containing the vessel barcode was carried out using "cold" thermocycling as described herein.

After performing the reverse transcription reactions of the RNA molecules, the resulting cDNA molecules can be barcoded with a molecular barcode and a vessel barcode and amplified by one or more PCR reactions, such as a first and/or a second PCR reaction. The first and/or second PCR reaction can utilize a pair of primers or a plurality of primer pairs. The first and/or second PCR reaction can utilize a plurality of forward/reverse primers and a reverse primer. The first and/or second PCR reaction can utilize a plurality of forward/reverse primers and a forward primer. A first and/or second primer of a plurality of forward/reverse primers can be a forward/reverse primer containing a region complementary to the cDNA molecules or barcoded cDNA molecules. A first and/or second primer of a plurality of forward/reverse primers can be a forward/reverse primer containing a region complementary to the barcoded cDNA molecules.

In some embodiments, a plurality of forward/reverse primers comprises one or more forward/reverse primers wherein each of the forward/reverse primers in the plurality of forward/reverse primers comprises a region complementary to one or more upstream or downstream regions to a V segment of the cDNAs or barcoded cDNAs. For example, a plurality of forward/reverse primers comprises a forward/reverse primer comprising a region complementary to a upstream or downstream region to a V segment of the cDNAs or barcoded cDNAs and one or more other forward/reverse primers comprising a region complementary to one or more other upstream or downstream regions to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs and a second forward/reverse primer comprising a region complementary to a second upstream or downstream region to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs, a second forward/reverse primer comprising a region complementary to a second upstream or downstream region to a V segment of the cDNAs or barcoded cDNAs, and a third forward/reverse primer comprising a region complementary to a third upstream or downstream region to a V segment of the cDNAs or barcoded cDNAs, etc. The primers in the plurality of forward/reverse primers can be used to anneal to all possible upstream or downstream regions of all V segments expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a C segment of the cDNAs or barcoded cDNAs. For example, a plurality of forward/reverse primers comprises a forward/reverse primer comprising a region complementary to a upstream or downstream region to a C segment of the cDNAs or barcoded cDNAs and one or more other forward/reverse primers comprising a region complementary to one or more other upstream or downstream regions to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs and a second forward/reverse primer comprising a region complementary to a second upstream or downstream region to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs, a second forward/reverse primer comprising a region complementary to a second upstream or downstream region to a C segment of the cDNAs or barcoded cDNAs, and a third forward/reverse primer comprising a region complementary to a third upstream or downstream region to a C segment of the cDNAs or barcoded cDNAs, etc. The primers in the plurality of forward/reverse primers can be used to anneal to all possible upstream or downstream regions of all C segments expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a molecular barcode of the barcoded cDNAs. For example, a plurality of forward/reverse primers comprises a forward/reverse primer comprising a region complementary to a upstream or downstream region to a molecular barcode of the barcoded cDNAs and one or more other forward/reverse primers comprising a region complementary to one or more other upstream or downstream regions to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs and a second forward/reverse primer comprising a region complementary to a second upstream or downstream region to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs, a second forward/reverse primer comprising a region complementary to a second upstream or downstream region to a molecular barcode of the barcoded cDNAs, and a third forward/reverse primer comprising a region complementary to a third upstream or downstream region to a molecular barcode of the barcoded cDNAs, etc. The plurality of forward/reverse primers can be used to anneal to all possible upstream or downstream regions of all molecular barcodes expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a vessel barcode of the barcoded cDNAs. For example, a plurality of forward/reverse primers comprises a forward/reverse primer comprising a region complementary to a upstream or downstream region to a vessel barcode of the barcoded cDNAs and one or more other forward/reverse primers comprising a region complementary to one or more other upstream or downstream regions to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs and a second forward/reverse primer comprising a region complementary to a second upstream or downstream region to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs, a second forward/reverse primer comprising a region complementary to a second upstream or downstream region to a vessel barcode of the barcoded cDNAs, and a third forward/reverse primer comprising a region complementary to a third upstream or downstream region to a vessel barcode of the barcoded cDNAs, etc. The primers in the plurality of forward/reverse primers can be used to anneal to all possible upstream or downstream regions of all vessel barcodes expressed by the cells, such as immune B-cells or T-cells, in the sample.

The forward/reverse primers in the plurality of forward/reverse primers further comprise a region that is not complementary to a region of the RNA. In some embodiments, the region that is not complementary to a region of the RNA is 5' to a region of the forward/reverse primers that is complementary to the RNA (i.e., upstream or downstream regions of a V segment). In some embodiments, the region that is not complementary to a region of the RNA is 3' to a region of the forward/reverse primers that is complementary to the RNA. In some embodiments, the region that is not complementary to a region of the RNA is a 5' overhang region. In some embodiments, the region that is not complementary to a region of the RNA comprises a priming site for amplification and/or a second sequencing reaction. In some embodiments, the region that is not complementary to a region of the RNA comprises a priming site for amplification and/or a third sequencing reaction. In some embodiments, the region that is not complementary to a region of the RNA comprises a priming site for a second and a third sequencing reaction. In some embodiments, the sequence of the priming site for the second and the third sequencing reaction are the same. Using the one or more forward/reverse primers and a reverse primer as described herein, the cDNA molecules are amplified using suitable reagents known in the art. In some embodiments, a region is complementary to a region of the RNA, such as the constant region or a poly-A tail of mRNA.

5. Barcodes

A barcode can be a molecular barcode or a vessel barcode. In some embodiments, a barcode, such as a molecular barcode or a vessel barcode, can each have a length within a range of from 2 to 36 nucleotides, 4 to 36 nucleotides, or from 6 to 30 nucleotides, or from 8 to 20 nucleotides, 2 to 20 nucleotides, 4 to 20 nucleotides, or from 6 to 20 nucleotides. In certain aspects, the melting temperatures of barcodes within a set are within 10° C. of one another, within 5° C. of one another, or within 2° C. of one another. In certain aspects, the melting temperatures of barcodes within a set are not within 10° C. of one another, within 5° C. of one another, or within 2° C. of one another. In other aspects, barcodes are members of a minimally cross-hybridizing set. For example, the nucleotide sequence of each member of such a set can be sufficiently different from that of every other member of the set that no member can form a stable duplex with the complement of any other member under stringent hybridization conditions. In some embodiments, the nucleotide sequence of each member of a minimally cross-hybridizing set differs from those of every other member by at least two nucleotides. Barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:1 1046; and Brenner (2004) Genome Biol. 5:240.

As used herein, a molecular barcode comprises information that is unique to a single molecule from a single cell or from a single vessel, or two or more molecules of a plurality or library of molecules from two or more single cells or from two or more single vessels. As used herein, a vessel barcode comprises information that is unique to polynucleotides from a single cell or from a single vessel, compared to polynucleotides from a different single cell or from a different single vessel. In some embodiments the unique information comprises a unique sequence of nucleotides. For example, the sequence of the molecular barcode or a vessel barcode can be determined by determining the identity and order of the unique or random sequence of nucleotides comprising the molecular barcode or a vessel barcode. In some embodiments, the first adaptor includes a vessel barcode sequence.

In some embodiments the unique information cannot be used to identify the sequence of a target polynucleotide. For example, a molecular barcode may be attached to one target polynucleotide, but the molecular barcode cannot be used to determine the target polynucleotide to which it is attached. In some embodiments the unique information is not a known sequence linked to the identity of the sequence of a target polynucleotide. For example, a vessel barcode may be attached to one or more target polynucleotides, but the vessel barcode cannot be used to determine which of the one or more target polynucleotides to which it is attached. In some embodiments, the unique information comprises a random sequence of nucleotides. In some embodiments the unique information comprises one or more unique sequences of nucleotides on a polynucleotide. In some embodiments the unique information comprises a degenerate nucleotide sequence or degenerate barcode. A degenerate barcode can comprise a variable nucleotide base composition or sequence. For example, a degenerate bar code can be a random sequence. In some embodiments, a complement sequence of a molecular barcode or a vessel barcode is also a molecular barcode or a vessel barcode sequence.

A molecular barcode or vessel barcode can comprise any length of nucleotides. For example a molecular barcode or a vessel barcode can comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. For example a molecular barcode or a vessel barcode can comprise at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. In some embodiments, a molecular barcode or a vessel barcode has a particular length of nucleotides. For example, a molecular barcode or a vessel barcode can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length.

In some embodiments, each molecular barcode or a vessel barcode in a plurality of molecular barcodes or vessel barcodes has at least about 2 nucleotides. For example, each molecular barcode or a vessel barcode in a plurality of molecular barcodes or vessel barcodes can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each molecular barcode or a vessel barcode in a plurality of molecular barcodes or vessel barcodes has at most about 1000 nucleotides. For example, each molecular barcode or a vessel barcode in a plurality of molecular barcodes or vessel barcodes can be at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each molecular barcode or a vessel barcode in a plurality of molecular barcodes or vessel barcodes has the same length of nucleotides. For example, each molecular barcode or a vessel barcode in a plurality of molecular barcodes or vessel barcodes can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, one or more molecular barcodes or vessel barcodes in a plurality of molecular barcodes or vessel barcodes have a different length of nucleotides. For example one or more first molecular barcodes or vessel barcodes in a plurality of molecular barcodes or vessel barcodes can have about, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides and one or more second molecular barcodes or vessel barcodes in a plurality of molecular barcodes or vessel barcodes can have about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides, wherein the number of nucleotides of the one or more first molecular barcodes or vessel barcodes is different than the one or more second molecular barcodes or vessel barcodes.

The number of molecular barcodes can be in excess of the total number of molecules to be labeled in a plurality of vessels. The number of vessel barcodes can be in excess of the total number of molecules to be labeled in a plurality of vessels. For example, the number of molecular barcodes or vessel barcodes can be at least about 2, 3, 4, 5, 6, 7, 8, 9, 10, 15, 20, 30, 40, 50, 60, 70, 80, 90, or 100 times greater than the total number of molecules to be labeled in a plurality of vessels.

The number of different molecular barcodes can be in excess of the total number of molecules to be labeled in a plurality of vessels. In some embodiments, the number of different molecular barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the total number of molecules to be labeled in a plurality of vessels.

The number of different molecular barcodes in a single vessel can be in excess of the number of different molecules to be labeled in the single vessel. In some embodiments, the number of different molecular barcodes in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of different vessel barcodes can be less than the total number of molecules to be labeled in a plurality of vessels. In some embodiments, the number of different vessel barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times less than the total number of molecules to be labeled in a plurality of vessels.

The number of amplified product molecules from a vessel barcoded polynucleotide molecule in a single vessel can be in excess of the number of different molecules to be labeled in the single vessel. In some embodiments, the number of amplified product molecules from a vessel barcoded polynucleotide molecule in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of vessel barcoded polynucleotide molecules in a single vessel can be less than the number of different molecules to be labeled in the single vessel. In some embodiments, the number of vessel barcoded polynucleotide molecules in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times less than the number of different molecules to be labeled in the single vessel.

The number of vessel barcoded polynucleotide molecules in a single vessel can be one molecule. The number of unamplified vessel barcoded polynucleotide molecules in a single vessel can be one molecule.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have the same concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have the same concentration.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have a different concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have a different concentration.

The molecular barcodes or vessel barcodes in a population of molecular barcodes or vessel barcodes can have at least 10, 15, 20, 25, 30, 35, 40, 45, 50, 60, 70, 80, 90, 100, 200, 300, 400, 500, 600, 700, 800, 900, 1000 or more different sequences. For example, the molecular barcodes or vessel barcodes in a population can have at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, 1,000,000 or more different sequences. Thus, a plurality of molecular barcodes or vessel barcodes can be used to generate at least 10, 15, 20, 25, 30, 35, 40, 45, 50, 60, 70, 80, 90, 100, 200, 300, 400, 500, 600, 700, 800, 900, 1000 or more different sequences from one or more polynucleotides, such as target polynucleotides. For example, a plurality of molecular barcodes or vessel barcodes can be used to generate at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from one or more polynucleotides, such as target polynucleotides. For example, a plurality of molecular barcodes or vessel barcodes can be used to generate at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600, 000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600, 000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more target polynucleotides.

In some embodiments, one or more molecular barcodes are used to group or bin sequences. In some embodiments, one or more molecular barcodes are used to group or bin sequences, wherein the sequences in each bin contain the same molecular barcode. In some embodiments, one or more molecular barcodes or vessel barcodes are used to group or bin sequences, wherein the sequences in each bin comprise an amplicon set. In some embodiments, one or more molecular barcodes are used to group or bin sequences, wherein the sequences in each bin comprise a plurality of sequences wherein the polynucleotides from which the plurality of sequences were generated were derived from the same polynucleotide molecule in an amplification reaction.

In some embodiments, one or more vessel barcodes are used to group or bin sequences. In some embodiments, one or more vessel barcodes are used to group or bin sequences, wherein the sequences in each bin contain the same vessel barcode. In some embodiments, one or more vessel barcodes are used to group or bin sequences, wherein the sequences in each bin comprise one or more amplicon sets. In some embodiments, one or more vessel barcodes are used to group or bin sequences, wherein the sequences in each bin comprise a plurality of sequences wherein the polynucleotides from which the plurality of sequences were generated were derived from the polynucleotides from a single vessel or single cell.

In some embodiments, one or more molecular barcodes and vessel barcodes are used to group or bin sequences. In some embodiments, one or more molecular barcodes and vessel barcodes are used to group or bin sequences, wherein the sequences in each bin contain the same molecular barcode and same vessel barcode. In some embodiments, one or more molecular barcodes and vessel barcodes are used to group or bin sequences, wherein the sequences in each bin comprise one or more amplicon sets. In some embodiments, one or more molecular barcodes and vessel barcodes are used to group or bin sequences, wherein the sequences in each bin comprise a plurality of sequences wherein the polynucleotides from which the plurality of sequences were generated were derived from the same polynucleotide in an amplification reaction and from the same single cell or vessel. In some embodiments, one or more molecular barcodes and vessel barcodes are not used to align sequences.

In some embodiments, one or more molecular barcodes are not used to align sequences. In some embodiments, one or more molecular barcodes are used to align sequences. In some embodiments, one or more molecular barcodes are used to group or bin sequences, and a target specific region is used to align sequences. In some embodiments, one or more vessel barcodes are not used to align sequences. In some embodiments, one or more vessel barcodes are used to align sequences. In some embodiments, one or more vessel barcodes are used to group or bin sequences, and a target specific region is used to align sequences. In some embodiments, one or more molecular barcodes and vessel barcodes are used to align sequences. In some embodiments, one or more molecular barcodes and vessel barcodes are used to group or bin sequences, and a target specific region is used to align sequences.

In some embodiments, the aligned sequences contain the same molecular barcode. In some embodiments, the aligned sequences contain the same vessel barcode. In some embodiments, the aligned sequences contain the same molecular barcode and vessel barcode. In some embodiments, one or more molecular barcodes or vessel barcodes are used align sequences, wherein the aligned sequences comprise two or more sequences from an amplicon set. In some embodiments, one or more molecular barcodes or vessel barcodes are used to align sequences, wherein the aligned sequences comprise a plurality of sequences wherein the polynucleotides from which the plurality of sequences were generated were derived from the same polynucleotide molecule in an amplification reaction. In some embodiments, one or more molecular barcodes or vessel barcodes are used to align sequences, wherein the aligned sequences comprise a plurality of sequences wherein the polynucleotides from which the plurality of sequences were generated were derived from a single cell or single vessel.

C. Adaptor Ligation

Prior to adaptor ligation, the dual barcoded polynucleotides or amplicons can be purified and/or selected for size. The size of the dual-barcoded polynucleotides can be selected to optimize the selected method for sequencing. The desired polynucleotide size is determined by the limitations of the sequencing instrumentation and by the specific sequencing application. In some examples the desired polynucleotide size is 0 base pairs (bp) to 100,000 bp (100 kilobases (kb)), 50 bp to 50 kb, 100 bp to 25 kb. In some embodiments, a short-read sequencer is used to sequence the polynucleotides generated herein. Generally, optimal polynucleotide sizes for short-read sequencers range in length from about 20 base pairs (bp) to 2000 bp, 50 bp to 1500 bp, 50 bp to 1250 bp, 50 bp to 1000 bp, 50 bp to 750 bp, 50 bp to 500 bp, 100 bp to 1500 bp, 100 bp to 1250 bp, 100 bp to 1000 bp, 100 bp to 750 bp, 100 bp to 500 bp, 200 bp to 1500 bp, 200 bp to 1250 bp, 200 bp to 1000 bp, 200 bp to 750 bp or 250 bp to 500 bp.

In some embodiments, a long-read sequencer is used to sequence the polynucleotides generated herein. Generally, optimal polynucleotide sizes for short-read sequencers range in length from about 1 kilobase (kb) to 100 kb, such as 1 kb to 50 kb, 5 kb to 25 kb, 5 kb to 20 kb, or approximately 1 kb, 5 kb, 10 kb, 15 kb, or 20 kb.

To generate a collection of polynucleotides of the desired size, the collection of polynucleotides can be sized by modifying the conditions of the reverse transcription or primer extension reactions, such as modifying the time of the extension step of the reactions. In some embodiments, the collection of polynucleotides can be fragmented or sized to a desired length by physical methods (i.e., acoustic shearing and sonication) or enzymatic methods (i.e., non-specific endonuclease cocktails and transposase tagmentation reactions). Polynucleotides of the desired size can be isolated by agarose gel electrophoresis, such as denaturing gel electrophoresis, size exclusion methods, or automated methods or commercial kits (Quail et al, Electrophoresis (2012) 33(23):3521-3528; Duhaime et al., Environ Microbiol (2012) 14(9):2526-2537).

In some embodiments, double stranded dual-barcoded polynucleotides are purified prior to size selection, such as by affinity purification. In some embodiments, the double stranded dual-barcoded polynucleotides are denatured prior to size selection. In some embodiments, the double-stranded dual-barcoded polynucleotides are denatured by disrupting the hydrogen bonds between complementary strands of DNA. In some embodiments, denaturation of double stranded DNA is effected by application of acid or base, a concentrated inorganic sale, an organic solvent, (e.g., alcohol or chloroform), radiation or heat. In some embodiments, denaturation of double stranded DNA is effected by exposure to chemical agents such as formamide, guanidine, sodium salicylate, dimethyl sulfoxide (DMS), propylene glycol, urea, or NaOH. In some embodiments, double stranded DNA molecules are treated with NaOH, such as 0.1 M NaOH to generate single stranded molecules.

Following size selection and/or purification, a second adaptor can be added to the adaptor-tagged, dual barcoded polynucleotides, which are polynucleotides generated by the method containing a first adaptor with a universal priming sequence, a vessel barcode and a molecular barcode. The adaptor contains a universal priming sequence, which can be used for amplification or sequencing of the adaptor-tagged dual barcoded polynucleotides. The adaptors can contain any known universal priming sequence or fragment thereof. Exemplary universal priming sequences include P7, C7, P5 or C5 priming sequences.

Addition of the second adaptor can be effected using any known method. The adaptor can be added to a single-stranded polynucleotide or a double-stranded polynucleotide. In some examples, the adaptor is added to a single-stranded polynucleotide. In other examples, an adaptor, such as a double-stranded adaptor is added to a double-stranded polynucleotide. In some embodiments, a ligase is used to ligate a single-stranded adaptor. For example, a Thermostable App ligase (NEB) or CircLigase II (Epicentre) can be used to ligate a second adaptor to a single-stranded adaptor to a single-stranded, adaptor-tagged, dual-barcoded polynucleotide.

In some embodiments a second adaptor can be added to single-stranded, adaptor-tagged dual-barcoded polynucleotides by annealing a degenerate splint adaptor. For example a second adaptor can be added by adding a splint adaptor duplex an end of the single-stranded, adaptor-tagged dual-barcoded polynucleotide. Such splint adaptor duplexes contain a paired double stranded oligonucleotide that has a degenerate overhang at one end of the molecule. The degenerate overhang can be 1, 2, 3, 4, 5, 6, 7, 8, 9, 10, 11, 12, 13, 14, 15, 16, 17, 18, 19, or 20 bases. The degenerate nucleotides of the overhang portion of the molecule are annealed to the end of the single-stranded, adaptor-tagged dual-barcoded polynucleotide opposite the end of the first adaptor sequence. In some embodiments of the method, a splint adaptor duplex with a 3'overhang is annealed to the 3' end of the single-stranded, adaptor-tagged dual-barcoded polynucleotide, opposite the first adaptor. In some embodiments of the method, a splint adaptor duplex with a 5'overhang is annealed to the 5' end of the single-stranded, adaptor-tagged dual-barcoded polynucleotide, opposite the first adaptor. A ligase, such as a blunt/TA ligase can facilitate annealing a splint adaptor duplex with the single-stranded, adaptor-tagged dual-barcoded polynucleotides.

In some embodiments of the method, enzymatic addition of non-templated nucleotides can be added to an end of single-stranded, adaptor-tagged dual-barcoded polynucleotides, to which an adaptor is annealed. In some embodiments, a second adaptor is annealed directly to the non-templated nucleotides using complementary base pairing. In some embodiments, a splint adaptor duplex can be annealed to the non-templated nucleotides to effect addition of the adaptor to the end of the molecule. In some embodiments, the adaptor is added to the 3' end of the single-stranded, adaptor-tagged dual-barcoded polynucleotides. In some embodiments, the adaptor is added to the 5' end of the single-stranded, adaptor-tagged dual-barcoded polynucleotides. A ligase, such as a blunt/TA ligase can facilitate annealing the second adaptor or splint adaptor duplex with the single-stranded, adaptor-tagged dual-barcoded polynucleotides.

The second adaptor contains a universal priming sequence or a universal priming site or a contiguous portion of a universal priming sequence or universal priming site sufficient to anneal to a complementary sequence. Universal priming sequences or universal priming sites contain oligonucleotide sequences that are complementary to universal primers or a contiguous portion thereof. Exemplary universal primers are listed in Section D below.

D. Amplification and Sequencing

The sample containing dual barcoded polynucleotides, with a first and second adaptor at or near opposite ends of the dual barcoded polynucleotides, corresponding to one or more target polynucleotide sequence(s) and/or all or part of the transcriptome of the cell, as generated in the procedures above, can be amplified to generate multiple copies of the dual barcoded polynucleotide library. The amplification can be performed prior to sequencing. In some embodiments, primers with sequencing adaptors can be used to amplify one or more sequences in the library. In some embodiments, selected transcripts, are amplified and prepared for sequencing.

Figure 2:
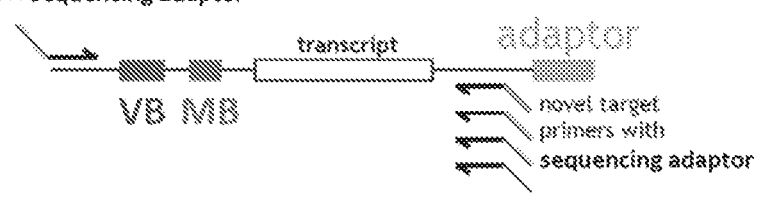
FIG. 2 depicts amplification and sequencing of dual barcoded transcripts, exemplary methods described herein. (Top) Amplification and sequencing of transcripts encoding a target gene of interest using a primer specific to the universal priming sequence of the first adaptor and a target-specific primer, each primer linked to a sequencing adaptor for sequencing. (Middle) Amplification and sequencing of all transcripts in the library, e.g., the transcriptome, or portion thereof, of one or more cells, using primers specific to the universal priming sequence of the first adaptor and the universal priming sequence of the second adaptor. (Bottom) Amplification and sequencing of transcriptome for a selected cell of interest, such as a cell determined to contain mRNA transcripts of a target gene of interest, using a primer specific for the determined vessel barcode (VB) common to polynucleotides from the same cell and a primer specific to the universal priming sequence of the second adaptor.

In some embodiments, adaptor primers with sequencing adaptors are used to amplify all transcripts in the library, and prepare the same for sequencing. In some embodiments, an adaptor primer with a sequencing adaptor and a target-specific primer with a sequencing adaptor are used to amplify a target gene, and prepare the target gene for sequencing. In some embodiments, a cell-specific primer, such as a primer to the vessel barcode, with a sequencing adaptor and a primer to the adaptor at the opposite end of the transcript from the vessel barcode with a sequencing adaptor is used to amplify the transcriptome of a selected cell and prepare the same for sequencing. FIG. 2 depicts exemplary selected amplification of polynucleotides in the generated library through use of selected primers as described herein.

1. Amplification

The sample containing the target polynucleotide can comprise DNA corresponding to the complete mRNA transcript, or fragment(s) thereof, which can be amplified. In some cases, the average length of the corresponding mRNA transcript, or fragment(s) thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some cases, a target sequence from a relatively short template, such as a sample containing a template that is about 40, 45, 50, 55, 60, 65, 70, 75, 80, 85, 90, 95, or 100 bases, is amplified.

An amplification reaction can comprise one or more additives. In some cases, the one or more additives are dimethyl sulfoxide (DMSO), glycerol, betaine (mono)hydrate N,N,N-trimethylglycine=[carboxymethyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-C1) and tetrapropylammonium chloride (TPrA-Cl), nonionic detergent (e.g., Triton X-100, TWEEN® 20, Nonidet P-40 (NP-40)), or PREXCEL-Q. In some cases, an amplification reaction comprises 0, 1, 2, 3, 4, 5, 6, 7, 8, 9, or 10 different additives. In other cases, an amplification reaction comprises at least 0, 1, 2, 3, 4, 5, 6, 7, 8, 9, or 10 different additives.

Thermocycling reactions can be performed on samples contained in reaction volumes (e.g., droplets). Droplets can be polydisperse or preferably monodisperse, generated through agitation, sonication or microfluidically through a T-channel junction or other means by those familiar with the art. Densities can exceed 20,000 droplets/404 (1 nL droplets), 200,000 droplets/404 (100 pL droplets). The droplets can remain intact during thermocycling. Droplets can remain intact during thermocycling at densities of greater than about 10,000 droplets/4, 100,000 droplets/4, 200,000 droplets/4, 300,000 droplets/4, 400,000 droplets/4, 500,000 droplets/4, 600,000 droplets/4, 700,000 droplets/4, 800,000 droplets/4, 900,000 droplets/4, or 1,000,000 droplets/4. In other cases, two or more droplets do not coalesce during thermocycling. In other cases, greater than 100 or greater than 1,000 droplets do not coalesce during thermocycling.

Any DNA polymerase that catalyzes primer extension can be used, including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. In some cases, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification.

Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1-45, 10-45, 20-45, 30-45, 35-45, 10-40, 10-30, 10-25, 10-20, 10-15, 20-35, 25-35, 30-35, or 35-40.

Amplification of target nucleic acids can be performed by any known means. Target nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (reverse transcription-PCR), single cell PCR, restriction fragment length polymorphism PCR (PCR-RFLP), PCR-RFLP/reverse transcription-PCR-RFLP, hot start PCR, nested PCR, in situ polony PCR, in situ rolling circle amplification (RCA), digital PCR (dPCR), droplet digital PCR (ddPCR), bridge PCR, picoliter PCR and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate polynucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification can be isothermal amplification, e.g., isothermal linear amplification.

In some embodiments, amplification does not occur on a solid support. In some embodiments, amplification does not occur on a solid support in a droplet. In some embodiments, amplification does occur on a solid support when the amplification is not in a droplet.

An amplification reaction can comprise one or more additives. In some embodiments, the one or more additives are dimethyl sulfoxide (DMSO), glycerol, betaine (mono) hydrate (N,N,N-trimethylglycine=[carboxymethyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-C1) and tetrapropylammonium chloride (TPrA-Cl), nonionic detergent (e.g., Triton X-100, TWEEN® 20, Nonidet P-40 (NP-40)), or PREXCEL-Q. In some embodiments, an amplification reaction can comprise 0, 1, 2, 3, 4, 5, 6, 7, 8, 9, or 10 different additives. In other cases, an amplification reaction can comprise at least 0, 1, 2, 3, 4, 5, 6, 7, 8, 9, or 10 different additives.

Generally, one or more pairs of primers can be used in an amplification reaction; one primer of a primer pair can be a forward primer and one primer of a primer pair can be a reverse primer.

In some cases, a first pair of primers can be used in the amplification reaction; one primer of the first pair can be a forward primer complementary to a sequence of a first target polynucleotide molecule and one primer of the first pair can be reverse primer can be complementary to a second sequence of the first target polynucleotide molecule, and a first target locus can reside between the first sequence and the second sequence. In some embodiments, the first target locus comprises a $V_H$ or Vα or Vγ sequence.

In some cases, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a $V_L$ or Vβ or Vδ sequence.

In some cases, a third pair of primers can be used in the amplification reaction; one primer of the third pair can be a forward primer complementary to a first sequence of a third target polynucleotide molecule and one primer of the third pair can be a reverse primer complementary to a second sequence of the third target polynucleotide molecule, and a third target locus can reside between the first sequence and the second sequence. In some embodiments, the third target locus comprises a barcode, such as a molecular barcode or vessel barcode.

In some cases, multiple pairs of primers can be used in the amplification reaction. In some examples one primer of a primer pair can be a forward primer complementary to a first adaptor sequence and one primer of the primer pair can be a reverse primer to a second adaptor sequence. In some examples one primer of a primer pair can be a forward primer complementary to a second adaptor sequence and one primer of the primer pair can be a reverse primer to a first adaptor sequence.

The length of the forward primer and the reverse primer can depend on the sequence of the target polynucleotide and the target locus. For example, the length and/or T of the forward primer and reverse primer can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some cases, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

A primer can be a single-stranded DNA prior to binding a template polynucleotide. In some cases, the primer initially comprises double-stranded sequence. The appropriate length of a primer can depend on the intended use of the primer but can range from about 6 to about 50 nucleotides, or from about 15 to about 35 nucleotides. Short primer molecules can generally require cooler temperatures to form sufficiently stable hybrid complexes with a template. In some embodiments, a primer need not reflect the exact sequence of the template nucleic acid, but can be sufficiently complementary to hybridize with a template. In some cases, a primer can be partially double-stranded before binding to a template polynucleotide. A primer with double-stranded sequence can have a hairpin loop of about, more than about, or less than about 3, 4, 5, 6, 7, 8, 9, 10, 11, 12, 13, 14, 15, 16, 17, 18, 19, or 20 bases. A double stranded portion of a primer can be about, more than about, less than about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base-pairs. The design of suitable primers for the amplification of a given target sequence is well known in the art.

Primers can incorporate additional features that allow for the detection or immobilization of the primer but do not alter a basic property of the primer (e.g., acting as a point of initiation of DNA synthesis). For example, primers can contain an additional nucleic acid sequence at the 5' end which does not hybridize to a target nucleic acid, but which facilitates cloning or further amplification, or sequencing of an amplified product. For example, the additional sequence can comprise a primer binding site, such as a universal primer binding site which can be an adaptor. A region of the primer which is sufficiently complementary to a template to hybridize can be referred to herein as a hybridizing region.

In another case, a primer utilized in methods and compositions described herein can comprise one or more universal nucleosides. Non-limiting examples of universal nucleosides are 5-nitroindole and inosine, as described in U.S. Appl. Pub. Nos. 2009/0325169 and 2010/0167353.

Primers can be designed according to known parameters for avoiding secondary structures and self-hybridization.

Different primer pairs can anneal and melt at about the same temperatures, for example, within 1° C., 2° C., 3° C., 4° C., 5° C., 6° C., 7° C., 8° C., 9° C. or 10° C. of another primer pair. In some cases, greater than 1, 2, 3, 4, 5, 6, 7, 8, 9, 10, 15, 20, 25, 30, 35, 40, 45, 50, 100, 200, 500, 1000, 5000, 10,000 or more primers are initially used. Such primers can hybridize to target polynucleotides described herein.

Primers can be prepared by a variety of methods including but not limited to cloning of appropriate sequences and direct chemical synthesis using methods well known in the art (Narang et al, Methods Enzymol. 68:90 (1979); Brown et al, Methods Enzymol. 68:109 (1979)). Primers can also be obtained from commercial sources. The primers can have an identical melting temperature. The primers can have non-identical melting temperatures. The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (T=2(A+T)+4(G+C)). Computer programs can also be used to design primers. The $T_M$ (melting or annealing temperature) of each primer can be calculated using software programs. The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers can be incorporated into the products from each loci of interest; thus the $T_M$ can be recalculated based on both the sequences of the 5' half and the 3' half of each primer.

Conducting the one or more reactions of the methods disclosed herein can comprise the use of one or more primers. As used herein, a primer comprises a double-stranded, single-stranded, or partially single-stranded polynucleotide that is sufficiently complementary to hybridize to a template polynucleotide. A primer can be a single-stranded DNA prior to binding a template polynucleotide. In some embodiments, the primer initially comprises double-stranded sequence. A primer site includes the area of the template to which a primer hybridizes. In some embodiments, primers are capable of acting as a point of initiation for template-directed nucleic acid synthesis. For example, primers can initiate template-directed nucleic acid synthesis when four different nucleotides and a polymerization agent or enzyme, such as DNA or RNA polymerase or reverse transcriptase.

A primer pair includes 2 primers: a first primer with a 5' upstream region that hybridizes with a 5' end of a template sequence, and a second primer with a 3' downstream region that hybridizes with the complement of the 3' end of the template sequence. A primer set includes two or more primers: a first primer or first plurality of primers with a 5' upstream region that hybridizes with a 5' end of a template sequence or plurality of template sequences, and a second primer or second plurality of primers with a 3' downstream region that hybridizes with the complement of the 3' end of the template sequence or plurality of template sequences.

In some embodiments, a primer comprises a target specific sequence. In some embodiments, a primer comprises a sample barcode sequence. In some embodiments, a primer comprises a universal priming sequence. In some embodiments, a primer comprises a PCR priming sequence. In some embodiments, a primer comprises a PCR priming sequence used to initiate amplification of a polynucleotide. (Dieffenbach, PCR Primer: A Laboratory Manual, 2nd Edition (Cold Spring Harbor Press, New York (2003)). The universal primer binding site or sequence allows the attachment of a universal primer to a polynucleotide and/or amplicon. Universal primers are well known in the art and include, but are not limited to, −47F (M13F), alfaMF, AOX3', AOX5', BGHr, CMV-30, CMV-50, CVMf, LACrmt, lambda gt 10F, lambda gt 10R, lambda gt 11F, lambda gt 11R, M13 rev, M13Forward (−20), M13Reverse, male, pQEproseq, pQE, pA-120, pet4, pGAP Forward, pGLRVpr3, pGLpr2R, pKLAC14, pQEFS, pQERS, pucU1, pucU2, reversA, seqIREStam, seqIRESzpet, seqori, seqPCR, seqpIRES-, seqpIRES+, seqpSecTag, seqpSecTag+, seqretro+PSI, SP6, T3-prom, T7-prom, and T7-termInv.

As used herein, attach can refer to both or either covalent interactions and noncovalent interactions. Attachment of the universal primer to the universal primer binding site may be used for amplification, detection, and/or sequencing of the polynucleotide and/or amplicon. The universal primer binding site may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. In some embodiments, the universal primer binding site comprises 1-10, 10-20, 10-30 or 10-100 nucleotides or base pairs. In some embodiments, the universal primer binding site comprises from about 1-90, 1-80, 1-70, 1-60, 1-50, 1-40, 1-30, 1-20, 1-10, 2-90, 2-80, 2-70, 2-60, 2-50, 2-40, 2-30, 2-20, 2-10, 1-900, 1-800, 1-700, 1-600, 1-500, 1-400, 1-300, 1-200, 1-100, 2-900, 2-800, 2-700, 2-600, 2-500, 2-400, 2-300, 2-200, 2-100, 5-90, 5-80, 5-70, 5-60, 5-50, 5-40, 5-30, 5-20, 5-10, 10-90, 10-80, 10-70, 10-60, 10-50, 10-40, 10-30, 10-20, 10-10, 5-900, 5-800, 5-700, 5-600, 5-500, 5-400, 5-300, 5-200, 5-100, 10-900, 10-800, 10-700, 10-600, 10-500, 10-400, 10-300, 10-200, 10-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can have a length compatible with its use in synthesis of primer extension products. A primer can be a polynucleotide that is 8 to 200 nucleotides in length. The length of a primer can depend on the sequence of the template polynucleotide and the template locus. For example, the length and/or melting temperature (TM) of a primer or primer set can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, primers are about 8-100 nucleotides in length, for example, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, or 20-60 nucleotides in length and any length there between. In some embodiments, primers are at most about 10, 12, 15, 20, 21, 22, 23, 24, 25, 26, 27, 28, 29, 30, 35, 40, 45, 50, 55, 60, 65, 70, 75, 80, 85, 90, 95 or 100 nucleotides in length.

Generally, one or more pairs of primers can be used in an exponential amplification reaction; one primer of a primer pair can be a forward primer and one primer of a primer pair can be a reverse primer. In some embodiments, a first pair of primers can be used in the exponential amplification reaction; one primer of the first pair can be a forward primer complementary to a sequence of a first template polynucleotide molecule and one primer of the first pair can be a reverse primer complementary to a second sequence of the first template polynucleotide molecule, and a first template locus can reside between the first sequence and the second sequence. In some embodiments, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a variable light chain antibody sequence. In some embodiments, a third pair of primers can be used in the amplification reaction; one primer of the third pair can be a forward primer complementary to a first sequence of a third template polynucleotide molecule and one primer of the third pair can be a reverse primer complementary to a second sequence of the third template polynucleotide molecule, and a third template locus can reside between the first sequence and the second sequence.

The one or more primers can anneal to at least a portion of a plurality of template polynucleotides. The one or more primers can anneal to the 3' end and/or 5' end of the plurality of template polynucleotides. The one or more primers can anneal to an internal region of the plurality of template polynucleotides. The internal region can be at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends or 5' ends the plurality of template polynucleotides. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. In some embodiments, the one or more custom primers anneal to an SBC, a target specific region, complements thereof, or any combination thereof. The one or more primers can comprise a universal primer. The one or more primers primer can be designed to amplify or perform primer extension, reverse transcription, linear extension, non-exponential amplification, exponential amplification, PCR, or any other amplification method of one or more target or template polynucleotides The target specific region can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs in some embodiments, the target specific region comprises from about 5-10, 10-15, 10-20, 10-30, 15-30, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, 20-60, 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can be designed according to known parameters for avoiding secondary structures and self-hybridization. In some embodiments, different primer pairs can anneal and melt at about the same temperatures, for example, within 1° C., 2° C., 3° C., 4° C., 5° C., 6° C., 7° C., 8° C., 9° C. or 10° C. of another primer pair. In some embodiments, one or more primers in a plurality of primers can anneal and melt at about the same temperatures, for example, within 1, 2, 3, 4, 5, 6, 7, 8, 9 or 10° C. of another primer in the plurality of primers. In some embodiments, one or more primers in a plurality can anneal and melt at different temperatures than another primer in the plurality of primers.

A plurality of primers for one or more steps of the methods described herein can comprise a plurality of primers comprising about, at most about, or at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1,000,000, 50,000,000, 100,000,000 different primers. For example, each primer in a plurality of primers can comprise a different target or template specific region or sequence.

FIG. 2 depicts exemplary amplification reactions for amplification of the polynucleotide library provided herein, generated by the methods provided herein. In the exemplary methods provided herein, amplification of the library for the purposes of sequencing use primers linked to a sequencing adaptor to be used for sequencing, such as next-generation sequencing. Such primers are known and described herein. Sequencing adaptor-tagged primers are used in the exemplary applications provided below.

In some embodiments, a target gene is amplified for sequencing. In some embodiments, the target gene is amplified using a primer directed to an adaptor sequence at one end of the polynucleotide and a target specific primer positioned to sequence the full-length target polypeptide or a selected portion thereof. In some examples the target sequence can be present in the library from a single cell or a plurality of cells. In some embodiments, one or more target sequences is amplified using primers specific to a universal priming sequence of the polynucleotide and one or more target-specific primers. In some embodiments, two or more target sequences are amplified, each with universal sequence and target-specific primers as described. In some embodiments the two or more target sequences are linked, such as two target sequences that are co-expressed in a cell, for example, target sequences that are expressed as a dimer (e.g., a heterodimer). Thus, using the provided embodiment, paired sequence information, such as full-length paired sequence information can be obtained using the provided methods.

In some embodiments the entire prepared library of polynucleotides can be amplified for sequencing using primers specific to the universal priming sequence of the first adaptor and the universal priming sequence of the second adaptor. Amplification of the polynucleotide libraries provided herein using primers specific to the universal priming sequences at the two ends of the polynucleotides of the library, can provide the transcriptome or genome, or portion thereof, of all cells used to make the library. Such transcriptomic information can be used for mining at later time points and/or used to evaluate expression (at the transcript level) of several genes within the population of cells from which the sample was prepared. In some embodiments, the transcriptomic information of all cells can be analyzed and used to generate clusters of cells with similar transcript expression profiles from the total population of cells from which the library was produced.

In some embodiments, the polynucleotides from a single cell can be specifically amplified and sequenced using a primer specific to the vessel barcode sequence and a primer specific to a universal priming site present in the second adaptor. In such embodiments, one or more target sequence(s) is/are amplified as described above, and the vessel barcode(s) is/are identified in the target sequence(s) that are identified as of interest. As all polynucleotides from the same cell are barcoded with the same vessel barcode, this application of the method yields sequence information of all polynucleotides from the selected cell or cells. The amplification of all the polynucleotides in the library from the selected cell or cells can then provide expression profiles or genetic profiles of the cell or cells that express the one or more particular target sequences.

2. Sequencing

After performing one or more of the methods or method steps described herein, a library of polynucleotides generated can be sequenced.

Sequencing can be performed by any sequencing method known in the art. In some embodiments, sequencing can be performed in high throughput. Suitable next generation sequencing technologies include the 454 Life Sciences platform (Roche, Branford, CT) (Margulies et al., Nature, 437, 376-380 (2005)); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, CA; Bibkova et al, Genome Res. 16, 383-393 (2006); and U.S. Pat. Nos. 6,306,597, 7,598,035, 7,232,656), or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453); or the Helicos True Single Molecule DNA sequencing technology (Harris et al, Science, 320, 106-109 (2008); and U.S. Pat. Nos. 7,037,687, 7,645,596, 7,169,560, and 7,769,400), the single molecule, real-time (SMRT™) technology of Pacific Biosciences, and sequencing (Soni et al, Clin. Chem. 53, 1996-2001 (2007)). These systems allow multiplexed parallel sequencing of many polynucleotides isolated from a sample (Dear, Brief Funct. Genomic Proteomic, 1(4), 397-416 (2003) and McCaughan et al, J. Pathol, 220, 297-306 (2010)).

In some embodiments, polynucleotides are sequenced by sequencing by ligation of dye-modified probes, pyrosequencing, or single-molecule sequencing. Determining the sequence of a polynucleotide may be performed by sequencing methods such as Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, and VisiGen Biotechnologies approach. Alternatively, determining the sequence of polynucleotides may use sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, MA). Sequencing can comprise MiSeq sequencing. Sequencing can comprise HiSeq sequencing. In some embodiments, determining the sequence of a polynucleotide comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of a polynucleotide can be determined by electron microscopy or a chemical-sensitive field effect transistor (chemFET) array.

A method can further comprise sequencing one or more polynucleotides in the library. A method can further comprise aligning one or more polynucleotide sequences, sequence reads, amplicon sequences, or amplicon set sequences in the library to each other.

As used herein, aligning comprises comparing a test sequence, such as a sequence read, to one or more other test sequences, reference sequences, or a combination thereof. In some embodiments, aligning can be used to determine a consensus sequence from a plurality of sequences or aligned sequences. In some embodiments, aligning comprises determining a consensus sequence from a plurality of sequences that each has an identical molecular barcode or vessel barcode. In some embodiments, the length of a sequence aligned for comparison purposes is at least 30%, at least 40%, at least 50%, at least 60%, at least 70%, at least 80%, at least 90%, or at least 95%, of the length of a reference sequence. The actual comparison of the two or more sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

Sequencing can comprise sequencing at least about 10, 20, 30, 40, 50, 60, 70, 80, 90, 100 or more nucleotides or base pairs of the polynucleotides. In some embodiments, sequencing comprises sequencing at least about 200, 300, 400, 500, 600, 700, 800, 900, 1000, or more nucleotides or base pairs of the polynucleotides. In other instances, sequencing comprises sequencing at least about 1500, 2000, 3000, 4000, 5000, 6000, 7000, 8000, 9000, 10,000, or more nucleotides or base pairs of the polynucleotides.

Sequencing can comprise at least about 200, 300, 400, 500, 600, 700, 800, 900, 1000 or more sequencing reads per run. As used herein, a sequence read comprises a sequence of nucleotides determined from a sequence or stream of data generated by a sequencing technique. In some embodiments, sequencing comprises sequencing at least about 1500, 2000, 3000, 4000, 5000, 6000, 7000, 8000, 9000, 10,000, or more sequencing reads per run. Sequencing can comprise more than, less than, or equal to about 1,000,000,000 sequencing reads per run. Sequencing can comprise more than, less than, or equal to about 200,000,000 reads per run.

In some embodiments, the number of sequence reads used to determine a consensus sequence is from about 2-1000 sequence reads. For example, the number of sequence reads used to determine a consensus sequence can be from about 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 sequence reads. In some embodiments, the number of sequence reads used to determine a consensus sequence is at least about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 50,000,000, or 100,000,000 reads. In some embodiments, the number of sequence reads used to determine a consensus sequence is at most about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 50,000,000, or 100,000,000 reads.

A method can comprise sequencing misreads. A method can comprise determining the number of misreads, such as for determining a reaction condition or designing primer sequences. Comparing the number of misreads generated under one or more first conditions or sets of conditions can be used to determine a preferred condition or condition set. For example, a first method can be carried out at a high salt concentration during a PCR reaction, and a second method can be carried out at a low salt concentration during a PCR reaction, wherein the first and second method are carried out substantially the same aside from the salt concentration difference. If the first method results in a higher number of misreads, such as a higher number of misreads for a particular target polynucleotide sequence or primer, a lower salt reaction condition can be determined to be preferred for that particular target polynucleotide sequence or primer.

II. Cloning and Expression of Target Genes

In some embodiments, target genes identified and sequenced according to the provided methods can be cloned into vectors for expression in or from cells. An expression library of target genes, such as immune receptors, e.g. antibodies or TCRs, can be generated.

"Antibody expression library" or "TCR expression library" or "expression library" as used herein can refer to a collection of molecules (i.e., two or more molecules) at either the nucleic acid or protein level. Thus, this term can refer to a collection of expression vectors which encode a plurality of antibody or TCR molecules (i.e., at the nucleic acid level) or can refer to a collection of antibody or TCR molecules after they have been expressed in an appropriate expression system (i.e., at the protein level). Alternatively the expression vectors/expression library may be contained in suitable host cells in which they can be expressed. The antibody molecules which are encoded or expressed in the expression libraries of the invention can be in any appropriate format, e.g., may be whole antibody or TCR molecules or may be antibody or TCR fragments, e.g., single chain antibodies (e.g., scFv antibodies), Fv antibodies, Fab' antibodies, (Fab')$_2$ fragments, diabodies, etc. The terms "encoding" and "coding for" as is nucleic acid sequence "encoding 'V' coding for" or a DNA coding sequence of or a nucleotide sequence "encoding 'V' coding for" a particular enzyme, as well as other synonymous terms, refer to a DNA sequence which is transcribed and translated into an enzyme when placed under the control of appropriate regulatory sequences. A "promoter sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence includes the minimum number of bases with elements necessary to initiate transcription at levels detectable above background. However, after the RNA polymerase binds the sequence and transcription is initiated at the start codon (3' terminus with a promoter), transcription proceeds downstream in the 3' direction. Within the promoter sequence will be found a transcription initiation site (conveniently defined by mapping with nuclease SI) as well as protein binding domains (consensus sequences) responsible for the binding of RNA polymerase.

Antibody or TCR molecules identified by, derived from, selected from, or obtainable from the antibody or TCR expression libraries of the invention form a yet further aspect of the invention. Again these antibody or TCR molecules may be proteins or nucleic acids encoding antibody or TCR molecules, which nucleic acids may in turn be incorporated into an appropriate expression vector and/or be contained in a suitable host cell.

The cDNA pool can be subjected to a PCR reaction with polynucleotides that hybridize to a constant region of the heavy chain of antibody genes and polynucleotides that hybridize to the 5' end of the $V_H$ or Vα or Vγ chain region of antibody or TCR genes. The cDNA pool can be subjected to a PCR reaction with polynucleotides that hybridize to a constant region of the heavy chain or alpha or gamma chain of antibody or TCR genes and polynucleotides that hybridize to region 5' to the 5' end of the $V_H$ or Vα or Vγ chain region of a barcoded polynucleotide comprising an antibody or TCR sequence. A PCR reaction can also setup for the amplification of the $V_L$ or Vβ or Vγ chain pool of e.g., kappa and lambda classes. The cDNA pool can be subjected to a PCR reaction with polynucleotides that hybridize to a constant region of the light chain of antibody genes and polynucleotides that hybridize to the 5' end of the $V_L$ or Vβ or Vγ chain region of antibody or TCR genes. The cDNA pool can be subjected to a PCR reaction with polynucleotides that hybridize to a constant region of the light chain of antibody genes and polynucleotides that hybridize to region 5' to the 5' end of the $V_L$ or Vβ or Vγ chain region of a barcoded polynucleotide comprising an antibody or TCR sequence. Such oligonucleotides or primers may be designed based on known and publicly available immunoglobulin or TCR gene sequence database information.

In some embodiments, $V_H$ and $V_L$ or Vα and Vβ or Vγ and Vδ sequences can be conveniently obtained from a library of $V_H$ and $V_L$ or Vα and Vβ or Vγ and Vδ sequences produced by PCR amplification using one or more primers that are not specific for heavy or light chain genes and, in particular, for one or both the terminal regions of the $V_H$ and $V_L$ or Vα and Vβ or Vγ and Vδ polynucleotides. In some embodiments, $V_H$ and $V_L$ sequences can be conveniently obtained from a library of $V_H$ and $V_L$ or Vα and Vβ or Vγ and Vδ sequences produced by PCR amplification using primers specific to a region of the vessel barcoded polynucleotide. In some embodiments, $V_H$ and $V_L$ sequences can be conveniently obtained from a library of $V_H$ and $V_L$ or Vα and Vβ or Vγ and Vδ sequences produced by PCR amplification using C-gene family-specific primers or C-gene-specific primers. In some embodiments, $V_H$ and $V_L$ sequences can be conveniently obtained from a library of $V_H$ and $V_L$ or Vα and Vβ or Vγ and Vδ sequences produced by PCR amplification using a primer set with a first primer specific to a region of the vessel barcoded polynucleotide and a second primer or plurality of second primers that are C-gene family-specific primers or C-gene-specific primers. In some embodiments, $V_H$ and $V_L$ or Vα and Vβ or Vγ and Vδ sequences can be conveniently obtained from a library of $V_H$ and $V_L$ or Vα and Vβ or Vγ and Vδ sequences produced by PCR amplification using a primer set with a first primer specific to a region of the vessel barcoded polynucleotide and a second primer specific to a universal sequence.

In some embodiments, upon reverse transcription, the resulting cDNA sequences may be amplified by PCR using one or more primers specific for immunoglobulin genes and, in particular, for one or both the terminal regions of the VH and VL or Vα and Vβ or Vγ and Vδ polynucleotides. In some embodiments, VH and VL sequences can be obtained from a library of VH and VL or Vα and Vβ or Vγ and Vδ sequences produced by PCR amplification using V-gene family-specific primers or V gene-specific primers (Nicholls et al, J. Immunol. Meth., 1993, 165:81; WO93/12227) or are designed according to standard art-known methods based on available sequence information. (The VH and VL or Vα and Vβ or Vγ and Vδ sequences can be ligated, usually with an intervening spacer sequence (e.g., encoding an in-frame flexible peptide spacer), forming a cassette encoding a single-chain antibody). V region sequences can be conveniently cloned as cDNAs or PCR amplification products for immunoglobulin-express sing cells. The VH and VL or Vα and Vβ or Vγ and Vδ regions are sequenced, optionally, in the methods described herein and particularly after certain steps as noted (e.g., after single cell PCR; after mammalian or other cell surface display, after FACS screening, and the like). Sequencing can be used, among other reasons, to verify that the level of diversity is at an acceptable level. Sequencing can include high-throughput sequencing, deep sequencing (in which the same gene is sequenced from a plurality of individual samples to identify differences in the sequences), or combinations of the two.

In some embodiments, it is unnecessary to physically link the natural VH and VL or Vα and Vβ or Vγ and Vδ combinations using the methods described herein. In some embodiments, cDNAs, barcoded polynucleotides, or PCR amplified barcoded cDNAs are not physically linked. In some embodiments, cDNAs, barcoded polynucleotides, or PCR amplified barcoded cDNAs are not physically linked in the same reaction or vessel.

In some embodiments, the natural VH and VL or Vα and Vβ or Vγ and Vδ combinations are physically linked, using, in addition to the cDNA primers, one primer or plurality of primers for the 5' end of the VH or Vα or Vγ gene and another primer or plurality of primers for the 5' end of the VL or Vβ or Vδ gene. These primers also contain complementary tails of extra sequence, to allow the self-assembly of the VH and VL or Vα and Vβ or Vγ and Vδ genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin-labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences may be recovered from cells for use in further method steps described herein. For example, the recovered DNA can be PCR amplified using terminal primers, if necessary, and cloned into vectors which may be plasmids, phages, cosmids, phagemids, viral vectors or combinations thereof as detailed below. Convenient restriction enzyme sites may be incorporated into the hybridized sequences to facilitate cloning. These vectors may also be saved as a library of linked variable regions for later use.

In some embodiments in which it is desired to provide additional VH and VL or Vα and Vβ or Vγ and Vδ combinations, an expression system is chosen to facilitate this. For example, bacteriophage expression systems allow for the random recombination of heavy- and light-chain sequences. Other suitable expression systems are known to those skilled in the art.

It should be noted that in the case of VH and $V_L$ or Vα and Vβ or Vγ and Vδ sequences derived from nonhumans, in some embodiments, it can be preferable to chimerize these sequences with a fully human Fc. As used herein "chimerized" refers to an immunoglobulin or TCR, wherein the heavy and light chain variable regions or Vα and Vβ or Vγ and Vδ regions are not of human origin and wherein the constant regions of the heavy and light chains or Vα and Vβ or Vγ and Vδ chains are of human origin. This is affected by amplifying and cloning the variable domains into a human Fc. The human Fc can be part of the vector, or in a separate molecule, and library of Fc's could also be used. In a preferred embodiment the chimerized molecules grown in mammalian cells such as CHO cells, screened with FACS twice to enrich the cell population for cells expressing the antibody of interest. The chimerized antibodies or TCRs are characterized, by either sequencing followed by functional characterization, or direct functional characterization or kinetics. Growth, screening and characterization are described in detail below.

It is important to note that the above described PCR reactions are described for cloning the antibodies in the IgG form. These are preferred as they are generally associated with a more mature immune response and generally exhibit higher affinity than IgM antibodies, thereby making them more desirable for certain therapeutic and diagnostic applications. Clearly, however, polynucleotides can be designed which will allow the cloning of one or more of the other forms of immunoglobulin molecules, e.g., IgM, IgA, IgE and IgD if desired or appropriate.

Once an antibody or TCR has been identified and the appropriate population of said cells have been isolated at an appropriate time and optionally enriched as described above, the antibody or TCR expression libraries need not be generated immediately, providing the genetic material contained in the cells can be kept intact thereby enabling the library to be made at a later date. Thus, for example the cells, a cell lysate, or nucleic acid, e.g., RNA or DNA derived therefrom, can be stored until a later date by appropriate methods, e.g., by freezing, and the expression libraries generated at a later date when desired.

Once the library of expression vectors has been generated, the encoded antibody molecules can then be expressed in an appropriate expression system and screened using appropriate techniques which are well known and documented in the art. Thus the above defined method of the invention may comprise the further steps of expressing the library of expression vectors in an appropriate expression system and screening the expressed library for antibodies with desired properties, as explained in further detail below.

As indicated herein, polynucleotides prepared by the methods of the disclosure which comprise a polynucleotide encoding antibody or TCR sequences can include, but are not limited to, those encoding the amino acid sequence of an antibody or TCR fragment, by itself, the noncoding sequence for the entire antibody or TCR or a portion thereof, the coding sequence for an antibody or TCR, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example-ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody or TCR comprising an antibody or TCR fragment or portion.

The primary PCR products can then optionally be subjected to a secondary PCR reaction with new polynucleotide sets that hybridize to the 5' and 3' ends of the antibody or TCR variable domains $V_H$, $V_L$ kappa and $V_L$ lambda or V$\alpha$ and v or V$\gamma$ and V$\delta$ (as appropriate depending on whether the primary PCR reaction with which the new polynucleotide sets are used was designed to amplify portions of the heavy or light chain antibody genes or V$\alpha$ or V$\beta$ TCR genes or V$\gamma$ or V$\delta$ TCR genes). These polynucleotides advantageously include DNA sequences specific for a defined set of restriction enzymes (i.e., restriction enzyme sites) for subsequent cloning. The selected restriction enzymes must be selected so as not to cut within human antibody or TCR V-gene segments. Such polynucleotides may be designed based on known and publicly available immunoglobulin or TCR gene sequence and restriction enzyme database information. However, preferred restriction enzyme sites to be included are Ncol, Hind III, M and Notl. The products of such secondary PCR reactions are repertoires of various V-heavy, V-light kappa and V-light lambda antibody fragments/domains. This type of secondary PCR reaction is therefore generally carried out when the expression library format of interest is a scFv or Fv format, wherein only the $V_H$ and $V_L$ or V$\alpha$ and V or V$\gamma$ and V$\delta$ domains of an antibody or TCR are present.

PCR products can also be subjected to a PCR reaction with new primer sets that hybridize to the 5' and 3' ends of the barcoded polynucleotides. These polynucleotides can advantageously include DNA sequences specific for a defined set of restriction enzymes (i.e., restriction enzyme sites) for subsequent cloning. The selected restriction enzymes must be selected so as not to cut within human antibody or TCR V-gene segments. Such polynucleotides may be designed based on known and publicly available immunoglobulin or TCR gene sequence and restriction enzyme database information. However, preferred restriction enzyme sites to be included are Ncol, Hind III, Mlul and Notl. The products of such secondary PCR reactions are repertoires of various $V_H$, $V_L$ kappa and $V_L$ lambda antibody fragments/domains or V$\alpha$ and V$\beta$ or V$\gamma$ and V$\delta$ TCR fragments/domains.

One of skill in the art will recognize that heavy or light chain or V$\alpha$ or V$\beta$ chain or V$\gamma$ or V$\delta$ chain Fv or Fab fragments, or single-chain antibodies or TCRs may also be used with this system. A heavy or light chain or V$\alpha$ or V$\beta$ chain or V$\gamma$ or V$\delta$ chain can be mutagenized followed by the addition of the complementary chain to the solution. The two chains are then allowed to combine and form a functional antibody fragment. Addition of random non-specific light or heavy chain or V$\alpha$ or V$\beta$ chain or V$\gamma$ or V$\delta$ chain sequences allows for the production of a combinatorial system to generate a library of diverse members.

Libraries of such repertoires of cloned fragments comprising the variable heavy chain or V$\alpha$ chain or V$\gamma$ chain regions, or fragments thereof, and/or variable light chain or V$\beta$ chain or V$\delta$ chain regions, or fragments thereof, of antibody or TCR genes derived from the B or T lymphocytes of immuno-challenged hosts as defined herein form further aspects of the invention. These libraries comprising cloned variable regions may optionally be inserted into expression vectors to form expression libraries.

In some embodiments, the PCR reactions can be set up so as to retain all or part of the constant regions of the various antibody or TCR chains contained in the isolated immune cell population. This is desirable when the expression library format is a Fab format, wherein the heavy or alpha or gamma chain component comprises $V_H$ or V$\alpha$ or V$\gamma$ and $C_H$ or C$\alpha$ or C$\gamma$ domains and the light chain or V$\beta$ chain or V$\gamma$ chain component comprises $V_L$ or V$\beta$ or V$\delta$ chain and CL or $\beta$ or $\delta$ domains. Again, libraries of such cloned fragments comprising all or part of the constant regions of antibody or TCR chains form further aspects of the invention.

These nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adaptor, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adaptors, and linkers is well known in the art. (See, e.g., Current Protocols in Molecular Biology (CPMB) (Fred M. Ausubel, et al. ed., John Wiley and Sons, Inc.); or J. Sambrook et al., "Molecular Cloning: A Laboratory Manual," 1989, 2nd Ed., Cold Spring Harbour Laboratory Press: New York, N.Y.).

The libraries disclosed herein may be used in a variety of applications. As used herein, a library comprises a plurality of molecules. In some embodiments, a library comprises a plurality of polynucleotides. In some embodiments, a library comprises a plurality of primers. In some embodiments, a library comprises a plurality of sequence reads from one or more polynucleotides, amplicons, or amplicon sets. A library can be stored and used multiple times to generate samples for analysis. Some applications include, for example, genotyping polymorphisms, studying RNA processing, and selecting clonal representatives to do sequencing according to the methods provided herein. Libraries comprising a plurality of polynucleotides, such as primers or libraries for sequencing or amplification, can be generated, wherein a plurality of polynucleotides comprises at least about 2, 3, 4, 5, 6, 7, 8, 9, 10, 11, 12, 13, 14, 15, 20, 25, 30, 35, 40, 45, 50, 60, 70, 90, 100, 200, 300, 400, 500, 600, 700, 800, 900, 1000, 15000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more molecular barcodes or vessel barcodes. In some embodiments, libraries of polynucleotides comprise a plurality of at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more unique polynucleotides, wherein each unique polynucleotide comprises one or more molecular barcodes and vessel barcodes.

III. Transcriptome Analysis

In some embodiments, the provided methods can be used to elucidate transcriptome information for cells, which can be combined with the capture of the target polynucleotide sequence, e.g., antibody or TCR, of a particular cell. In some embodiments, a cell or a plurality of cells identified by the target polynucleotide sequence can be characterized by their transcriptional cell state, including with respect to a particular state, feature or attribute of the cell. In some embodiments, individualized transcriptome profiles of cells can be determined and provided information related to one or more features of a cell. Examples of such features include, but are not limited to, activation state, proliferation state, exhaustion state, transition state, cell cycle stage or other parameter associated with the functional or phenotypic state of the cell.

In some embodiments, the transcriptional state information can be used to identify cells expressing a particular target gene, e.g., antibody or TCR, that exhibit a desired or interesting response. In some aspects, the provided methods permit matching of the transcriptome profile of a cell to the target polynucleotide, e.g., antibody or TCR, amplified or sequenced from the cell. In particular embodiments, the transcriptome information and sequence of the target polynucleotide is matched by virtue of the amplified and sequenced transcriptome and target polynucleotides having the same vessel barcode, which identifies transcriptome profiles and target polynucleotides that were derived from the same cell.

Various methods for processing transcriptome data are known in the art. In some aspects, data obtained from the methods can be visualized on a map. A map of the number and location of targets from a sample can be constructed using information generated using the methods described herein. The map can be used to locate a physical location of a target. The map can be used to identify the location of multiple targets.

In some embodiments, the system comprises computer-readable media that includes code for providing data analysis for the sequence datasets generated from the provided methods. Examples of data analysis functionality that can be provided by the data analysis software include, but are not limited to, (i) algorithms for decoding/demultiplexing of the sample vessel barcode, molecular barcode, and target sequence or transcriptome data provided by sequencing the polynucleotide library, (ii) algorithms for determining the number of reads per gene per cell, and the number of unique transcript molecules per gene per cell, based on the data, and creating summary tables, (iii) statistical analysis of the sequence data, e.g., for clustering of cells by gene expression data, or for predicting confidence intervals for determinations of the number of transcript molecules per gene per cell, etc., (iv) algorithms for identifying sub-populations of rare cells, for example, using principal component analysis, hierarchical clustering, k-mean clustering, self-organizing maps, neural networks etc., (v) sequence alignment capabilities for alignment of gene sequence data with known reference sequences and detection of mutation, polymorphic markers and splice variants, and (vi) automated clustering of molecular labels to compensate for amplification or sequencing errors.

In some embodiments, computational programs can be employed to produce transcriptome assemblies. Exemplary computational programs for short-read assemblies include those described in Robertson et al., Nat Methods. 2010; 7:909-12; Grabherr et al., Nat Biotechnol. 2011; 29:644-52; Schulz et al., Bioinformatics. 2012; 28:1086-92, and Xie et al., Bioinformatics. 2014; 30:1660-6. Transcriptome assembly can be challenging due to large variation in expression levels among transcripts, sequencing bias and alternative splicing. Thus, merging transcriptome assemblies based on k-mer lengths, or using a fixed k-mer value, can be used to offset the different degrees of transcript abundancies and improve transcriptome assembly (see, e.g., Robertson et al., Nat Methods. 2010; 7:909-12, Grabherr et al., Nat Biotechnol. 2011; 29:644-52 and Surget-Groba Genome Res. 2010; 20:1432-40).

In some embodiments, commercially available software can be used to perform all or a portion of the data analysis.

In some embodiments, the data analysis software can include options for outputting the sequencing results in useful graphical formats, e.g., heat maps that indicate the number of copies of one or more genes occurring in each cell of a collection of cells. In some embodiments, the data analysis software can further comprise algorithms for extracting biological meaning from the sequencing results, for example, by correlating the number of copies of one or more genes occurring in each cell of a collection of cells with a type of cell, a type of rare cell, or a cell derived from a subject having a specific disease or condition. In some embodiments, the data analysis software can further comprise algorithms for comparing populations of cells across different biological samples.

In some embodiments, all of the data analysis functionality can be packaged within a single software package. In some embodiments, the complete set of data analysis capabilities can comprise a suite of software packages. In some embodiments, the data analysis software can be a standalone package that is made available to users independently of the assay instrument system. In some embodiments, the software can be web-based, and can allow users to share data.

In some examples, cluster analysis can be performed to identify one or more different cell populations. In some examples the cell populations are clustered based on the expression of one or more target genes. Presence, up-regulation or down-regulation of known genes or transcripts, representative of a transcriptional cell state, can be used to cluster cells within a plurality of cells.

In some embodiments, transcriptome genes of interest are identified by their vessel barcodes and are matched or joined to the output of the amplification and sequencing of the full-length target molecule of interest, e.g., antibody or TCR. Accordingly, by practice of the provided methods, each vessel barcode is matched or can be annotated with gene counts (e.g., transcriptome) and target molecule (e.g., full-length antibody or TCR) information.

In some embodiments, an expression profile, represented by the nucleic acid sequences present in the transcriptome can be generated. The expression profiles can be generated of a subset of cells, such as cells that express one or more target genes, and that share a vessel barcode.

IV. Diagnostics

In some embodiments, a method can further comprise diagnosing, prognosing, monitoring, treating, ameliorating and/or preventing in a subject a disease, disorder, symptom and/or condition. In some embodiments, a method can further comprise diagnosing, prognosing, monitoring, treating, ameliorating and/or preventing in a subject a disease, disorder, symptom and/or condition, based on a presence, absence, or level of a target polynucleotide and/or a particular transcriptional cell state, such as a cell state described herein above. In some embodiments, a method can further comprise diagnosing, prognosing, monitoring, treating, ameliorating and/or preventing in a subject a disease, disorder, symptom and/or condition, based on a presence, absence, or level of one or more target polynucleotides and/or the transcriptional state of one or more cells.

In some embodiments, a method can further comprise diagnosing, prognosing, monitoring, treating, ameliorating and/or preventing in a subject a disease, disorder, symptom and/or condition based on a presence, absence, level, or sequence of one or more of the sequences obtained using the methods described herein. For example, a diagnosis of a disease can be made based on a presence, absence, level, or sequence of a variant sequence obtained using the methods described herein. In some embodiments, a method can further comprise diagnosing, prognosing, monitoring, treating, ameliorating and/or preventing in a subject a disease, disorder, symptom and/or condition based on a presence, absence, level, or sequence, one or more of the sequence reads obtained using the methods described herein. In some embodiments, a method can further comprise diagnosing, prognosing, monitoring, treating, ameliorating and/or preventing in a subject a disease, disorder, symptom and/or condition based on a presence, absence, level, or sequence of one or more of the consensus sequences obtained using the methods described herein. In some embodiments, a method can further comprise diagnosing, prognosing, monitoring, treating, ameliorating and/or preventing in a subject a disease, disorder, symptom and/or condition based on a determination of a level (e.g., an amount or concentration) of a target polynucleotide in a sample. A level of a target polynucleotide in a sample can be determined based on one or more sequence reads, sequences, consensus sequences, or any combination thereof. A level of each of a plurality of target polynucleotides in a sample can be determined using the methods described herein. A level of each of a plurality of target polynucleotide in a sample can be determined based on a number of sequence reads, sequences, consensus sequences, or any combination thereof of each target polynucleotide in the plurality. For example, a level of a first target polynucleotide and a level of a second target polynucleotide can be determined using the methods described herein.

In some embodiments, first and second target polynucleotides of a plurality of target polynucleotides are the same. For example, a first target polynucleotide can comprise a first copy of an mRNA molecule and a second target polynucleotide can comprise a second copy of an mRNA molecule. In some embodiments, the first and second target polynucleotides are different. For example, a first target polynucleotide can comprise a first mRNA molecule and a second target polynucleotide can comprise a second mRNA molecule transcribed from a different gene than the first mRNA molecule. For example, a first target polynucleotide can comprise a first allele and a second target polynucleotide can comprise a second allele. For example, a first target polynucleotide can comprise a wild-type sequence and a second target polynucleotide can comprise a variant sequence.

In some embodiments, a method can further comprise diagnosing or prognosing a subject with a disease, disorder, symptom and/or condition with at least 50% confidence. For example, a diagnosis or prognosis of a subject with a disease, disorder, symptom and/or condition can be determined with at least 50%, 55%, 60%, 65%, 70%, 75%, 80%, 85%, 90%, 95%, 98%, 99%, or 100% confidence. In some embodiments, a diagnosis or prognosis of a subject with a disease, disorder, symptom and/or condition can be determined with a 50%-100% confidence. For example, a diagnosis or prognosis of a subject with a disease, disorder, symptom and/or condition can be determined with a 60%-100%, 70%-100%, 80%-100%, 90%-100%, 50%-90%, 50%-80%, 50%-70%, 50%-60%, 60%-90%, 60%-80%, 60%-70%, 70%-90%, 70%-80%, or 80%-90% confidence.

In some embodiments, the presence, absence, level, sequence, or any combination thereof, of a target polynucleotide in the subject, such as a biomarker, can be determined with at least 50% confidence. For example, the presence, absence, level, sequence, or any combination thereof, of a target polynucleotide in the subject can be determined with at least 50%, 55%, 60%, 65%, 70%, 75%, 80%, 85%, 90%, 95%, 98%, 99%, or 100% confidence. In some embodiments, the presence, absence, level, sequence, or any combination thereof, of a target polynucleotide in the subject can be determined with a 50%-100% confidence. For example, the presence, absence, level, sequence, or any combination thereof, of a target polynucleotide in the subject can be determined with a 60%-100%, 70%-100%, 80%-100%, 90%-100%, 50%-90%, 50%-80%, 50%-70%, 50%-60%, 60%-90%, 60%-80%, 60%-70%, 70%-90%, 70%-80%, or 80%-90% confidence.

V. Enzymes

The methods and kits disclosed herein may comprise one or more enzymes. Examples of enzymes include, but are not limited to ligases, reverse transcriptases, polymerases, and restriction nucleases.

In some embodiments, attachment of an adaptor to polynucleotides comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods and kits disclosed herein may further comprise the use of one or more reverse transcriptases. In some embodiments, the reverse transcriptase is a HIV-1 reverse transcriptase, MMLV reverse transcriptase, AMV reverse transcriptase, and telomerase reverse transcriptase. In some embodiments, the reverse transcriptase is M-MLV reverse transcriptase.

In some embodiments, the methods and kits disclosed herein comprise the use of one or more proteases In some embodiments, the methods and kits disclosed herein comprise the use of one or more polymerases. Examples of polymerases include, but are not limited to, DNA polymerases and RNA polymerases. In some embodiments, the DNA polymerase is a DNA polymerase I, DNA polymerase II, DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, Sulfolobus DNA Polymerase IV, Taq DNA Polymerase, 9° NTMm DNA Polymerase, Deep VentR™ (exo-) DNA Polymerase, Deep VentR™ DNA Polymerase, Hemo KlenTaq™, LongAmp® Taq DNA Polymerase, OneTaq® DNA Polymerase, Phusion® DNA Polymerase, Q5™ High-Fidelity DNA Polymerase, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, phi29 DNA Polymerase, T4 DNA Polymerase, T7 DNA Polymerase, Terminal Transferase, Titanium® Taq Polymerase, KAPA Taq DNA Polymerase and KAPA Taq Hot Start DNA Polymerase.

In some embodiments, the polymerase is an RNA polymerases such as RNA polymerase I, RNA polymerase II, RNA polymerase III, E. coli Poly(A) polymerase, phi6 RNA polymerase (RdRP), Poly(U) polymerase, SP6 RNA polymerase, and T7 RNA polymerase.

VI. Kits and Additional Reagents

Provided herein are articles of manufacture or kits that comprise one or more reagents for carrying out the provided methods. Kits can optionally include one or more components such as instructions for use, devices and additional reagents (e.g., sterilized water or saline solutions for dilution and/or reconstitution of reagents or components), and components, such as tubes, containers and syringes for practice of the methods. In some embodiments, the kits can further contain reagents for collection of samples or preparation and processing of samples. In some embodiments, the kits can be provided as articles of manufacture that include packing materials for the packaging of the reagents and components of the kit. For example, the kits can contain containers, bottles, tubes, vial and any packaging material suitable for separating or organizing the components of the kit.

The methods and kits disclosed herein may comprise the use of one or more reagents. Examples of reagents include, but are not limited to, PCR reagents, ligation reagents, reverse transcription reagents, enzyme reagents, hybridization reagents, sample preparation reagents, affinity capture reagents, solid supports such as beads, and reagents for nucleic acid purification and/or isolation.

A solid support can comprise virtually any insoluble or solid material, and often a solid support composition is selected that is insoluble in water. For example, a solid support can comprise or consist essentially of silica gel, glass (e.g., controlled-pore glass (CPG)), nylon, Sephadex®, Sepharose®, cellulose, a metal surface (e.g., steel, gold, silver, aluminum, silicon and copper), a magnetic material, a plastic material (e.g., polyethylene, polypropylene, polyamide, polyester, polyvinylidene difluoride (PVDF)) and the like. Examples of beads for use according to the embodiments can include an affinity moiety that allows the bead to interact with a nucleic acid molecule. A solid phase (e.g., a bead) can comprise a member of a binding pair (e.g., avidin, streptavidin or derivative thereof). For instance, the bead may be a streptavidin-coated bead and a nucleic acid molecule for immobilization on the bead can include a biotin moiety. In some cases, each polynucleotide molecule can include two affinity moieties, such as biotin, to further stabilize the polynucleotide. Beads can include additional features for use in immobilizing nucleic acids or that can be used in a downstream screening or selection processes. For example, the bead may include a binding moiety, a fluorescent label or a fluorescent quencher. In some cases, the bead can be magnetic. In some instances, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide-dT conjugated beads, silica beads, silica-like beads, anti-biotin microbead, anti-fluorochrome microbead, and BcMag™ Carboxy-Terminated Magnetic Beads. Beads or particles may be swellable (e.g., polymeric beads such as Wang resin) or non-swellable (e.g., CPG). In some embodiments a solid phase is substantially hydrophilic. In some embodiments a solid phase (e.g., a bead) is substantially hydrophobic. In some embodiments a solid phase comprises a member of a binding pair (e.g., avidin, streptavidin or derivative thereof) and is substantially hydrophobic or substantially hydrophilic. In some embodiments, a solid phase comprises a member of a binding pair (e.g., avidin, streptavidin or derivative thereof) and has a binding capacity greater than about 1350 picomoles of free capture agent (e.g., free biotin) per mg solid support. In some embodiments the binding capacity of solid phase comprising a member of a binding pair is greater than 800, 900, 1000, 1100, 1200, 1250, 1300, 1350, 1400, 1450, 1500, 1600, 1800, 2000 picomoles of free capture agent per mg solid support. Other examples of beads that are suitable for the invention are gold colloids or beads such as polystyrene beads or silica beads. Substantially any bead radii may be used. Examples of beads may include beads having a radius ranging from 150 nanometers to 10 microns. Other sizes may also be used.

The methods and kits disclosed herein may comprise the use of one or more buffers. Examples of buffers include, but are not limited to, wash buffers, ligation buffers, hybridization buffers, amplification buffers, and reverse transcription buffers. In some embodiments, the hybridization buffer is a commercially available buffer, such as TMAC Hyb solution, SSPE hybridization solution, and ECONO™ hybridization buffer. The buffers disclosed herein may comprise one or more detergents.

The methods and kits disclosed herein may comprise the use of one or more carriers. Carriers may enhance or improve the efficiency of one or more reactions disclosed herein (e.g., ligation reaction, reverse transcription, amplification, hybridization). Carriers may decrease or prevent non-specific loss of the molecules or any products thereof (e.g., a polynucleotide and/or amplicon). For example, the carrier may decrease non-specific loss of a polynucleotide through absorption to surfaces. The carrier may decrease the affinity of a polynucleotide to a surface or substrate (e.g., container, Eppendorf tube, pipet tip). Alternatively, the carrier may increase the affinity of a polynucleotide to a surface or substrate (e.g., bead, array, glass, slide, or chip). Carriers may protect the polynucleotide from degradation. For example, carriers may protect an RNA molecule from ribonucleases. Alternatively, carriers may protect a DNA molecule from a DNase. Examples of carriers include, but are not limited to, polynucleotides such as DNA and/or RNA, or polypeptides. Examples of DNA carriers include plasmids, vectors, polyadenylated DNA, and DNA polynucleotides. Examples of RNA carriers include polyadenylated RNA, phage RNA, phage MS2 RNA, *E. coli* RNA, yeast RNA, yeast tRNA, mammalian RNA, mammalian tRNA, short polyadenylated synthetic ribonucleotides and RNA polynucleotides. The RNA carrier may be a polyadenylated RNA. Alternatively, the RNA carrier may be a non-polyadenylated RNA. In some embodiments, the carrier is from a bacteria, yeast, or virus. For example, the carrier may be a polynucleotide or a polypeptide derived from a bacteria, yeast or virus. For example, the carrier is a protein from *Bacillus subtilis*. In another example, the carrier is a polynucleotide from *Escherichia coli*. Alternatively, the carrier is a polynucleotide or peptide from a mammal (e.g., human, mouse, goat, rat, cow, sheep, pig, dog, or rabbit), avian, amphibian, or reptile.

The methods and kits disclosed herein may comprise the use of one or more control agents. Control agents may include control polynucleotides, inactive enzymes, and/or non-specific competitors. Alternatively, the control agents comprise bright hybridization, bright probe controls, nucleic acid templates, spike-in controls, PCR amplification controls. The PCR amplification controls may be positive controls. In other instances, the PCR amplification controls are negative controls. The nucleic acid template controls may be of known concentrations. The control agents may comprise one or more labels.

Spike-in controls may be templates that are added to a reaction or sample. For example, a spike-in template may be added to an amplification reaction. The spike-in template may be added to the amplification reaction any time after the first amplification cycle. In some embodiments, the spike-in template is added to an amplification reaction after cycle number 2, 3, 4, 5, 6, 7, 8, 9, 10, 11, 12, 13, 14, 15, 20, 25, 30, 35, 40, 45, or 50. The spike-in template may be added to the amplification reaction any time before the last amplification cycle. The spike-in template may comprise one or more nucleotides or nucleic acid base pairs. The spike-in template may comprise DNA, RNA, or any combination thereof. The spike-in template may comprise one or more labels.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed methods and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

While some embodiments described herein have been shown and described herein, such embodiments are provided by way of example only. Numerous variations, changes, and substitutions will now occur to those skilled in the art without departing from the disclosure provided herein. It should be understood that various alternatives to the embodiments described herein can be employed in practicing the methods described herein.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-91 19102); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al, Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al, Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998).

VII. Definitions

The terminology used herein is for the purpose of describing particular cases only and is not intended to be limiting. Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

The terms "polypeptide" and "protein" are used interchangeably to refer to a polymer of amino acid residues, and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

A polymerase chain reaction (PCR) refers to an in vitro amplification reaction of polynucleotide sequences by the simultaneous primer extension of complementary strands of a double stranded polynucleotide. PCR reactions produce copies of a template polynucleotide flanked by primer binding sites. The result, with two primers, is an exponential increase in template polynucleotide copy number of both strands with each cycle, because with each cycle both strands are replicated. The polynucleotide duplex has termini corresponding to the ends of primers used. PCR can comprise one or more repetitions of denaturing a template polynucleotide, annealing primers to primer binding sites, and extending the primers by a DNA or RNA polymerase in the presence of nucleotides. Particular temperatures, durations at each step, and rates of change between steps depend on many factors well-known to those of ordinary skill in the art. (McPherson et al., IRL Press, Oxford (1991 and 1995)). For example, in a conventional PCR using Taq DNA polymerase, a double stranded template polynucleotide can be denatured at a temperature $>90°$ C., primers can be annealed at a temperature in the range 50-75° C., and primers can be extended at a temperature in the range 72-78° C. In some embodiments, PCR comprises Reverse transcription PCR (RT-PCR), real-time PCR, nested PCR, quantitative PCR, multiplexed PCR, or the like. In some embodiments, PCR does not comprise RT-PCR. (U.S. Pat. Nos. 5,168,038, 5,210,015, 6,174,670, 6,569,627, and 5,925,517; Mackay et al., Nucleic Acids Research, 30: 1292-1305 (2002)). RT-PCR comprises a PCR reaction preceded by a reverse transcription reaction and a resulting cDNA is amplified, Nested PCR comprises a two-stage PCR wherein an amplicon of a first PCR reaction using a first set of primers becomes the sample for a second PCR reaction using a second primer set, at least one of which binds to an interior location of an amplicon of a first PCR reaction. Multiplexed PCR comprises a PCR reaction, wherein a plurality of polynucleotide sequences is subjected to PCR in the same reaction mixture simultaneously. PCR reaction volumes can be anywhere from 0.2 pL-1000 µL. Quantitative PCR comprises a PCR reaction designed to measure an absolute or relative amount, abundance, or concentration of one or more sequences in a sample. Quantitative measurements can include comparing one or more reference sequences or standards to a polynucleotide sequence of interest. (Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); Becker-Andre et al., Nucleic Acids Research, 17: 9437-9446 (1989)).

"Nucleotide," "nucleoside," "nucleotide residue," and "nucleoside residue," as used herein, can mean a deoxyribonucleotide or ribonucleotide residue, or other similar nucleoside analogue capable of serving as a component of a primer suitable for use in an amplification reaction (e.g., PCR reaction). Such nucleosides and derivatives thereof can be used as the building blocks of the primers described herein, except where indicated otherwise. Nothing in this application is meant to preclude the utilization of nucleoside derivatives or bases that have been chemical modified to enhance their stability or usefulness in an amplification reaction, provided that the chemical modification does not interfere with their recognition by a polymerase as deoxyguanine, deoxycytosine, deoxythymidine, or deoxyadenine, as appropriate. In some embodiments, nucleotide analogs can stabilize hybrid formation. In some embodiments, nucleotide analogs can destabilize hybrid formation. In some embodiments, nucleotide analogs can enhance hybridization specificity. In some embodiments, nucleotide analogs can reduce hybridization specificity.

A "nucleic acid", or grammatical equivalents, refers to either a single nucleotide or at least two nucleotides covalently linked together.

A "polynucleotide" or grammatical equivalents refers to at least two nucleotides covalently linked together. A polynucleotide comprises a molecule containing two or more nucleotides. A polynucleotide comprises polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatives of nucleotide bases. The backbone of the polynucleotide can comprise sugars and phosphate groups, or modified or substituted sugar or phosphate groups. A polynucleotide may comprise modified nucleotides, such as methylated nucleotides and nucleotide analogs. The sequence of nucleotides may be interrupted by non-nucleotide components. A polynucleotide can include other molecules, such as another hybridized polynucleotide. Polynucleotides include sequences of deoxyribonucleic acid (DNA), ribonucleic acid (RNA), or both. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Polynucleotides can be isolated from natural sources, recombinant, or artificially synthesized.

Polynucleotides can include nonstandard nucleotides, such as nucleotide analogs or modified nucleotides. In some embodiments, nonstandard nucleotides can stabilize hybrid formation. In some embodiments, nonstandard nucleotides can destabilize hybrid formation. In some embodiments, nonstandard nucleotides can enhance hybridization specificity. In some embodiments, nonstandard nucleotides can reduce hybridization specificity. Examples of nonstandard nucleotide modifications include 2' O-Me, 2' O-allyl, 2' 0-propargyl, 2' O-alkyl, 2' fluoro, 2' arabino, 2' xylo, 2' fluoro arabino, phosphorothioate, phosphorodithioate, phosphoroamidates, 2' Amino, 5-alkyl-substituted pyrimidine, 3' deoxyguanosine, 5-halo-substituted pyrimidine, alkyl-substituted purine, halo-substituted purine, bicyclic nucleotides, 2'MOE, PNA molecules, LNA-molecules, LNA-like molecules, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methyl guanine, 5-methylaminomethyluracil, 5-methoxyaminomethyl-2-thiouracil, beta-D-mannosylqueosine, 5'5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxy acetic acid (v), 5-methyl-2-thiouracil, 3-(3-amino-3-N-2-carboxypropyl) uracil, (acp3)w, 2,6-diaminopurine, and derivatives thereof.

A "subject", "individual", "host" or "patient" refers to a living organism such as a mammal. Examples of subjects and hosts include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., *Xenopus*), and non-mammalian invertebrates, as well as transgenic species thereof. In certain aspects, a subject refers to a single organism (e.g., human). In certain aspects, or a group of individuals composing a small cohort having either a common immune factor to study and/or disease, and/or a cohort of individuals without the disease (e.g., negative/normal control) are provided. A subject from whom samples are obtained can either be inflicted with a disease and/or disorder (e.g., one or more allergies, infections, cancers or autoimmune disorders or the like) and can be compared against a negative control subject which is not affected by the disease.

A "kit" refers to a delivery system for delivering materials or reagents for carrying out a method disclosed herein. In some embodiments, kits include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains a plurality of primers.

A "polypeptide" refers in some aspects to a molecule comprising at least two amino acids. In some embodiments, the polypeptide consists of a single peptide. In some embodiments, a polypeptide comprises two or more peptides. For example, a polypeptide can comprise at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 peptides or amino acids. Examples of polypeptides include, but are not limited to, amino acid chains, proteins, peptides, hormones, polypeptide saccharides, lipids, glycolipids, phospholipids, antibodies, enzymes, kinases, receptors, transcription factors, and ligands.

A "sample" refers in some aspects to a biological, environmental, medical, subject, or patient sample or a sample containing a polynucleotide, such as a target polynucleotide.

"Pharmaceutically acceptable" refers to molecular entities and compositions that are physiologically tolerable and do not typically produce an allergic or similar untoward reaction, such as gastric upset, dizziness and the like, when administered to a human.

"Prevention" refers to prophylaxis, prevention of onset of symptoms, prevention of progression of a disease or disorder associated with excess levels of protein or correlated with protein activity.

"Inhibition," "treatment" and "treating" are used interchangeably and refer to, for example, stasis of symptoms, prolongation of survival, partial or full amelioration of symptoms, and partial or full eradication of a condition, disease or disorder associated with excess levels of protein or correlated with protein activity. For example, treatment of cancer includes, but is not limited to, stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between. Similarly, treatment or partial elimination can include a percent reduction in growth or tumor size and/or volume of about 1%, 2%, 3%, 4%, 5%, 10%, 20%, 30%, 40%, 50%, 60%, 70%, 80%, 90%, 95% or any percentage reduction in between.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The section heading used herein are for organizational purposes only and are not to be construed as limiting the subject matter described.

VIII. Exemplary Embodiments

Among the provided embodiments are:

1. A method of producing a polynucleotide library, the method comprising adding a second adaptor to each of a plurality of barcoded single-stranded polynucleotides at or near a terminal end that is opposite a first adaptor attached to each of the barcoded single-stranded polynucleotides, the plurality of barcoded single-stranded polynucleotides comprising:
  (i) one or more target single-stranded polynucleotide(s) comprising an amplicon of one or more target polynucleotide(s), or a complement(s) thereof, present in a cell of a population of cells; and
  (ii) a collection of single-stranded polynucleotides that each comprise an amplicon of a polynucleotide, or a complement thereof, in the cell; and
  wherein each of the plurality of barcoded single-stranded polynucleotides comprise a vessel barcode that is the same for all polynucleotides from (i) and (ii) from the same cell of the population of cells.

2. The method of embodiment 1, wherein the plurality of barcoded single-stranded polynucleotides comprises polynucleotides of (i) and (ii) of a plurality of cells in the population of cells.

3. The method of embodiment 1 or embodiment 2, wherein each of the plurality of barcoded single-stranded polynucleotides further comprises a molecular barcode that is unique to each single-stranded polynucleotide.

4. The method of any of embodiments 1-3, wherein the collection of single-stranded polynucleotides from each cell of the population of cells, collectively, comprise complementary DNA (cDNA) strands of a transcriptome or a partial transcriptome.

5. The method of any of embodiments 1-4, wherein the transcriptome or partial transcriptome, collectively, comprises at least 60%, 70%, 75%, 80%, 85% 90% 95%, 96%, 97%, 98%, 99% or 100% of the transcripts present in the genome of the cell.

6. The method of any of embodiments 1-5, wherein each of the barcoded single-stranded polynucleotides has a size that is greater than or greater than about 50 base pairs, greater than 100 base pairs, or greater than 200 base pairs.

7. The method of any of embodiments 1-6, wherein each of the barcoded single-stranded polynucleotides has a size from or from about 50 base pairs (bp) to 1500 bp, 50 bp to 1250 bp, 50 bp to 1000 bp, 50 bp to 750 bp, 50 bp to 500 bp, 100 bp to 1500 bp, 100 bp to 1250 bp, 100 bp to 1000 bp, 100 bp to 750 bp, 100 bp to 500 bp, 200 bp to 1500 bp, 200 bp to 1250 bp, 200 bp to 1000 bp, 200 bp to 750 bp or 250 bp to 500 bp.

8. The method of any of embodiments 1-7, wherein adding the second adaptor is carried out in a homogenous mixture comprising the plurality of barcoded-single stranded polynucleotides.

9. The method of any of embodiments 1-8, wherein the first adaptor comprises the vessel barcode.

10. A method of producing a polynucleotide library, the method comprising:
  (a) lysing cells within each of a plurality of vessels, wherein each of said vessels comprises a cell from a sample comprising a population of cells;
  (b) producing, in each vessel, a plurality of complementary polynucleotides, said producing of said plurality of complementary polynucleotides comprising (i) producing one or more target polynucleotide(s) that is complementary to one or more target polynucleotide(s) present in the cell using one or more target-specific primers; and (ii) producing a collection of polynucleotides, each of which complementary to a polynucleotide in the cell, using random oligo primers.

11. The method of embodiment 10, wherein each of said vessels further comprises a plurality of molecular barcoded oligonucleotides, one or a pool of vessel barcoded oligonucleotides, and, optionally, a first adaptor, and the method further comprises:
  (c) attaching to a plurality of, optionally each of the plurality of, complementary polynucleotides one of the plurality of molecular barcoded oligonucleotides, thereby generating a plurality of molecular barcoded polynucleotides each comprising a molecular barcode, optionally wherein the molecular barcode of each of the molecular barcoded polynucleotides is distinct from the molecular barcodes comprised by other molecular barcoded polynucleotides within the plurality and/or is a unique molecular barcode;
  (d) attaching one of the one or a pool of vessel barcoded oligonucleotides and the first adaptor, or an amplified product thereof, to a plurality of, optionally each of, the barcoded polynucleotides, thereby generating a plurality of dual-barcoded polynucleotides, wherein each of the dual-barcoded polynucleotides in the same vessel comprise the same vessel barcode.

12. The method of embodiment 11, further comprising (e) producing a single-stranded amplicon of a plurality of, optionally each of, the plurality of dual-barcoded polynucleotides.

13. The method of embodiment 11, further comprising (f) adding a second adaptor to each of the single-stranded amplicons, wherein the first adaptor and second adaptor are present at or near opposite ends of each of the dual-barcoded single-stranded polynucleotides.

14. A method of producing a polynucleotide library, the method comprising:
   (a) lysing cells within each of a plurality of vessels, wherein each of said vessels comprises a cell from a sample comprising a population of cells, a plurality of molecular barcoded oligonucleotides, and one or a pool of vessel barcoded oligonucleotides, and, optionally, a first adaptor;
   (b) producing, in each vessel, a plurality of complementary polynucleotides, said producing said plurality comprising (i) producing one or more target polynucleotide(s) that is complementary to one or more target polynucleotide(s) present in the cell; and (ii) producing a collection of polynucleotides that each are individually complementary to a polynucleotide in the cell;
   (c) attaching to each complementary polynucleotide one of the plurality of molecular barcoded oligonucleotides, thereby generating a plurality of barcoded polynucleotides each comprising a unique molecular barcode;
   (d) attaching one of the one or a pool of vessel barcoded oligonucleotides, or an amplified products thereof, to each of the barcoded polynucleotides, thereby generating a plurality of dual-barcoded polynucleotides, wherein each of the dual-barcoded polynucleotides in the same vessel comprise the same vessel barcode;
   (e) producing a single-stranded amplicon of each of the plurality of dual-barcoded polynucleotides; and
   (f) adding a second adaptor to each of the single-stranded amplicons, thereby adding the second adaptor to a dual-barcoded single-stranded polynucleotide, wherein the first adaptor and second adaptor are present at or near opposite ends of each of the dual-barcoded single-stranded polynucleotides.

15. The method of any of embodiments 11-14, wherein the first adaptor comprises the vessel barcoded oligonucleotide.

16. The method of any of embodiments 10-15, wherein the collection of polynucleotides from each cell of the population of cells, collectively, comprise sequences complementary to transcripts of a transcriptome or a partial transcriptome of a cell.

17. The method of any of embodiment 16, wherein the transcriptome or partial transcriptome comprises at least 60%, 70%, 75%, 80%, 85% 90% 95%, 96%, 97%, 98%, 99% or 100% of the transcripts present in the genome of the cell.

18. The method of any of embodiments 1-17, wherein the one or more target polynucleotide(s) and/or the polynucleotide in the cell is a DNA.

19. The method of any of embodiments 1-18, wherein the one or more target polynucleotide(s) and/or the polynucleotide in the cell is an RNA.

20. The method of embodiment 19, wherein the RNA is an mRNA. 21. The method of any of embodiments 10-20, wherein each of or one or more of the complementary polynucleotides of (b) is a cDNA.

22. The method of any of embodiments 1-21, wherein each of or one or more of the barcoded single-stranded polynucleotides is a strand of a cDNA.

23. The method of any of embodiments 1-22, wherein the first adaptor and/or second adaptor comprise at least one universal priming site.

24. The method of any of embodiments 1-23, wherein:
   the first adaptor and second adaptor are different; and/or the first adaptor comprises a first universal priming site and the second adaptor comprises a second universal priming site, optionally wherein the first universal priming site and second universal priming site are different.

25. The method of embodiment 24, wherein the first universal priming site and/or second universal priming site is or comprises a P7 priming site (C7) or a contiguous portion thereof or a P5 priming site (C5) or a contiguous portion thereof, optionally wherein the contiguous portion thereof is sufficient to anneal to a complementary sequence.

26. The method of embodiment 24 or embodiment 25, wherein the first universal priming site is or comprises the P7 priming site (C7) or a contiguous portion thereof and the second universal priming site is or comprises the P5 priming site (C5) or a contiguous portion thereof.

27. The method of embodiment 25 or embodiment 26, wherein the P7 priming site (C7) comprises the sequence AGATCGGAAGAGCACACGTCTGAACTCCA (SEQ ID NO:77), or is a contiguous portion thereof.

28. The method of embodiment 25 or embodiment 26, wherein the P5 priming site comprises the sequence AGATCGGAAGAGCGTCGTGTAGGGAAAGAGTGTA-GATCTCGGTGGTCGCCGTATCA TT (SEQ ID NO:78), or is a contiguous portion thereof.

29. The method of any of embodiments 25-28, wherein the contiguous portion comprises at least or at least about 15, 20, 25 or 30 nucleotides in length.

30. The method of any of embodiments 25, 26, 28 or 29, wherein the P5 priming site is a contiguous portion set forth in SEQ ID NO:25 (AGATCGGAAGAGCGTCGTGT).

31. The method of any of embodiments 1-9 and 13-30, wherein adding the second adaptor comprises hybridizing a splint oligonucleotide to each of the barcoded single-stranded polynucleotides in the presence of an oligonucleotide comprising the second universal priming site, wherein the splint oligonucleotide comprises (i) a sequence complementary to the second universal priming site and (ii) a degenerate overhang sequence capable of randomly annealing to the 3' end of the barcoded single-stranded polynucleotide.

32. The method of embodiment 31, wherein, prior to the hybridizing, the splint oligonucleotide and the oligonucleotide comprising the second universal priming site are annealed to form a splint-adaptor duplex.

33. The method of embodiment 31 or embodiment 32, wherein the degenerate overhang sequence comprises the sequence $(N)_{3-12}$, wherein N is any nucleotide.

34. The method of any of embodiments 31-33, wherein the degenerate overhang sequence comprises the sequence NNNNNN, wherein N is any nucleotide (SEQ ID NO:24).

35. The method of any of embodiments 31-34, wherein the splint oligonucleotide comprises the sequence ACACGACGCTCTTCCGATCTNNNNNN, wherein N is any amino acid (SEQ ID NO:26).

36. The method of any of embodiments 31-35, wherein the oligonucleotide comprising the second universal priming site comprises the sequence AGATCG-GAAGAGCGTCGTGT (SEQ ID NO:25).

37. The method of any of embodiments 1-9 and 11-36, wherein the vessel barcoded oligonucleotide comprises at least or about at least 3, 4, 5, 6, 7, 8, 9, 10, 15, 20, 30, 40 or 50 nucleotides.

38. The method of any of embodiments 1-9 and 11-37, wherein the vessel barcoded oligonucleotide comprises from or from about 10 to 30 nucleotides.

39. The method of any of embodiments 1-38, wherein the vessel barcoded oligonucleotide comprises a degenerate sequence.

40. The method of any of embodiments 1-9 and 11-39, wherein the vessel barcoded oligonucleotide comprises the sequence $(N)_{14-17}$, wherein N is any nucleotide, optionally wherein at least one or two N in the sequence is W, wherein W is adenine or thymine.

41. The method of any of embodiments 1-9 and 11-40, wherein the vessel barcoded oligonucleotide comprises the sequence NNNNWNNNNWNNNN (SEQ ID NO:80), WNNNNWNNNNWNNNN (SEQ ID NO:81), NWNNNWNNNNWNNNN (SEQ ID NO:82) or NNWNNNNWNNNNWNNNN (SEQ ID NO:83), wherein N is any nucleotide and W is adenine or thymine.

42. The method of any of embodiments 11-41, wherein each vessel comprises a pool of first adaptors, wherein each vessel barcoded oligonucleotide of the pool of first adaptors comprise at least one base-shift or base addition compared to at least one of the other vessel barcoded oligonucleotides in the pool.

43. The method of embodiment 42, wherein the vessel barcoded oligonucleotides of the pool of first adaptors comprises the sequences NNNNWNNNNWNNNN (SEQ ID NO:80), WNNNNWNNNNWNNNN (SEQ ID NO:81), NWNNNWNNNNWNNNN (SEQ ID NO:82) and NNWNNNNWNNNNWNNNN (SEQ ID NO:83), wherein N is any nucleotide and W is adenine or thymine.

44. The method of any of embodiments 11-43, wherein in step (d) the method further comprises amplifying the one or pool of vessel barcoded oligonucleotides or first adaptors comprising the one or pool of vessel barcoded oligonucleotides, wherein the amplifying is performed prior to or simultaneously with attaching the vessel barcoded oligonucleotide.

45. The method of any of embodiments 11-44, wherein attaching the vessel barcoded oligonucleotide comprises hybridizing a region of the vessel barcoded oligonucleotide to a region of each of the complementary polynucleotides or to a region of each of the molecular barcoded polynucleotides comprising a molecular barcode.

46. The method of embodiment 45, wherein the region comprises a 3' tagging polynucleotide that is complementary to a 5' terminal region of the molecular barcode of the molecular barcoded polynucleotides.

47. The method of any of embodiments 10-46, wherein in step (b):
the one or more target polynucleotide(s) are produced by reverse transcription of the target polynucleotide(s) in the presence of a reverse transcriptase and one or more target-specific primer(s) complementary to a target sequence of the target polynucleotide(s); and/or
the collection of polynucleotides are produced by reverse transcription of polynucleotides in the cell in the presence of a reverse transcriptase and a one or more transcriptome primers complementary to a polynucleotide in the cell.

48. The method of any of embodiments 1-47, wherein the one or more target polynucleotide(s) comprises a polynucleotide of an immune molecule or chain thereof.

49. The method of any of embodiments 1-48, wherein the one or more target polynucleotide(s) comprises at least two target polynucleotides, each comprising a polynucleotide of an immune molecule chain.

50. The method of any of embodiments 1-49, wherein the one or more target polynucleotide(s) comprises a polynucleotide of a TCR or a chain thereof.

51. The method of any of embodiments 1-50, wherein the one or more target polynucleotides comprises a first polynucleotide of a T-cell receptor alpha (TCRα) and a second polynucleotide of a T-cell receptor (TCRβ).

52. The method of any of embodiments 1-50, wherein the one or more target polynucleotide(s) comprises a first polynucleotide of a T-cell receptor gamma (TCRγ) and a second polynucleotide of a T-cell receptor delta (TCRdelta).

53. The method of any of embodiments 1-49, wherein the one or more target polynucleotide(s) comprises a polynucleotide of an antibody or a chain thereof.

54. The method of any of embodiments 1-49 and 53, wherein the one or more target polynucleotide(s) comprises a first polynucleotide of a heavy chain immunoglobulin (IgH) polynucleotide and a second polynucleotide of a light chain immunoglobulin (IgL) polynucleotide.

55. The method of any of embodiments 47-54, wherein the one or more target-specific primers and/or the one or more transcriptome primers comprise a poly (T) sequence.

56. The method of any of embodiments 47-54, wherein the one or more transcriptome primers comprises a mixture of random hexamer oligonucleotide primers.

57. The method of any of embodiments 47-56, wherein the one or more target-specific primers comprises one or more primers complementary to a sequence(s) of the target sequence(s) of the target polynucleotide.

58. The method of embodiment 57, wherein the one or more target-specific primers comprises at least a first primer and a second primer.

59. The method of embodiment 57 or embodiment 58, wherein the one or more target-specific primers comprise primers to a target sequence of a plurality of immune molecules or a chain thereof.

60. The method of embodiment 59, wherein the immune molecule is a T cell receptor or an antibody.

61. The method of any of embodiments 58-60, wherein at least the first primer is complementary to a target sequence of a polynucleotide of a first chain of an immune molecule and a second primer is complementary to a target sequence of a polynucleotide of a second chain of the immune molecule.

62. The method of any of embodiments 58-61, wherein the first and second primer are complementary to a target sequence of different TCR chain polynucleotides of a TCR.

63. The method of any of embodiments 58-62, wherein:
the first primer is complementary to a target sequence of a TCRalpha polynucleotide sequence and the second primer is complementary to a target sequence of a TCRbeta polynucleotide sequence; or
the first primer is complementary to a target sequence of a TCRgamma polynucleotide sequence and the second primer is complementary to a target sequence of a TCRdelta polynucleotide sequence.

64. The method of embodiment 62 or embodiment 63, wherein the target sequence of the TCR chain polynucleotides is a constant region sequence.

65. The method of any of embodiments 58-64, wherein:
the first primer is complementary to a target sequence of a TCRalpha constant region polynucleotide sequence and the second primer is complementary to a target sequence of a TCRbeta constant region polynucleotide sequence; or
the first primer is complementary to a target sequence of a TCRgamma constant region polynucleotide sequence and the second primer is complementary to a target sequence of a TCRdelta constant region polynucleotide sequence.

66. The method of any of embodiments 58-61, wherein at least the first and second primer are complementary to a target sequence of different antibody chain polynucleotides of an antibody.

67. The method of any of embodiments 58-61 and 66, wherein the first primer is complementary to a target sequence of a heavy chain immunoglobulin (IgH) polynucleotide sequence and the second primer is complementary to a target sequence of a light chain immunoglobulin (IgL) polynucleotide sequence.

68. The method of embodiment 66 or embodiment 67, wherein the target sequence of the antibody chain polynucleotides is a constant region sequence.

69. The method of any of embodiments 58-61 and 66-68, wherein the first primer is complementary to a target sequence of a heavy chain constant region (CH) polynucleotide sequence and the second primer is complementary to a target sequence of a light chain constant region (CL) polynucleotide sequence.

70. The method of embodiment 68 or embodiment 69, wherein:
the target sequence of the CH polynucleotide is from IgM, IgD, IgA, IgE or IgG, or combinations thereof; and/or
the target sequence of the CL polynucleotide sequence is from Igkappa, Iglambda or combinations thereof.

71. The method of any of embodiments 1-70, wherein the one or more target polynucleotide(s) comprises a full-length coding sequence.

72. The method of any of embodiments 10-71, wherein the one or more target polynucleotide(s) and the collection of polynucleotides are produced in the vessel in the same reaction volume.

73. The method of any of embodiments 10-72, wherein, in step (b), producing the plurality of complementary polynucleotides comprises use of a non-template terminal transferase, wherein three or more non-template nucleotides, ribonucleotides or analogs thereof are added to the 3' end of each produced complementary polynucleotide.

74. The method of embodiment 73, wherein the non-template terminal transferase is a reverse transcriptase or a polymerase.

75. The method of embodiment 73 or embodiment 74, wherein the non-template terminal transferase is a reverse transcriptase, and wherein the reverse transcriptase is selected from Superscript II reverse transcriptase, Maxima reverse transcriptase, Protoscript II reverse transcriptase, Maloney murine leukemia virus reverse transcriptase (MMLV-RT), HighScriber reverse transcriptase, avian myeloblastosis virus (AMV) reverse transcriptase, any reverse transcriptase comprising terminal deoxynucleotidyl transferase activity, and combinations thereof.

76. The method of any of embodiments 11-75, wherein, in step (c) the attaching comprises hybridizing a region of one of the molecular barcoded oligonucleotides to the three or more non-template nucleotides of each of the complementary polynucleotide.

77. The method of any of embodiments 73-75, wherein the plurality of molecular barcoded oligonucleotides are provided as a plurality of template switch oligonucleotides each comprising a 3' portion complementary to the three or more non-template nucleotides.

78. The method of embodiment 77, wherein the template switch oligonucleotide further comprises a 5' terminal region that is complementary to a 3' tagging oligonucleotide of the first adaptor comprising the vessel barcode.

79. The method of any of embodiments 11-78, wherein:
the reverse transcriptase has template switching activity;
at least some strands of the plurality of produced complementary polynucleotides comprises a 3' overhang comprising three or more non-template nucleotides;
the plurality of molecular barcoded oligonucleotides are provided as a plurality of template switch oligonucleotides each comprising (1) a 5' terminal region that is complementary to a 3' tagging oligonucleotide of the first adaptor comprising the vessel barcode, (2) the molecular barcode and (3) a 3' portion complementary to the three of more non-template nucleotides of the 3' overhang; and
the template switch oligonucleotide serves as a template for the reverse transcriptase, such that the molecular barcode is incorporated into each complementary polynucleotide.

80. The method of any of embodiments 77-79, wherein the 3' portion complementary to the three or more non-template nucleotides comprises a nucleotide, ribonucleotide or analog thereof.

81. The method of any of embodiments 73-80, wherein the three or more non-template nucleotides comprises three or more C nucleotides and the 3' portion complementary to three of more non-template nucleotides comprises one or more G nucleotides or a ribonucleotide or analog thereof.

82. The method of any of embodiments 73-77, wherein the template switch oligonucleotide further comprise a 3' modified nucleotide that blocks extension by a reverse transcriptase or a DNA polymerase.

83. The method of embodiment 82, wherein the modification is a deoxy, phosphate, amino, or alkyl modification of the 3' nucleotide.

84. The method of any of embodiments 11-83, wherein step (d) further comprises extending each of the plurality of complementary molecular barcoded polynucleotides after the attaching.

85. The method of any of embodiments 1-84, wherein the vessel is a well, an emulsion, or a droplet.

86. The method of any of embodiments 12-85, comprising, prior to step (e), combining the contents of two or more of the plurality of vessels, thereby generating a homogenous mixture comprising the two or more of the plurality of dual-barcoded single-stranded polynucleotides.

87. The method of embodiment 86, wherein combining the contents of the plurality of vessels comprises breaking two or more of the plurality of vessels and pooling the dual-barcoded single-stranded polynucleotides from the two or more broken vessels.

88. The method of embodiment 86 or embodiment 87, comprising, prior to step (e), selecting or purifying dual-barcoded single-stranded polynucleotides having a size that is greater than or greater than about 50 base pairs, greater than 100 base pairs, or greater than 200 base pairs.

89. The method of any of embodiments 86-88, comprising, prior to step (e), selecting or purifying dual-barcoded single-stranded polynucleotides having a size from or from about 50 base pairs (bp) to 1500 bp, 50 bp to 1250 bp, 50 bp to 1000 bp, 50 bp to 750 bp, 50 bp to 500 bp, 100 bp to 1500 bp, 100 bp to 1250 bp, 100 bp to 1000 bp, 100 bp to 750 bp, 100 bp to 500 bp, 200 bp to 1500 bp, 200 bp to 1250 bp, 200 bp to 1000 bp, 200 bp to 750 bp or 250 bp to 500 bp.

90. The method of any of embodiments 1-89, wherein the dual-barcoded single-stranded polynucleotides comprise in order (5' to 3'): the first adaptor, the vessel barcode, the molecular barcode and the second adaptor.

91. The method of any of embodiments 1-90, wherein the first adaptor is positioned at or near the 5' region of the dual-barcoded single-stranded polynucleotide.

92. The method of any of embodiments 1-91, wherein the second adaptor is positioned at or near the 3' region of the dual-barcoded single-stranded polynucleotide.

93. The method of any of embodiments 10-92 wherein one or more of steps (a)-(f) is carried out in solution and/or is not carried out in the presence of a solid support, optionally a bead.

94. The method of any of embodiments 11-93, wherein at least steps (c) and (d) are carried out in solution and/or are not carried out in the presence of a solid support, optionally a bead.

95. The method of any of embodiments 10-94, wherein each of steps (a)-(e) is carried out in solution and/or is not carried out in the presence of a solid support, optionally a bead.

96. The method of any of embodiments 1-95, wherein the population of cells comprises at least or about at least $1\times10^3$, $5\times10^3$, $1\times10^4$, $5\times10^4$, $1\times10^5$, $5\times10^5$, $1\times10^6$, or $5\times10^6$ cells.

97. The method of any of embodiments 1-96, wherein the population of cells is from a biological sample from a subject.

98. The method of embodiment 97, wherein the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

99. The method of any of embodiments 1-98, wherein the population of cells comprises immune cells.

100. The method of any of embodiments 1-99, wherein the immune cells comprise lymphocytes or antigen presenting cells.

101. The method of any of embodiments 1-100, wherein the immune cell is a lymphocyte or a subtype thereof, a B cell or a subtype thereof, a T cell or a subtype thereof, or a combination thereof.

102. The method of embodiment 101, wherein the immune cell is a T cell that is a CD4+ and/or CD8+ T cell.

103. The method of any of embodiments 1-102, wherein the population of cells is enriched for or comprises central memory T cells, effector memory T cells, naïve T cells, stem central memory T cells, effector T cells and regulatory T cells.

104. The method of any of embodiments 1-101, wherein the population of cells is enriched for memory B-cells, naïve B-cells or plasmablast B-cells.

105. The method of any of embodiments 97-104, wherein the subject is a human subject.

106. The method of any of embodiments 97-105, wherein the subject has a cancer, an infection or an autoimmune condition.

107. The method of embodiment 106, wherein the infection is a viral, bacterial or fungal infection.

108. The method of any of embodiments 1-107, further comprising amplifying the plurality of barcoded single-stranded polynucleotides, thereby generating a plurality of polynucleotide templates.

109. The method of any of embodiments 1-108, wherein amplification is carried out in the presence of a first primer set comprising a first primer complementary to the first adaptor sequence and a second primer complementary to the second adaptor sequence.

110. The method of embodiment 109, wherein the first and/or second primer is a universal primer.

111. The method of embodiment 110, wherein the first and/or second primer is complementary to the P7 priming site (C7) or a contiguous portion thereof or the P5 priming site (C5) or a contiguous portion thereof.

112. The method of embodiment 110 or embodiment 111, wherein the first primer is complementary to the P7 priming site (C7) or a contiguous portion thereof and the second primer is complementary to the P5 priming site (C5) or a contiguous portion thereof.

113. The method of embodiment 111 or embodiment 112, wherein:
the primer that is complementary to the P7 priming site (C7) or a contiguous portion thereof has or comprises the sequence CAAGCAGAAGACGGCATACGAGAT (SEQ ID NO:39); and/or
the primer that is complementary to the P5 priming site (C5) or a contiguous portion thereof comprises the sequence ACACGACGCTCTTCCGATCT (SEQ ID NO:27).

114. The method of any of embodiments 109-113, wherein the first and/or second primer further comprises a sequencing adaptor.

115. The method of embodiment 114, wherein:
the primer that is complementary to the P7 priming site (C7) or a contiguous portion thereof further comprises the sequence CAAGCAGAAGACGGCATACGAGAT[NNNNNN]GTGACTGGAGTTCAGACGTGTGCTCTTCCGATCT (SEQ ID NO:28); and/or
the primer that is complementary to the P5 priming site (C5) or a contiguous portion thereof comprises the sequence AATGATACGGCGACCACCGAGATCTACACTCTTTCCCTACACGACGCTCTTCC (SEQ ID NO:76).

116. The method of embodiment 115, further comprising purifying each of the plurality of barcoded polynucleotides.

117. A polynucleotide library comprising a plurality of barcoded polynucleotides produced by the method of any of embodiments 1-116.

118. A polynucleotide library, comprising a plurality of barcoded polynucleotides, wherein the plurality of barcoded polynucleotides comprise (i) one or more target polynucleotide(s) comprising an amplicon of one or more target polynucleotide(s) present in a cell of a population of cells; and (ii) a collection of polynucleotides that each comprise an amplicon of a polynucleotide in the cell, wherein each barcoded polynucleotide comprises:
a first adaptor comprising a first universal priming site that is complementary to a first universal primer;
a vessel barcode that is the same for all barcoded polynucleotides from (i) and (ii) from the same cell of the population of cells; and
a second adaptor sequence comprising a second universal priming site that is complementary to a second universal primer.

119. The polynucleotide library of embodiment 118, wherein each of the plurality of barcoded polynucleotides templates comprises a molecular barcode that is unique to each polynucleotide template.

120. The polynucleotide library of embodiment 118 or embodiment 119, wherein the collection of barcoded polynucleotide templates from each cell of the population of cells, collectively, comprise complementary DNA (cDNA) strands of a transcriptome or a partial transcriptome.

121. The polynucleotide library of any of embodiments 118-120, wherein the transcriptome or partial transcriptome, collectively, comprises at least 60%, 70%, 75%, 80%, 85% 90% 95%, 96%, 97%, 98%, 99% or 100% of the transcripts present in the genome of the cell.

122. The polynucleotide library of any of embodiments 118-121, wherein each of the barcoded polynucleotide templates has a size that is greater than or greater than about 50 base pairs, greater than 100 base pairs, or greater than 200 base pairs.

123. The polynucleotide library of any of embodiments 118-122, wherein each of the barcoded single-stranded polynucleotides has a size from or from about 50 base pairs (bp) to 1500 bp, 50 bp to 1250 bp, 50 bp to 1000 bp, 50 bp to 750 bp, 50 bp to 500 bp, 100 bp to 1500 bp, 100 bp to 1250 bp, 100 bp to 1000 bp, 100 bp to 750 bp, 100 bp to 500 bp, 200 bp to 1500 bp, 200 bp to 1250 bp, 200 bp to 1000 bp, 200 bp to 750 bp or 250 bp to 500 bp.

124. The polynucleotide library of any of embodiments 118-123, wherein the first adaptor comprises the vessel barcode.

125. The polynucleotide library of any of embodiments 118-124, wherein the first adaptor and second adaptor are different.

126. The polynucleotide library of any of embodiments 118-125, wherein the first universal priming site and/or second universal priming site is or comprises a P7 priming site (C7) or a contiguous portion thereof or a P5 priming site (C5) or a contiguous portion thereof, optionally wherein the contiguous portion thereof is sufficient to anneal to a complementary sequence.

127. The polynucleotide library of any of embodiments 118-126, wherein the first universal priming site is or comprises the P7 priming site (C7) or a contiguous portion thereof and the second universal priming site is or comprises the P5 priming site (C5) or a contiguous portion thereof.

128. The polynucleotide library of embodiment 126 or embodiment 127, wherein the P7 priming site (C7) comprises the sequence AGATCGGAAGAGCACACGTCT-GAACTCCA (SEQ ID NO:77), or is a contiguous portion thereof.

129. The polynucleotide library of embodiment 126 or embodiment 127, wherein the P5 priming site comprises the sequence AGATCGGAAGAGCGTCGTGTAGG-GAAAGAGTGTAGATCTCGGTGGTCGCCGTATCA TT (SEQ ID NO:78), or is a contiguous portion thereof.

130. The polynucleotide library of any of embodiments 126-129, wherein the contiguous portion comprises at least or at least about 15, 20, 25 or 30 nucleotides in length.

131. The polynucleotide library of embodiment 129 or embodiment 130, wherein the P5 priming site is a contiguous portion set forth in SEQ ID NO:25 (AGATCG-GAAGAGCGTCGTGT).

132. The polynucleotide library of any of embodiments 118-131, wherein the vessel barcoded oligonucleotide comprises at least or about at least 3, 4, 5, 6, 7, 8, 9, 10, 15, 20, 30, 40 or 50 nucleotides.

133. The polynucleotide library of any of embodiments 118-132, wherein the vessel barcoded oligonucleotide comprises from or from about 10 to 30 nucleotides.

134. The polynucleotide library of any of embodiments 118-133, wherein the one or more target polynucleotide(s) comprises a polynucleotide of an immune molecule or chain thereof.

135. The polynucleotide library of any of embodiments 118-134, wherein the one or more target polynucleotide(s) comprises at least two target polynucleotides, each comprising a polynucleotide of an immune molecule chain.

136. The polynucleotide library of any of embodiments 118-135, wherein the one or more target polynucleotide(s) comprises a polynucleotide of a TCR or a chain thereof.

137. The polynucleotide library of any of embodiments 118-136, wherein the one or more target polynucleotides comprises a first polynucleotide of a T-cell receptor alpha (TCRα) and a second polynucleotide of a T-cell receptor (TCRβ).

138. The polynucleotide library of any of embodiments 118-136, wherein the one or more target polynucleotide(s) comprises a first polynucleotide of a T-cell receptor gamma (TCRγ) and a second polynucleotide of a T-cell receptor delta (TCRdelta).

139. The polynucleotide library of any of embodiments 118-135, wherein the one or more target polynucleotide(s) comprises a polynucleotide of an antibody or a chain thereof.

140. The polynucleotide library of any of embodiments 118-135 and 139, wherein the one or more target polynucleotide(s) comprises a first polynucleotide of a heavy chain immunoglobulin (IgH) polynucleotide and a second polynucleotide of a light chain immunoglobulin (IgL) polynucleotide.

141. The polynucleotide library of any of embodiments 118-140, wherein the barcoded polynucleotides comprise in order (5' to 3'): the first adaptor, the vessel barcode, the molecular barcode and the second adaptor.

142. The polynucleotide library of any of embodiments 118-1141, wherein the first adaptor is positioned at or near the 5' region of the dual-barcoded single-stranded polynucleotide.

143. The polynucleotide library of any of embodiments 118-137, wherein the second adaptor is positioned at or near the 3' region of the dual-barcoded single-stranded polynucleotide.

144. A method for sequencing, comprising sequencing one or more the plurality of barcoded polynucleotides produced by any of embodiments 1-116 or from the polynucleotide library of any of embodiments 118-141.

145. The method of embodiment 144, wherein the transcriptome from the plurality of barcoded polynucleotides is sequenced.

146. The method of embodiment 145, further comprising amplifying the whole transcriptome or a portion thereof prior to the sequencing.

147. The method of embodiment 146, wherein amplification is carried out using a first primer set comprising a first primer and second primer specific for the first and second adaptor sequences, respectively.

148. The method of embodiment 146 or embodiment 147, wherein the one or more target polynucleotide(s) from the plurality of barcoded polynucleotides is sequenced.

149. The method of embodiment 148, further comprising amplifying the one or more target polynucleotide(s) from the plurality of polynucleotide templates prior to the sequencing.

150. The method of embodiment 149, wherein the full-length sequence(s) of the one or more target polynucleotide(s) is amplified.

151. The method of embodiment 149 or embodiment 150, wherein amplification is carried out in the presence of a second primer set comprising one or more first primer complementary to one or more target polynucleotide and a second primer complementary to the first adaptor sequence.

152. The method of embodiment 151, wherein the second primer of the second primer set is complementary to the P7 priming site (C7) or a contiguous portion thereof or the P5 priming site (C5) or a contiguous portion thereof.

153. The method of embodiment 151 or embodiment 152, wherein the second primer of the second primer set is complementary to the P7 priming site (C7) or a contiguous portion thereof.

154. The method of any of embodiments 151-153, wherein the second primer of the second primer set has or comprises the sequence CAAGCAGAAGACGGCATACGAGAT (SEQ ID NO:39) or CAAGCAGAAGACGG-CATACGAGAT[NNNNNN]GTGACTGGAGTTCA-GACGTGTGCT CTTCCGATCT (SEQ ID NO:28).

155. The method of any of embodiments 151-154, wherein the one or more first primer complementary to the one or more target polynucleotide is specific to a target sequence of an immune molecule or a chain thereof.

156. The method of embodiment 155, wherein the immune molecule is a T cell receptor or an antibody.

157. The method of embodiment 155 or embodiment 156, wherein the one or more first primers is specific to a target sequence of a constant region of the immune molecule.

158. The method of any of embodiments 155-157, wherein the immune molecule is a TCR and the one or more first primers comprise AGTCTCTCAGCTGGTACACGG (SEQ ID NO:37), ATGGCTCAAACACAGCGACCTC (SEQ ID NO:38) or a combination thereof.

159. The method of any of embodiments 155-158, wherein the immune molecule is an antibody and the one or more first primers comprise any of SEQ ID NOS: 29-36 or a combination thereof.

160. The method of any of embodiments 144-159, comprising determining the cell origin of the one or more barcoded polynucleotides(s).

161. The method of embodiment 160, wherein determining the cell origin comprises identifying sequence information that have the same vessel barcode as being from the same cell.

162. The method of any of embodiments 144-161, wherein the target polynucleotide is an immune molecule comprising a first polynucleotide chain and a second polynucleotide chain and the method comprises matching the first polynucleotide chain and the second polynucleotide chain to the same cell by the presence of the same vessel barcode.

163. The method of any of embodiments 154-162, further comprises quantitating or determining the number of polynucleotides with the same molecular barcode.

164. The method of any of embodiments 154-163, wherein the method comprises identifying transcriptome sequences and target polynucleotide sequences that have the same vessel barcode, thereby identifying transcriptome information of the cell bearing the target polynucleotide(s).

165. A method for transcriptome analysis, the method comprising:
(a) sequencing a target polynucleotide from barcoded polynucleotides from the plurality of barcoded polynucleotides produced by the method of any of embodiments 1-116 or from the plurality of barcoded polynucleotides of the polynucleotide library of any of embodiments 118-141, thereby generating sequence information for the target polynucleotide from the plurality of cells;
(b) sequencing the whole transcriptome or a portion thereof from the from the plurality of barcoded polynucleotides produced by the method of any of embodiments 1-116 or from the plurality of barcoded polynucleotides of the polynucleotide library of any of embodiments 118-141, thereby generating transcriptome data from the plurality of cells; and
(c) identifying sequence information from (a) and from (b) that have the same vessel barcode as being from the same cell.

166. A method of analyzing a transcriptome of a selected single cell, comprising:
(a) amplifying and sequencing a target polynucleotide from the plurality of barcoded polynucleotides produced by the method of any of embodiments 1-116 or from a plurality of the plurality of barcoded polynucleotides of the polynucleotide library of any of embodiments 118-141, thereby generating sequence information for each of the target polynucleotide in at least one of the plurality of cells;
(b) identifying a vessel barcode(s) associated with one of the target polynucleotide sequenced in (a), thereby identifying a selected single cell bearing the target polynucleotide;
(c) amplifying and sequencing the transcriptome or a portion thereof from the plurality of barcoded polynucleotides of the cell bearing the vessel barcode, thereby generating transcriptome data from the selected target polypeptide-expressing cell.

167. The method of embodiment 166, wherein the transcriptome or portion thereof is amplified or sequenced from the selected cell using a primer specific to the vessel barcode identified in (b) and a primer specific to the second adaptor sequence of the barcoded polynucleotides.

168. A method for transcriptome analysis, comprising matching sequence information of the transcriptome or a portion thereof and at least one of the target polynucleotide(s) that are from the same cell, wherein the sequence information is determined from the plurality of barcoded polynucleotides produced by the method of any of embodiments 1-114 or from the plurality of polynucleotide templates of the polynucleotide library of any of embodiments 118-141 or is determined from the method of any of embodiments 154-164.

169. The method of embodiment 168, wherein sequences that have the same vessel barcode are matched as being from the same cell.

170. The method of any of embodiments 165-169, wherein the transcriptome data comprise a parameter, characteristic, feature or phenotype associated with the function or activity of the cell.

171. The method of embodiment 170, wherein the transcriptome data is associated with the activation, exhaustion or proliferation activity of the cell.

IX. Examples

The following examples are included for illustrative purposes only and are not intended to limit the scope of the invention.

Example 1—Barcoding of Transcripts in Emulsion for Single-Cell Polynucleotide Sequencing A. Preparation of Cells Single cell suspensions for carrying out single-cell polynucleotide sequencing were obtained from total peripheral blood mononuclear cells (PBMCs). Approximately 50 mL blood was drawn into Vacutainer CPT Cell Preparation Tubes with sodium heparin (BD), centrifuged for 20 min at 1800×g, washed twice in cell preparation buffer (1×PBS supplemented with 2% fetal bovine serum and 2 mM EDTA), using spins at 200×g to remove platelets, and the resulting PBMCs were cryopreserved in RPMI-1640 medium (Life Technologies)+20% fetal bovine serum+10% DMSO at −80° C. until needed. Prior to emulsion generation, PBMCs were thawed, washed twice by centrifugation (200×g for 10 min) in Cell Buffer: 1× Dulbecco's Phosphate-Buffered Saline (PBS). The cells were then diluted in Cell Buffer to a cell concentration of $3.5 \times 10^6$ cells/mL. The suspension was then pipetted through a 20 μm cell strainer.

B. Barcoding in Emulsion

An emulsion was formed containing the prepared cells and a reaction mixture. The reaction mix was prepared as a 2× concentrate which was mixed at a 1:1 volume ratio with the cell suspension during the droplet formation process.

1. Preparation of the Emulsion Reaction Mixture

An emulsion reaction mixture, containing the reagents and oligonucleotides in Table E1 below, was mixed at room temperature in a PCR-clean hood.

2. Generating Dual-Barcoded Transcript Libraries from Single Cells

Figure 1B:
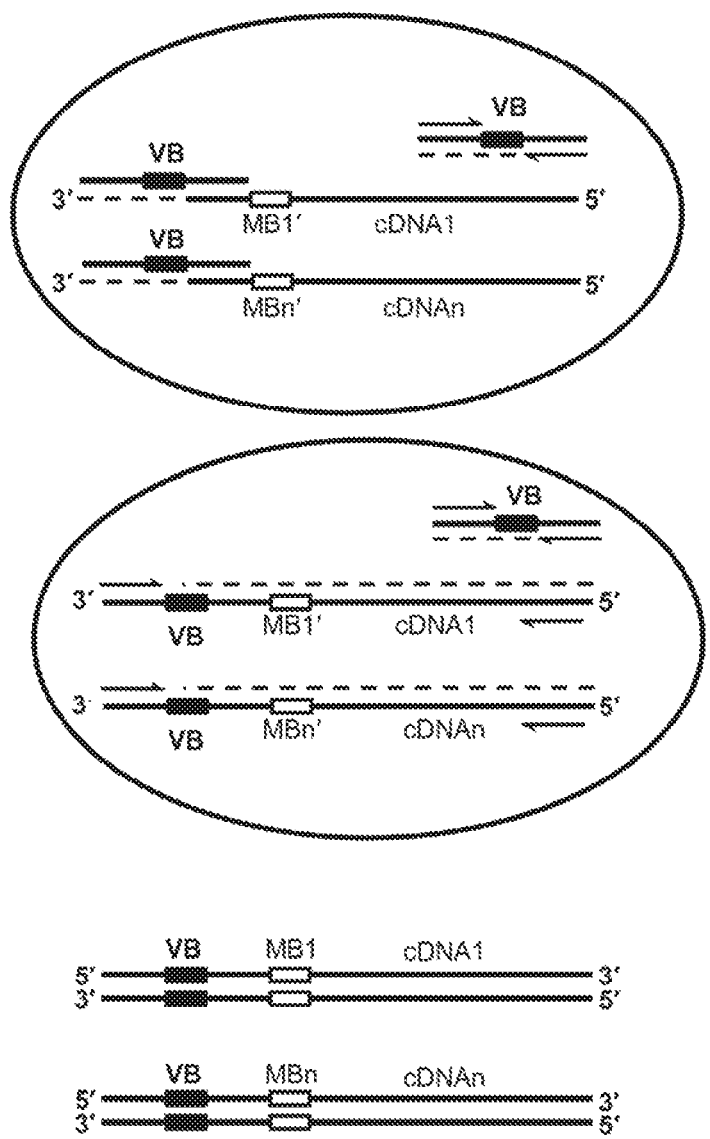
FIG. 1B depicts a schematic of an amplification phase of an exemplary method described herein. The sketch represents a method of amplifying and barcoding two or more polynucleotides, such as a target polynucleotide and one or more genomic or transcriptomic polynucleotides, or paired sequences, such as paired variable Ig (e.g., $V_H$ and $V_L$ mRNAs) and TCR sequences (e.g., $V\alpha/V\beta$ and $V\gamma/V\delta$ mRNAs), for library preparation and immune sequencing. (Top) Independent amplification of Vessel Barcodes (VBs) generates a plurality of copies of identical VBs in each droplet. Molecular barcoded (MB) cDNA molecules are simultaneously tagged with the VBs during annealing and extension phases of amplification. (Middle) Simultaneous amplification of dual barcoded cDNA molecules during amplification cycle. (Bottom) Exemplary dual barcoded cDNA molecules ready for further processing (e.g., purification, size selection, adaptor ligation, amplification, and sequencing).

An overview of an exemplary method of generating dual-barcoded polynucleotide libraries is depicted in FIG. 1A and FIG. 1B. An emulsion was formed using the prepared cells and the reaction mixture. The emulsion generation platform included three Mitos P-Pumps (Dolomite Microfluidics) driven by a single air compressor, each with a Mitos Flow Rate sensor, to allow computer-controlled flow of two aqueous phases and one fluorophilic oil continuous phase into a fluorophilically-coated quartz Dolomite Small 2-Reagent chip. One aqueous input channel contained the cells at the required density to produce the desired cells-per-droplet occupancy level (in some embodiments this

TABLE E1

Emulsion Reaction Mixture

Reagent

Tris-Cl, pH 8.0

MgSO$_4$

DTT dNTPs each

5'biotin oligo-dT

Template switch oligo

VB template molecules/μL

VB primer fwd

VB primer rev

Protease inhibitor (X)

Enzymatic RNase inhibitor (U/μL)

MMLV RNaseH-reverse transcriptase

DNA polymerase

Triton X-100 (% v/v)

Water

Oligonucleotide Sequences

| | |
|---|---|
| 5'biotin oligo-dT anchored reverse transcription primer | /5BiosG//iSp18/TTT TTT TTT TTT TTT TTT TTT TTT T V N (SEQ ID NO: 1) |
| Vessel barcode template | ATCCATCCACGACTGACGGACGTATTAAANNNNWNNNNWNN NNAGATCGGAAGAGCACACGTCTGAACTCCAGTCACC (SEQ ID NO: 2) |
| Template switch oligo | AATACGTCCGTCAGTCGTGGATGNNTNNANNTrGrGG (SEQ ID NO: 3) |
| Vessel barcode forward | CATCCACGACTGACGGACGTATT (SEQ ID NO: 4) |
| Vessel barcode reverse | GTGACTGGAGTTCAGACGTGTGCT (SEQ ID NO: 5) |

/5BiosG/ = 5'biotin modification
/iSp18/ = 18-carbon spacer
V = A, C, or G
N = any base
rG = riboguanosine
W = A or T desired cells-per-droplet occupancy level is one), while the second aqueous channel contained lysis and the reaction mixture.

A 100 µL Hamilton Microliter syringe was used to overload a 100 µL internal diameter PEEK tubing sample loop in two injections of approximately 100 µL each of the reaction mixture. A 100 µL Hamilton Gastight syringe was used to load approximately 110 µL of the cell suspension into a ~110 µL, 0.2 mm internal diameter FEP tubing loop. The loop was attached to a mechanical rotator that was constantly inverting the cell loop approximately once every 1-2 seconds to prevent cells from settling and/or bunching. The emulsion was formed by focused flow jetting of the aqueous phases at identical flow rates through a Dolomite 2-reagent chip with simultaneous oil flow from the two oil channels in the chip. The outer oil channels contained 0.5-5.0% (w/v) polyethylene glycol-based surfactant in HFE7500 (Novec 7500) fluorocarbon oil. The emulsion jet was run at a constant flow rate (equal in cell phase and reaction phase channels). The emulsion chip output was collected through a 12 cm, 0.5 mm internal diameter PEEK tube, by dropping into 0.2 mL PCR strip tubes (Eppendorf) that were kept at approximately 0° C. in a chilled block.

Excess oil was removed from the bottom of each tube with a capillary micropipette. Each emulsion fraction was gently overlayed with 40 µL of Overlay Solution: 25 mM Na-EDTA, pH 8.0.

The emulsions were incubated in a thermal cycler for the transcript tagging reaction. Briefly, during a 45 min reverse transcription (RT) step, RNA was reverse transcribed at 42° C. with a polyA-specific RT primer (oligo-dT primer) (SEQ ID NO:1), with template-switch-based addition of a universal adaptor sequence (SEQ ID NO:3) containing a randomized molecular barcode (see, e.g., FIG. 1A). Following RT, emulsions were subjected to 40 cycles of thermocycling (each cycle: 82° C. for 10 sec, 65° C. for 25 sec) to perform PCR amplification of the vessel barcode templates (SEQ ID NO:2), which were diluted in the initial lysis and reaction mix to 30,000 copies (cp)/µL, generating a concentration in the final mixture of 15,000 cp/µL or ~1 per ~65 pL droplet (see, e.g., FIG. 1B). One end of the vessel barcode (also referred to herein as "droplet barcode") contains the Illumina read 2 ("P7") primer site (SEQ ID NO:77), whereas the other end matches the common sequence of the universal adaptor oligonucleotide (SEQ ID NO:4). Therefore, during PCR, template-switched cDNAs could anneal to amplified vessel barcode strands and become spliced by overlap extension to produce full-length products containing the molecular barcode and vessel barcode sequences.

The methods described above can be adapted to add an adaptor as described in Example 5 and used for transcriptome and target-specific analysis as described in Examples 6-8.

Example 2—Barcoding of Transcripts in Emulsion Using Target-Specific Primers for Single-Cell Polynucleotide Sequencing A. Preparation of Cells 50 mL blood were drawn into Vacutainer CPT Cell Preparation Tubes with sodium heparin (BD), centrifuged for 20 min at 1800× g, washed twice in cell preparation buffer (1× PBS supplemented with 2% fetal bovine serum and 2 mM EDTA), using spins at 200× g to remove platelets, and the resulting PBMCs were cryopreserved in RPMI-1640 medium (Life Technologies)+20% fetal bovine serum+10% DMSO at −80° C. until needed. Prior to emulsion generation, PBMCs were thawed, washed twice in cell preparation buffer and counter. B-cells were isolated using a negative selection-based human B-cell enrichment kit (Stem Cell Technologies). Cells were passed through a 20 micron cell strainer and diluted to 6.2E+06 cells/ml (3 million B-cell experiment) or 3.1E+06 cells/ml (PGT-donor and ovarian tumor experiments) in cell preparation buffer.

B. Immune Receptor Barcoding in Emulsion

The emulsion generation platform consisted of three Mitos P-Pumps (Dolomite Microfluidics) driven by a single air compressor, each with a Mitos Flow Rate sensor, to allow computer-controlled flow of two aqueous phases and one fluorophilic oil continuous phase into a fluorophilically-coated quartz Dolomite Small 2-Reagent chip. One aqueous input channel contained the cells at the required density to produce the desire cells-per-droplet occupancy level, while the second aqueous channel contained lysis and reaction mix, consisting of reaction buffer and oligonucleotides as set forth in Table E2 below, 5 units/µL MuMLV-based reverse transcriptase (Thermo Scientific) and 0.1 units/µL Herculase II PCR polymerase. A 100-µL Hamilton Microliter syringe was used to overload a 100-µL internal diameter PEEK tubing sample loop in two injections of ~100 µL each of LR mix. A 100-µL Hamilton Gastight syringe was used to load ~110 µL of the cell suspension into a ~100-µL, 0.2-mm internal diameter FEP tubing loop. The emulsion was formed by focused flow jetting of the aqueous phases at identical flow rates through the 2-reagent chip with simultaneous oil flow from the two oil channels in the chip. The emulsion leaving the chip exit channel was dripped into 0.2-ml PCR strip tubes (Eppendorf) on a cold block, after which excess oil was removed by pipetting from the bottom of the tube, 40 µL of overlay solution was added (25 mM Na-EDTA, pH 8.0) and tubes were transferred to a standard thermocycler for the transcript tagging reaction.

TABLE E2

| Target-Specific RT Primers | |
|---|---|
| IgM-RT | /biotin/TGTGAGGTGGCTGCGTACTTG (SEQ ID NO: 84) |
| IgG-RT | /biotin/AGGACAGCCGGGAAGGTGT (SEQ ID NO: 85) |
| IgD-RT | /biotin/CACGCATTTGTACTCGCCTTG (SEQ ID NO: 86) |
| IgA-RT | /biotin/CTGGCTRGGTGGGAAGTTTCT (SEQ ID NO: 87) |
| IgE-RT | /biotin/GGTGGCATAGTGACCAGAGA (SEQ ID NO: 88) |

TABLE E2-continued

Target-Specific RT Primers

| | |
|---|---|
| IgK-RT | /biotin/TATTCAGCAGGCACACAACAGA (SEQ ID NO: 89) |
| IgL-RT | /biotin/AGTGTGGCCTTGTTGGCTTG (SEQ ID NO: 90) |
| TCR-A-RT | /biotin/GGGAGATCTCTGCTTCTGATG (SEQ ID NO: 91) |
| TCR-B-RT | /biotin/GGTGAATAGGCAGACAGACTTG (SEQ ID NO: 92) |
| CD4-RT | /biotin/GGCAGTCAATCCGAACACT (SEQ ID NO: 93) |
| CD-8-RT | /biotin/CTACAAAGTGGGCCCTTCTG (SEQ ID NO: 94) |
| IgA-nested | ACACGACGCTCTTCCGATCTGGCTCAGCGGGAAGACCTTG (SEQ ID NO: 44) |
| IgE-nested | ACACGACGCTCTTCCGATCTGGGAAGACGGATGGGCTCTG (SEQ ID NO: 48) |
| IgM-nested | ACACGACGCTCTTCCGATCTGAGACGAGGTGGAAAAGGGTTG (SEQ ID NO: 52) |
| IgD-nested | ACACGACGCTCTTCCGATCTGGAACACATCCGGAGCCTTG (SEQ ID NO: 56) |
| IgG-nested | ACACGACGCTCTTCCGATCTCCAGGGGAAGACSGATG (SEQ ID NO: 40) |
| IgL-nested | ACACGACGCTCTTCCGATCTAGGGYGGGAACAGAGTGAC (SEQ ID NO: 60) |
| IgK-nested | ACACGACGCTCTTCCGATCTGACAGATGGTGCAGCCACAG (SEQ ID NO: 64) |
| TRA-nested | ACACGACGCTCTTCCGATCTCACGGCAGGGTCAGGGTTC (SEQ ID NO: 68) |
| TRB-nested | ACACGACGCTCTTCCGATCTCGACCTCGGGTGGGAACAC (SEQ ID NO: 72) |
| CD4-nested | ACACGACGCTCTTCCGATCTTGTGGCCTTGCCGAGGGAGG (SEQ ID NO: 95) |
| CD8-nested | ACACGACGCTCTTCCGATCTTGCGGAATCCCAGAGGGCCA (SEQ ID NO: 96) |
| C7-bc-P7 | CAAGCAGAAGACGGCATACGAGATNNNNNNNGTGACTGGAGTTCAGACGTGTGCTCTTCCGATCT (SEQ ID NO: 97) |
| C5-P5 | AATGATACGGCGACCACCGAGATCTACACTCTTTCCCTACACGACGCTCTTCCGATCT (SEQ ID NO: 98) |

During a 45-min reverse transcription (RT) step, RNA was reverse transcribed at 42° C. with target-specific RT primers (Table E2) with template-switch-based addition of a universal adaptor sequence containing a randomized molecular barcode as previously described (Shugay, M. et al. Towards error-free profiling of immune repertoires. *Nat. Methods* 11, 653-655 (2014); Islam, S. et al. Highly multiplexed and strand-specific single-cell RNA 5' end sequencing. *Nat. Protoc.* 7, 813-828 (2012)) (see, e.g., FIG. 1A). Following RT, emulsions were subjected to 40 cycles of thermocycling (each cycle: 82° C. for 10 sec, 65° C. for 25 sec) to perform PCR amplification of the droplet barcode templates, which were diluted in the initial lysis and reaction mix to 30,000 cp/μL, generating a concentration in the final mixture of 15,000 cp/μL or ~1 per ~65 pL droplet. One end of the vessel barcode (droplet barcode) comprised the Illumina read 2 ("P7") primer site (SEQ ID NO:77), whereas the other end matched the common sequence of the universal adaptor oligonucleotide (SEQ ID NO:4) (see, e.g., FIG. 1B). Therefore, during PCR, template-switched cDNAs can anneal to amplified vessel barcode strands and become spliced by overlap extension to produce full-length products containing target, molecular barcode and vessel barcode sequences.

The methods described above can be adapted to include primers to reverse transcribe the transcriptome or a portion thereof, such as by inclusion of random hexamer oligonucleotides during the reverse transcription phase. These methods also can be adapted to add an adaptor as described in Example 5 and used for transcriptome and target-specific analysis as described in Examples 6-8.

Example 3—Method of Barcoding Transcripts of a Target Sequence and Transcriptome in Emulsion for Single-Cell Polynucleotide Sequencing A. Preparation of Cells Cryopreserved PBMC suspension was thawed rapidly and added to 10 volumes of RPMI+10% FBS at room temperature. Cells were pelleted by centrifugation at 350×g for 8 minutes and resuspended in RPMI+10% FBS at 2×10^6 cells/mL. PBMCs were rested in a tissue culture incubator for approximately 16 hours.

Rested PBMCs were co-cultured with autologous antigen-presenting cells at a ratio of approximately 10:1 PBMC: APCs. In this case, the APCs were autologous monocyte-derived dendritic cells that had been exposed to irradiated, HSV-infected HeLa cells. The co-culture was incubated for 5 hours. Without intending to be limiting to the method described herein, it is contemplated that an incubation time of about 5 hours is sufficient to allow antigen-specific cells to express new mRNAs in response to antigen, or in response to cytokines released into the media by other cells.

The PBMCs were removed from co-culture by gentle pipetting up and down and moving to a new tube. The cells were placed on ice and washed in CELL buffer (20 g/L fish skin gelatin (Biotium), 155 mM KCl, 0.05% sodium azide, 5 mM HEPES-Na pH 7.5)+2 mM EDTA, then in CELL buffer, and finally strained through a 20-micron mesh strainer and resuspended in CELL buffer. The cells were counted and viability assessed by staining with acridine orange-propidium iodide. The final cell density was adjusted to 3.5×10^6 viable (propidium iodide-negative) cells/mL and kept on ice.

Immediately before emulsion generation, the cell suspension was heated and placed back on ice for 1 min.

B. Barcoding in Emulsion

As in the previous example, an emulsion was formed containing the prepared cells and a reaction mixture for a subsequent transcript tagging reaction to add a molecular barcode and vessel barcode to single cell polynucleotide molecules. The reaction mix is prepared as a 2× concentrate, which is mixed at a 1:1 volume ratio with the cell suspension during the droplet formation process.

1. Preparation of the Emulsion Reaction Mixture

The reaction mix, containing the reagents and oligonucleotides in Table E3 below, was prepared. The VB oligos 1 (SEQ ID NO:6), 2 (SEQ ID NO:7), 3 (SEQ ID NO:8), and 4 (SEQ ID NO:9) were added as an equimolar mixture to produce a base-shifted (staggered) ensemble of amplicons to increase diversity during sequencing. The reaction mixture was loaded into the reaction sample loop of the emulsion generation apparatus described in the previous example.

TABLE E3

| Emulsion Reaction Mixture |
| --- |
| Component |
| Water |
| HEPES-Na, pH 8.0 |
| Triton X-100 (Surfact-Amps, Thermo Sci) |
| dNTPs (each of dATP/dCTP/dTTP/dGTP) |
| VB oligos (containing C7 adaptor sequence) |
| Reverse VB primer |
| Forward VB primer |
| Gene-specific RT primer(s) (each) |
| Template switch oligo (MB barcode) |
| RNase inhibitor |
| Random hexamer oligonucleotides |
| protease inhibitor |
| MgSO$_4$ |
| Dithiothreitol |
| Sodium bicarbonate |
| GTP |
| Guanidine hydrochloride |
| Ammonium sulfate |
| EvaGreen Dye (Biotium) |
| Herculase II fusion polymerase (Agilent) |

TABLE E3-continued

Emulsion Reaction Mixture

Maxima H- reverse transcriptase (Thermo)

| Oligo | Sequence (5'-3') |
|---|---|
| VB (vessel barcode) oligo 1 | T*A*C*G*TCTACGCGCTGCTCTG CCACGACTGACGGACGTATT NNNNWNNNNWNNNNAGATCGGAAG AGCACACGTCTGAACTCCA*G*T*C*A (SEQ ID NO: 6) |
| VB (vessel barcode) oligo 2 | T*A*C*G*TCTACGCGCTGCTCTG CCACGACTGACGGACGTATT WNNNNWNNNNWNNNNAGATCGGAAG AGCACACGTCTGAACTCCA*G*T*C*A (SEQ ID NO: 7) |
| VB (vessel barcode) oligo 3 | T*A*C*G*TCTACGCGCTGCTCTG CCACGACTGACGGACGTATT NWNNNNWNNNNWNNNNAGATCGGAAG AGCACACGTCTGAACTCCA*G*T*C*A (SEQ ID NO: 8) |
| VB (vessel barcode) oligo 4 | T*A*C*G*TCTACGCGCTGCTCTG CCACGACTGACGGACGTATT NNWNNNNWNNNNWNNNNAGATCGGAAG AGCACACGTCTGAACTCCA*G*T*C*A (SEQ ID NO: 9) |
| Forward VB primer | GTGACTGGAGTTCAGACGTGTGCT (SEQ ID NO: 10) |
| Reverse VB primer | TACGTCTACGCGCTGCTCTG (SEQ ID NO: 11) |
| IgG constant RT primer | AGGACAGCC mGmGmG AAGGTGT (SEQ ID NO: 12) |
| IgL constant RT primer | GCTCCCGG mG T mAmG AAGTCA (SEQ ID NO: 13) |
| IgK constant RT primer | GGCCTCTCTG mGmGmA TAGAAGT (SEQ ID NO: 14) |
| IgM constant RT primer | TGTGAGGTGGCT mGmCmG TACTTG (SEQ ID NO: 15) |
| IgA constant RT primer | CTGGCTRGGTG mGmGmA AGTTTCT (SEQ ID NO: 16) |
| IgD constant RT primer | CACGCATTTGT mAmC T mC GCCTTG (SEQ ID NO: 17) |
| IgE constant RT primer | GATGGTGGC mA T mAmG TGACCAG (SEQ ID NO: 18) |
| TRA constant RT primer | TGTTTGAGAATCAA mAmA T mC GGTGAA (SEQ ID NO: 19) |
| TRB constant RT primer | ACGTGGTC mGmGmG AAGAAG (SEQ ID NO: 20) |
| TRG constant RT primer | CAAGAAGACAAA mGmG T mA TGTTCC (SEQ ID NO: 21) |
| TRD constant RT primer | TCTTCTTGGAT mGmAmC ACGAGA (SEQ ID NO: 22) |
| Template switch oligo (Trilink) | AATACGTCCGTCAGTCGTGGATGU/(N)//(N)/T/(N)//(N)/A/(N) //(N)/T/[(po)rG]//[(po)rG]//{3-deoxy guanosine}/ (SEQ ID NO: 23) |

\* indicates a phosphorothioate linkage
N = A/T/C/G
W = A/T
mA/mG/mC = 2' O-methyl A/G/C
U = 2'deoxy uridine
(po)rG = riboguanosine (RNA base)

2. Generating Dual-Barcoded Transcript Libraries from Single Cells

An emulsion was formed using the prepared cells and the reaction mixture. The emulsion generation platform included three Mitos P-Pumps (Dolomite Microfluidics) driven by a single air compressor, each with a Mitos Flow Rate sensor, to allow computer-controlled flow of two aqueous phases and one fluorophilic oil continuous phase into a fluorophilically-coated quartz Dolomite Small 2-Reagent chip. One aqueous input channel contained the cells at the required density to produce the desired cells-per-droplet occupancy level, while the second aqueous channel contained lysis and the reaction mixture.

A 100 µL Hamilton Microliter syringe was used to overload a 100 µL internal diameter PEEK tubing sample loop in two injections of approximately 100 µL each of the reaction mixture. A 100 µL Hamilton Gastight syringe was used to load approximately 110 µL of the cell suspension into a ~110 µL, 0.2 mm internal diameter FEP tubing loop. The loop was attached to a mechanical rotator that was constantly inverting the cell loop approximately once every 1-2 seconds to prevent cells from settling and/or bunching. The emulsion was formed by focused flow jetting of the aqueous phases at identical flow rates through a Dolomite 2-reagent chip with simultaneous oil flow from the two oil channels in the chip. The outer oil channels contained 0.5-5.0% (w/v) polyethylene glycol-based surfactant in HFE7500 (Novec 7500) fluorocarbon oil. The emulsion jet was run at a constant flow rate (equal in cell phase and reaction phase channels). The emulsion chip output was collected through a 12 cm, 0.5 mm internal diameter PEEK tube, by dropping into 4 replicate 0.2 mL PCR strip tubes (Eppendorf) that were kept at approximately 0° C. in a chilled block. Excess oil was removed from the bottom of each tube with a capillary micropipette.

The emulsions were incubated in a thermal cycler for the transcript tagging reaction. Briefly, the reaction was pre-chilled at 4° C. for 10 minutes. Then, during a 45 min reverse transcription (RT) step, RNA was reverse transcribed at 37° C., with target-specific primers or with random priming based on binding of the hexamer oligonucleotides, and template-switch-based addition of a universal adaptor sequence containing a randomized molecular barcode, generating cDNA molecules each with a unique molecular identifier (barcode). Following RT, the temperature was held at 94° C. for 10 min. Emulsions were then subjected to 50 cycles of thermocycling (each cycle: 83° C. for 10 sec (denaturation), 65° C. for 25 sec (extension)) to amplify the vessel barcode oligo. After amplification of the VB oligo, the emulsion was subjected to 10 cycles of higher temperature thermocycling (each cycle: 95° C. for 10 sec (denaturation), 63° C. for 25 sec (annealing), 72° C. for 2 min 20 sec (extension)). After the thermocycling cycles were complete, the emulsion was held at 4° C.

Example 4—Purification of Dual-Barcoded cDNA

For each emulsion fraction tube, following dual-barcoding cDNA transcripts generated in the above Examples, the emulsion was broken (after PCR) by mixing with an equal volume of 1:1 (v:v) perfluorooctanol:FC-40, and EDTA was added to a final concentration of 5 mM to stop DNA polymerization. Approximately 0.1 volume of Qiagen Protease was added and the broken emulsion was incubated at 50° C. for 10 to 15 minutes, followed by heat inactivation of the protease by incubating the tubes at 95° C. for 3 minutes. The tube was briefly centrifuged and the upper aqueous phase was transferred to a new tube.

The dual-barcoded cDNA was concentrated and desalted by purification with 1.8 volumes of AMPure XP (Beckman Coulter) according to the manufacturer's directions. cDNA was eluted from the beads and denatured by adding 8 µL of 0.1 M sodium hydroxide+1 mM EDTA and heating to 50° C. for 3 minutes. If full length products contained biotin due to 5' biotinylation of the RT primer, such full length products were separated from excess droplet barcode PCR products by cleanup on streptavidin beads, After adding 2 µL of 6×DNA loading dye (New England Biolabs), the denatured single-stranded cDNA was separated on a 1.5% (w/v) agarose gel in 30 mM NaOH+1 mM EDTA at 5 V/cm for 35 minutes. After the pH of the gel was neutralized, gel containing cDNA within the size range corresponding to 100-1000 nt was excised, and cDNA was purified from the excised agarose with a DNA recovery kit (e.g., Zymoclean™ Gel DNA Recovery Kit, Zymo Research), with elution into 20 µL of 10 mM Tris-Cl, pH 8.5+0.05% TWEEN® 20. The cDNA was further desalted with 1.8 volumes of AMPure XP beads and eluted into 10.5 µL of 10 mM Tris-Cl, pH 8.0+0.05% TWEEN® 20 by heating at 95° C. for 10 sec and precipitated by placing on ice.

Example 5—Ligation of 3' Adaptor Sequence to Dual-Barcoded cDNA Transcripts

An adaptor sequence, containing a known priming site, was added to the dual-barcoded cDNA transcripts generated as described in Example 3, and after purification as described in Example 4. The addition of the adaptor sequence permits amplification, cloning, or sequencing, such as next-gen sequencing, of the all of the transcripts with a known primer. Several adaptor sequences are known and routinely used for sequencing, such as the exemplary P5 adaptor sequence used herein.

1. Methods of 3' Adaptor Sequence Addition

Several methods were used for adding an adaptor sequence to the unknown 3' end of single-stranded, dual-barcoded cDNA sequences. Ligases, such as Thermostable App ligase (NEB) and CircLigase II (Epicentre), that ligate an ssDNA adaptor, were used to add an adaptor sequence to the 3' end of the dual-barcoded cDNA transcripts. A commercial kit (Swift Biosciences Accel-NGS 1S DNA Kit), based on enzymatic addition of non-templated nucleotides to the 3' end of the cDNA, was also used to add an adaptor sequence. In addition, methods that use a degenerate splint annealed to the adaptor that overhangs the 3' end of the cDNA were used, with degenerate overhangs up to 6 nucleotides (i.e., NNNNNN; SEQ ID NO:24). For the degenerate overhangs, NNNNNN (SEQ ID NO:24) appeared to work the best in the protocols tested.

2. Addition of 3' Adaptor Sequence to Dual-Barcoded cDNA Using a Degenerate Splint with a 6-Nucleotide Overhang A splint-adaptor duplex molecule was formed by mixing the oligonucleotides containing a short P5 priming sequence, /5Phos/AGATCGGAAGAGCGTCGTGT/3AmMO/(SEQ ID NO:25) and a splint oligonucleotide set forth as ACACGACGCTCTTCCGATCT NNNNNN/3AmMO/(SEQ ID NO:26) at a ratio of 1.2:1. Annealing buffer was added to 30 mM HEPES-Na pH 7.5, 0.1 M KCl. The solution was heated at 85° C. for 2 minutes in a thermocycler and allowed to cool to 37° C. for at a rate of 0.1° C./sec.

Dual-barcoded cDNA transcripts, recovered from part A above, were then mixed with the splint-adaptor solution. The adaptors were then ligated to the cDNA transcripts, by adding an equal volume of Blunt/TA Ligase Master Mix (New England Biolabs) to the mixture and incubating at room temperature. Excess adaptor DNA was removed by purifying the mixture with AMPure XP and eluting the DNA in 10 mM Tris-Cl, pH 8.0+0.05% TWEEN® 20.

Example 6—PCR Amplification and Sequencing of Transcriptome Library

A. Amplifying the Library of Polynucleotides

Purified dual-barcoded and universal adaptor-labeled sequences were PCR amplified for 8 cycles, using a forward primer complementary to the C7 universal adaptor sequence (SEQ ID NO:28), located 5' of the dual barcode and coding sequence of the transcript (5' end of the cDNA transcript), and a reverse primer complementary the P5 universal adaptor sequence (SEQ ID NO:27), located 3' of the dual barcode and coding sequence of the transcript (3' end of the cDNA transcript) (PCR0).

The PCR0 reaction mixture (containing adaptor-ligated cDNA (generated in Example 5) DNA polymerase, a C7 forward primer, a P5 reverse primer, dNTPs, and reaction buffer) was initially denatured at 98° C. for 1 min, followed by 8 cycles of thermocycling (each cycle: 98° C. for 10 sec, 69° C. for 20 sec, 72° C. for 10 sec) and a final extension time of 2 min at 72° C. Following completion of the PCR, the mixture was held at 4° C.

Each PCR0-generated cDNA sequence contained a C7 adaptor sequence, sequences of a vessel barcode (for host cell identification), a molecular barcode (for transcript identification), a transcript, and a P5 adaptor sequence. The amplified library (PCR0 product) was then purified using AMPure XP beads and eluted in 10 mM Tris-Cl, pH 8.0+ 0.05% TWEEN® 20.

The purified transcriptome library was then used to sequence one or more of the following: one or more full-length targeted gene(s), such as an immune receptor, the transcriptome of all cells in the emulsion, and/or the transcriptome of one or more selected cell(s) within the emulsion as described below.

B. Sequencing Targeted Genes
1. PCR1: Amplification of Target Gene(s)

To amplify a selected target gene, PCR0 product was amplified using the universal forward primer used for PCR0 (C7-index-P7 primer; SEQ ID NO: 28) and a reverse primer specific to the desired target (s) (e.g., immunoglobulin- or T-cell receptor-specific primers). Exemplary target primers used for the PCR1 reaction are set forth in Table E4 below.

TABLE E4

Exemplary Target-Specific Reverse Primer Sequences

| Target | Primer sequence 5' to 3' |
|---|---|
| IgG constant | AAGTAGTCCTTGACCAGGCAGC (SEQ ID NO: 29) |
| IgL constant | GGCTTGAAGCTCCTCAGAGGA (SEQ ID NO: 30) |
| IgK constant | AGGCACACAACAGAGGCAGTTC (SEQ ID NO: 31) |
| IgM constant | CGACGGGGAATTCTCACAGGAG (SEQ ID NO: 32) |
| IgD constant | TGTCTGCACCCTGATATGATGG (SEQ ID NO: 33) |
| IgA constant 1 | GGGTGCTGCAGAGGCTCAG (SEQ ID NO: 34) |
| IgA constant 2 | GGGTGCTGTCGAGGCTCAG (SEQ ID NO: 35) |
| IgE constant | GGAATGTTTTTGCAGCAGCGGG (SEQ ID NO: 36) |
| TRA constant | AGTCTCTCAGCTGGTACACGG (SEQ ID NO: 37) |
| TRB constant | ATGGCTCAAACACAGCGACCTC (SEQ ID NO: 38) |

The PCR1 reaction mixture (containing PCR0 product (generated in part A above), DNA polymerase, a C7-index-P7 forward primer, a target-specific reverse primer, dNTPs and reaction buffer) was initially denatured at 98° C. for 1 min, followed by 10 cycles of thermocycling (each cycle: 98° C. for 10 sec, 61° C. for 20 sec, 72° C. for 20 sec) and a final extension time of 2 min at 72° C. Following completion of PCR1, the mixture was held at 4° C. The PCR1 product (target gene sequence(s)) was purified with AMPure XP beads, and eluted in 10 mM Tris-Cl, pH 8.0+0.05% TWEEN® 20.

2. PCR2: Amplification of Target Gene, Adding 3'Sequencing Adaptor Sequence

Purified PCR1 product was amplified, using a C7 forward primer (SEQ ID NO: 39) and a target-specific reverse primer containing a universal priming P5short sequence. Exemplary primers used for the PCR2 reaction are set forth in Table E5 below.

TABLE E5

Exemplary PCR2 primers

| Target | Sequence 5' to 3' |
|---|---|
| C7 | CAAGCAGAAGACGGCATACGAGAT (SEQ ID NO: 39) |
| IgG | ACACGACGCTCTTCCGATCTCCAGGGGAAGACSGATG (SEQ ID NO: 40) |
| IgG | ACACGACGCTCTTCCGATCTNCCAGGGGAAGACSGATG (SEQ ID NO: 41) |
| IgG | ACACGACGCTCTTCCGATCTNNCCAGGGGAAGACSGATG (SEQ ID NO: 42) |

TABLE E5-continued

Exemplary PCR2 primers

| Target | Sequence 5' to 3' |
|---|---|
| IgG | ACACGACGCTCTTCCGATCTNNNCCAGGGGGAAGACSGATG (SEQ ID NO: 43) |
| IgA | ACACGACGCTCTTCCGATCTGGCTCAGCGGGAAGACCTTG (SEQ ID NO: 44) |
| IgA | ACACGACGCTCTTCCGATCTNGGCTCAGCGGGAAGACCTTG (SEQ ID NO: 45) |
| IgA | ACACGACGCTCTTCCGATCTNNGGCTCAGCGGGAAGACCTTG (SEQ ID NO: 46) |
| IgA | ACACGACGCTCTTCCGATCTNNNGGCTCAGCGGGAAGACCTTG (SEQ ID NO: 47) |
| IgE | ACACGACGCTCTTCCGATCTGGGAAGACGGATGGGCTCTG (SEQ ID NO: 48) |
| IgE | ACACGACGCTCTTCCGATCTNGGGAAGACGGATGGGCTCTG (SEQ ID NO: 49) |
| IgE | ACACGACGCTCTTCCGATCTNNGGGAAGACGGATGGGCTCTG (SEQ ID NO: 50) |
| IgE | ACACGACGCTCTTCCGATCTNNNGGGAAGACGGATGGGCTCTG (SEQ ID NO: 51) |
| IgM | ACACGACGCTCTTCCGATCTGAGACGAGGTGGAAAAGGGTTG (SEQ ID NO: 52) |
| IgM | ACACGACGCTCTTCCGATCTNGAGACGAGGTGGAAAAGGGTTG (SEQ ID NO: 53) |
| IgM | ACACGACGCTCTTCCGATCTNNGAGACGAGGTGGAAAAGGGTTG (SEQ ID NO: 54) |
| IgM | ACACGACGCTCTTCCGATCTNNNGAGACGAGGTGGAAAAGGGTTG (SEQ ID NO: 55) |
| IgD | ACACGACGCTCTTCCGATCTGGAACACATCCGGAGCCTTG (SEQ ID NO: 56) |
| IgD | ACACGACGCTCTTCCGATCTNGGAACACATCCGGAGCCTTG (SEQ ID NO: 57) |
| IgD | ACACGACGCTCTTCCGATCTNNGGAACACATCCGGAGCCTTG (SEQ ID NO: 58) |
| IgD | ACACGACGCTCTTCCGATCTNNNGGAACACATCCGGAGCCTTG (SEQ ID NO: 59) |
| IgL | ACACGACGCTCTTCCGATCTAGGGYGGGAACAGAGTGAC (SEQ ID NO: 60) |
| IgL | ACACGACGCTCTTCCGATCTNAGGGYGGGAACAGAGTGAC (SEQ ID NO: 61) |
| IgL | ACACGACGCTCTTCCGATCTNNAGGGYGGGAACAGAGTGAC (SEQ ID NO: 62) |
| IgL | ACACGACGCTCTTCCGATCTNNNAGGGYGGGAACAGAGTGAC (SEQ ID NO: 63) |
| IgK | ACACGACGCTCTTCCGATCTGACAGATGGTGCAGCCACAG (SEQ ID NO: 64) |
| IgK | ACACGACGCTCTTCCGATCTNGACAGATGGTGCAGCCACAG (SEQ ID NO: 65) |
| IgK | ACACGACGCTCTTCCGATCTNNGACAGATGGTGCAGCCACAG (SEQ ID NO: 66) |
| IgK | ACACGACGCTCTTCCGATCTNNNGACAGATGGTGCAGCCACAG (SEQ ID NO: 67) |

TABLE E5-continued

Exemplary PCR2 primers

| Target | Sequence 5' to 3' |
|---|---|
| TRA | ACACGACGCTCTTCCGATCTCACGGCAGGGTCAGGGTTC (SEQ ID NO: 68) |
| TRA | ACACGACGCTCTTCCGATCTNCACGGCAGGGTCAGGGTTC (SEQ ID NO: 69) |
| TRA | ACACGACGCTCTTCCGATCTNNCACGGCAGGGTCAGGGTTC (SEQ ID NO: 70) |
| TRA | ACACGACGCTCTTCCGATCTNNNCACGGCAGGGTCAGGGTTC (SEQ ID NO: 71) |
| TRB | ACACGACGCTCTTCCGATCTCGACCTCGGGTGGGAACAC (SEQ ID NO: 72) |
| TRB | ACACGACGCTCTTCCGATCTNCGACCTCGGGTGGGAACAC (SEQ ID NO: 73) |
| TRB | ACACGACGCTCTTCCGATCTNNCGACCTCGGGTGGGAACAC (SEQ ID NO: 74) |
| TRB | ACACGACGCTCTTCCGATCTNNNCGACCTCGGGTGGGAACAC (SEQ ID NO: 75) |

The PCR2 reaction mixture (containing PCR1 product (generated in part B1 above), DNA polymerase, a C7 forward primer (SEQ ID NO: 39), a target-specific-short P5 reverse primer, dNTPs and reaction buffer) was initially denatured at 98° C. for 1 min, followed by 6 cycles of thermocycling (each cycle: 98° C. for 10 sec, 65° C. for 20 sec, 72° C. for 20 sec) and a final extension time of 2 min at 72° C. Following completion of PCR2, the mixture was held at 4° C. The PCR2 product (target gene sequence(s)) was purified with AMPure XP beads, and eluted 10 mM Tris-Cl, pH 8.0+0.05% TWEEN® 20.

3. Quantitative PCR (qPCR3) and Sequencing of Target Gene

Purified PCR2 or PCR0 product was used for quantitative PCR (qPCR) to determine the number of amplification cycles to achieve the qPCR3 endpoint. Pre-amplified adaptor-ligated material from PCR0, or full-length IG or TR material from PCR2, were amplified with C7 (forward; SEQ ID NO:39) and C5-P5 (reverse; SEQ ID NO:76) primers.

Briefly, the qPCR3 reaction mixture (containing PCR0 or PCR2 product (generated in parts A or B1 above, respectively), DNA polymerase, a C7 forward primer (SEQ ID NO:39), a C5-P5 reverse primer (SEQ ID NO:76), dNTPs, EvaGreen, and reaction buffer) was initially denatured at 98° C. for 1 min, followed by 3 cycles of thermocycling (each cycle: 98° C. for 10 sec, 60° C. for 20 sec, 72° C. for 20 sec), followed by 30 cycles of a second round of thermocycling (each cycle: 98° C. for 10 sec, 70° C. for 20 sec, 72° C. for 20 sec). The qPCR intensity plot was inspected to determine the amplification cycle at which fluorescence intensity was maximal but amplification of DNA had not yet ended. This was determined to be the final cycle number for the qPCR3 endpoint.

After determining the number of PCR cycles required to amplify each library to exponential phase, the same PCR was repeated in a non-quantitative fashion to the desired number of cycles and purified with 1 AMPure XP and eluted in 10 mM Tris-Cl, pH 8.0+0.05% TWEEN® 20. Optionally, qPCR3 results were normalized by DASH (Gu et al., Genome Biology 2016, 17:41). Results were analyzed on an Agilent Tapestation D1000 tape, quantified with the KAPA NGS Quant Kit for Illumina, and sequenced with either the Illumina NextSeq high output 75-cycle kit (for example, 32 cycles Read 1, 6 cycles Index Read 17, 54 cycles Read 2) for the adaptor-ligated library, or the Illumina MiSeq V3 600-cycle kit (for example, 325 cycles Read 1, 6 cycles Index Read 17, 300 cycles Read 2) for the full-length IG and TR libraries. In some cases, the NextSeq sequencer used 56 cycles of a Read1, 6 cycles of an Index Read 17 and 33 cycles of Read2.

C. Sequencing Transcriptomes from all Cells

To generate a transcriptome library from all cells, PCR1, PCR2 and qPCR3 reactions are carried out as described above, except replacing the target-specific reverse primers with universal reverse primers directed to the 3' adaptor sequence (e.g., SEQ ID NOS: 27 and 76), for use in combination with the universal forward primers (e.g., SEQ ID NOS: 28 and 39) for amplification. Thus, universal forward and reverse primers can be used to sequence of all the transcripts of all cells in the emulsion.

D. Sequencing Transcriptome from Selected Cells

To generate a transcriptome library from selected cells, PCR1, PCR2 and qPCR3 reactions are carried out as described above, except using forward primers that are complementary to the vessel barcode (VB) of a desired cell or cells, such as a cell or cells containing an Ig molecule or TCR of interest sequenced in part A above, and universal reverse primers directed to the 3' adaptor sequence (e.g., SEQ ID NOS: 27 and 76).

Example 7—Analysis of Sequence Data

Illumina MiSeq reads were processed to generate full length consensus sequences for mRNA molecules and droplets, annotated with IgBLAST and IMGT/HighV-QUEST, and processed with custom scripts and the Change-0 package to generate statistics and figures. MiSeq reads were de-multiplexed using Illumina software. Positions with less than Phred quality 5 were masked with Ns. Isotype-specific primers, vessel barcodes (VBs), molecular barcodes (MBs), and adaptor sequences were identified in the amplicon and trimmed, using pRESTO MaskPrimers-cut with a maximum error of 0.2.

A. Analysis of Selected Immune Receptor Sequence Data
Sequence Data

In one example, full-length sequences of targeted immune receptors were prepared and sequenced. A read 1 consensus sequence and a read 2 consensus sequence was generated separately for each mRNA from reads grouped by unique molecular identifier (UMI) comprising the VB and MB together, which are PCR replicates arising from the same original mRNA molecule of origin. UMI read groups were aligned with MUSCLE, and pRESTO was used to build consensus sequences with the following parameters: maxdiv=0.1; bf PRIMER; prfreq=0.6; maxmiss=0.5; q=5; >60% of called PCR primer sequence agreement for the read group; maximum nucleotide diversity=0.1; using majority rule on indel positions; and masking alignment columns with low posterior (consensus) quality. Paired end consensus sequences were then stitched in two rounds. First, ungapped alignment of each read pair's consensus sequence termini was optimized using a Z-score approximation and scored with a binomial p-value as implemented in pRESTO AssemblePairs-align with the following parameters: minimum length=8; alpha $1\times10^5$; and maximum error=0.3. For read pairs failing to stitch this way, stitching was attempted using the human BCR and TCR germline V exons to scaffold each read prior to stitching or gapped readjoining, using pRESTO's AssemblePairs-reference parameters: minimum identity=0.5; e value 1×10 5.

1. V D J Segment Annotation and Isotype Confirmation

IgBLAST, Change-0, and custom scripts were used to identify the germline V(D)J genes of origin, trim mRNA sequences to a V(D)J region, identify CDR3 regions, and calculate the mutation from germline V nucleotide sequences. IgBLAST counts Ns as mismatches but mRNA sequences with more than 6 V-region Ns were filtered for mutation analyses and cross-fraction pairing precision analysis. For IG heavy chains, isotype identity was confirmed by matching non-primer C-regions (constant region exons) to expected sequences using pRESTO MaskPrimers-score parameters: start=0; maximum error=0.2. Amplicons with discordant primer/non-primer C-region calls were discarded, except for two primer/non-primer combinations where a specific primer crosstalk event was resolved by visual inspection.

2. Grouping V(D)J Sequences into Clonal Lineages

V(D)J sequences were grouped into clones using single-linkage clustering with a weighted intraclonal distance. Clustering was performed with Change-0 package Define-Clones—by group parameters: model=min; gene=first; dist=4.0; norm=none. First, all functional Ig $V_H$ chains' droplet consensus sequences were binned into V-J junction bins, such that sequences possibly arising from the same initial recombination event were binned together (based on best matching Ig $V_H$ gene, best matching Ig $J_H$ gene, and junction length as identified by IMGT/HighV-QUEST. The intraclonal distance threshold was chosen by generating a histogram of nearest-neighbor distances within each Ig $V_H$ bin using the distToNearest function of Change-0's shm package, and visually inspecting the histogram for a natural distance cutoff (in the trough of a bimodal histogram). Light chains' clonal clusters were defined using the same distance model and threshold.

3. Droplet Filtering, Pairing Fidelity Calculation

Heavy-light pairing confidence was assessed in two independent ways: using intradroplet mRNA sequence agreement, and inter-replicate pair agreement. Intradroplet mRNA agreement was defined as mean pairwise nucleotide difference (Nei's pi<0.02) of V(D)J sequences within a locus. mRNA sequences were trimmed down to V(D)J nucleotide coding sequences using IgBLAST annotations. Within each droplet all productive mRNA sequences were grouped by V locus. Within each group, multiple sequences were aligned using MUSCLE as implemented in pRESTO AlignSets using default parameters. Droplet consensus chains were built from multiple mRNAs per locus using the pRESTO parameters: BuildConsensus.py; maximum div=0.2; maximum miss=0.5. Randomly shuffled droplets were used to select the diversity cutoff pi<0.02. In shuffled droplets, less than 0.01% of heavy chain loci (<0.2% of light chain loci) met this criteria. Multi-cell or immune-receptor included droplets were separated for further precision analysis.

Pairing precision was calculated based on observation of the same clone-pair across multiple replicates (separate emulsion experiments), focusing on those VDJ clusters likely containing only a single lineage, i.e., arising from a single V(D)J and VJ rearrangement followed by expansion. Similar VDJ rearrangements can arise within an individual multiple independent times, leading to the same heavy chain V(D)J rearrangement natively paired with multiple different light chain VJ rearrangements. Because rare V(D)J rearrangements would provide a more accurate measure of the technical precision achieved by the methods described herein, long heavy CDR3s (CDR3H) for a focus for this analysis (as a proxy for rarer V(D)J rearrangements). Sequences with >6Ns were also removed to increase clonal assignment confidence. Pairing precision increased with CDR 3 H length to over 96% for the longest quartile of clones observed across fractions (2,604 clones with junction length ≥54 nt). Because the probability of clone-pair agreements is the joint probability of true pairs in two independent experiments, pairing precision was estimated as the square root of the pairing agreement across replicates, calculated as follows where $d_{h1}{}^f$ is the number of vessel barcodes d with paired heavy clone h and light clone 1, and found in physical fraction f. Mean (squared) pairing precision for each experiment is estimated by averaging, over heavy clones h and all pairs of fractions (f, g), the agreement of paired light clones (1, k):

$$(\text{precision}^2) =$$

$$\text{mean}(P_f P_g) = \frac{\text{consistent heavy light pairs across fractions}}{\text{total pairs where heavy clone seen across fractions}}$$

$$\frac{\text{consistent heavy tight pairs}}{\text{consistent pairs} + \text{inconsistent pairs}} = \frac{\Sigma_h \left( \sum_{i=k}^{f+g} d_{hl}^f \cdot d_{hk}^g \right)}{\Sigma_k \left( \sum_{i=k}^{f+g} d_{kl}^f \cdot d_{hk}^g + \sum_{i \neq k}^{f+g} d_{hl}^f \cdot d_{hk}^g \right)}$$

$$\{\text{precision}^2\} = \frac{33157}{35922}$$

Therefore the mean precision of each experiment, (to within the variance in precision between experiments) was 96.1% according to this exemplary experiment.

B. Transcriptome Sequence Data Analysis

For transcriptome sequence data, reads comprising the same VB were collapsed, and sequences were aligned to a human reference genome to identify transcripts (HiSAT2). The alignment of the output file was manipulated using samtools, and reads were assigned to transcripts by genomic location.

For each VB-genome mapping, the reads were collapsed by MB. A matrix was built of MB counts, mapped to each individual reference gene per droplet. These data were then merged with target data, e.g., immune receptor sequence data processed as described above in part A. Data from each VB (droplet) were annotated with gene counts and receptor information. The combined data sets were then analyzed to examine the single-cell RNA sequence profile (scRNAseq). Dimensional reduction, clustering and visualization were carried out using t-SNE, Seurat, ZIFA, PCA, LDA, and other exemplary programs.

Example 8—Exemplary High Throuphut Transcriptome Sequence Data Analysis and Plotting from a Multitude of Single Cells About 7,000 PBMCs were prepared and the transcriptomes and full-length BCR and TCR receptors were sequenced as generally described in Examples 4A and 4B, above.

Prior to analysis by Illumina NextSeq, the transcriptome sequencing libraries of the emulsion, prepared as described in Example 4B, were analyzed by D1000 DNA tapestation. The transcriptome was represented by sequences ranging in size from approximately 170-900 bp. The full-length TCR sequences, sequenced by targeted-sequencing described in Example 4A, were also analyzed by D1000 DNA tapestation prior to NextSeq analysis, which indicated TCR alpha and beta peaks at 628 and 664 bp, respectively.

Figure 3:
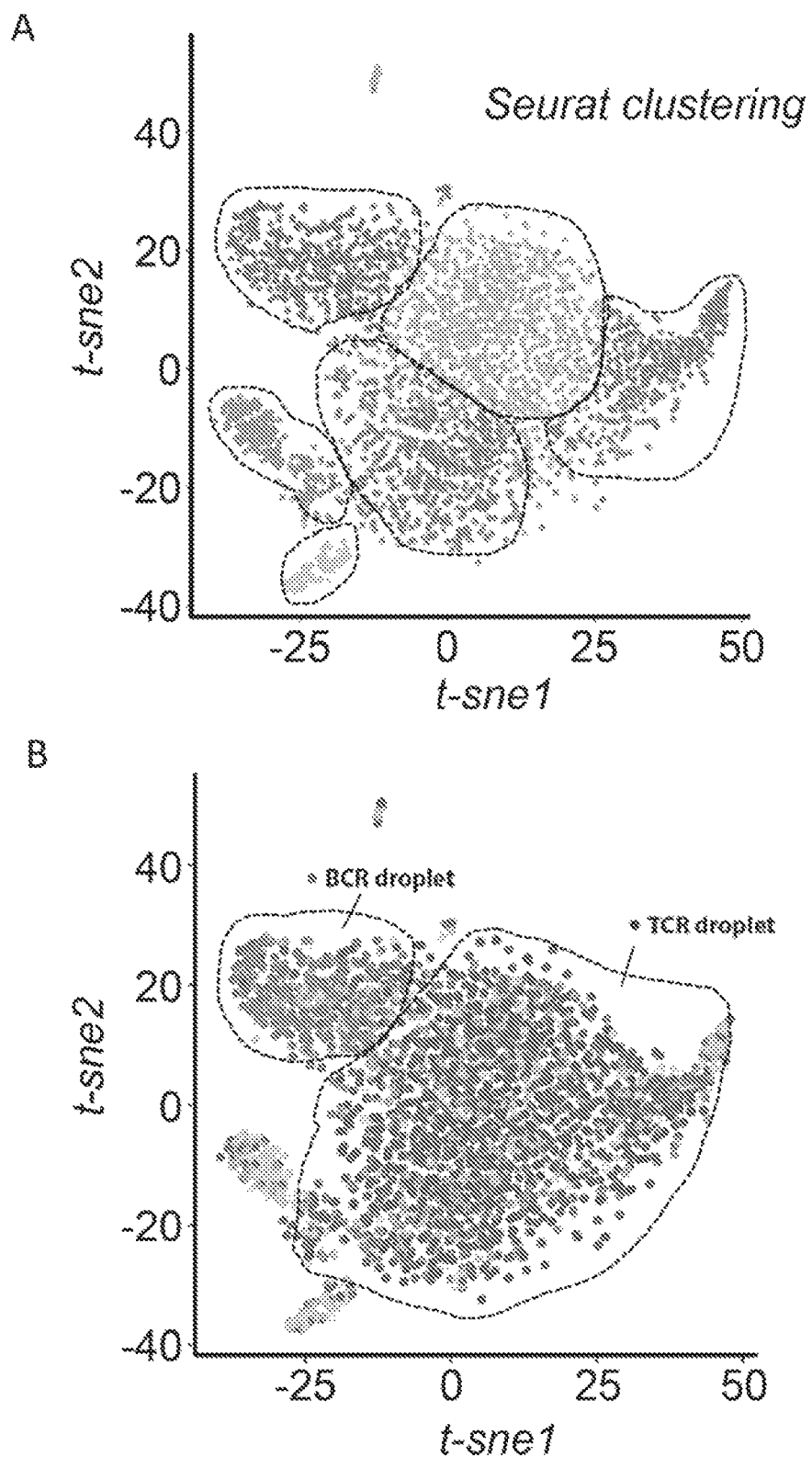
FIG. 3 depicts t-SNE plots of single-cell transcriptome data, colored by inferred cluster identity according to the Seurat software tool (A; dashed lines indicate clusters of events exhibiting predominantly the same color) or colored by the type of full-length immune receptor sequenced, B cell receptor (BCR) or T cell receptor (TCR) (B; dashed lines indicate clusters of events exhibiting predominantly the same color).

After NextSeq analysis, all droplet cell profiles with >1,000 reads (n=6,707) were analyzed by t-distributed stochastic neighbor embedding (t-SNE) and Seurat clustering. The multidimensional, single-cell transcriptome data were visualized using t-SNE plots, and the cells were color-coded based on Seurat clustering of cells with a similar transcriptional profile (FIG. 3A) or by the nature of the sequenced immune receptor (i.e., BCR (red/medium grey) or TCR (green/dark grey)) (FIG. 3B), demonstrating clustering of cells with similar phenotypes.

Transcriptome data for exemplary genes in sequenced cells were analyzed and sequence information with the same vessel barcode as the sequenced immune receptor were identified as being from the same cell. Single-cell transcriptome data for the exemplary genes in the transcriptome were color-coded based on a heat map of levels of expression and are shown for Toll-like receptor 7 (TLR7; FIG. 4A), T-cell surface glycoprotein CD3 epsilon chain (CD3E; FIG. 4B), natural killer cell granule protein 7 (NKG7; FIG. 4C), MRC1 mannose receptor C-type 1 (MRC1; FIG. 4D).

These results indicate that genome-wide RNA expression profiles can be captured alongside immune receptors in a high throughput manner, since gene markers associated with T cells (CD3E) or B cells (TLR7) generally clustered together in cells expressing a full-length TCR or BCR, respectively. Likewise, gene markers that are not associated with T cells or B cells, such as the exemplary NK cell marker NKG7 or the exemplary monocyte marker MRC1, did not appear to cluster in cells with the full-length TCR or BCR immune receptors.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| # | SEQUENCE | ANNOTATION |
|---|----------|------------|
| 1 | /5BiosG//iSp18/TTT TTT TTT TTT TTT TTT TTT TTT T V N | 5'biotin oligo-dT anchored reverse transcription primer |
| 2 | ATCCATCCACGACTGACGGACGTATTAAANNNNWNNN NWNNNNAGATCGGAAGAGCACACGTCTGAACTCCAGT CACC | vessel barcode template oligo |
| 3 | AATACGTCCGTCAGTCGTGGATGNNNTNNANNTrGrGG | template switch oligo |
| 4 | CATCCACGACTGACGGACGTATT | vessel barcode forward primer/universal adaptor oligonucleotide |
| 5 | GTGACTGGAGTTCAGACGTGTGCT | vessel barcode reverse primer |
| 6 | T*A*C*G*TCTACGCGCTGCTCTG CCACGACTGACGGACGTATT NNNNWNNNNWNNNNAGATCGGAAG AGCACACGTCTGAACTCCA*G*T*C*A | vessel barcode oligo 1 |
| 7 | T*A*C*G*TCTACGCGCTGCTCTG CCACGACTGACGGACGTATT WNNNNWNNNNWNNNNAAGATCGGAAG AGCACACGTCTGAACTCCA*G*T*C*A | vessel barcode oligo 2 |
| 8 | T*A*C*G*TCTACGCGCTGCTCTG CCACGACTGACGGACGTATT NWNNNNWNNNNWNNNNAGATCGGAAG AGCACACGTCTGAACTCCA*G*T*C*A | vessel barcode oligo 3 |
| 9 | T*A*C*G*TCTACGCGCTGCTCTG CCACGACTGACGGACGTATT NNWNNNNWNNNNWNNNNAGATCGGAAG AGCACACGTCTGAACTCCA*G*T*C*A | vessel barcode oligo 4 |

-continued

| # | SEQUENCE | ANNOTATION |
|---|---|---|
| 10 | GTGACTGGAGTTCAGACGTGTGCT | vessel barcode forward primer |
| 11 | TACGTCTACGCGCTGCTCTG | vessel barcode reverse primer |
| 12 | AGGACAGCC mGmGmG AAGGTGT | IgG constant RT primer |
| 13 | GCTCCCGG mG T mAmG AAGTCA | IgL constant RT primer |
| 14 | GGCCTCTCTG mGmGmA TAGAAGT | IgK constant RT primer |
| 15 | TGTGAGGTGGCT mGmCmG TACTTG | IgM constant RT primer |
| 16 | CTGGCTRGGTG mGmGmA AGTTTCT | IgA constant RT primer |
| 17 | CACGCATTTGT mAmC T mC GCCTTG | IgD constant RT primer |
| 18 | GATGGTGGC mA T mAmG TGACCAG | IgE constant RT primer |
| 19 | TGTTTGAGAATCAA mAmA T mC GGTGAA | TRA constant RT primer |
| 20 | ACGTGGTC mGmGmG GAAGAAG | TRB constant RT primer |
| 21 | CAAGAAGACAAA mGmG T mA TGTTCC | TRG constant RT primer |
| 22 | TCTTCTTGGAT mGmAmC ACGAGA | TRD constant RT primer |
| 23 | AATACGTCCGTCAGTCGTGGATGU/(N)//(N)/T/(N)//(N)/A/(N)//(N)/T/[(po)rG]//[(po)rG]//{3-deoxy guanosine}/ | template switch oligo (Trilink) |
| 24 | NNNNNN | degenerate overhangs |
| 25 | /5Phos/AGATCGGAAGAGCGTCGTGT/3AmMO | short P5 priming sequence |
| 26 | ACACGACGCTCTTCCGATCT NNNNNN/3AmMO/ | splint oligonucleotide |
| 27 | ACACGACGCTCTTCCGATCT | short P5 reverse primer |
| 28 | CAAGCAGAAGACGGCATACGAGAT[NNNNNN]GTGACTGGAGTTCAGACGTGTGCTCTTCCGATCT | C7-index-P7 forward primer |
| 29 | AAGTAGTCCTTGACCAGGCAGC | IgG constant reverse primer sequence |
| 30 | GGCTTGAAGCTCCTCAGAGGA | IgL constant reverse primer sequence |
| 31 | AGGCACACAACAGAGGCAGTTC | IgK constant reverse primer sequence |
| 32 | CGACGGGGAATTCTCACAGGAG | IgM constant reverse primer sequence |
| 33 | TGTCTGCACCCTGATATGATGG | IgD constant reverse primer sequence |
| 34 | GGGTGCTGCAGAGGCTCAG | IgA constant 1 reverse primer sequence |
| 35 | GGGTGCTGTCGAGGCTCAG | IgA constant 2 reverse primer sequence |
| 36 | GGAATGTTTTTGCAGCAGCGGG | IgE constant reverse primer sequence |
| 37 | AGTCTCTCAGCTGGTACACGG | TRA constant reverse primer sequence |
| 38 | ATGGCTCAAACACAGCGACCTC | TRB constant reverse primer sequence |
| 39 | CAAGCAGAAGACGGCATACGAGAT | C7 |

| # | SEQUENCE | ANNOTATION |
|---|---|---|
| 40 | ACACGACGCTCTTCCGATCTCCAGGGGGAAGACSGATG | IgG adaptor-tagged target-specific reverse primer sequence |
| 41 | ACACGACGCTCTTCCGATCTNCCAGGGGGAAGACSGATG | IgG adaptor-tagged target-specific reverse primer sequence |
| 42 | ACACGACGCTCTTCCGATCTNNCCAGGGGGAAGACSGATG | IgG adaptor-tagged target-specific reverse primer sequence |
| 43 | ACACGACGCTCTTCCGATCTNNNCCAGGGGGAAGACSGATG | IgG adaptor-tagged target-specific reverse primer sequence |
| 44 | ACACGACGCTCTTCCGATCTGGCTCAGCGGGAAGACCTTG | IgA adaptor-tagged target-specific reverse primer sequence |
| 45 | ACACGACGCTCTTCCGATCTNGGCTCAGCGGGAAGACCTTG | IgA adaptor-tagged target-specific reverse primer sequence |
| 46 | ACACGACGCTCTTCCGATCTNNGGCTCAGCGGGAAGACCTTG | IgA adaptor-tagged target-specific reverse primer sequence |
| 47 | ACACGACGCTCTTCCGATCTNNNGGCTCAGCGGGAAGACCTTG | IgA adaptor-tagged target-specific reverse primer sequence |
| 48 | ACACGACGCTCTTCCGATCTGGGAAGACGGATGGGCTCTG | IgE adaptor-tagged target-specific reverse primer sequence |
| 49 | ACACGACGCTCTTCCGATCTNGGGAAGACGGATGGGCTCTG | IgE adaptor-tagged target-specific reverse primer sequence |
| 50 | ACACGACGCTCTTCCGATCTNNGGGAAGACGGATGGGCTCTG | IgE adaptor-tagged target-specific reverse primer sequence |
| 51 | ACACGACGCTCTTCCGATCTNNNGGGAAGACGGATGGGCTCTG | IgE adaptor-tagged target-specific reverse primer sequence |
| 52 | ACACGACGCTCTTCCGATCTGAGACGAGGTGGAAAAGGGTTG | IgM adaptor-tagged target-specific reverse primer sequence |
| 53 | ACACGACGCTCTTCCGATCTNGAGACGAGGTGGAAAAGGGTTG | IgM adaptor-tagged target-specific reverse primer sequence |
| 54 | ACACGACGCTCTTCCGATCTNNGAGACGAGGTGGAAAAGGGTTG | IgM adaptor-tagged target-specific reverse primer sequence |
| 55 | ACACGACGCTCTTCCGATCTNNNGAGACGAGGTGGAAAAGGGTTG | IgM adaptor-tagged target-specific reverse primer sequence |
| 56 | ACACGACGCTCTTCCGATCTGGAACACATCCGGAGCCTTG | IgD adaptor-tagged target-specific reverse primer sequence |
| 57 | ACACGACGCTCTTCCGATCTNGGAACACATCCGGAGCCTTG | IgD adaptor-tagged target-specific reverse primer sequence |

| # | SEQUENCE | ANNOTATION |
|---|---|---|
| 58 | ACACGACGCTCTTCCGATCTNNGGAACACATCCGGAGCCTTG | IgD adaptor-tagged target-specific reverse primer sequence |
| 59 | ACACGACGCTCTTCCGATCTNNNGGAACACATCCGGAGCCTTG | IgD adaptor-tagged target-specific reverse primer sequence |
| 60 | ACACGACGCTCTTCCGATCTAGGGYGGGAACAGAGTGAC | IgL adaptor-tagged target-specific reverse primer sequence |
| 61 | ACACGACGCTCTTCCGATCTNAGGGYGGGAACAGAGTGAC | IgL adaptor-tagged target-specific reverse primer sequence |
| 62 | ACACGACGCTCTTCCGATCTNNAGGGYGGGAACAGAGTGAC | IgL adaptor-tagged target-specific reverse primer sequence |
| 63 | ACACGACGCTCTTCCGATCTNNNAGGGYGGGAACAGAGTGAC | IgL adaptor-tagged target-specific reverse primer sequence |
| 64 | ACACGACGCTCTTCCGATCTGACAGATGGTGCAGCCACAG | IgK adaptor-tagged target-specific reverse primer sequence |
| 65 | ACACGACGCTCTTCCGATCTNGACAGATGGTGCAGCCACAG | IgK adaptor-tagged target-specific reverse primer sequence |
| 66 | ACACGACGCTCTTCCGATCTNNGACAGATGGTGCAGCCACAG | IgK adaptor-tagged target-specific reverse primer sequence |
| 67 | ACACGACGCTCTTCCGATCTNNNGACAGATGGTGCAGCCACAG | IgK adaptor-tagged target-specific reverse primer sequence |
| 68 | ACACGACGCTCTTCCGATCTCACGGCAGGGTCAGGGTTC | TRA adaptor-tagged target-specific reverse primer sequence |
| 69 | ACACGACGCTCTTCCGATCTNCACGGCAGGGTCAGGGTTC | TRA adaptor-tagged target-specific reverse primer sequence |
| 70 | ACACGACGCTCTTCCGATCTNNCACGGCAGGGTCAGGGTTC | TRA adaptor-tagged target-specific reverse primer sequence |
| 71 | ACACGACGCTCTTCCGATCTNNNCACGGCAGGGTCAGGGTTC | TRA adaptor-tagged target-specific reverse primer sequence |
| 72 | ACACGACGCTCTTCCGATCTCGACCTCGGGTGGGAACAC | TRB adaptor-tagged target-specific reverse primer sequence |
| 73 | ACACGACGCTCTTCCGATCTNCGACCTCGGGTGGGAACAC | TRB adaptor-tagged target-specific reverse primer sequence |
| 74 | ACACGACGCTCTTCCGATCTNNCGACCTCGGGTGGGAACAC | TRB adaptor-tagged target-specific reverse primer sequence |
| 75 | ACACGACGCTCTTCCGATCTNNNCGACCTCGGGTGGGAACAC | TRB adaptor-tagged target-specific reverse primer sequence |
| 76 | AATGATACGGCGACCACCGAGATCTACACTCTTTCCCTACACGACGCTCTTCC | C5-P5 reverse primer |

| # | SEQUENCE | ANNOTATION |
|---|---|---|
| 77 | AGATCGGAAGAGCACACGTCTGAACTCCA | P7 priming site (C7) |
| 78 | AGATCGGAAGAGCGTCGTGTAGGGAAAGAGTGTAGATCTCGGTGGTCGCCGTATCATT | P5 priming site |
| 79 | ACACGACGCTCTTCCGATCTN | Universal adaptor; N is any nucleotide |
| 80 | NNNNWNNNNWNNNN | Universal adaptor; N is any nucleotide and W is adenine or thymine |
| 81 | WNNNNWNNNNWNNNN | Universal adaptor; N is any nucleotide and W is adenine or thymine |
| 82 | NWNNNWNNNNWNNNN | Universal adaptor; N is any nucleotide and W is adenine or thymine |
| 83 | NNWNNNNWNNNNWNNNN | Universal adaptor; N is any nucleotide and W is adenine or thymine |
| 84 | /biotin/TGTGAGGTGGCTGCGTACTTG | IgM-RT primer |
| 85 | /biotin/AGGACAGCCGGGAAGGTGT | IgG-RT primer |
| 86 | /biotin/CACGCATTTGTACTCGCCTTG | IgD-RT primer |
| 87 | /biotin/CTGGCTRGGTGGGAAGTTTCT | IgA-RT primer |
| 88 | /biotin/GGTGGCATAGTGACCAGAGA | IgE-RT primer |
| 89 | /biotin/TATTCAGCAGGCACACAACAGA | IgK-RT primer |
| 90 | /biotin/AGTGTGGCCTTGTTGGCTTG | IgL-RT primer |
| 91 | /biotin/GGGAGATCTCTGCTTCTGATG | TCR-A-RT primer |
| 92 | /biotin/GGTGAATAGGCAGACAGACTTG | TCR-B-RT primer |
| 93 | /biotin/GGCAGTCAATCCGAACACT | CD4-RT primer |
| 94 | /biotin/CTACAAAGTGGGCCCTTCTG | CD-8-RT primer |
| 95 | ACACGACGCTCTTCCGATCTTGTGGCCTTGCCGAGGGAGG | CD4-nested primer |
| 96 | ACACGACGCTCTTCCGATCTTGCGGAATCCCAGAGGGCCA | CD8-nested primer |
| 97 | CAAGCAGAAGACGGCATACGAGATNNNNNNGTGACTGGAGTTCAGACGTGTGCTCTTCCGATCT | C7-bc-P7 primer |
| 98 | AATGATACGGCGACCACCGAGATCTACACTCTTTCCCTACACGACGCTCTTCCGATCT | C5-P5 primer |
| 99 | NNNNWNNNNWNNNNWNNNNW | Vessel barcode sequence |
| 100 | NNNNWISCNNNWISCNNN | Vessel barcode sequence |

What is claimed:

1. A method of producing a polynucleotide library, the method comprising:
   (a) lysing a cell within each of a plurality of vessels, wherein each of said vessels comprises a cell from a population of cells and further comprises a plurality of molecular barcoded oligonucleotides, one or a pool of vessel barcoded oligonucleotides, and a first adaptor or a pool of first adaptors;
   (b) producing, in each vessel, a plurality of complementary polynucleotides, said producing comprising:
      (i) producing one or more target polynucleotide(s) that is complementary to one or more target polynucleotide transcript(s) present in the cell using one or more target-specific primers, wherein the one or more target polynucleotide(s) comprises a full-length coding sequence of a target gene; and
      (ii) producing a collection of polynucleotides using random oligomer primers, wherein each of the polynucleotides in the collection of polynucleotides is individually complementary to a polynucleotide transcript in the cell;
   (c) attaching to a plurality of the complementary polynucleotides one of the plurality of molecular barcoded oligonucleotides, thereby generating a plurality of molecular barcoded polynucleotides each comprising a molecular barcode;
   (d) attaching one of the one or a pool of vessel barcoded oligonucleotides, or an amplified product thereof, and the first adaptor or one of the pool of first adaptors or an amplified product thereof, to a plurality of the molecular barcoded polynucleotides, thereby generating a plurality of dual-barcoded polynucleotides comprising a molecular barcode and a vessel barcode;
   (e) producing a single-stranded amplicon of the plurality of dual-barcoded polynucleotides, thereby generating dual-barcoded single-stranded polynucleotides;
   (f) adding a second adaptor to each of the single-stranded amplicons, wherein the first adaptor and second adaptor are present at or near opposite ends of each of the dual-barcoded single-stranded polynucleotides; wherein the first adaptor and/or second adaptor comprise at least one universal priming site;
   (g) sequencing one or more target polynucleotide(s) from the plurality of barcoded polynucleotides; and
   (h) sequencing the whole transcriptome or a portion thereof from the plurality of barcoded polynucleotides;
   wherein sequence information from (g) and from (h) that have the same vessel barcode is identified as being from the same cell; and
   wherein:
      the complete transcriptome or a portion thereof is amplified prior to the sequencing, wherein amplification is carried out using a first primer set comprising a first primer and second primer specific for the first and second adaptor sequences, respectively;
      the one or more target polynucleotide(s) from the plurality of barcoded polynucleotides is amplified prior to the sequencing, wherein the full-length sequence(s) of the one or more target polynucleotide(s) is amplified;
      the cell origin of the one or more barcoded polynucleotide(s) is determined; and/or
      the number of polynucleotides with the same barcode is quantitated or determined.

2. The method of claim 1, wherein the collection of polynucleotides from each cell of the vessel, collectively, comprise sequences complementary to polynucleotide transcripts of a transcriptome or a partial transcriptome of each cell.

3. The method of claim 2, wherein the transcriptome or partial transcriptome, collectively, comprises at least 60%, 70%, 75%, 80%, 85%, 90% 95%, 96%, 97%, 98%, 99% or 100% of the transcripts present in the cell.

4. The method of claim 1, wherein: each of the dual-barcoded polynucleotides comprises a molecular barcode and a vessel barcode; and each of the dual-barcoded polynucleotides in the same vessel comprise the same vessel barcode.

5. The method of claim 1, wherein the first adaptor contains a first universal priming site and the second adaptor contains a second universal priming site.

6. The method of claim 1, wherein the first adaptor comprises the vessel barcoded oligonucleotide.

7. The method of claim 1, wherein each of or one or more of the complementary polynucleotides of (b) is a cDNA.

8. The method of claim 1, wherein each of or one or more of the barcoded single-stranded polynucleotide(s) is a strand of a cDNA.

9. The method of claim 5, wherein adding the second adaptor comprises hybridizing a splint oligonucleotide to each of the dual-barcoded single-stranded polynucleotides in the presence of an oligonucleotide comprising the second universal priming site, wherein the splint oligonucleotide comprises (i) a sequence complementary to the second universal priming site and (ii) a degenerate overhang sequence capable of randomly annealing to the 3' end of the barcoded single-stranded polynucleotide; and prior to the hybridizing, the splint oligonucleotide and the oligonucleotide comprising the second universal priming site are annealed to form a splint-adaptor duplex.

10. The method of claim 9, wherein:
the degenerate overhang sequence comprises the sequence NNNNNN, wherein N is any nucleotide (SEQ ID NO:24);
the splint oligonucleotide comprises the sequence ACACGACGCTCTTCCGATCTNNNNNN, wherein Nis any nucleotide (SEQ ID NO:26); and/or
the oligonucleotide comprising the second universal priming site comprises the sequence AGATCG-GAAGAGCGTCGTGT (SEQ ID NO:25).

11. The method of claim 1, wherein the vessel barcode-oligonucleotide comprises a degenerate sequence or the sequence $(N)_{14-17}$, wherein Nis any nucleotide.

12. The method of claim 1, wherein each vessel comprises a pool of first adaptors that comprises a pool of vessel barcoded oligonucleotides, wherein each vessel barcoded oligonucleotide of the pool of first adaptors comprises at least one base-shift or base addition compared to at least one of the other vessel barcoded oligonucleotides in the pool.

13. The method of claim 1, wherein in step (d) the method further comprises:
(i) amplifying the one or pool of vessel barcoded oligonucleotides; or amplifying the one or pool of the first adaptors, wherein the first adaptors comprise the one or pool of vessel barcoded oligonucleotides,
wherein the amplifying is performed prior to or simultaneously with attaching the vessel barcoded oligonucleotide; and/or
(ii) extending each of the plurality of the molecular barcoded polynucleotides after the attaching to generate the plurality of dual-barcoded polynucleotides.

14. The method of claim 1, wherein, in step (b):
the one or more target polynucleotide(s) are produced by reverse transcription of the target polynucleotide transcript(s) in the presence of a reverse transcriptase and one or more target-specific primer(s) complementary to a target sequence of the target polynucleotide(s); and/or
the collection of polynucleotides are produced by reverse transcription of polynucleotide transcripts in the cell in the presence of a reverse transcriptase and one or more random oligomer primers complementary to a polynucleotide transcript in the cell, wherein the one or more random oligomer primers comprise a poly (T) sequence or a mixture of random hexamer oligonucleotide primers; and/or
producing the plurality of complementary polynucleotides comprises use of a non-template terminal transferase, wherein three or more non-template nucleotides, ribonucleotides or analogs thereof are added to the 3' end of each produced complementary polynucleotide.

15. The method of claim 1, wherein the one or more target polynucleotides comprises:
a first polynucleotide of a T-cell receptor alpha (TCRα) polynucleotide and a second polynucleotide of a T-cell receptor (TCRβ) polynucleotide;
a first polynucleotide of a T-cell receptor gamma (TCRγ) polynucleotide and a second polynucleotide of a T-cell receptor delta (TCRδ) polynucleotide; or
a first polynucleotide of a heavy chain immunoglobulin (IgH) polynucleotide and a second polynucleotide of a light chain immunoglobulin (IgL) polynucleotide.

16. The method of claim 1, wherein the one or more target polynucleotide(s) and the collection of polynucleotides are produced in the vessel in the same reaction volume.

17. The method of claim 1, wherein:
in step (b), producing the plurality of complementary polynucleotides comprises use of a non-template terminal transferase, wherein three or more non-template nucleotides, ribonucleotides or analogs thereof are added to the 3' end of each produced complementary polynucleotide; and
in step (c), the attaching comprises hybridizing a region of one of the plurality of molecular barcoded oligonucleotides to the three or more non-template nucleotides of each of the complementary polynucleotides, wherein the plurality of molecular barcoded oligonucleotides are provided as a plurality of template switch oligonucleotides each comprising a 3' portion complementary to the three or more non-template nucleotides; and/or the template switch oligonucleotide further comprises a 5' terminal region that is complementary to a portion of the first adaptor, wherein the first adaptor comprises the vessel barcoded oligonucleotide.

18. The method of claim 1, wherein the vessel is a well, an emulsion, a droplet, or a microcapsule.

19. The method of claim 1, wherein the dual-barcoded single-stranded-polynucleotides comprise in order (5' to 3'): the first adaptor, the vessel barcode, the molecular barcode and the second adaptor.

20. The method of claim 1, wherein:
one or more of steps (a)-(f) is carried out in solution and/or is not carried out in the presence of a solid support.

21. The method of claim 1, wherein the population of cells comprises at least or about at least $1\times10^3$ cells.

22. The method of claim 1, wherein the population of cells comprises a lymphocyte or a subtype thereof, a B cell or a subtype thereof, a T cell or a subtype thereof, or a combination thereof.

23. The method of claim 1, further comprising amplifying the plurality of dual-barcoded single-stranded polynucleotides, thereby generating a plurality of polynucleotide templates, wherein amplification of the plurality of dual-barcoded single-stranded polynucleotides is carried out in the presence of a first primer set comprising a first primer complementary to the first adaptor sequence and a second primer complementary to the second adaptor sequence.

24. The method of claim 1, wherein one or more of the plurality of barcoded polynucleotides is sequenced.

25. The method of claim 24, wherein:
the complete transcriptome or a portion thereof is amplified prior to the sequencing, wherein amplification is carried out using a first primer set comprising a first primer and second primer specific for the first and second adaptor sequences, respectively;
the one or more target polynucleotide(s) from the plurality of barcoded polynucleotides is amplified prior to the sequencing, wherein the full-length sequence(s) of the one or more target polynucleotide(s) is amplified;
the cell origin of the one or more barcoded polynucleotide(s) is determined; and/or
the number of polynucleotides with the same barcode is quantitated or determined.

26. The method of claim 1, wherein transcriptome data from the plurality of cells is generated.

27. The method of claim 26, wherein the transcriptome data comprise a parameter, characteristic, feature or phenotype associated with the function or activity of the cell; and/or the transcriptome data is associated with the activation, exhaustion or proliferation activity of the cell.

28. The method of claim 1, further comprising:
   (a) identifying the vessel barcode(s) associated with one of the target polynucleotide(s) sequenced in (g);
   (b) identifying a selected single cell bearing the target polynucleotide; and
   (c) generating transcriptome data from the selected target polypeptide-expressing cell.

29. The method of claim 1, wherein the one or more target-specific primers comprises one or more primers complementary to a sequence(s) of the target sequence(s) of the target polynucleotide.

30. The method of claim 29, wherein the one or more target-specific primers comprise primers to a target sequence of a plurality of target polynucleotides each encoding an immune molecule or a chain thereof.

31. The method of claim 11, wherein at least one or two N in the sequence is W, wherein W is adenine or thymine.

32. The method of claim 1, wherein at least steps (c) and (d) are carried out in solution and/or are not carried out in the presence of a solid support.

33. The method of claim 1, wherein each of steps (a)-(e) is carried out in solution and/or is not carried out in the presence of a solid support.

* * * * *

SEQUENCE LISTING

<160> NUMBER OF SEQ ID NOS: 100

<210> SEQ ID NO 1
<211> LENGTH: 27
<212> TYPE: DNA
<213> ORGANISM: Artificial Sequence
<220> FEATURE:

```
<223> OTHER INFORMATION: 5'biotin oligo-dT anchored reverse
      transcription primer
<220> FEATURE:
<221> NAME/KEY: misc_feature
<222> LOCATION: 1
<223> OTHER INFORMATION: 5' biotin modification with an 18-carbon spacer
<220> FEATURE:
<221> NAME/KEY: misc_feature
<222> LOCATION: 27
<223> OTHER INFORMATION: n = A,T,C or G

<400> SEQUENCE: 1
tttttttttt tttttttttt tttttvn                                     27

<210> SEQ ID NO 2
<211> LENGTH: 78
<212> TYPE: DNA
<213> ORGANISM: Artificial Sequence
<220> FEATURE:
<223> OTHER INFORMATION: vessel barcode template oligo
<220> FEATURE:
<221> NAME/KEY: misc_feature
<222> LOCATION: 30, 31, 32, 33, 35, 36, 37, 38, 40, 41, 42, 43
<223> OTHER INFORMATION: n = A,T,C or G

<400> SEQUENCE: 2
atccatccac gactgacgga cgtattaaan nnnwnnnnwn nnnagatcgg aagagcacac   60
gtctgaactc cagtcacc                                                78

<210> SEQ ID NO 3
<211> LENGTH: 35
<212> TYPE: DNA
<213> ORGANISM: Artificial Sequence
<220> FEATURE:
<223> OTHER INFORMATION: template switch oligo
<220> FEATURE:
<221> NAME/KEY: misc_feature
<222> LOCATION: 33
<223> OTHER INFORMATION: riboguanosine
<220> FEATURE:
<221> NAME/KEY: misc_feature
<222> LOCATION: 34
<223> OTHER INFORMATION: riboguanosine
<220> FEATURE:
<221> NAME/KEY: misc_feature
<222> LOCATION: 24, 25, 27, 28, 30, 31
<223> OTHER INFORMATION: n = A,T,C or G

<400> SEQUENCE: 3
aatacgtccg tcagtcgtgg atgnntnnan ntggg                             35

<210> SEQ ID NO 4
<211> LENGTH: 23
<212> TYPE: DNA
<213> ORGANISM: Artificial Sequence
<220> FEATURE:
<223> OTHER INFORMATION: vessel barcode forward primer/universal adaptor
      oligonucleotide

<400> SEQUENCE: 4
catccacgac tgacggacgt att                                          23

<210> SEQ ID NO 5
<211> LENGTH: 24
<212> TYPE: DNA
<213> ORGANISM: Artificial Sequence
<220> FEATURE:
<223> OTHER INFORMATION: vessel barcode reverse primer

<400> SEQUENCE: 5
```

```
gtgactggag ttcagacgtg tgct                                            24
```

<210> SEQ ID NO 6
<211> LENGTH: 87
<212> TYPE: DNA
<213> ORGANISM: Artificial Sequence
<220> FEATURE:
<223> OTHER INFORMATION: vessel barcode oligo 1
<220> FEATURE:
<221> NAME/KEY: misc_feature
<222> LOCATION: (1)...(5)
<223> OTHER INFORMATION: phosphorothioate linkage
<220> FEATURE:
<221> NAME/KEY: misc_feature
<222> LOCATION: (83)...(87)
<223> OTHER INFORMATION: phosphorothioate linkage
<220> FEATURE:
<221> NAME/KEY: misc_feature
<222> LOCATION: 41, 42, 43, 44, 46, 47, 48, 49, 51, 52, 53, 54
<223> OTHER INFORMATION: n = A,T,C or G

<400> SEQUENCE: 6

```
tacgtctacg cgctgctctg ccacgactga cggacgtatt nnnnwnnnnw nnnnagatcg     60
gaagagcaca cgtctgaact ccagtca                                         87
```

<210> SEQ ID NO 7
<211> LENGTH: 88
<212> TYPE: DNA
<213> ORGANISM: Artificial Sequence
<220> FEATURE:
<223> OTHER INFORMATION: vessel barcode oligo 2
<220> FEATURE:
<221> NAME/KEY: misc_feature
<222> LOCATION: (1)...(5)
<223> OTHER INFORMATION: phosphorothioate linkage
<220> FEATURE:
<221> NAME/KEY: misc_feature
<222> LOCATION: (84)...(88)
<223> OTHER INFORMATION: phosphorothioate linkage
<220> FEATURE:
<221> NAME/KEY: misc_feature
<222> LOCATION: 42, 43, 44, 45, 47, 48, 49, 50, 52, 53, 54, 55
<223> OTHER INFORMATION: n = A,T,C or G

<400> SEQUENCE: 7

```
tacgtctacg cgctgctctg ccacgactga cggacgtatt wnnnnwnnnn wnnnnagatc     60
ggaagagcac acgtctgaac tccagtca                                        88
```

<210> SEQ ID NO 8
<211> LENGTH: 89
<212> TYPE: DNA
<213> ORGANISM: Artificial Sequence
<220> FEATURE:
<223> OTHER INFORMATION: vessel barcode oligo 3
<220> FEATURE:
<221> NAME/KEY: misc_feature
<222> LOCATION: (1)...(5)
<223> OTHER INFORMATION: phosphorothioate linkage
<220> FEATURE:
<221> NAME/KEY: misc_feature
<222> LOCATION: (85)...(89)
<223> OTHER INFORMATION: phosphorothioate linkage
<220> FEATURE:
<221> NAME/KEY: misc_feature
<222> LOCATION: 41, 43, 44, 45, 46, 48, 49, 50, 51, 53, 54, 55, 56
<223> OTHER INFORMATION: n = A,T,C or G

<400> SEQUENCE: 8

```
tacgtctacg cgctgctctg ccacgactga cggacgtatt nwnnnnwnnn nwnnnnagat     60
```
cggaagagca cacgtctgaa ctccagtca                                        89

<210> SEQ ID NO 9
<211> LENGTH: 90
<212> TYPE: DNA
<213> ORGANISM: Artificial Sequence
<220> FEATURE:
<223> OTHER INFORMATION: vessel barcode oligo 4
<220> FEATURE:
<221> NAME/KEY: misc_feature
<222> LOCATION: (1)...(5)
<223> OTHER INFORMATION: phosphorothioate
<220> FEATURE:
<221> NAME/KEY: misc_feature
<222> LOCATION: (86)...(90)
<223> OTHER INFORMATION: phosphorothioate
<220> FEATURE:
<221> NAME/KEY: misc_feature
<222> LOCATION: 41, 42, 44, 45, 46, 47, 49, 50, 51, 52, 54, 55, 56, 57
<223> OTHER INFORMATION: n = A,T,C or G

<400> SEQUENCE: 9
tacgtctacg cgctgctctg ccacgactga cggacgtatt nnwnnnnwnn nnwnnnnaga      60
tcggaagagc acacgtctga actccagtca                                       90

<210> SEQ ID NO 10
<211> LENGTH: 24
<212> TYPE: DNA
<213> ORGANISM: Artificial Sequence
<220> FEATURE:
<223> OTHER INFORMATION: vessel barcode forward primer

<400> SEQUENCE: 10
gtgactggag ttcagacgtg tgct                                             24

<210> SEQ ID NO 11
<211> LENGTH: 20
<212> TYPE: DNA
<213> ORGANISM: Artificial Sequence
<220> FEATURE:
<223> OTHER INFORMATION: vessel barcode reverse primer

<400> SEQUENCE: 11
tacgtctacg cgctgctctg                                                  20

<210> SEQ ID NO 12
<211> LENGTH: 19
<212> TYPE: DNA
<213> ORGANISM: Artificial Sequence
<220> FEATURE:
<223> OTHER INFORMATION: IgG constant RT primer
<220> FEATURE:
<221> NAME/KEY: modified_base
<222> LOCATION: 10
<223> OTHER INFORMATION: gm
<220> FEATURE:
<221> NAME/KEY: modified_base
<222> LOCATION: 11
<223> OTHER INFORMATION: gm
<220> FEATURE:
<221> NAME/KEY: modified_base
<222> LOCATION: 12
<223> OTHER INFORMATION: gm

<400> SEQUENCE: 12
aggacagccg ggaaggtgt                                                   19

<210> SEQ ID NO 13
<211> LENGTH: 18

-continued

```
<212> TYPE: DNA
<213> ORGANISM: Artificial Sequence
<220> FEATURE:
<223> OTHER INFORMATION: IgL constant RT primer
<220> FEATURE:
<221> NAME/KEY: modified_base
<222> LOCATION: 9
<223> OTHER INFORMATION: gm
<220> FEATURE:
<221> NAME/KEY: modified_base
<222> LOCATION: 11
<223> OTHER INFORMATION: 2'-O-methyl-adenosine
<220> FEATURE:
<221> NAME/KEY: modified_base
<222> LOCATION: 12
<223> OTHER INFORMATION: gm

<400> SEQUENCE: 13
gctcccgggt agaagtca                                                18

<210> SEQ ID NO 14
<211> LENGTH: 20
<212> TYPE: DNA
<213> ORGANISM: Artificial Sequence
<220> FEATURE:
<223> OTHER INFORMATION: IgK constant RT primer
<220> FEATURE:
<221> NAME/KEY: modified_base
<222> LOCATION: 11
<223> OTHER INFORMATION: gm
<220> FEATURE:
<221> NAME/KEY: modified_base
<222> LOCATION: 12
<223> OTHER INFORMATION: gm
<220> FEATURE:
<221> NAME/KEY: modified_base
<222> LOCATION: 13
<223> OTHER INFORMATION: 2'-O-methyl-adenosine

<400> SEQUENCE: 14
ggcctctctg ggatagaagt                                              20

<210> SEQ ID NO 15
<211> LENGTH: 21
<212> TYPE: DNA
<213> ORGANISM: Artificial Sequence
<220> FEATURE:
<223> OTHER INFORMATION: IgM constant RT primer
<220> FEATURE:
<221> NAME/KEY: modified_base
<222> LOCATION: 13
<223> OTHER INFORMATION: gm
<220> FEATURE:
<221> NAME/KEY: modified_base
<222> LOCATION: 14
<223> OTHER INFORMATION: cm
<220> FEATURE:
<221> NAME/KEY: modified_base
<222> LOCATION: 15
<223> OTHER INFORMATION: gm

<400> SEQUENCE: 15
tgtgaggtgg ctgcgtactt g                                            21

<210> SEQ ID NO 16
<211> LENGTH: 21
<212> TYPE: DNA
<213> ORGANISM: Artificial Sequence
<220> FEATURE:
<223> OTHER INFORMATION: IgA constant RT primer
<220> FEATURE:
<221> NAME/KEY: modified_base
<222> LOCATION: 12
```

```
<223> OTHER INFORMATION: gm
<220> FEATURE:
<221> NAME/KEY: modified_base
<222> LOCATION: 13
<223> OTHER INFORMATION: gm
<220> FEATURE:
<221> NAME/KEY: modified_base
<222> LOCATION: 14
<223> OTHER INFORMATION: 2'-O-methyladenosine

<400> SEQUENCE: 16
ctggctrggt gggaagtttc t                                              21

<210> SEQ ID NO 17
<211> LENGTH: 21
<212> TYPE: DNA
<213> ORGANISM: Artificial Sequence
<220> FEATURE:
<223> OTHER INFORMATION: IgD constant RT primer
<220> FEATURE:
<221> NAME/KEY: modified_base
<222> LOCATION: 12
<223> OTHER INFORMATION: 2'-O-methyladenosine
<220> FEATURE:
<221> NAME/KEY: modified_base
<222> LOCATION: 13
<223> OTHER INFORMATION: gmcm
<220> FEATURE:
<221> NAME/KEY: modified_base
<222> LOCATION: 15
<223> OTHER INFORMATION: cm

<400> SEQUENCE: 17
cacgcatttg tactcgcctt g                                              21

<210> SEQ ID NO 18
<211> LENGTH: 20
<212> TYPE: DNA
<213> ORGANISM: Artificial Sequence
<220> FEATURE:
<223> OTHER INFORMATION: IgE constant RT primer
<220> FEATURE:
<221> NAME/KEY: modified_base
<222> LOCATION: 10
<223> OTHER INFORMATION: 2'-O-methyladenosine
<220> FEATURE:
<221> NAME/KEY: modified_base
<222> LOCATION: 12
<223> OTHER INFORMATION: 2'-O-methyladenosine
<220> FEATURE:
<221> NAME/KEY: modified_base
<222> LOCATION: 13
<223> OTHER INFORMATION: gm

<400> SEQUENCE: 18
gatggtggca tagtgaccag                                                20

<210> SEQ ID NO 19
<211> LENGTH: 24
<212> TYPE: DNA
<213> ORGANISM: Artificial Sequence
<220> FEATURE:
<223> OTHER INFORMATION: TRA constant RT primer
<220> FEATURE:
<221> NAME/KEY: modified_base
<222> LOCATION: 15
<223> OTHER INFORMATION: 2'-O-methyladenosine
<220> FEATURE:
<221> NAME/KEY: modified_base
<222> LOCATION: 16
<223> OTHER INFORMATION: 2'-O-methyladenosine
<220> FEATURE:
<221> NAME/KEY: modified_base
```

```
<222> LOCATION: 18
<223> OTHER INFORMATION: cm

<400> SEQUENCE: 19
tgtttgagaa tcaaaatcgg tgaa                                          24

<210> SEQ ID NO 20
<211> LENGTH: 18
<212> TYPE: DNA
<213> ORGANISM: Artificial Sequence
<220> FEATURE:
<223> OTHER INFORMATION: TRB constant RT primer
<220> FEATURE:
<221> NAME/KEY: modified_base
<222> LOCATION: 9
<223> OTHER INFORMATION: gm
<220> FEATURE:
<221> NAME/KEY: modified_base
<222> LOCATION: 10
<223> OTHER INFORMATION: gm
<220> FEATURE:
<221> NAME/KEY: modified_base
<222> LOCATION: 11
<223> OTHER INFORMATION: gm

<400> SEQUENCE: 20
acgtggtcgg ggaagaag                                                 18

<210> SEQ ID NO 21
<211> LENGTH: 22
<212> TYPE: DNA
<213> ORGANISM: Artificial Sequence
<220> FEATURE:
<223> OTHER INFORMATION: TRG constant RT primer
<220> FEATURE:
<221> NAME/KEY: modified_base
<222> LOCATION: 13
<223> OTHER INFORMATION: ac4cgm
<220> FEATURE:
<221> NAME/KEY: modified_base
<222> LOCATION: 14
<223> OTHER INFORMATION: gm
<220> FEATURE:
<221> NAME/KEY: modified_base
<222> LOCATION: 16
<223> OTHER INFORMATION: 2'-O-methyladenosine

<400> SEQUENCE: 21
caagaagaca aaggtatgtt cc                                            22

<210> SEQ ID NO 22
<211> LENGTH: 20
<212> TYPE: DNA
<213> ORGANISM: Artificial Sequence
<220> FEATURE:
<223> OTHER INFORMATION: TRD constant RT primer
<220> FEATURE:
<221> NAME/KEY: modified_base
<222> LOCATION: 12
<223> OTHER INFORMATION: gm
<220> FEATURE:
<221> NAME/KEY: modified_base
<222> LOCATION: 13
<223> OTHER INFORMATION: 2'-O-methyladenosine
<220> FEATURE:
<221> NAME/KEY: modified_base
<222> LOCATION: 14
<223> OTHER INFORMATION: cm

<400> SEQUENCE: 22
tcttcttgga tgacacgaga                                               20
```

```
<210> SEQ ID NO 23
<211> LENGTH: 36
<212> TYPE: DNA
<213> ORGANISM: Artificial Sequence
<220> FEATURE:
<223> OTHER INFORMATION: template switch oligo
<220> FEATURE:
<221> NAME/KEY: modified_base
<222> LOCATION: 24
<223> OTHER INFORMATION: 2'-deoxyuridine
<220> FEATURE:
<221> NAME/KEY: misc_feature
<222> LOCATION: 34
<223> OTHER INFORMATION: riboguanosine
<220> FEATURE:
<221> NAME/KEY: misc_feature
<222> LOCATION: 35
<223> OTHER INFORMATION: riboguanosine
<220> FEATURE:
<221> NAME/KEY: modified_base
<222> LOCATION: 36
<223> OTHER INFORMATION: 3-deoxyguanosine
<220> FEATURE:
<221> NAME/KEY: misc_feature
<222> LOCATION: 25, 26, 28, 29, 31, 32
<223> OTHER INFORMATION: n = A,T,C or G

<400> SEQUENCE: 23
aatacgtccg tcagtcgtgg atgunntnna nntggg                             36

<210> SEQ ID NO 24
<211> LENGTH: 6
<212> TYPE: DNA
<213> ORGANISM: Artificial Sequence
<220> FEATURE:
<223> OTHER INFORMATION: degenerate overhang
<220> FEATURE:
<221> NAME/KEY: misc_feature
<222> LOCATION: 1, 2, 3, 4, 5, 6
<223> OTHER INFORMATION: n = A,T,C or G

<400> SEQUENCE: 24 nnnnnn                                                               6

<210> SEQ ID NO 25
<211> LENGTH: 20
<212> TYPE: DNA
<213> ORGANISM: Artificial Sequence
<220> FEATURE:
<223> OTHER INFORMATION: short P5 priming sequence
<220> FEATURE:
<221> NAME/KEY: modified_base
<222> LOCATION: 1
<223> OTHER INFORMATION: phosphorylated adenosine
<220> FEATURE:
<221> NAME/KEY: modified_base
<222> LOCATION: 20
<223> OTHER INFORMATION: 3' amnino modified (3AmMO) thymine

<400> SEQUENCE: 25
agatcggaag agcgtcgtgt                                               20

<210> SEQ ID NO 26
<211> LENGTH: 26
<212> TYPE: DNA
<213> ORGANISM: Artificial Sequence
<220> FEATURE:
<223> OTHER INFORMATION: splint oligonucleotide
<220> FEATURE:
<221> NAME/KEY: modified_base
<222> LOCATION: 26
<223> OTHER INFORMATION: 3'amino modified (3AmMO) nucleotide (a, g, c,
```

```
                or t)
<220> FEATURE:
<221> NAME/KEY: misc_feature
<222> LOCATION: 21, 22, 23, 24, 25, 26
<223> OTHER INFORMATION: n = A,T,C or G

<400> SEQUENCE: 26
acacgacgct cttccgatct nnnnnn                                          26

<210> SEQ ID NO 27
<211> LENGTH: 20
<212> TYPE: DNA
<213> ORGANISM: Artificial Sequence
<220> FEATURE:
<223> OTHER INFORMATION: short P5 reverse primer

<400> SEQUENCE: 27
acacgacgct cttccgatct                                                 20

<210> SEQ ID NO 28
<211> LENGTH: 64
<212> TYPE: DNA
<213> ORGANISM: Artificial Sequence
<220> FEATURE:
<223> OTHER INFORMATION: C7-index-P7 forward primer
<220> FEATURE:
<221> NAME/KEY: misc_feature
<222> LOCATION: 25, 26, 27, 28, 29, 30
<223> OTHER INFORMATION: n = A,T,C or G

<400> SEQUENCE: 28
caagcagaag acggcatacg agatnnnnnn gtgactggag ttcagacgtg tgctcttccg     60
atct                                                                 64

<210> SEQ ID NO 29
<211> LENGTH: 22
<212> TYPE: DNA
<213> ORGANISM: Artificial Sequence
<220> FEATURE:
<223> OTHER INFORMATION: IgG constant reverse primer sequence

<400> SEQUENCE: 29
aagtagtcct tgaccaggca gc                                              22

<210> SEQ ID NO 30
<211> LENGTH: 21
<212> TYPE: DNA
<213> ORGANISM: Artificial Sequence
<220> FEATURE:
<223> OTHER INFORMATION: IgL constant reverse primer sequence

<400> SEQUENCE: 30
ggcttgaagc tcctcagagg a                                               21

<210> SEQ ID NO 31
<211> LENGTH: 22
<212> TYPE: DNA
<213> ORGANISM: Artificial Sequence
<220> FEATURE:
<223> OTHER INFORMATION: IgK constant reverse primer sequence

<400> SEQUENCE: 31
aggcacacaa cagaggcagt tc                                              22

<210> SEQ ID NO 32
<211> LENGTH: 22
```

```
<212> TYPE: DNA
<213> ORGANISM: Artificial Sequence
<220> FEATURE:
<223> OTHER INFORMATION: IgM constant reverse primer sequence

<400> SEQUENCE: 32
cgacggggaa ttctcacagg ag                                             22

<210> SEQ ID NO 33
<211> LENGTH: 22
<212> TYPE: DNA
<213> ORGANISM: Artificial Sequence
<220> FEATURE:
<223> OTHER INFORMATION: IgD constant reverse primer sequence

<400> SEQUENCE: 33
tgtctgcacc ctgatatgat gg                                             22

<210> SEQ ID NO 34
<211> LENGTH: 19
<212> TYPE: DNA
<213> ORGANISM: Artificial Sequence
<220> FEATURE:
<223> OTHER INFORMATION: IgA constant 1 reverse primer sequence

<400> SEQUENCE: 34
gggtgctgca gaggctcag                                                 19

<210> SEQ ID NO 35
<211> LENGTH: 19
<212> TYPE: DNA
<213> ORGANISM: Artificial Sequence
<220> FEATURE:
<223> OTHER INFORMATION: IgA constant 2 reverse primer sequence

<400> SEQUENCE: 35
gggtgctgtc gaggctcag                                                 19

<210> SEQ ID NO 36
<211> LENGTH: 22
<212> TYPE: DNA
<213> ORGANISM: Artificial Sequence
<220> FEATURE:
<223> OTHER INFORMATION: IgE constant reverse primer sequence

<400> SEQUENCE: 36 ggaatgttttt tgcagcagcg gg                                            22

<210> SEQ ID NO 37
<211> LENGTH: 21
<212> TYPE: DNA
<213> ORGANISM: Artificial Sequence
<220> FEATURE:
<223> OTHER INFORMATION: TRA constant reverse primer sequence

<400> SEQUENCE: 37
agtctctcag ctggtacacg g                                              21

<210> SEQ ID NO 38
<211> LENGTH: 22
<212> TYPE: DNA
<213> ORGANISM: Artificial Sequence
<220> FEATURE:
<223> OTHER INFORMATION: TRB constant reverse primer sequence

<400> SEQUENCE: 38
```
atggctcaaa cacagcgacc tc                                            22

<210> SEQ ID NO 39
<211> LENGTH: 24
<212> TYPE: DNA
<213> ORGANISM: Artificial Sequence
<220> FEATURE:
<223> OTHER INFORMATION: C7

<400> SEQUENCE: 39
caagcagaag acggcatacg agat                                          24

<210> SEQ ID NO 40
<211> LENGTH: 38
<212> TYPE: DNA
<213> ORGANISM: Artificial Sequence
<220> FEATURE:
<223> OTHER INFORMATION: IgG adapter-tagged target-specific reverse
      primer sequence

<400> SEQUENCE: 40
acacgacgct cttccgatct ccaggggaa gacsgatg                             38

<210> SEQ ID NO 41
<211> LENGTH: 39
<212> TYPE: DNA
<213> ORGANISM: Artificial Sequence
<220> FEATURE:
<223> OTHER INFORMATION: IgG adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 41
acacgacgct cttccgatct nccaggggga agacsgatg                           39

<210> SEQ ID NO 42
<211> LENGTH: 40
<212> TYPE: DNA
<213> ORGANISM: Artificial Sequence
<220> FEATURE:
<223> OTHER INFORMATION: IgG adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 42
acacgacgct cttccgatct nnccaggggg aagacsgatg                          40

<210> SEQ ID NO 43
<211> LENGTH: 41
<212> TYPE: DNA
<213> ORGANISM: Artificial Sequence
<220> FEATURE:
<223> OTHER INFORMATION: IgG adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 43
acacgacgct cttccgatct nnnccagggg gaagacsgat g                        41

-continued

<210> SEQ ID NO 44
<211> LENGTH: 40
<212> TYPE: DNA
<213> ORGANISM: Artificial Sequence
<220> FEATURE:
<223> OTHER INFORMATION: IgA adapter-tagged target-specific reverse
      primer sequence

<400> SEQUENCE: 44
acacgacgct cttccgatct ggctcagcgg gaagaccttg                          40

<210> SEQ ID NO 45
<211> LENGTH: 41
<212> TYPE: DNA
<213> ORGANISM: Artificial Sequence
<220> FEATURE:
<223> OTHER INFORMATION: IgA adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 45
acacgacgct cttccgatct nggctcagcg ggaagacctt g                        41

<210> SEQ ID NO 46
<211> LENGTH: 42
<212> TYPE: DNA
<213> ORGANISM: Artificial Sequence
<220> FEATURE:
<223> OTHER INFORMATION: IgA adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 46
acacgacgct cttccgatct nnggctcagc gggaagacct tg                       42

<210> SEQ ID NO 47
<211> LENGTH: 43
<212> TYPE: DNA
<213> ORGANISM: Artificial Sequence
<220> FEATURE:
<223> OTHER INFORMATION: IgA adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 47
acacgacgct cttccgatct nnnggctcag cgggaagacc ttg                      43

<210> SEQ ID NO 48
<211> LENGTH: 40
<212> TYPE: DNA
<213> ORGANISM: Artificial Sequence
<220> FEATURE:
<223> OTHER INFORMATION: IgE adapter-tagged target-specific reverse
      primer sequence

<400> SEQUENCE: 48
acacgacgct cttccgatct gggaagacgg atgggctctg                          40

<210> SEQ ID NO 49
<211> LENGTH: 41

```
<212> TYPE: DNA
<213> ORGANISM: Artificial Sequence
<220> FEATURE:
<223> OTHER INFORMATION: IgE adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 49
acacgacgct cttccgatct ngggaagacg gatgggtctc g                    41

<210> SEQ ID NO 50
<211> LENGTH: 42
<212> TYPE: DNA
<213> ORGANISM: Artificial Sequence
<220> FEATURE:
<223> OTHER INFORMATION: IgE adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 50
acacgacgct cttccgatct nngggaagac ggatgggctc tg                   42

<210> SEQ ID NO 51
<211> LENGTH: 43
<212> TYPE: DNA
<213> ORGANISM: Artificial Sequence
<220> FEATURE:
<223> OTHER INFORMATION: IgE adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 51
acacgacgct cttccgatct nnngggaaga cggatgggct ctg                  43

<210> SEQ ID NO 52
<211> LENGTH: 42
<212> TYPE: DNA
<213> ORGANISM: Artificial Sequence
<220> FEATURE:
<223> OTHER INFORMATION: IgM adapter-tagged target-specific reverse
      primer sequence

<400> SEQUENCE: 52
acacgacgct cttccgatct gagacgaggt ggaaaagggt tg                   42

<210> SEQ ID NO 53
<211> LENGTH: 43
<212> TYPE: DNA
<213> ORGANISM: Artificial Sequence
<220> FEATURE:
<223> OTHER INFORMATION: IgM adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 53
acacgacgct cttccgatct ngagacgagg tggaaaaggg ttg                  43
```

```
<210> SEQ ID NO 54
<211> LENGTH: 44
<212> TYPE: DNA
<213> ORGANISM: Artificial Sequence
<220> FEATURE:
<223> OTHER INFORMATION: IgM adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 54
acacgacgct cttccgatct nngagacgag gtggaaaagg gttg                44

<210> SEQ ID NO 55
<211> LENGTH: 45
<212> TYPE: DNA
<213> ORGANISM: Artificial Sequence
<220> FEATURE:
<223> OTHER INFORMATION: IgM adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 55
acacgacgct cttccgatct nnngagacga ggtggaaaag ggttg               45

<210> SEQ ID NO 56
<211> LENGTH: 40
<212> TYPE: DNA
<213> ORGANISM: Artificial Sequence
<220> FEATURE:
<223> OTHER INFORMATION: IgD adapter-tagged target-specific reverse
      primer sequence

<400> SEQUENCE: 56
acacgacgct cttccgatct ggaacacatc cggagccttg                     40

<210> SEQ ID NO 57
<211> LENGTH: 41
<212> TYPE: DNA
<213> ORGANISM: Artificial Sequence
<220> FEATURE:
<223> OTHER INFORMATION: IgD adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 57
acacgacgct cttccgatct ngaacacat ccggagcctt g                    41

<210> SEQ ID NO 58
<211> LENGTH: 42
<212> TYPE: DNA
<213> ORGANISM: Artificial Sequence
<220> FEATURE:
<223> OTHER INFORMATION: IgD adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 58
acacgacgct cttccgatct nnggaacaca tccggagcct tg                  42
```

<210> SEQ ID NO 59
<211> LENGTH: 43
<212> TYPE: DNA
<213> ORGANISM: Artificial Sequence
<220> FEATURE:
<223> OTHER INFORMATION: IgD adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 59
acacgacgct cttccgatct nnnggaacac atccggagcc ttg                43

<210> SEQ ID NO 60
<211> LENGTH: 39
<212> TYPE: DNA
<213> ORGANISM: Artificial Sequence
<220> FEATURE:
<223> OTHER INFORMATION: IgL adapter-tagged target-specific reverse
      primer sequence

<400> SEQUENCE: 60
acacgacgct cttccgatct agggygggaa cagagtgac                     39

<210> SEQ ID NO 61
<211> LENGTH: 40
<212> TYPE: DNA
<213> ORGANISM: Artificial Sequence
<220> FEATURE:
<223> OTHER INFORMATION: IgL adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 61
acacgacgct cttccgatct nagggyggga acagagtgac                    40

<210> SEQ ID NO 62
<211> LENGTH: 41
<212> TYPE: DNA
<213> ORGANISM: Artificial Sequence
<220> FEATURE:
<223> OTHER INFORMATION: IgL adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 62
acacgacgct cttccgatct nnagggyggg aacagagtga c                  41

<210> SEQ ID NO 63
<211> LENGTH: 42
<212> TYPE: DNA
<213> ORGANISM: Artificial Sequence
<220> FEATURE:
<223> OTHER INFORMATION: IgL adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 63
acacgacgct cttccgatct nnnagggygg gaacagagtg ac					42

<210> SEQ ID NO 64
<211> LENGTH: 40
<212> TYPE: DNA
<213> ORGANISM: Artificial Sequence
<220> FEATURE:
<223> OTHER INFORMATION: IgK adapter-tagged target-specific reverse
      primer sequence

<400> SEQUENCE: 64
acacgacgct cttccgatct gacagatggt gcagccacag					40

<210> SEQ ID NO 65
<211> LENGTH: 41
<212> TYPE: DNA
<213> ORGANISM: Artificial Sequence
<220> FEATURE:
<223> OTHER INFORMATION: IgK adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 65
acacgacgct cttccgatct ngacagatgg tgcagccaca g					41

<210> SEQ ID NO 66
<211> LENGTH: 42
<212> TYPE: DNA
<213> ORGANISM: Artificial Sequence
<220> FEATURE:
<223> OTHER INFORMATION: IgK adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 66
acacgacgct cttccgatct nngacagatg gtgcagccac ag					42

<210> SEQ ID NO 67
<211> LENGTH: 43
<212> TYPE: DNA
<213> ORGANISM: Artificial Sequence
<220> FEATURE:
<223> OTHER INFORMATION: IgK adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 67
acacgacgct cttccgatct nnngacagat ggtgcagcca cag					43

<210> SEQ ID NO 68
<211> LENGTH: 39
<212> TYPE: DNA
<213> ORGANISM: Artificial Sequence
<220> FEATURE:
<223> OTHER INFORMATION: TRA adapter-tagged target-specific reverse
      primer sequence

<400> SEQUENCE: 68
acacgacgct cttccgatct cacggcaggg tcagggttc					39

```
<210> SEQ ID NO 69
<211> LENGTH: 40
<212> TYPE: DNA
<213> ORGANISM: Artificial Sequence
<220> FEATURE:
<223> OTHER INFORMATION: TRA adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 69
acacgacgct cttccgatct ncacggcagg gtcagggttc                           40

<210> SEQ ID NO 70
<211> LENGTH: 41
<212> TYPE: DNA
<213> ORGANISM: Artificial Sequence
<220> FEATURE:
<223> OTHER INFORMATION: TRA adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 70
acacgacgct cttccgatct nncacggcag ggtcagggtt c                         41

<210> SEQ ID NO 71
<211> LENGTH: 42
<212> TYPE: DNA
<213> ORGANISM: Artificial Sequence
<220> FEATURE:
<223> OTHER INFORMATION: TRA adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 71
acacgacgct cttccgatct nnncacggca gggtcagggt tc                        42

<210> SEQ ID NO 72
<211> LENGTH: 39
<212> TYPE: DNA
<213> ORGANISM: Artificial Sequence
<220> FEATURE:
<223> OTHER INFORMATION: TRB adapter-tagged target-specific reverse
      primer sequence

<400> SEQUENCE: 72
acacgacgct cttccgatct cgacctcggg tgggaacac                            39

<210> SEQ ID NO 73
<211> LENGTH: 40
<212> TYPE: DNA
<213> ORGANISM: Artificial Sequence
<220> FEATURE:
<223> OTHER INFORMATION: TRB adapter-tagged target-specific reverse
      primer sequence
<220> FEATURE:
<221> NAME/KEY: misc_feature
<222> LOCATION: 21
<223> OTHER INFORMATION: n = A,T,C or G

<400> SEQUENCE: 73
```

```
acacgacgct cttccgatct ncgacctcgg gtgggaacac                    40
```

<210> SEQ ID NO 74
<211> LENGTH: 41
<212> TYPE: DNA
<213> ORGANISM: Artificial Sequence
<220> FEATURE:
<223> OTHER INFORMATION: TRB adapter-tagged target-specific reverse
      primer sequence
<220> FEATURE:
<221> NAME/KEY: misc_feature
<222> LOCATION: 21, 22
<223> OTHER INFORMATION: n = A,T,C or G

<400> SEQUENCE: 74

```
acacgacgct cttccgatct nncgacctcg ggtgggaaca c                  41
```

<210> SEQ ID NO 75
<211> LENGTH: 42
<212> TYPE: DNA
<213> ORGANISM: Artificial Sequence
<220> FEATURE:
<223> OTHER INFORMATION: TRB adapter-tagged target-specific reverse
      primer sequence
<220> FEATURE:
<221> NAME/KEY: misc_feature
<222> LOCATION: 21, 22, 23
<223> OTHER INFORMATION: n = A,T,C or G

<400> SEQUENCE: 75

```
acacgacgct cttccgatct nnncgacctc gggtgggaac ac                 42
```

<210> SEQ ID NO 76
<211> LENGTH: 53
<212> TYPE: DNA
<213> ORGANISM: Artificial Sequence
<220> FEATURE:
<223> OTHER INFORMATION: C5-P5 reverse primer

<400> SEQUENCE: 76

```
aatgatacgg cgaccaccga gatctacact ctttccctac acgacgctct tcc     53
```

<210> SEQ ID NO 77
<211> LENGTH: 29
<212> TYPE: DNA
<213> ORGANISM: Artificial Sequence
<220> FEATURE:
<223> OTHER INFORMATION: P7 priming site (C7)

<400> SEQUENCE: 77

```
agatcggaag agcacacgtc tgaactcca                                29
```

<210> SEQ ID NO 78
<211> LENGTH: 58
<212> TYPE: DNA
<213> ORGANISM: Artificial Sequence
<220> FEATURE:
<223> OTHER INFORMATION: P5 priming site

<400> SEQUENCE: 78

```
agatcggaag agcgtcgtgt agggaaagag tgtagatctc ggtggtcgcc gtatcatt   58
```

<210> SEQ ID NO 79
<211> LENGTH: 26
<212> TYPE: DNA
<213> ORGANISM: Artificial Sequence
<220> FEATURE:

```
<223> OTHER INFORMATION: Universal adaptor
<220> FEATURE:
<221> NAME/KEY: misc_feature
<222> LOCATION: 21, 22, 23, 24, 25, 26
<223> OTHER INFORMATION: n = A,T,C or G

<400> SEQUENCE: 79
acacgacgct cttccgatct nnnnnn                                          26

<210> SEQ ID NO 80
<211> LENGTH: 14
<212> TYPE: DNA
<213> ORGANISM: Artificial Sequence
<220> FEATURE:
<223> OTHER INFORMATION: Universal adaptor
<220> FEATURE:
<221> NAME/KEY: misc_feature
<222> LOCATION: 1, 2, 3, 4, 6, 7, 8, 9, 11, 12, 13, 14
<223> OTHER INFORMATION: n = A,T,C or G

<400> SEQUENCE: 80
nnnnwnnnnw nnnn                                                       14

<210> SEQ ID NO 81
<211> LENGTH: 15
<212> TYPE: DNA
<213> ORGANISM: Artificial Sequence
<220> FEATURE:
<223> OTHER INFORMATION: Universal adaptor
<220> FEATURE:
<221> NAME/KEY: misc_feature
<222> LOCATION: 2, 3, 4, 5, 7, 8, 9, 10, 12, 13, 14, 15
<223> OTHER INFORMATION: n = A,T,C or G

<400> SEQUENCE: 81
wnnnnwnnnn wnnnn                                                      15

<210> SEQ ID NO 82
<211> LENGTH: 15
<212> TYPE: DNA
<213> ORGANISM: Artificial Sequence
<220> FEATURE:
<223> OTHER INFORMATION: Universal adaptor
<220> FEATURE:
<221> NAME/KEY: misc_feature
<222> LOCATION: 1, 3, 4, 5, 7, 8, 9, 10, 12, 13, 14, 15
<223> OTHER INFORMATION: n = A,T,C or G

<400> SEQUENCE: 82
nwnnnwnnnn wnnnn                                                      15

<210> SEQ ID NO 83
<211> LENGTH: 17
<212> TYPE: DNA
<213> ORGANISM: Artificial Sequence
<220> FEATURE:
<223> OTHER INFORMATION: Universal adaptor
<220> FEATURE:
<221> NAME/KEY: misc_feature
<222> LOCATION: 1, 2, 4, 5, 6, 7, 9, 10, 11, 12, 14, 15, 16, 17
<223> OTHER INFORMATION: n = A,T,C or G

<400> SEQUENCE: 83
nnwnnnnwnn nnwnnnn                                                    17

<210> SEQ ID NO 84
<211> LENGTH: 21
<212> TYPE: DNA
<213> ORGANISM: Artificial Sequence
```

```
<220> FEATURE:
<223> OTHER INFORMATION: IgM-RT primer
<220> FEATURE:
<221> NAME/KEY: modified_base
<222> LOCATION: 1
<223> OTHER INFORMATION: biotinylated thymine

<400> SEQUENCE: 84
tgtgaggtgg ctgcgtactt g                                              21

<210> SEQ ID NO 85
<211> LENGTH: 19
<212> TYPE: DNA
<213> ORGANISM: Artificial Sequence
<220> FEATURE:
<223> OTHER INFORMATION: IgG-RT primer
<220> FEATURE:
<221> NAME/KEY: modified_base
<222> LOCATION: 1
<223> OTHER INFORMATION: biotinylated adenine

<400> SEQUENCE: 85
aggacagccg ggaaggtgt                                                 19

<210> SEQ ID NO 86
<211> LENGTH: 21
<212> TYPE: DNA
<213> ORGANISM: Artificial Sequence
<220> FEATURE:
<223> OTHER INFORMATION: IgD-RT primer
<220> FEATURE:
<221> NAME/KEY: modified_base
<222> LOCATION: 1
<223> OTHER INFORMATION: biotinylated cytosine

<400> SEQUENCE: 86
cacgcatttg tactcgcctt g                                              21

<210> SEQ ID NO 87
<211> LENGTH: 21
<212> TYPE: DNA
<213> ORGANISM: Artificial Sequence
<220> FEATURE:
<223> OTHER INFORMATION: IgA-RT primer
<220> FEATURE:
<221> NAME/KEY: modified_base
<222> LOCATION: 1
<223> OTHER INFORMATION: biotinylated cytosine

<400> SEQUENCE: 87
ctggctrggt gggaagtttc t                                              21

<210> SEQ ID NO 88
<211> LENGTH: 20
<212> TYPE: DNA
<213> ORGANISM: Artificial Sequence
<220> FEATURE:
<223> OTHER INFORMATION: IgE-RT primer
<220> FEATURE:
<221> NAME/KEY: modified_base
<222> LOCATION: 1
<223> OTHER INFORMATION: biotinylated guanine

<400> SEQUENCE: 88
ggtggcatag tgaccagaga                                                20

<210> SEQ ID NO 89
<211> LENGTH: 22
<212> TYPE: DNA
```

```
<213> ORGANISM: Artificial Sequence
<220> FEATURE:
<223> OTHER INFORMATION: IgK-RT primer
<220> FEATURE:
<221> NAME/KEY: modified_base
<222> LOCATION: 1
<223> OTHER INFORMATION: biotinylated thymine

<400> SEQUENCE: 89
tattcagcag gcacacaaca ga                                              22

<210> SEQ ID NO 90
<211> LENGTH: 20
<212> TYPE: DNA
<213> ORGANISM: Artificial Sequence
<220> FEATURE:
<223> OTHER INFORMATION: IgL-RT primer
<220> FEATURE:
<221> NAME/KEY: modified_base
<222> LOCATION: 1
<223> OTHER INFORMATION: biotinylated adenine

<400> SEQUENCE: 90
agtgtggcct tgttggcttg                                                 20

<210> SEQ ID NO 91
<211> LENGTH: 21
<212> TYPE: DNA
<213> ORGANISM: Artificial Sequence
<220> FEATURE:
<223> OTHER INFORMATION: TCR-A-RT primer
<220> FEATURE:
<221> NAME/KEY: modified_base
<222> LOCATION: 1
<223> OTHER INFORMATION: biotinylated guanine

<400> SEQUENCE: 91
gggagatctc tgcttctgat g                                               21

<210> SEQ ID NO 92
<211> LENGTH: 22
<212> TYPE: DNA
<213> ORGANISM: Artificial Sequence
<220> FEATURE:
<223> OTHER INFORMATION: TCR-B-RT primer
<220> FEATURE:
<221> NAME/KEY: modified_base
<222> LOCATION: 1
<223> OTHER INFORMATION: biotinylated guanine

<400> SEQUENCE: 92
ggtgaatagg cagacagact tg                                              22

<210> SEQ ID NO 93
<211> LENGTH: 19
<212> TYPE: DNA
<213> ORGANISM: Artificial Sequence
<220> FEATURE:
<223> OTHER INFORMATION: CD4-RT primer
<220> FEATURE:
<221> NAME/KEY: modified_base
<222> LOCATION: 1
<223> OTHER INFORMATION: biotinylated guanine

<400> SEQUENCE: 93
ggcagtcaat ccgaacact                                                  19

<210> SEQ ID NO 94
<211> LENGTH: 20
```

```
<212> TYPE: DNA
<213> ORGANISM: Artificial Sequence
<220> FEATURE:
<223> OTHER INFORMATION: CD-8-RT primer
<220> FEATURE:
<221> NAME/KEY: modified_base
<222> LOCATION: 1
<223> OTHER INFORMATION: biotinylated cytosine

<400> SEQUENCE: 94
ctacaaagtg ggcccttctg                                             20

<210> SEQ ID NO 95
<211> LENGTH: 40
<212> TYPE: DNA
<213> ORGANISM: Artificial Sequence
<220> FEATURE:
<223> OTHER INFORMATION: CD4-nested primer

<400> SEQUENCE: 95
acacgacgct cttccgatct tgtggccttg ccgagggagg                        40

<210> SEQ ID NO 96
<211> LENGTH: 40
<212> TYPE: DNA
<213> ORGANISM: Artificial Sequence
<220> FEATURE:
<223> OTHER INFORMATION: CD8-nested primer

<400> SEQUENCE: 96
acacgacgct cttccgatct tgcggaatcc cagagggcca                        40

<210> SEQ ID NO 97
<211> LENGTH: 64
<212> TYPE: DNA
<213> ORGANISM: Artificial Sequence
<220> FEATURE:
<223> OTHER INFORMATION: C7-bc-P7 primer
<220> FEATURE:
<221> NAME/KEY: misc_feature
<222> LOCATION: 25, 26, 27, 28, 29, 30
<223> OTHER INFORMATION: n = A,T,C or G

<400> SEQUENCE: 97
caagcagaag acggcatacg agatnnnnnn gtgactggag ttcagacgtg tgctcttccg  60
atct                                                              64

<210> SEQ ID NO 98
<211> LENGTH: 58
<212> TYPE: DNA
<213> ORGANISM: Artificial Sequence
<220> FEATURE:
<223> OTHER INFORMATION: C5-P5 primer

<400> SEQUENCE: 98
aatgatacgg cgaccaccga gatctacact ctttccctac acgacgctct tccgatct    58

<210> SEQ ID NO 99
<211> LENGTH: 20
<212> TYPE: DNA
<213> ORGANISM: Artificial Sequence
<220> FEATURE:
<223> OTHER INFORMATION: Vessel barcode sequence
<220> FEATURE:
<221> NAME/KEY: misc_feature
<222> LOCATION: 1, 2, 3, 4, 6, 7, 8, 9, 11, 12, 13, 14, 16, 17, 18, 19
<223> OTHER INFORMATION: n = A,T,C or G
```

```
<400> SEQUENCE: 99
nnnnwnnnnw nnnnwnnnnw                                              20

<210> SEQ ID NO 100
<211> LENGTH: 18
<212> TYPE: DNA
<213> ORGANISM: Artificial Sequence
<220> FEATURE:
<223> OTHER INFORMATION: Vessel barcode sequence
<220> FEATURE:
<221> NAME/KEY: misc_feature
<222> LOCATION: 1, 2, 3, 4, 6, 9, 10, 11, 13, 16, 17, 18
<223> OTHER INFORMATION: n = A,T,C or G

<400> SEQUENCE: 100
nnnnwnscnn nwnscnnn                                                18
```